(12) United States Patent
Loosmore et al.

(10) Patent No.: US 6,184,371 B1
(45) Date of Patent: Feb. 6, 2001

(54) LACTOFERRIN RECEPTOR GENES OF MORAXELLA

(75) Inventors: Sheena M. Loosmore, Aurora; Run-Pan Du; Quijun Wang, both of Thornhill; Yan-Ping Yang; Michel H. Klein, both of Willowdale, all of (CA)

(73) Assignee: Connaught Laboratories Limited, Toronto (CA)

( * ) Notice: Under 35 U.S.C. 154(b), the term of this patent shall be extended for 0 days.

(21) Appl. No.: 09/074,658

(22) Filed: May 8, 1998

Related U.S. Application Data

(63) Continuation-in-part of application No. 08/867,941, filed on Jun. 3, 1997, now Pat. No. 5,977,337.

(51) Int. Cl.$^7$ .................................................. C07H 21/04

(52) U.S. Cl. ...................... 536/23.7; 536/23.1; 536/24.3; 536/24.32; 435/320.1; 435/69.1; 435/69.3; 435/69.7; 435/252.3; 424/200.1; 424/251.1

(58) Field of Search ................................. 536/23.1, 23.7, 536/24.3, 24.32; 435/320.1, 69.1, 69.3, 69.7, 252.3; 424/251.1, 200.1

(56) References Cited

U.S. PATENT DOCUMENTS

| 4,258,029 | 3/1981 | Moloney et al. . |
| 4,855,283 | 8/1989 | Lockhoff et al. . |
| 4,952,496 | 3/1990 | Studier et al. . |
| 5,194,254 | 3/1993 | Barber et al. . |

FOREIGN PATENT DOCUMENTS

| 2162193 | 5/1997 | (CA) . |
| WO 90/12591 | 11/1990 | (WO) . |
| WO 92/17167 | 10/1992 | (WO) . |
| WO 94/12641 | 6/1994 | (WO) . |
| WO 95/34308 | 12/1995 | (WO) . |
| WO 96/12733 | 5/1996 | (WO) . |

OTHER PUBLICATIONS

1. Brorson, J–E., A. Axelsson, and S.E. Holm. 1976. Studies on *Branhamella catarrhalis* (*Neisseria catarrhalis*) with special reference to maxillary sinusitis. Scan. J. Infect. Dis. 8:151–155.
2. Catlin, B.W., 1990. *Branhamella catarrhalis*: an organism gaining respect as a pathogen. Clin. Microbiol. Rev. 3: 293–320.
3. Hager, H., A. Verghese, S. Alvarez, and S.L. Berk. 1987. *Branhamella catarrhalis* respiratory infections. Rev. Infect. Dis. 9:1140–1149.
4. McLeod, D.T., F. Ahmad, M.J. Croughan, and M.A. Calder. 1986. Bronchopulmonary infection due to *M. catarrhalis*. Clinical features and therapeutic response. Drugs 31 (Suppl.3) : 109–112.

5. Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.
6. Ninane, G., J. Joly, and M. Kraytman. 1978. Bronchopulmonary infection due to *Branhamella catarrhalis* 11 cases assessed by transtracheal puncture. Br.Med.Jr. 1:276–278.
7. Srinivasan, G., M.J. Raff, W.C. Templeton, S.J. Givens, R.C. Graves, and J.C. Mel. 1981. *Branhamella catarrhalis* pneumonia. Report of two cases and review of the literature. Am. Rev. Respir. Dis. 123:553–555.
8. West, M., S.L. Berk, and J.K. Smith. 1982. *Branhamella catarrhalis* pneumonia., South. Med. J. 75:1021–1023.
9. Christensen, J.J., and B. Bruun. 1985. Bacteremia caused by a beta–lactamase producing strain of *Branhamella catarrhalis*. Acta. Pathol. Microbiol. Immunol. Scand. Sect. B 93:273–275.
10. Craig, D.B., and P.A. Wehrle. 1983. *Branhamella catarrhalis* septic arthritis. J. Rheumatol. 10:985–986.
11. Guthrie, R., K. Bakenhaster, R. Nelson, and R. Woskobnick. 1988. *Branhamella catarrhalis* sepsis: a case report and review of the literature. J. Infect. Dis. 158:907–908.
12. Hiroshi, Saito, E.J. Anaissie, N. Khardori, and G.P. Bodey. 1988. *Branhamella catarrhalis* septicemia in patients with leukemia. Cancer 61:2315–2317.
13. O'Neill, J.H., and P.W. Mathieson. 1987. Meningitis due to *Branhamella catarrhalis*. Aust. N.Z. J. Med. 17:241–242.
14. Murphy, T.F. 1989. The surface of *Branhamella catarrhalis*: a systematic approach to the surface antigens of an emerging pathogen. Pediatr. Infect. Dis. J. 8:S75–S77.
15. Van Hare, G.F., P.A. Shurin, C.D. Marchant, N.A. Cartelli, C.E. Johnson, D. Fulton, S. Carlin, and C.H. Kim. Acute otitis media caused by *Branhamella catarrhalis*: biology and therapy. Rev. Infect. Dis. 9:16–27.
16. Jorgensen, J.H., Doern, G.V., Maher, L.A., Howell, A.W., and Redding, J.S., 1990 Antimicrobial resistance among respiratory isolates of *Haemophilus influenza*, *Moraxella catarrhalis*, and *Streptococcus pneumoniae* in the United States. Antibiocrob. Agents Chemother. 34: 2075–2080.
17. Schryvers, A.B. and Lee, B.C. (1988) Comparative analysis of the transferrin and lactoferrin binding proteins in the family Neisseriaceae. Can. J. Microbiol. 35, 409–415.
18. O'Hagan, DT. 1992. Oral deleivery of faccines. Formulation and clinical pharmaco kinetic considerations. Clin. Pharmacokinet 22(t) : 1–10.

(List continued on next page.)

*Primary Examiner*—Jennifer Graser
(74) *Attorney, Agent, or Firm*—Sim & McBurney

(57) ABSTRACT

Purified and isolated nucleic acid molecules are provided which encode lactoferrin receptor proteins of Moraxella, such as *M. catarrhalis*, or a fragment or an analog of the lactoferrin receptor protein. The nucleic acid sequence may be used to produce recombinant lactoferrin receptor proteins Lbp1, Lbp2 and ORF3 of the strain of Moraxella free of other proteins of the Moraxella strain for purposes of diagnostics and medical treatment. Furthermore, the nucleic acid molecule may be used in the diagnosis of infection.

5 Claims, 130 Drawing Sheets

OTHER PUBLICATIONS

19. Ulmer et al. 1993. Curr. Opinion Invest. Drugs 2:983–989..

20. Lockhoff, O., Glycolipids as immunomodulators: Synthesis and properties, 1991, pp. 1611–1630.

21. Nixon–George A., et al., 1990. The adjuvant effect of stearyl tyrosine on a recombinant subunit hepatitis B surface antigen. J. Immunol 144 (12) : 4798–4802.

22. Wallace, R.J. et al., 1990. Antibiotic susceptibilites and drug resistance in *Moraxella (Branhaemella) catarrhalis*. Am. J. Med. 88 (5A) : 465–505.

26. Legrain M, et al. 1993. Cloning and characterization of *Neisseria meningitides* genes encoding the transferrin–binding proteins Tbp1 and Tbp2. Gene 130 (1) : 73–80.

28. Anderson JE, Sparling PF, Cornelissen CN. 1994. Gonococcal transferrin–binding protein 2 facilitates but is not essential for transferrin utilization. J Bacteriol 176 (11) : 3162–3170.

31. Pettersson, A. et al. 1993. Molecular Characterization of the 98–Kilodalton Iron–Regulated Outer membrane Protein of *Neisseria meningitides*. Infect. Immun. 61 (ti) : 4724–4733.

32. Ogunnariwo, J.A., Woo, T.K.W., Lo, R.Y.C., Gonzalez, G.C., and Schryvers, A.B. (1997) Characterization of the *Pasteurella haemolytica* transferrin receptor genes and the recombinant receptor proteins. *Microbial Pathog* 23:273–284.

33. Yang, Y.P., Myers, L.E., McGuinness, U., Chong, P., Kwok, Y., Klein, M.H., and Harkness, R.E. (1997) The outer membrane protein, CD, extracted from *Moraxella (Branhamella) catarrhalis* is a potential vaccine antigen that induces bactericidal antibodies. *FEMS Immun Med Microbiol* 17:187–199.

37. Waterman, M.S., Smith, T.F., and Beyer, W.A. 1976. Advan. Math. 20:367–387.

39. Smith, T.F., and Waterman, M.S. 1981 Identification of common molecular subsequences. J. Mol. Biol. 147:195–197.

42. Du, R–P et al; vol. 66, No. 8, Aug. 1998; pp. 3656–3665.

FIG. 1A

Alignment of translated 2.2kb lbpA PCR fragments

```
MNQSKQNNKSKKSKQVLKLSALSLGLLNITQVALANTTADK                          Tbp1
MSKSITKTQTPSVHTMTTHRLNLAIKAALFGVAVLPLSVWAQENTQTDAN                 Lbp1

AEATDKTNLVVVLDETVVTAKKNAPVSRKANEVTGLGKVVKTAETINKEQ                 Tbp1
SDAKDTKTPVVYLDAITVTAAPSA---RFDTDVTGLGKTVKTADTLAKEQ                 Lbp1

VLNIRDLTRYDPGIAVVEQGRGASSGYSIRGMDKNRVAVLVDGINQAQHY                 Tbp1
VQGIRDLVRYETGVSVVEQGRGGSSGFAIHGVDKNRVGITVDGIAQIQSY                 Lbp1

--QGPVAGKNYAAGGAINEIEYENVRSVEISKGANSSEYGSGALSGSVAFVT               Tbp1
ALKDESTKRAGAGSGAMNEIEIENIAAVAINKGGNALEAGSGALGGSVAFHT               Lbp1

KTADDIIKDGKDWGVQTKTAYASKNNAWVNSVAAAGKAGSFSGLIIYTDR                 Tbp1
KDVSDVLKSGKNLGAQSKTTYNSKNDHFSQTLAAAGKTERVEAMVQYTYR                 Lbp1
                                          QYT-R                    PCR4
                                          QYT-R                    PCR5

RGQEYKAHDDAYQGSQSFDRAVATTDPNNRTFLIANECANGNYEACAAGG                 Tbp1
KGKENKAHSDLNGINQSLYRLGAWQQKYDLRKPNELFAGTSYITESCLAS                 Lbp1
KG-ENKAHSDLNGINQSLYRLGAWQQKYDLRKPNELFAGTSYITESCLAS                 PCR4
KG-ENKAHSDLNGINQSLYRLGAWQQKYDLRKPNELFAGTSYITESCLAS                 PCR5

QTKLQAKPTNVRDKVNVKDYTGPNRLIPNPLTQDSKSLLLRPGYQLNDKH                 Tbp1
DDPKSCVQYPYVYTKARPDGIGNRNFSELSDAEKAQYLASTHPHEVVSAK                 Lbp1
DDPKSCVQYPYVYTKARPDGIGNRNFSELSDAEKAQYLASTHPHEVVSAK                 PCR4
DDPKSCVQYPYVYTKARPDGIGNRNFSELSDAEKAQYLASTHPHEVVSAK                 PCR5
```

FIG.1B

```
YVGGVYEITKQNYAMQDKTVPAYLAVHDIEKSRLSNHAQANGYYQGNNLGERIRDT  Tbp1
DYTGIYRLLPDPMDYRSDSYLARLNIKITPNLVSKLLLEDTKQTYNIRDM        Lbp1
DYTGIYRLLPDPMDYRSDSYLARLNIKITPNLVXKLLLEDTKQTYNIRDM        PCR4
DYTGTYRLLPDPMDYRSDSYLARLNIKITPNLVSKLLLEDTKQTYNIRDM        PCR5

IGPDSGYGINYAHGVFYDEKHQKDRLGLEYVYDSKGENKWFDDVRSYDKQDIT     Tbp1
RHCSYHGARLGNDGKPANGGSIVLCDDYQEYLNANDASQALFRPGANDAP        Lbp1
RHCSYHGARLGNDGKPANGGSIVLCDDYQEYLNANDASQALFRPGANDAP        PCR4
RHCSYHGARLGNDGKPANGGSIVLCDDYQEYLNANDASQASFRPGANDAP        PCR5

LRSQLTNTHCSTYPHIDKNCTPDVNKPFSVKEVDNNAYKEQHNLIKAVFN        Tbp1
IPKLAYARSSVFNQEHGKTRYGLSFEFKPDTPWFKQAKLNLHQQNIQIIN        Lbp1
IPKLAYARSSVFNQEHGKTRYGLSFEFKPDTPWFKQAKLNLHQQNIQIIN        PCR4
IPKLAYARSSVFNQEHGKTRYGLGFEFKPDTPWFKQAKLNLHQQNIQIIN        PCR5

KKMALGSTHHHINLQVGYDKFNSSLSRVEYRLATHQSYQKLDYTPPSNPL        Tbp1
HDIKKSCSQYPKVDLNCGISEIGHYEYQNNYRYKEGRASLTGKLDFNFDL        Lbp1
HDIKKSCSQYPKVDSNCGISEIGHYEYQXNYRYKEGRASLTGKLDFNFDL        PCR4

PDKFKPILGSNNKPICLDAYGYGHDHPQACNAKNSTYQNFAIKKGIEQYN        Tbp1
LGQHDLTVLAGADKVKSQFRANNPRRTIIDTTQGDAIIDESTLTAQEQAK        Lbp1
LGQHDLTVLAGTDKVKSQFRANNPRRTIIDTTQGDAIIDESTLTAQEQAK        PCR4
```

FIG.1C

```
QKTNTDKIDYQAIIDQYDKQNPNSTLKPFEKIKQSLGQEKYNKIDELGFK                          Tbp1
FKQSGAAWIVKNRLGRLEEKDACGNANECERAPIHGSNQYVGINNLYTPN                          Lbp1
FKQSGAAWIVKNRLGRLEEKDACGNANECERAPIHGSNQYVGINNLYTPN                          PCR4

AYKDLRNEWAGWTNDNSQQNANKGTDNIYQPNQATVVKDDKCKYSETNSY                          Tbp1
DYVDLSFGGRLDKQRIHSTDSNIISKTYTNKSYNFGAAVHLTPDFSLLYK                          Lbp1
DYVDXSFGGRLDKQRIHSTDSNIISKTYTNKSYNFGAAVHLTPDFSLLYK                          PCR4
              TDSNIISKTYTNKSYNFGAAVHXTPDFSLLYK                              PCR5

ADCSTTRHISGDNYFIALKDNMTINKYVDLGLGARYDRIKHKSDVPLVDNSASNQLSWNFGVV             Tbp1
TAKGFRTPSFYELYNYNSTAAQHKNDPDVSFPKRAVDVKPETSNTNEYGF                          Lbp1
TAKGFRTPSFYELYNYNSTAAQHKNDPDVSFPKRAVDVKPETSNTNEYGF                          PCR4
TAKGFRTPSFYELYNYNSTAAQHKNDPDVSFPKRAVDVKPETSNTNEYGF                          PCR5

VKPTNWLDIAYRSSQGFRMPSFSEMYGERFGVTIGKGTQHGCKGLYYICQQTV                       Tbp1
RYQHPWGDVEMSMFKSRYKDMLDKAIPNLTKAQQEYCKAHLDSNECVGNP                          Lbp1
RYQHPWGDVEMSMFKSRYKDMLDKAIPNLTKAQQEYCRAHLDSNECVGNP                          PCR4
RYQHPWGDIEMSMFKSRYKDMLDKAIPNLTKAQQEYCKAHLDSNECVGNP                          PCR5

HQTKLKPEKSFNQEIGATLHNHLGSLEVSYFKNRYTDLIVGKSEEIRTLT                          Tbp1
PTPKTSDEVFANLYNATIKGVSVKGKLDLHAMTSKLPDGLEMTLGYGHTK                          Lbp1
PTPKTSDEVFANLYNATIKGVSVKGKLDLHAMTSKLPDGLEMTLGYGHTK                          PCR4
PTPKTSDEVFANLYNATIKGVSVKGKLDLHAMTSKLPDGLEMTLGYGHTK                          PCR5

QGDNAGKQRGKGDLGFHNGQDADLTGINIIGRLDLNAANSRLPYGLYSTL                          Tbp1
```

FIG.1D

```
AYNKVDVKGKTLNPTLAGTNILFDAIQPSRYVVGLGYDAPSQKWGANAIF            Tbp1
LGKFDYIAPKDADGWYQARPAFWDAITPARYVVGLNYDHPSQVWGIGTTL            Lbp1
LGKFXYIAPKDADGWYQARPAFWDAITPARYVVGLNYDHPSQVWGIGATL            PCR4
LGKFXYIAPKDADGWYQARPAFWDAITPARYVVGLNYDHPSQVWGIGTTL            PCR5

HSDAKNPSELLADKNLGNGNIQTKQATKAKSTPWQTL-DLSGYVNIKDNFT           Tbp1
THSKQKDENELSALRIR-NGKRETQTLTHTIPKAYTLLDMTGYYSPTESIT           Lbp1
THSKQKDENELSALRIR-NGKRETQTLTHTIPKAYTLLDMTGYYSPTESIT           PCR4
THSKQKDENELSALRIR-NGKREIQTLTHTIPKAYTLLDMTGYYSPTESIT           PCR5

LRAGVYNVFNTYYTTWEALRQTAKGAVNQHTGLSQDKHYGRYAAPGRNYQLALEMKF*    Tbp1
ARLGINNVLNTRYTTWEAARQ------LPSEAASSTQSTRYIAPGRSYFASLEMKF*     Lbp1
ARLGINNVLNTRYTTWEAARQ------LPSEAASSTQSTRYIAPGRSYFASLEMKF*     PCR4
ARLGINNVLNTRYTTWEAARQ------LPSEAASSTQSTRYIAPGRSYFASLEMKF*     PCR5
```

FIG. 2A

M. catarrhalis 4223 lfr sequence

```
AAGCTTAGCATGATGGCATCGGCTGATTGT CTTTTGCCTTGTTGTGTGTTTGTGGGAGT
         10        20        30         40        50        60
                                          -35
TGATTGTACTTACCTTAGTGGTGGATGCTT GGGCTGATTTAATAAAGCGGTCTTCACAAC
         70        80        90        100       110       120
                                     -10
                                         RBS        Lbp2  MET SER THR
ACACCAAACGAGATATCACCATGAGTACTG VAL LYS THR PRO HIS ILE PHE TYR GLN LYS A
         130       140       150  TCAAAACCCCACATTTCTACCAAAAAC
                                         160       170       180

RG THR LEU SER LEU ALA ILE ALA SER ILE   PHE ALA ALA LEU VAL MET THR GLY CYS ARG S
GCACCCTTAGCCTTGCCATCGCCAGTATTT           TTGCTGCCCTTGGTGATGACAGGCTGCCGCT
         190       200       210                  220       230       240
```

FIG.2B

ER ASP ASP ILE SER VAL ASN ALA PRO ASN
CTGATGACATCAGCGTCAATGCACCCAATG
        250        260        270

VAL THR GLN LEU PRO GLN GLY THR VAL SER P
TTACCCAACTGCCCCAAGGCACGGTTTCAC
        280        290        300

RO ILE PRO ASN THR GLY HIS ASP ASN THR
CAATACCGAACACAGGTCATGACAACACCA
        310        320        330

ASN ASN THR ASN GLN GLY ASN ASN THR A
ATAACACCAACAATCAGGGCAACAACACGG
        340        350        360

SP ASN SER THR SER THR THR ASP PRO ASN
ATAACAGCACCAGCACCAACTGACCCAAATG
        370        380        390

GLY ASP ASN ASN GLN LEU THR GLN ALA GLN L
GCGATAACAACCAAACTGACACAAGCACAAA
        400        410        420

FIG.2C

```
YS  THR ALA ALA ALA GLY PHE PHE VAL
AGA CCG CCG CTG CCG GCA GGG TTT TTT GTG A
        430             440             450

MET GLY LYS ILE ARG ASP THR SER PRO LYS A
              T GGG TAA AAT TCG TGA TAC CAG CCC AAA AAA
                        460             470             480

SN  ASP PRO ASP TYR SER ASN ASP LEU VAL
A TGA CCC AGA TTA TAG CAA TGA TTT AGT TAC
        490             500             510

GLN GLN TRP GLN GLY LYS LEU TYR VAL GLY I
              A GCA GTG GCA AGG CAA ATT ATA TGT TGG TA
                        520             530             540

LE  ASP ALA HIS ARG PRO ASP GLY ILE GLY
T TGA TGC CCA TCG CCC AGA TGG CAT CGG CA
        550             560             570

THR GLY LYS ASN LEU ARG GLN PRO ILE THR A
              C AGG TAA AAA CTT GCG TCA GCC CAT CAC CG
                        580             590             600
```

FIG.2D

LA ASN ASP ILE LYS PRO LEU TYR PHE ASN
CCAATGACATCAAACCCTTGTATTTTAACA
    610              620            630

LYS PHE PRO ALA LEU SER ASP LEU HIS LEU A
ATTCCCTGCATTGTCTGATTTGCATTTAG
    640              650            660

SP SER GLU ARG HIS ARG PHE ASP PRO LYS
ACAGTGAACGCCCACCGTTTTGACCCCAAAA
    670              680            690

LYS LEU ASN THR ILE LYS VAL TYR GLY TYR G
AGCTAAACACCATTAAAGTGTATGGTTATG
    700              710            720

LY ASN LEU THR THR PRO SER LYS ASN ASN
GCAACTTAACAACACCCCTCTAAAAACAACA
    730              740            750

THR TYR ILE ASN HIS GLN GLN ALA ASP ASN L
CTTACATCAATCATCAGCAAGCTGATAATTA
    760              770            780

FIG.2E

```
YS  LYS ASN ASN LYS PRO VAL ASP PRO TYR
  A G A A A A A T A A C A A G C C T G T T G A C C C T T A T
                        790                 800                 810
                                  GLU ASN ILE ARG PHE GLY TYR LEU GLU LEU G
                                  G A A A A T A T C C G T T T T G G G T A T C T T G A A C T A C
                                                  820                 830                 840

LN  GLY SER SER LEU THR GLN LYS ASN ALA
  A A G G A A G C A G T C T G A C C C A A A A A A T G C C G
                        850                 860                 870
                                  ASP THR PRO ASN ASP LYS ASP ARG ILE PRO L
                                  A T A C T C C A A A T G A C A A A G A C C G C A T T C C C A
                                                  880                 890                 900

YS  PRO MET PRO ILE LEU PHE TYR HIS GLY
  A A C C C A T G C C C A T T T T G T T T T A T C A C G G A G
                        910                 920                 930
                                  GLU ASN ALA SER SER GLN LEU PRO SER ALA G
                                  A A A A C G C C A G C C A G C C C A G T G C C C A G T G C T G
                                                  940                 950                 960
```

FIG.2F

```
LY  LYS PHE ASN TYR THR GLY ASN TRP LEU
G T A A A T T T A A C T A C A C A G G C A A C T G G C T G T
                        970                 980                 990
                        TYR LEU SER ASP VAL LYS LYS ARG PRO ALA  L
                        A C C T A A G T G A T G T C A A A A A C G C C C T G C A C
                                1000                1010                1020

EU  SER ALA SER ASP ASP ARG VAL GLY VAL
T T T C A G C A T C A G A T G A T C G A G T G G G G G T C T
                        1030                1040                1050
                        TYR LEU ASN ALA SER GLY LYS SER ASN GLU  G
                        A T C T C A A T G C C A G T G G C A A A T C C A A T G A G G
                                1060                1070                1080

LY  ASP VAL VAL SER ALA ALA HIS ILE TYR
G C G A T G T G T C G T C A G T G C C G C C A C A T T T A T C
                        1090                1100                1110
                        LEU ASN GLY PHE GLN TYR LYS HIS THR PRO  A
                        T A A A C G G C T T T C A A T A T A A G C A C A C G C C T G
                                1120                1130                1140
```

FIG. 2G

```
LA  THR TYR GLN VAL ASP PHE ASP THR ASN
C C A C T T T A T C A G G T G G A T T T T G A C A C A A A C T
            1150                1160                1170
                    SER LEU THR GLY LYS LEU SER TYR TYR ASP A
                    C A T T A A C A G G C A A G C T G T C T T A T T A T G A C A
                            1180                1190                1200

SN  PRO ASN GLN GLN THR ALA GLN GLY LYS
A T C C C A A C C A G C A A A C T G C C C A A G G C A A A T
            1210                1220                1230
                    TYR ILE LYS SER GLN PHE ASP THR THR LYS L
                    A C A T C A A A A G C C A A T T T G A C A C T A C C A A A A
                            1240                1250                1260

YS  VAL ASN GLU THR ASP VAL TYR GLN ILE
A A G T C A A T G A A A C C G A T G T G T A T C A A A T T G
            1270                1280                1290
                    ASP ALA LYS ILE ASN GLY ASN ARG PHE VAL G
                    A T G C C A A A A T C A A C G G C A A C C G C T T C G T C G
                            1300                1310                1320
```

FIG.2H

LY  THR  ALA  LYS  SER  LEU  VAL  ASN  GLU  ASN
G T A C G G C C A A A T C T T T G G T T A A T G A G A A C A
                  1330                             1340                         1350

THR  GLU  THR  ALA  PRO  PHE  ILE  LYS  GLU  LEU  P
C A G A A A C C G C A C C T T T T A T C A A A G A G C T G T
                  1360                         1370                       1380

HE  SER  LYS  LYS  ALA  ASN  PRO  ASN  ASN  PRO
T C T C C A A A A A G C C A A T C C C A A T A A C C C A A
                  1390                         1400                       1410

ASN  PRO  ASN  SER  ASP  THR  LEU  GLU  GLY  GLY  P
A C C C T A A T T C A G A C A C G C T A G A A G G C G G G T
                  1420                         1430                       1440

HE  TYR  GLY  GLU  SER  GLY  ASP  GLU  LEU  ALA
T T T A T G G T G A G T C G G G C G A T G A G C T G G C G G
                  1450                         1460                       1470

GLY  LYS  PHE  LEU  SER  ASN  ASP  ASN  ALA  SER  T
G T A A A T T T T T A T C C A A T G A C A A C G C A T C T T
                  1480                         1490                       1500

FIG. 2I.

```
YR  VAL VAL PHE GLY GLY LYS ARG ASP LYS
    ATGTGGGTCTTTGGTGGTAAACGAGACAAAA
                    1510              1520              1530
    THR ASP LYS PRO VAL ALA THR LYS THR VAL T
    CAGACAAACCTGTCGCCACAAAACGGTGT
              1540              1550              1560

YR  PHE SER ALA GLY PHE GLU LYS PRO SER
    ATTTAGTGCAGGCTTTGAAAAACCTAGCA
                    1570              1580              1590
    THR SER PHE VAL ASP ASN GLU THR ILE GLY A
    CCAGTTTTGTGGATAATGAAACGATTGGCA
              1600              1610              1620

RG  ILE ILE ASN SER LYS LYS LEU ASN ASP
    GAATTATTAACAGCAAAAAGTTAAATGATG
                    1630              1640              1650
    ALA VAL ASN GLU LYS ILE ASP ASN GLY ASP I
    CGGTGAATGAGAAAATTGATAATGGTGATA
              1660              1670              1680
```

FIG.2J

```
LE  PRO THR SER ASP GLU ARG TYR ASP GLU
    TTCCTACCAGTGATGAACGCTATGATGAAT
    1690                    1700
                                      PHE PRO TRP GLY GLU LYS LYS ALA GLU PHE  T
                                          TTCCTTGGGGCGAAAAAAGCAGAATTCA
                                          1720                    1730      1740

HR  LYS LYS VAL SER SER THR GLN ALA
    CCAAAAAGTCAGCAGCACCCAAGCCG
    1750                    1760
                                      VAL PRO ALA TYR PHE GLY GLN HIS ASP LYS  P
                                          TGCCAGCTTATTTTGGGCAACATGATAAAT
                                          1780                    1790      1800

HE  TYR PHE ASN GLY ASN TYR TYR ASP LEU
    TTTATTTTAATGGCAACTATTATGACCTAT
    1810                    1820      1830
                                      SER ALA SER SER VAL ASP LYS LEU ALA PRO  A
                                          CAGCCCAGCAGTGTTGATAAATTGGCCCCTG
                                          1840                    1850      1860
```

FIG.2K

```
LA  ASP ALA VAL LYS ALA ASN GLN SER ILE
    CCGATGCTGTCAAAGCCAACCAATCCATTA
          1870              1880             1890
    LYS GLU LYS TYR PRO ASN ALA THR LEU ASN  L
    AAGAAAAATACCCTAATGCCACACTAAATA
          1900             1910             1920

YS  ASP ASN GLN VAL THR ALA ILE VAL LEU
    AGGACAACCAAGTTACCGCCATCGTGCTAC
          1930             1940             1950
    GLN GLU ALA LYS ASP ASN LYS PRO TYR THR  A
    AAGAAGCCAAAGATAATAAGCCTTATACCG
          1960             1970             1980

LA  ILE ARG ALA LYS SER TYR GLN HIS ILE
    CCATTCGTGCCAAAAGCTATCAGCACATCA
          1990             2000             2010
    SER PHE GLY GLU THR LEU TYR ASN ASP ALA  A
    GTTTTGGCGAGACGCTGTATACGATGCCAA
          2020             2030             2040
```

FIG. 2L

```
SN  GLN THR PRO THR ARG SER TYR PHE VAL
    ACCAAACCCCAACACGCAGTTATTTTGTGC
            2050              2060              2070
    GLN GLY GLY ARG ALA ASP THR SER THR L
    AAGGCGGGTAGGGCAGATACCAGCACCACGC
            2080              2090              2100

EU  PRO LYS ALA GLY LYS PHE THR TYR ASN
    TGCCCAAGGCAGGTAAATTCACTTACAACG
            2110              2120              2130
    GLY LEU TRP ALA GLY TYR LEU ILE GLN LYS L
    GTCTTTGGGCAGGCTATCTTATCCAAAAAA
            2140              2150              2160

YS  ASP LYS GLY TYR SER ASN ASN GLU GLU
    AGGACAAAGGTTATAGCAATAATGAAGAAA
            2170              2180              2190
    THR ILE LYS LYS LYS GLY HIS GLN ASP TYR L
    CCATCAAGAAAAAAGGCCATCAAGATTATC
            2200              2210              2220
```

FIG.2M

```
EU  LEU THR GLU ASP PHE THR PRO GLU ASP
T G T T A A C C G A G A A G A C T T C A C C C C A G A A G A T G
                    2230                        2240                        2250
          ASP ASP ASP LEU THR ALA SER ASP ASP S
          A T G A C G A T G A T T T G A C C G C A T C T G A T G A T T
                    2260                        2270                        2280

ER  GLN ASP ASP ALA HIS GLY ASP ASP
C A C A A G A T G A T G A T G C A C A T G G C G A T G A T G
                    2290                        2300                        2310
          ASP LEU ILE ALA SER ASP ASP SER GLN ASP A
          A T T T G A T T G C A T C T G A T G A T T C A C A A G A T G
                    2320                        2330                        2340

SP  ASP ALA ASP GLY ASP ASP SER ASP
A T G A C G C A G A T G G C G A T G A C G A T T C A G A T G
                    2350                        2360                        2370
          ASP LEU GLY ASP GLY ALA ASP ASP ALA ALA A
          A T T T G G G T G A T G G T G C A G A T G A C G C C G C C G
                    2380                        2390                        2400
```

FIG.2N

```
LA  GLY LYS VAL TYR HIS ALA GLY ASN ILE
C A G G C A A A G T G T A T C A T G C A G G T A A T A T T C
         2410                2420              2430

ARG PRO GLU PHE GLU ASN LYS TYR LEU PRO I
              G C C C T G A A T T G A A A A C A A A T A C T T G C C C A
                   2440              2450              2460

LE  ASN GLU PRO THR HIS GLU LYS THR PHE
T T A A T G A G C C T A C T T C A T G A A A A A C C T T T G
         2470              2480              2490

ALA LEU ASP GLY LYS ASN LYS ALA LYS PHE A
              C C C T A G A T G G T A A A A A T A A A G C T A A G T T T G
                   2500              2510              2520

SP  VAL ASP PHE ASP THR ASN SER LEU THR
A T G T G G A T T T T G A C A C C A A C A G C C T A A C T G
         2530              2540              2550

GLY LYS LEU ASN ASP GLU ARG GLY ASP ILE V
              G T A A A T T A A A C G A T G A G A G A G G T G A T A T C G
                   2560              2570              2580
```

FIG. 20

```
AL  PHE ASP ILE LYS ASN GLY LYS ILE ASP
    TCTTTGATATCAAAAATGGCAAAATTGATG
              2590              2600              2610
    GLY THR GLY PHE THR ALA LYS ALA ASP VAL P
    GCACAGGCTTTACCGCCAAAGCCGATGTGC
              2620              2630              2640

RO  ASN TYR ARG GLU VAL GLY ASN ASN
    CAAACTATCGTGAAGAAGTGGGTAACAACC
              2650              2660              2670
    GLN GLY GLY PHE LEU TYR ASN ILE LYS A
    AAGGTGGCGGTTTCTTATACAACATCAAAG
              2680              2690              2700

SP  ILE ASP VAL LYS GLY GLN PHE PHE GLY
    ATATTGATGTCAAGGGGCAATTTTTTGGCA
              2710              2720              2730
    THR ASN GLY GLU GLU LEU ALA GLY GLN LEU G
    CAAATGGCGAAGAGTTGGCAGGGCAGTTAC
              2740              2750              2760
```

FIG.2P

```
IN  TYR ASP LYS GLY ASP GLY ILE ASN ASP
AGTACGACAAAGGCGATGGCATCAATGACA
                                    2790
                     2780
              2770
                    THR ALA GLU LYS ALA GLY ALA VAL PHE GLY A
                    CCGCCGAAAAAGCAGGGGCTGTCTTTGGGG
                                                            2820
                                              2810
                         2800
LA VAL LYS ASP LYS ***
CTGTTAAAGATAAATAAAGCCCCCTTCATC
                                    2850
                    2840
     2830
                    ATCGTTTAGTCGCTTGACCGACAGTTGATG
                                              2870          2880
                         2860
ACGCCCCTTGGCAATGTCTTAAAACAGCACT
                                     2910
          2890           2900
                    TTGAAACAGTGCCTTGGGCGAATTCTTTGGA
                          2920         2930          2940
TAAATGCACCAGATTTGCCTTGGGCTAATA
                                   2970
          2950          2960
                                -35
                    TCTTGATAAAACATCGCCATAAAATAGAAA
                          2980         -10           3000
                                     2990
```

FIG. 2Q

```
                              RBS                          Lbp1
                                                           MET SER LYS
ATAAAGTTTAGGATTTTTTTATGTCAAAAT
         3010              3020            3030

2nd possible start
IS  THR MET THR THR HIS ARG LEU ASN LEU   SER ILE THR LYS THR GLN THR PRO SER VAL H
ATACCATGACCACCGCACCCGCTTAAACCTTG           CTATCACAAAAACACAAACAAACACCATCAGTCC
         3070            3080       3090          3040              3050              3060

ALA ILE LYS ALA ALA LEU PHE GLY VAL ALA V
                                          CCATCAAAAGCGGCGTTATTTGGTGTGGCAG
                                                  3100              3110              3120

AL  LEU PRO LEU SER VAL TRP ALA GLN GLU   ASN THR GLN THR ASP ALA ASN SER ASP ALA L
TTTTACCCCTATCCGTCTGGGCGCAAGAGA             ACACTCAGACAGATGCCAACTCTGATGCCA
         3130            3140       3150          3160              3170              3180
```

FIG.2R

```
YS  ASP THR LYS THR PRO VAL VAL TYR LEU
    AAGACACAAAACCCCTGTCTATTTAG
                3190                  3200                3210

ASP ALA ILE THR VAL THR ALA ALA PRO SER  A
    ATGCCATCACGGTAACCGCCGCCCCATCTG
                        3220              3230              3240

LA  PRO VAL SER ARG PHE ASP THR ASP VAL
    CCCCTGTTTCTCGGTTTGACACCGATGTAA
            3250              3260              3270

THR GLY LEU GLY LYS THR VAL LYS THR ALA  A
    CAGGGCTTGGCAAAACGGTCAAAACCGCTG
                3280              3290              3300

SP  THR LEU ALA LYS GLU GLN VAL GLN GLY
    ACACGCTGGCAAAAGAACAAGTGCAGGGC
            3310              3320              3330

ILE ARG ASP LEU VAL ARG TYR GLU THR GLY  V
    ATTCGTGATTTGGTGCGTTATGAAACTGGGG
                    3340              3350              3360
```

FIG.2S

```
AL  SER  VAL  VAL  GLU  GLN  GLY  ARG  GLY  GLY                SER  SER  GLY  PHE  ALA  ILE  HIS  GLY  VAL  ASP  L
T G A G T G T G G T T G A G C A G G G G C G T G G C A          G C A G C G G A T T T G C C A T T C A T G G C G T G G A T A
                        3370                           3380                              3390                      3400                           3410                    3420

YS  ASN  ARG  VAL  GLY  ILE  THR  VAL  ASP  GLY                ILE  ALA  GLN  ILE  GLN  SER  TYR  LYS  ASP  GLU  S
A A A A C C G A G T G G G C A T T A C C G T A G A T G G C A    T T G C C C A A A T T C A A T T C C T A C A A A G A T G A A T
                        3430                           3440                              3450                      3460                           3470                    3480

ER  THR  LYS  ARG  ALA  GLY  SER  GLY                          ALA  MET  ASN  GLU  ILE  GLU  ILE  GLU  ASN  ILE  A
C C A C C A A A C G A G C T G G T G C A G G C T C T G G G G    C G A T G A A T G A G A T A G A G A T T G A A A A C A T T G
                        3490                           3500                              3510                      3520                           3530                    3540
```

FIG.2T

```
LA  ALA VAL ALA ILE ASN LYS GLY GLY ASN
    CCGCCGTTGCCATCAATAAAGGTGGTAATG
                    3550              3560           3570
        ALA LEU GLU ALA GLY SER GLY ALA LEU GLY G
        CCCTAGAAGCAGGCTCTGGTGCGTTGGGCG
                3580            3590            3600

LY  SER VAL ALA PHE HIS THR LYS ASP VAL
    GTTCGGTGGCGTTTCATACCAAAGATGTGA
                    3610            3620            3630
        SER ASP VAL LEU LYS SER GLY LYS ASN LEU G
        GCGATGTCTTAAAATCTGGTAAAAATCTTG
                3640            3650            3660

LY  ALA GLN SER LYS THR THR TYR ASN SER
    GCGCTCAAAGCAAAACCACTTATAACAGCA
                    3670            3680            3690
        LYS ASN ASP HIS PHE SER GLN THR LEU ALA A
        AAAATGACCATTTTAGTCAGACGCTGGCAG
                3700            3710            3720
```

FIG.2U

```
LA  ALA  GLY  LYS  THR  GLU  LYS  THR  GLU  ARG  VAL  GLU  ALA
    CGGCAGGTAAAACCGAGCGTGTGGAAGCGA
    3730                              3740              3750

MET  VAL  GLN  TYR  THR  TYR  ARG  LYS  GLY  LYS  G
                    TGGTGCAATATACCTACCGTAAAGGCAAAG
                         3760              3770              3780

LU  ASN  LYS  ALA  HIS  SER  ASP  LEU  ASN  GLY
    AAAACAAAGCACACAGCGACCTAAATGGCA
    3790                              3800              3810

ILE  ASN  GLN  SER  LEU  TYR  ARG  LEU  GLY  ALA  T
                    TCAACCAAAGCCTATATCGCTTGGGTGCAT
                         3820              3830              3840

RP  GLN  GLN  LYS  TYR  ASP  LEU  ARG  LYS  PRO
    GGCAACAAAAATATGATTTAAGAAAAGCCCA
    3850                              3860              3870

ASN  GLU  LEU  PHE  ALA  GLY  THR  SER  TYR  ILE  T
                    ATGAACTGTTTGCAGGCACAAGCTACATCA
                         3880              3890              3900
```

FIG.2V

```
HR  GLU  SER  CYS  LEU  ALA  SER  ASP  ASP  PRO
C C G A A A G C T G T T T G G C A A G T G A T G A C C C A A
    3910                3920                3930

LYS  SER  CYS  VAL  GLN  TYR  PRO  TYR  VAL  TYR  T
                          A A A G C T G C G T A C A A T A C C C T T A T G T C T A C A
                              3940                3950                3960

HR  LYS  ALA  ARG  PRO  ASP  GLY  ILE  GLY  ASN
C C A A A G C C C C G G A C C A G A T G G C A T C G G C A A T C
    3970                3980                3990

ARG  ASN  PHE  SER  GLU  LEU  SER  ASP  ALA  GLU  L
                          G C A A T T T T T C T G A G T T A A G C G A T G C T G A A A
                              4000                4010                4020

YS  ALA  GLN  TYR  LEU  ALA  SER  THR  HIS  PRO
A A G C A C A A A T A T T T G G C A T C C A C G C C A C C C C C
    4030                4040                4050

HIS  GLU  VAL  VAL  SER  ALA  LYS  ASP  TYR  THR  G
                          A T G A G G G T T G T C T C T G C C A A A G A T T A T A C A G
                              4060                4070                4080
```

FIG.2W

```
LY  ILE TYR ARG LEU LEU PRO ASP PRO MET
GCA TTT ATC GGT TGT TAC CTG ACC CCA TGG
            4090            4100            4110
                ASP TYR ARG SER ASP SER TYR LEU ALA ARG L
                ACT ATC GTT CAG ACT CGT ATT TGG CAC GCC
                    4120            4130            4140

EU  ASN ILE LYS ILE THR PRO ASN LEU VAL
TTA ACA TCA AAA TCA CCC CAA ATC TGG TCA
            4150            4160            4170
                SER LYS LEU LEU LEU GLU ASP THR LYS GLN T
                GTA AAC TGT TAT TAG AAG ACA CCA AGC AAA
                    4180            4190            4200

HR  TYR ASN ILE ARG ASP MET ARG HIS CYS
CAT ACA ACA TTC GTG ATA TGC GTC ATT GTA
            4210            4220            4230
                SER TYR HIS GLY ALA ARG LEU GLY ASN ASP G
                GTT ACC ATG GGG CAA GAT TGG GCA ATG ATG
                    4240            4250            4260
```

FIG.2X

```
LY  LYS PRO ALA ASN GLY GLY SER ILE VAL
GT AAG CCT GCC AAT GGT GGC TCC ATT GTT C
        4270            4280            4290

LEU CYS ASP ASP TYR GLN GLU TYR LEU ASN A
                TTT GCG ATT ATC AAG AGT ATC TAA ACG
                        4300            4310            4320

LA ASN ASP ALA SER GLN ALA LEU PHE ARG
C CAA TGA CGG CAT CAC AAG CAT TAT TTA GAC
        4330            4340            4350

PRO GLY ALA ASN ASP ALA PRO ILE PRO LYS L
                CAG GTG CTA ATG ATG CCC CAT TCC AAA AC
                        4360            4370            4380

EU ALA TYR ALA ARG SER SER VAL PHE ASN
TGG CTT ATG CCA GAA GCA GTG TGT TTA ACC
        4390            4400            4410

GLN GLU HIS GLY LYS THR ARG TYR GLY LEU S
                AAG AGC ATG GCA AAA CTC GCT ATG GGT TAA
                        4420            4430            4440
```

FIG.2Y

```
ER  PHE GLU PHE LYS PRO ASP THR PRO TRP
GTTTTGAGTTTAAGCCTGACACGCCATGGT
              4450            4460            4470
                PHE LYS GLN ALA LYS LEU ASN LEU HIS GLN G
                TTAAGCAAGCAAAATTAAACCTACACCAAAC
                      4480            4490            4500

LN  ASN ILE GLN ILE ILE ASN HIS ASP ILE
AAAATATCCAAATCATTAACCATGACATTA
              4510            4520            4530
                LYS LYS SER CYS SER GLN TYR PRO LYS VAL A
                AAAAATCGTGCAGCCAATATCCTAAGGTGG
                      4540            4550            4560

SP  LEU ASN CYS GLY ILE SER GLU ILE GLY
ATTTAAATTGTGTGGCATCAGTGAAATTGGGC
              4570            4580            4590
                HIS TYR GLU TYR GLN ASN ASN TYR ARG TYR L
                ATTATGAATATCAAAAATAATTACCGTTATA
                      4600            4610            4620
```

FIG.2Z

```
YS  GLU GLY ARG ALA SER LEU THR GLY LYS
    AAGAAGGGCGTGCCAGCTTGACAGGCAAAC
                 4630                4640              4650
        LEU ASP PHE ASN PHE ASP LEU LEU GLY GLN H
        TTGATTTTAATTTTGACCTGCTGGGTCAGC
                 4660                4670              4680

IS  ASP LEU THR VAL LEU ALA GLY ALA ASP
    ACGATTTGACGGTGTTGGCTGGTGCAGATA
                 4690                4700              4710
        LYS VAL LYS SER GLN PHE ARG ALA ASN ASN P
        AAGTTAAAAGCCAATTTCGTGCCAACAACC
                 4720                4730              4740

RO  ARG ARG THR ILE ILE ILE ASP THR THR GLN
    CCAGACGCACAATCATTGACACCACCCAAG
                 4750                4760              4770
        GLY ASP ALA ILE ILE ASP GLU SER THR LEU T
        GCGATGCCATCATTGATGAAAGCACGCTGA
                 4780                4790              4800
```

FIG.2A'

```
HR  ALA GLN GLU GLN ALA LYS PHE LYS GLN
    CAGCACAGGAGCAAGCCAAATTTAAGCAAT
            4810          4820          4830
                    SER GLY ALA ALA TRP ILE VAL LYS ASN ARG L
                    CGGGGGCGGCATGGGATTGTCAAAAATCGCC
                            4840          4850          4860

EU  GLY ARG LEU GLU GLU LYS ASP ALA CYS
    TTGGACGCTTAGAAGAAAAAGACGCCCTGTG
            4870          4880          4890
                    GLY ASN ALA ASN GLU CYS GLU ARG ALA PRO I
                    GCAATGCCAATGAATGTGAACGCGCCCCA
                            4900          4910          4920

LE  HIS GLY SER ASN GLN TYR VAL GLY ILE
    TTCATGGCAGTAACCAATATGTGGGCATTA
            4930          4940          4950
                    ASN ASN LEU TYR THR PRO ASN ASP TYR VAL A
                    ACAACCTTTATACACCAAATGATTATGTGG
                            4960          4970          4980
```

FIG.2B'

```
SP  LEU SER PHE GLY GLY ARG LEU ASP LYS
A T T A A G T T T T G G T G G A C G C T T G G A T A A A C
        4990                            5000                    5010
                    GLN ARG ILE HIS SER THR ASP SER ASN ILE  I
                    A A C G C A T T C A C A G C A C C G A T T C A A A C A T C A
                            5020                    5030                    5040

LE  SER LYS THR TYR THR ASN LYS SER TYR
T C A G C A A A A C T T A C C A C C A A C A A A A G C T A T A
        5050                            5060                    5070
                    ASN PHE GLY ALA ALA VAL HIS LEU THR PRO  A
                    A T T T T G G A G C G G C G G T T C A T C T G A C A C C T G
                            5080                    5090                    5100

SP  PHE SER LEU LEU TYR LYS THR ALA LYS
A T T T T A G C C C T G T T G T A T A A A A C T G C C A A A G
        5110                            5120                    5130
                    GLY PHE ARG THR PRO SER PHE TYR GLU LEU  T
                    G C T T T C G T A C G C C A A G T T T T T A T G A A C T G T
                            5140                    5150                    5160
```

FIG.2C'

```
YR  ASN  TYR  ASN  SER  THR  ALA  ALA  GLN  HIS
A C A A C T A T A A C A G C A C C C G C C C C A G C A T A
            5170                5180                5190
                    LYS  ASN  ASP  PRO  ASP  VAL  SER  PHE  PRO  LYS  A
                    A A A A T G A C C C T G A T G T G T C T T T C C C A A A C
                            5200                5210                5220

RG  ALA  VAL  ASP  VAL  LYS  PRO  GLU  THR  SER
G A G C G G G T T G A T G T C A A A C C T G A A A C T T C C A
            5230                5240                5250
                    ASN  THR  ASN  GLU  TYR  GLY  PHE  ARG  TYR  GLN  H
                    A T A C C A A T G A A T A C G G C T T T C G C T A T C A G C
                            5260                5270                5280

IS  PRO  TRP  GLY  ASP  VAL  GLU  MET  SER  MET
A C C C T T G G G G G G A T G T T G A G A T G A G C A T G T
            5290                5300                5310
                    PHE  LYS  SER  ARG  TYR  LYS  ASP  MET  LEU  ASP  L
                    T C A A A A G C C G T T A C A A G G A C A T G T T A G A T A
                            5320                5330                5340
```

FIG.2D'

YS ALA ILE PRO ASN LEU THR LYS ALA GLN
AAGCCATACCGAACCTAACCAAAGCCCAAC
       5350                    5360                   5370

GLN GLU TYR CYS LYS ALA HIS LEU ASP SER A
AAGAGTATTGTAAGGCTCATTTGGATTCCA
       5380                   5390                    5400

SN GLU CYS VAL GLY ASN PRO PRO THR PRO
ATGAATGTGTTGGCAATCCGCCCACGCCCA
       5410                    5420                   5430

LYS THR SER ASP GLU VAL PHE ALA ASN LEU T
AAACCAGTGATGAGGTATTTGCCAACTTAT
       5440                    5450                   5460

YR ASN ALA THR ILE LYS GLY VAL SER VAL
ATAATGCCACCATCAAAGGGGTGAGTGTCA
       5470                    5480                   5490

LYS GLY LYS LEU ASP LEU HIS ALA MET THR S
AAGGCAAAACTGGATTTGCATGCCATGACAT
       5500                    5510                   5520

FIG.2E'

```
ER  LYS LEU PRO ASP GLY LEU GLU MET THR
C A A A A C T G C C A G A T G G T C T T G A A A T G A C C T
          5530                    5540                5550

LEU GLY TYR GLY HIS THR LYS LEU GLY LYS P
                        T G G G T T A T G G T C A T A C C A A A T T G G G G A A A T
                              5560                5570                5580

HE ASP TYR ILE ALA PRO LYS ASP ALA ASP
T T G A T T A C A T T G C A C C C A A A G A T G C C G A T G
          5590                    5600                5610

GLY TRP TYR GLN ALA ARG PRO ALA PHE TRP A
                        G T T G G T A T C A G G C T C G C C C T G C T T T T G G G
                              5620                5630                5640

SP ALA ILE THR PRO ALA ARG TYR VAL VAL
A T G C C A T C A C C C C A G C G C T A T G T G G T C G
          5650                    5660                5670

GLY LEU ASN TYR ASP HIS PRO SER GLN VAL T
                        G T C T A A A C T A T G A C C A C C C C A G T C A A G T A T
                              5680                5690                5700
```

FIG.2F

```
RP  GLY ILE GLY THR THR LEU THR HIS SER
    GGGGCATTGGCACAACTTTAACGCACAGCA
    5710                          5720                    5730
                                                              LYS GLN LYS ASP GLU ASN GLU LEU SER ALA L
                                                              AACAAAAAGATGAAAATGAGCTAAGTGCCC
                                                              5740                    5750                   5760

EU  ARG ILE ARG ASN GLY LYS ARG GLU THR
    TTAGAATCCGAAATGGCAAAAGAGAAACAC
    5770                          5780                    5790
                                                              GLN THR LEU THR HIS THR ILE PRO LYS ALA T
                                                              AAACCTTAACGCACACAATACCCAAAGCCT
                                                              5800                    5810                   5820

YR  THR LEU LEU ASP MET THR GLY TYR TYR
    ATACCTTACTGGACATGACAGGCTATTATA
    5830                          5840                    5850
                                                              SER PRO THR GLU SER ILE THR ALA ARG LEU G
                                                              GCCCAACTGAGAGCATCACCGCTCGTCTTG
                                                              5860                    5870                   5880
```

FIG.2G'

```
LY  ILE ASN ASN VAL LEU ASN THR ARG TYR
GTATCAACAATGTATTAACACCCGCTACA
              5890              5900              5910

THR THR TRP GLU ALA ALA ARG GLN LEU PRO  S
                CCACATGGGAAGCGGCACGCCAACTGCCCA
                              5920              5930              5940

ER  GLU ALA ALA SER SER THR GLN SER THR
GCGAAGCTGCAAGCAGTACCCAATCAACCC
              5950              5960              5970

ARG TYR ILE ALA PRO GLY ARG SER TYR PHE  A
                GTTACATTGCACCAGGTCGCAGTTACTTTG
                              5980              5990              6000

ORF3
                                      MET THR
LA  SER LEU GLU MET LYS PHE ***       MET LYS
CCAGTCTTGAAATGAAGTTTTAATATGACC
              6010              6020              6030

CYS LEU PRO LYS THR ASN PRO ALA LEU . LYS
                TGTTTACCAAAGACCAACCCTGCTTTAAAA
                              6040              6050              6060
```

FIG.2H'

VAL LYS HIS ARG PHE LEU LYS GLN VAL LEU
GTCAAGCACAGATTTTAAAGCAGGTGCTG
6070                      6080              6090

LYS GLN VAL LEU LEU LEU CYS VAL ASP THR LEU THR ALA
          TTATTGCTTTGTGTTGATACATTAACAGCA
          6100              6110              6120

GLN ALA TYR ALA HIS SER HIS HIS THR PRO
CAGGCGTACGCCCACAGCCATCATACGCCC
6130              6140              6150

ILE HIS THR PRO THR HIS GLU LEU PRO SER
ATTCATACACCCACGCATGAGCTGCCATCT
6160              6170              6180

ALA ASP ALA LEU SER ASP GLU GLY LEU GLY
GCTGATGCTTTATCAGATGAAGGCTTGGGT
6190              6200              6210

LYS ASP LEU GLY SER LEU ASP SER LEU ASP
AAGGATTTGGGCAGTTTGGACAGTTTGGAT
6220              6230              6240

FIG.2I'

```
SER PRO ASP GLY LEU GLY ASP GLY LEU GLY
A G C C C A G A T G G T T T G G G T G A T G G T T T A G G C
        6250                6260                6270
                                        ASP GLY LEU GLY ASP GLY LEU LYS SER ASP
                                        G A T G G T T T G G G T G A T G G C T T A A A A A G T G A T
                                                6280                6290                6300

LYS ALA PRO LEU PRO ILE ASN ALA LEU THR
A A A G C C C C T T T A C C C A T C A A C G C C C T T G A C C
        6310                6320                6330
                                        ALA HIS GLN THR ASN GLU SER GLN PRO ALA
                                        G C C C A T C A G A C C A A T G A G A G C C A G C C T G C C
                                                6340                6350                6360

PRO PRO SER VAL ASP VAL ASN PHE LEU LEU
C C A C C G A G C C G T A G A T G T C A A T T T T T T A C T T
        6370                6380                6390
                                        ALA GLN PRO GLU ALA PHE TYR HIS VAL PHE
                                        G C C C A G C C A G A G G C A T T T T A T C A T G T C T T T
                                                6400                6410                6420
```

FIG.2J'

```
HIS GLN ALA ILE VAL GLN ASP ASP VAL ALA
CATCAAGCGATTGTGCAAGATGATGTGGCA
              6430              6440              6450
                    THR LEU ARG LEU LEU PRO PHE TYR ASP
                    ACATTACGCTTGTTATTGCCATTTTATGAC
                          6460              6470              6480

ARG LEU PRO ASP ASP TYR GLN ASP ASP VAL
CGCCCTGCCTGATGATTATCAAGATGATGTT
              6490              6500              6510
                    LEU LEU PHE ALA GLN SER LYS LEU ALA
                    TTGTTTGTTATTTGCCCAAAGTAAACTTGCC
                          6520              6530              6540

LEU SER ASP GLY ASN THR LYS LEU ALA LEU
CTAAGTGATGGCAATACCAAATTGGCATTG
              6550              6560              6570
                    ASN LEU LEU THR ASP LEU SER ASN LYS GLU
                    AATCTGCTGACCGATTTGAGTAACAAAGAG
                          6580              6590              6600
```

FIG.2K'

```
PRO THR LEU THR ALA VAL LYS LEU GLN LEU
CCAACACTTACGGCGGTAAAATTACAACTT
      6610                6620           6630

ALA SER LEU LEU LEU THR ASN LYS HIS ASP
                    GCTTCCTTGTTGCTGACCAACAAGCACGAT
                          6640           6650           6660

LYS HIS ALA GLN MET VAL LEU ASP GLU LEU
AAACACGCCCAAATGGTGCTAGATGAACTC
      6670               6680           6690

LYS ASP ASP ALA HIS PHE LEU LYS LEU SER
                    AAAGATGATGCCCACTTTTAAAATTAAGC
                          6700           6710           6720

LYS LYS GLU GLN ARG TRP VAL LEU SER GLN
AAAAAAGAGCAAAGATGGGTGCTATCGCAA
      6730               6740           6750

SER ARG TYR LEU HIS LYS TYR LYS MET
                    AGTCGCTATTTACATAAAAATATAAAATG
                          6760           6770           6780
```

FIG.2L'

```
GLY LEU ASP LEU GLY ILE ASN TYR LEU HIS
GGC TTG GAT TTG GGC ATC AAC TAT CTG CAT
    6790                6800            6810
                                             LEU ASP ASN ILE ASN ALA ALA SER THR ILE
                                             TTG GAT AAT ATC AAC GCC GCC TCC ACC ATC
                                                6820            6830            6840

THR GLN PRO ASN ILE LYS LYS ASP ALA PRO
ACC CAG CCC AAT ATT AAA AAA GAT GCC CCA
    6850            6860            6870
                                             LYS PRO ALA HIS GLY LEU ALA LEU SER LEU
                                             AAA CCT GCT CAT GGG CTT GCC TTA TCG CTT
                                                6880            6890            6900

GLY VAL ASN LYS TYR THR PRO LEU SER HIS
GGT GTG AAT AAA TAC ACG CCG CTT AGT CAT
    6910            6920            6930
                                             GLY MET SER ILE TYR THR ALA LEU ASP VAL
                                             GGC ATG AGT ATT TAT ACA GCC CTA GAT GTT
                                                6940            6950            6960
```

FIG.2M'

```
ASP GLY LYS PHE TYR ASP ASP LYS SER HIS
GATGGTAAATTTTATGATGACAAAAGCCAC
       6970              6980           6990

ASN GLU LEU ALA VAL PHE ALA HIS ALA GLY
                    AATGAACTGGCGCGGTTTTGCTCATGCTGGA
                           7000              7010              7020

LEU ARG LYS ASP HIS GLN LYS GLY TYR VAL
CTAAGAAAGATCACCAAAAGGTTATGTT
       7030              7040           7050

ASP VAL VAL PRO PHE VAL GLY ARG ILE PHE
                    GATGTCGTACCTTTTGTTGGGCGTATTTTT
                           7060              7070              7080

ALA THR ASN GLN GLN HIS GLY ARG LEU SER
GCCACCAATCAGCAGCATGGCAGATTATCC
       7090              7100           7110

PRO ARG LYS ASP SER GLN GLY VAL ALA PHE
                    CCCAGAAAAGACAGTCAGGGGTGGCGTTT
                           7120              7130              7140
```

FIG.2N'

```
GLY SER HIS HIS ARG ILE ASN ASP LYS TRP
GGCAGCCATCATCGGATCAATGATAAATGG
        7150                7160              7170
                                    GLN ASN ALA PHE PHE ALA ARG MET GLU LYS
                                    CAAAATGCGTTTTTTGCACGCATGGAAAAA
                                            7180              7190              7200

GLY ASN TYR THR GLU ARG TYR GLN GLY TYR
GGCAATTATACCGAGCGTTATCAAGGTTAT
        7210              7220              7230
                                    ASP GLY LYS ARG TYR HIS VAL ASN ASP THR
                                    GATGGCAAGCGTTATCATGTGAATGACACC
                                            7240              7250              7260

ILE LEU LEU GLN ASP GLY PRO ASN ARG ARG
ATTTTGTTGCAAGATGGCCCAAATCGTCGT
        7270              7280              7290
                                    TYR SER LEU GLY VAL GLY TYR GLN LEU SER
                                    TACTCTTTGGGCGTGGGGTATCAGCTTAGC
                                            7300              7310              7320
```

FIG. 20'

```
HIS LEU GLN ASP ALA THR LYS SER SER HIS
CAT CTG CAA GAT GCA ACA AAA AGC AGT CAT
            7330              7340              7350
                    ALA THR LYS ILE HIS PHE GLY VAL LEU GLN
                    GCC ACA AAA GAT ACA TTT GGG GTG TTG CAA
                            7360              7370              7380

ARG LEU PRO ASN GLY LEU THR VAL GLN GLY
AGA TTG CCA AAT GGT CTG ACC GTG CAA GGT
            7390              7400              7410
                    ARG VAL SER ALA GLU ARG GLU ARG TYR HIS
                    AGA GTG AGT GCT GAG CGT GAG CGT TAT CAT
                            7420              7430              7440

GLY LYS LEU LEU ARG LEU VAL ASN PRO ASP
GGT AAA TTA TTG CGT CTG GTT AAT CCT GAT
            7450              7460              7470
                    ASP VAL TYR ARG THR ASP LYS THR LEU THR
                    GAT GTG TAT CGC ACA GAT AAA ACC CTA ACC
                            7480              7490              7500
```

FIG.2P'

```
LEU GLN THR SER ILE TRP HIS LYS ASP ILE
CTACAAACCTCCATTTGGCACAAAGACATT
         7510                  7520              7530
                    HIS TRP LEU GLY LEU THR PRO LYS LEU THR
                    CACTGGCTTGGATTAACGCCAAAGCTGACT
                         7540             7550             7560

TYR ARG TYR SER LYS ASN ASN SER ASN LEU
TATCGTTACAGTAAAAATAACAGTAACTTA
         7570                  7580              7590
                    PRO ALA LEU TYR SER HIS ASN LYS GLN ASN
                    CCAGCACTTTATAGCCATAACAAACAAAAT
                         7600             7610             7620

PHE TYR LEU GLU LEU GLY ARG SER PHE ***
TTTTATTTGGAGCTTGGGTCGTTTTAA
         7630                  7640              7650
```

FIG.4A  M. catarrhalis Q8 lfr sequence

```
AAGCTTAGCATGATGGCATCGGCTGATTGT CTTTTTGCCTTGTTGTGTTTGTGGGAGT
         10        20        30        40        50        60

TGATTGTACTTACCCTTAGTGGTGGATGCTT GGGCTGATTTAATTAAATTTAATCAAAGCG
         70        80        90       100       110       120
                                              -35              -10
                                                    RBS
                                                              Lpp2
                                                              MET SER THR VAL LYS THR PRO HIS ILE PHE
GTCTTCACAACACACCAAACGAGATATCAC CATGAGTACTGTCAAAACCCCCATATTT
        130       140       150       160       170       180

TYR GLN LYS ARG THR LEU SER LEU ALA ILE   ALA SER ILE PHE ALA ALA LEU VAL MET THR
CTACCAAAAACGCCACCCTTAGCCCTTGCCAT CGCCAGTATTTTTGCTGCCTTGGTGATGAC
        190       200       210       220       230       240
```

FIG.4B

```
GLY CYS ARG SER ASP ASP ILE SER VAL ASN
AGGCTGCCGCTCTGATGACATCAGCGTCAA
                 250              260           270

ALA PRO ASN VAL THR GLN LEU PRO GLN GLY
TGCACCCCAATGTTACCCAGCTGCCCCAAGG
       280           290            300

THR VAL SER PRO THR PRO ASN THR GLY HIS
CACGGGTTTCACCAACGCCGAACACAGGTCA
         310           320           330

ASP ASN ALA ASN THR ASN ASN GLN GLY
TGACAACGCCAATAACACCAACAATCAGGG
       340           350           360

ASN ASN THR ASP ASN SER THR SER THR THR
CAACAACACGGATAACAGCACCAGCACAAAC
        370           380           390

ASP PRO ASN GLY ASP ASN ASN GLN LEU THR
TGACCCAAATGGCGATAACAACCAACTGAC
       400           410            420
```

FIG.4C

```
GLN ALA GLN LYS THR ALA ALA ALA ALA GLY
ACAAGCGCAAAAAACTGCCGCCGCCGCAGG
            430              440         450
                                    PHE PHE VAL MET GLY LYS ILE ARG ASP THR
                                    GTTTTTTGTGATGGGTAAAATTCGTGATAC
                                              460              470              480

SER GLU LYS ASN ASP PRO ASP TYR SER ASP
CAGCGAAAAAAATGACCCCAGATTATAGTGAT
            490              500         510
                                    ASP LEU LYS GLN TRP LEU GLY LYS LEU
                                    TGATTTAAAACAGCAGTGGCTGGGCAAATT
                                              520              530         540

TYR VAL GLY ILE ASP ALA HIS ARG PRO ASP
ATATGTTGGTATTGATGCCCATCGCCCAGA
            550              560         570
                                    GLY ILE GLY LYS GLY LYS ASN LEU ARG GLN
                                    TGGCATCGGAAAAGGTAAAAACTTGCGTCA
                                              580              590              600
```

FIG.4D

```
PRO ILE THR ALA ASN ASP ILE LYS PRO LEU
GCCCATCACCGCCAATGACATCAAACCCTT T
         610             620           630

TYR PHE ASN LYS PHE PRO ALA LEU SER ASP
                    GTATTTTAACAAATTCCCTGCATTGTCTGA
                              640           650           660

LEU HIS LEU ASP SER GLU ARG HIS ARG PHE
TTTGCACTTAGACAGTGAACGCCATCGTTT
         670             680           690

ASP PRO GLN LYS ILE ASN THR ILE LYS VAL
                    TGACCCCCAAAAGATAAACACCATTAAAGT
                              700           710           720

TYR GLY TYR GLY ASN LEU THR THR PRO SER
GTATGGTTATGGTAACTTAACAACACCATC
         730             740           750

ASN ASN ASN THR HIS ILE ASN HIS GLN GLN
                    CAACAACAACACTCACATCAATCATCAGCA
                              760           770           780
```

FIG.4E

```
ALA ASP ASN LYS LYS ASN ASN LYS PRO VAL
AGCTGATAATAAGAAAAATAACAAGCCTGT
                 790            800      810

ASP PRO TYR GLU ASN ILE ARG PHE GLY TYR
TGACCCTTATGAAAATATCCGTTTTGGGTA
         820            830           840

LEU GLU LEU GLN GLY SER SER LEU THR GLN
TCTTGAACTACAAGGAAGCAGCCTGACCCA
         850            860           870

LYS ASN ALA ASP ASN GLN ASN GLU GLN ASP
AAAAAATGCCGATAATCAAAATGAGCAAGA
         880            890           900

ARG ILE PRO LYS PRO MET PRO ILE LEU PHE
CCGCATTCCCAAACCCATGCCCATTTTGTT
         910            920           930

TYR HIS GLY GLU ASN ALA SER SER GLN LEU
TTATCATGGAGAAAACGCCAGCAGCCAGCT
         940            950           960
```

FIG.4F

PRO SER ALA GLY LYS PHE ASN TYR THR GLY
GCCCAGCGCTGGTAAATTTAACTACACAGG
　　　　　970　　　　　　　　　980　　　　　　　　　990

ASN TRP LEU TYR LEU SER ASP VAL LYS LYS
CAACTGGCTGTACCTAAGTGATGTCAAAAA
　　　　　1000　　　　　　　　1010　　　　　　　　1020

ARG PRO ALA LEU SER ALA LEU SER PHE GLN HIS GLN ARG
ACGCCCCTGCCCTTTCAGCATCAGATGAGCG
　　　　　1030　　　　　　　　1040　　　　　　　　1050

VAL GLY VAL TYR LEU ASN ALA SER GLY LYS
AGTGGGGTCTATCTCAATGCCAGTGGCAA
　　　　　1060　　　　　　　　1070　　　　　　　　1080

ALA ASN GLU GLY ASP VAL VAL SER ALA ALA
AGCCAACGAGGGCGATGTCGTCAGTGCCGC
　　　　　1090　　　　　　　　1100　　　　　　　　1110

HIS ILE TYR LEU ASN GLY PHE GLN TYR LYS
CCACATTTATCTAAACGGCTTTCAATATAA
　　　　　1120　　　　　　　　1130　　　　　　　　1140

FIG. 4G

```
HIS THR PRO ALA THR TYR GLN VAL ASP PHE
GCACACGCCTGCCACTTATCAGGTGGATTT
              1150              1160              1170
```

```
                    ASP THR ASN SER LEU THR GLY LYS LEU SER
                    TGACACAAACTCATTAACAGGCAAGCTGTC
                         1180              1190              1200
```

```
TYR TYR ASP ASN PRO ASN GLN GLN ASN ASN
CTATTATGACAATCCCAATCAGCAAAATAA
              1210              1220              1230
```

```
                    LYS GLY GLU TYR LEU LYS SER GLN PHE ASP
                    TAAAGGCGAATATCTCAAAAGCCAATTTGA
                         1240              1250              1260
```

```
THR THR LYS LYS VAL ASN GLU THR ASP VAL
CACTACCAAAAAAGTCAATGAAACCGATGT
              1270              1280              1290
```

```
                    TYR GLN ILE ASP ALA LYS ILE ASN GLY ASN
                    GTATCAAATTGATGCCAAAATCAACGGTAA
                         1300              1310              1320
```

FIG.4H

```
ARG PHE VAL GLY THR ALA LYS SER LEU VAL
CCGCTTTGTCGGTACGGCCAAATCTTTGGT
                1330                    1340                    1350

ASN GLU LYS THR GLN THR ALA PRO PHE ILE
                              TAATGAGAAAACACAAACCGCACCTTTTAT
                                  1360                    1370                    1380

LYS GLU LEU PHE SER LYS LYS ALA ASN PRO
CAAAGAGCTGTTCTCCAAAAAGCCAACCC
                1390                    1400                    1410

ASN ASN PRO ASN PRO ASN SER ASP THR LEU
                              CAATAACCCAAACCCTAATTCAGACACGCT
                                  1420                    1430                    1440

GLU GLY GLY PHE TYR GLY SER GLY ASP
AGAAGGCGGATTTTATGGTGAGTCGGGCGA
                1450                    1460                    1470

GLU LEU ALA GLY LYS PHE LEU SER ASN ASP
                              TGAGCTGGCGGGTAAATTTTTATCCAATGA
                                  1480                    1490                    1500
```

FIG.4I

```
ASN ALA SER TYR VAL VAL PHE GLY GLY LYS
CAACGCATCTTTATGTGGTCTTTGGTGGCAA
                1510              1520              1530
                                                    ARG ASP LYS THR THR LYS PRO VAL ALA THR
                                                    ACGAGACAAAACGACTAAACCTGTCGCCAC
                                                         1540              1550              1560

LYS THR VAL TYR PHE SER ALA GLY PHE GLU
AAAAACGGTGTATTTTAGTGCAGGCTTTGA
                1570              1580              1590
                                                    LYS PRO SER THR SER PHE VAL ASP ASN GLU
                                                    AAAACCCAGCACCAGTTTTGTGGATAATGA
                                                         1600              1610              1620

THR ILE GLY GLY ILE ILE ASP ARG LYS GLY
AACGATTGGTGGAATTATTGACCGTAAAGG
                1630              1640              1650
                                                    LEU ASN ASN HIS ILE ASN GLU ASP GLU ILE
                                                    GTTAAAATAATCACATTAATGAAGATGAAAT
                                                         1660              1670              1680
```

FIG.4J

ILE PRO SER ASP ASP SER TYR TYR GLY TYR
TATTCCCAGTGATGATAGTTATTATGGATA
       1690                  1700                 1710

THR TRP GLY LYS PRO GLU LYS GLN PHE THR
TACTTGGGCAAGCCAGAGAAGCAGTTCAC
       1720                  1730                 1740

LYS LYS VAL SER SER THR GLN VAL VAL
CAAAAAAGTCAGCAGCACCCAAGTCGT
       1750                  1760                 1770

PRO ALA TYR PHE GLY GLN HIS ASP LYS PHE
GCCAGCTTATTTTGGGCAACATGATAAATT
       1780                  1790                 1800

TYR PHE ASN GLY ASN TYR TYR ASP LEU SER
TTATTTTAATGGCAACTATTATGACCTATC
       1810                  1820                 1830

ALA SER ARG VAL ASP LYS LEU ALA PRO ALA
AGCCAGTCGTGTTGATAAATTAGCCCCTGC
       1840                  1850                 1860

FIG.4K

ASP ALA VAL LYS ALA ASN GLN SER ILE LYS
CGATGCTGTCAAAGCCAACCAATCCATTAA
　　　　　1870　　　　　　　　1880　　　　　　　　1890

GLU LYS TYR PRO ASN ALA THR LEU ASN LYS
AGAAAAATACCCTAATGCCACACTAAATAA
　　　　　1900　　　　　　　　1910　　　　　　　　1920

ASP ASN GLN VAL THR ALA ILE VAL LEU GLN
GGACAACCAAGTTACCGCCATCGTGCTACA
　　　　　1930　　　　　　　　1940　　　　　　　　1950

GLU ALA LYS ASP ASN LYS PRO TYR THR ALA
AGAAGCCAAAGATAATAAGCCTTATACCGC
　　　　　1960　　　　　　　　1970　　　　　　　　1980

ILE ARG ALA LYS SER TYR GLN HIS ILE SER
CATTCGTGCCAAAAGCTATCAGCACATCAG
　　　　　1990　　　　　　　　2000　　　　　　　　2010

PHE GLY GLU THR LEU TYR ASN ASP ALA ASN
TTTTGGCGAGACGCTGTATAACGATGCCAA
　　　　　2020　　　　　　　　2030　　　　　　　　2040

FIG.4L

| GLN | THR | PRO | THR | ARG | SER | TYR | PHE | VAL | GLN | GLY | GLY | ARG | ALA | ASP | THR | SER | THR | THR | LEU |
|-----|-----|-----|-----|-----|-----|-----|-----|-----|-----|-----|-----|-----|-----|-----|-----|-----|-----|-----|-----|

C C A A A C C C C A A C A C G C A G T T A T T T T G T G C A A G G C G G G T A G G G C A G A T A C C A G C A C A A C T T T
              2050                      2060                      2070                      2080                      2090                      2100

| PRO | GLN | ALA | GLY | LYS | PHE | THR | TYR | ASN | GLY | LEU | TRP | ALA | GLY | TYR | LEU | THR | GLN | LYS | LYS |
|-----|-----|-----|-----|-----|-----|-----|-----|-----|-----|-----|-----|-----|-----|-----|-----|-----|-----|-----|-----|

G C C C C A G G C A G G T A A A T T C A C T T A C A A C G G T C T T T G G G C A G G C T A C C T G A C C C A A A A A A A
              2110                      2120                      2130                      2140                      2150                      2160

| ASP | LYS | GLY | TYR | SER | ASP | ASN | ALA | GLU | THR | ILE | LYS | GLU | LYS | GLY | HIS | PRO | GLY | TYR | LEU |
|-----|-----|-----|-----|-----|-----|-----|-----|-----|-----|-----|-----|-----|-----|-----|-----|-----|-----|-----|-----|

```
LEU THR GLU ASN PHE THR PRO GLU ASP ASP
GTTAACCGAAAACTTCACCCCAGAAGATGA
         2230              2240         2250

ASP ASP LEU THR ALA SER ASP ASP SER
                    TGACGATGATTTGACCGCATCTGATGATTC
                         2260         2270         2280

GLN ASP ASN THR HIS GLY ASP ASP ASP
ACAAGATGATAATACACATGGCGATGATGA
         2290         2300         2310

LEU ILE ALA SER ASP ASP SER GLN ASP ASP
                    TTTGATTGCATCTGATGATTCACAAGATGA
                         2320         2330         2340

ASP ALA ASP GLY ASP ASP ASP SER ASP ASP
TGACGCAGATGGAGAGATGACGATTCAGATGA
         2350         2360         2370

LEU GLY ASP GLY ALA ASP ASP ASP ALA ALA
                    TTTGGGTGATGGTGCAGATGATGACGCCGC
                         2380         2390         2400
```

FIG.4N

```
GLY LYS VAL TYR HIS ALA GLY ASN ILE ARG
AGGCAAAGTGTATCATGCAGGTAATATTCG
         2410              2420            2430

PRO GLU PHE GLU ASN LYS TYR LEU PRO ILE
                CCCTGAATTTGAAAACAAATACTTGCCCAT
                       2440          2450          2460

ASN GLU PRO THR HIS GLU LYS THR PHE ALA
TAATGAGCCTACTCATGAAAAAACCTTTGC
         2470            2480           2490

LEU ASP GLY LYS ASN LYS ALA LYS PHE GLU
                CCTAGATGGTAAAAATAAAGCTAAGTTTGA
                       2500          2510          2520

VAL ASP PHE ASN THR ASN SER LEU THR GLY
AGTGGATTTTAACACCAACAGCCTAACTGG
         2530            2540           2550

LYS LEU ASN ASP GLU ARG GLY ASP ILE VAL
                TAAATTAAACGATGAGAGAGGTGATATCGT
                       2560          2570          2580
```

FIG. 4O

```
PHE ASP ILE LYS ASN GLY LYS ILE ASP GLY
CTTTGATATCAAAAATGGCAAAATTGATGG
         2590              2600              2610
                    THR GLY PHE THR ALA LYS ALA ASP VAL PRO
                    CACAGGATTTACCGCCAAAGCCGATGTGCC
                              2620              2630              2640

ASN TYR ARG GLU GLU VAL GLY ASN ASN GLN
AAACTATCGTGAAGAAGTGGGTAACAACCA
         2650              2660              2670
                    GLY GLY GLY PHE LEU TYR ASN ILE LYS ASP
                    AGGTGGCGGGTTTCTTATACAACATCAAAGA
                              2680              2690              2700

ILE ASP VAL LYS GLY GLN PHE PHE GLY THR
TATTGATGTTAAGGGGCAATTTTTTGGCAC
         2710              2720              2730
                    ASN GLY GLU GLU LEU ALA GLY GLN LEU HIS
                    AAATGGCGAAGAGTTGGCAGGACAGTTACA
                              2740              2750              2760
```

FIG.4P

```
HIS ASP LYS GLY ASP GLY ILE ASN ASP THR
TCATGACAAAGGCGATGGCATCAATGACAC
         2770              2780         2790
                              ALA GLU LYS ALA GLY ALA VAL PHE GLY ALA
                              CGCCGAAAAAGCAGGGGCTGTCTTTGGGGC
                                    2800         2810         2820

VAL LYS ASP LYS ***
TGTTAAAGATAAATAAAGCCCCCCTTCATC
         2830         2840         2850
                              ATCGTTTAGTCGCTTGACCGACAGTTGATG
                                    2860         2870         2880

ACGCCCTTGGCAATGTCTTAAAACAGCACT
         2890         2900         2910
                              TTGAAACAGTGCCTTGGGCGAATTCTTGGA
                                    2920         2930         2940

TAAATGCACCAGATTTGCCTTGGGCTAATA
         2950         2960         2970
                        -10
                              TCTTGATAAAACATCGCCATAAAATAGAAA
                                    2980         2990         3000
                                           -35
```

FIG. 4Q

```
                              RBS                  Lbp1
                                                   MET SER LYS
ATAAAGTTTAGGATTTTTTTATGTCAAAA
         3010              3020            3030
                                                   SER ILE THR LYS THR GLN THR PRO SER VAL H
                                                   TCTATCACAAAAACACAAACACCATCAGTCC
                                                           3040            3050            3060

IS  THR MET THR THR HIS ARG LEU ASN LEU            ALA ILE LYS ALA ALA LEU PHE GLY VAL ALA V
ATACCATGACCACCACGCTTAAACCTTG                        CCATCAAAGCGGCGTTATTTGGTGTGGCAG
       3070            3080            3090                3100            3110            3120

AL  LEU PRO LEU SER VAL TRP ALA GLN GLU            ASN THR GLN THR ASP ALA ASN SER ASP ALA L
TTTTACCCCTATCCGTCTGGGCGCAAGAGA                      ACACTCAGACAGATGCCAACTCTGATGCCA
       3130            3140            3150                3160            3170            3180
```

FIG.4R

```
YS  ASP THR LYS THR PRO VAL VAL TYR LEU
A A G A C A C A A A A C C C C T G T C G T A T T T A G
                3190                        3210
                                                        ASP ALA ILE THR VAL THR ALA ALA PRO SER  A
                                                        A T G C C A T C A C G G T A A C C G C C C C A T C T G
                                                                    3220                        3240
                                                                                3230

LA  PRO VAL SER ARG PHE ASP THR ASP VAL
C C C C T G T T T C T C G G T T T G A C A C C G A T G T A A
                3250                        3270
                            3260
                                                        THR GLY LEU GLY LYS THR VAL LYS THR ALA  A
                                                        C A G G G C T T G G G C A A A A C C G T C A A A A C C G C T G
                                                                    3280                        3300
                                                                                3290

SP  THR LEU ALA LYS GLU GLN VAL GLN GLY
A C A C G C T G G C A A A A G A A C A A G T A C A G G G C A
                3310                        3330
                            3320
                                                        ILE ARG ASP LEU VAL ARG TYR GLU THR GLY  V
                                                        T T C G T G A T T T G G T G C G T T A T G A A A C T G G G G
                                                                    3340                        3360
                                                                                3350
```

FIG.4S

```
AL  SER VAL VAL GLU GLN GLY ARG GLY GLY
    TGAGTGTGGTTGAGCAGGGGCCGTGGTGGCA
                    3370            3380            3390
    SER SER GLY PHE ALA ILE HIS GLY VAL ASP L
    GCAGCGGATTTGCCATTCATGGCCGTGGATA
                    3400            3410            3420

YS  ASN ARG VAL GLY ILE THR VAL ASP GLY
    AAAACCGAGTGGGCATTACCGTAGATGGCA
                    3430            3440            3450
    ILE ALA GLN ILE GLN SER TYR LYS ASP GLU S
    TTGCCCAAATTCAATCCTACAAAGACGAAT
                    3460            3470            3480

ER  THR LYS ARG ALA GLY ALA GLY SER GLY
    CCACTAAGCGAGCTGGGGCAGGCTCTGGGG
                    3490            3500            3510
    ALA MET ASN GLU ILE GLU ILE GLU ASN ILE A
    CGATGAAACGAGATAGAGATTGAAAACATTG
                    3520            3530            3540
```

FIG.4T

```
LA  ALA VAL ALA ILE ASN LYS GLY GLY ASN
    CCGCCGTTGCCATCAATAAAGGCGGTAATG
                                      3570
    3550
         ALA LEU GLU ALA GLY SER GLY ALA LEU GLY  G
         CCTTAGAAGCAGGCTCTGGTGCGTTGGGTG
                              3580              3590              3600

LY  SER VAL ALA PHE HIS THR LYS ASP VAL
    GTTCGGTGGCGTTTCATACCAAAGATGTGA
                                      3630
    3610
         SER ASP VAL LEU LYS SER GLY ASN ASN LEU  G
         GCGATGTCTTAAAATCTGGTAACAATCTTG
                              3640              3650              3660

LY  ALA GLN SER LYS THR THR TYR ASN SER
    GTGCTCAAAGCAAAACCACTTATAACAGCA
                                      3690
    3670
         LYS ASN ASP PHE HIS PHE SER GLN THR LEU ALA  A
         AAAATGACCATTTTAGTCAGACGCTGGCAG
                              3700              3710              3720
```

FIG.4U

```
LA  ALA GLY LYS THR GLU THR VAL GLU ALA
    CGGCAGGTAAAACCGAGCGTGTGGAAGCGA
             3730              3740        3750
                 MET VAL GLN TYR THR TYR ARG LYS GLY LYS G
                 TGGTGCAATATACCTACCGTAAAGGCAAAG
                      3760              3770        3780

LU  ASN LYS ALA HIS SER ASP LEU ASN GLY
    AAAACAAAGCACACAGCGACCTAAATGGCA
             3790              3800        3810
                 ILE ASN GLN SER LEU TYR ARG LEU GLY ALA T
                 TCAACCAAAGCCTATATCGCTTGGGTGCAT
                      3820              3830        3840

RP  GLN GLN LYS TYR ASP LEU ARG LYS PRO
    GGCAACAAAAATATGATTTAAGAAAGCCTA
             3850              3860        3870
                 ASN GLU LEU PHE ALA GLY THR SER TYR ILE T
                 ACGAACTGTTTGCAGGCACAAGCTATATCA
                      3880              3890        3900
```

FIG.4V

HR GLU SER CYS LEU ALA SER ASP ASP PRO
CCGAAAGCTGTTTGGCAAGTGATGACCCAA
  3910                    3920              3930

LYS SER CYS VAL GLN TYR PRO TYR VAL TYR T
AAAGCTGCGTACAATACCCTTATGTCTACA
           3940              3950              3960

HR LYS ALA ARG PRO ASP GLY ILE GLY ASN
CCAAAGCCCCGACCAGATGGTATCGGCAATC
  3970                    3980              3990

ARG ASN PHE SER GLU LEU SER ASP ALA GLU L
GCAATTTTCTGAGTTAAGCGATGCTGAAA
           4000              4010              4020

YS ALA GLN TYR LEU ALA SER THR HIS PRO
AAGCACAAATATTTGGCGTCCACGCACCCCC
  4030                    4040              4050

HIS GLU VAL VAL SER ALA LYS ASP TYR THR G
ATGAGGTTGTCTCTGCCAAAGATTATACAG
           4060              4070              4080

FIG.4W

```
LY  THR TYR ARG LEU LEU PRO ASP PRO MET
GCACTTATCGGTTGTTACCTGACCCCATGG
        4090                    4100                   4110
                    ASP TYR ARG SER ASP SER TYR LEU ALA ARG L
                    ACTATCGTTCAGACTCGTATTTGGCACGCC
                        4120                    4130                   4140

EU  ASN ILE LYS ILE THR PRO ASN LEU VAL
TTAACATCAAAATCACCCCAAATTTGGTCA
        4150                    4160                   4170
                    SER LYS LEU LEU GLU ASP THR LYS GLN T
                    GTAAACTGTTATTAGAAGACACCAAGCAAA
                        4180                    4190                   4200

HR  TYR ASN ILE ARG ASP MET ARG HIS CYS S
CATACAACATTCGTGATATGCGTCATTGTA
        4210                    4220                   4230
                    ER  TYR HIS GLY ALA ARG LEU GLY ASN ASP G
                    GTTATCATGGGGCAAGATTGGGCAATGACG
                        4240                    4250                   4260
```

FIG. 4X

```
LY  LYS  PRO  ALA  ASN  GLY  GLY  SER  ILE  VAL
GTAAGCCCTGCCAATGGCGGCTCCATTGTCC
         4270              4280              4290

LEU  CYS  ASP  ASP  TYR  GLN  GLU  TYR  LEU  ASN  A
                TTTGCGATTATCAAGAGTATCTAAATG
                         4300              4310              4320

LA  ASN  ASP  ALA  SER  GLN  ALA  SER  PHE  ARG
CCAATGACGCATCACAAGCATCATTTAGAC
         4330              4340              4350

PRO  GLY  ALA  ASN  ASP  ALA  PRO  ILE  PRO  LYS  L
                CAGGGGCTAATGACGCCCCATTCCAAAAC
                         4360              4370              4380

EU  ALA  TYR  ALA  ARG  SER  SER  VAL  PHE  ASN
TGGCTTATGCCAGAAGCAGTGTTTAACC
         4390              4400              4410

GLN  GLU  HIS  GLY  LYS  THR  ARG  TYR  GLY  LEU  G
                AAGAGCATGGCAAAACTCGCTATGGGTTAG
                         4420              4430              4440
```

FIG.4Y

```
LY  PHE GLU PHE LYS PRO ASP THR PRO TRP
GTTTGAGTTTAAGCCCTGACACGCCATGGT
         4450                4460                4470
              PHE LYS GLN ALA LYS LEU ASN LEU HIS GLN G
              TTAAACAAGCAAAATTAAACCTACATCAAC
                   4480                4490                4500

LN  ASN ILE GLN ILE ILE ASN HIS ASP ILE
AAATATCCAAATCATTAACCATGACATTA
         4510                4520                4530
              LYS SER CYS SER GLN TYR PRO LYS VAL A
              AAAAATCGTGCAGCCAATATCCCAAGGTGG
                   4540                4550                4560

SP  LEU ASN CYS GLY ILE SER GLU ILE GLY
ATTTAAATTGTGGCATCAGTGAAATTGGGC
         4570                4580                4590
              HIS TYR GLU TYR GLN ASN ASN TYR ARG TYR L
              ATTATGAATATCAAAACAATTACCGTTATA
                   4600                4610                4620
```

FIG. 4Z

```
YS  GLU  GLY  ARG  THR  SER  LEU  THR  GLY  LYS
A A G A A G G G C G T A C C A G T T T G A C A G G C A A A C
                 4630                 4640                 4650
                      LEU  ASP  PHE  ASN  PHE  ASP  LEU  LEU  GLY  GLN  H
                      T T G A T T T T A A T T T T G A C C T G C T G G G C C A G C
                                4660                 4670                 4680

IS  ASP  LEU  THR  VAL  LEU  ALA  GLY  ALA  ASP
A C G A T T T G A C G G T G T T G G C T G G T G C A G A T A
                 4690                 4700                 4710
                      LYS  VAL  LYS  SER  GLN  PHE  ARG  ALA  ASN  ASN  P
                      A A G T T A A A A G C C A A T T T C G T G C C A A C A A C C
                                4720                 4730                 4740

RO  ARG  ARG  THR  ILE  ILE  ASP  THR  THR  GLN
C C A G A C G C A C A A T C A T T G A C A C C A C C C A A G
                 4750                 4760                 4770
                      GLY  ASP  ALA  ILE  ILE  ASP  GLU  SER  THR  LEU  T
                      G C G A T G C C A T C A T T G A T G A A A G C A C G C T G A
                                4780                 4790                 4800
```

FIG.4A'

```
HR  ALA GLN GLU GLN ALA LYS PHE LYS GLN           SER GLY ALA ALA TRP ILE VAL LYS ASN ARG L
CAG CAC AGG AGC AAG CCA AAT TTA AGC AAT           CAG GGG CAG CAT GGA TTG TCA AAA ATC GCT
         4810            4820           4830              4840           4850           4860

EU  GLY ARG LEU GLU GLU LYS ASP ALA CYS           GLY ASN ALA ASN GLU CYS GLU ARG ALA PRO I
TAG GAC GCT TAG AAG AAA AAG ACG CCT GTG           GCA ATG CCA ATG AAT GTG AAC GCG CGC CCA
         4870            4880           4890              4900           4910           4920

LE  HIS GLY SER ASN GLN TYR VAL GLY ILE           ASN ASN LEU TYR THR PRO ASN ASP TYR VAL A
TTC ATG GCA GTA ACC AAT ATG TGG GCA TTA           ACA ACC TTT ATA CAC CAA ATG ATT ATG TGG
         4930            4940           4950              4960           4970           4980
```

FIG.4B'

```
SP  LEU SER PHE GLY GLY ARG LEU ASP LYS                                I
ATTTAAGTTTTGGTGGACGCTTGGATAAAC
         4990                   5000                  5010
                GIN ARG ILE HIS SER THR ASP SER ASN ILE I
                AACGCATTCACAGCACCGATTCAAACATCA
                         5020                   5030                  5040

LE  SER LYS THR TYR THR ASN LYS SER TYR
TCAGCAAAACTTACACCAACAAAAGCTATA
         5050                   5060                  5070
                ASN PHE GLY ALA ALA VAL HIS LEU THR PRO A
                ATTTTGGAGCGGGCGGTTCATCTGACACCTG
                         5080                   5090                  5100

SP  PHE SER LEU LEU TYR LYS THR ALA LYS
ATTTTAGCCCTGTTGTATAAAACTGCCAAAG
         5110                   5120                  5130
                GLY PHE ARG THR PRO SER PHE TYR GLU LEU T
                GCTTTCGTACGCCAAGTTTTTATGAACTGT
                         5140                   5150                  5160
```

FIG.4C'

```
YR  ASN TYR ASN SER THR ALA ALA GLN HIS
A C A A C T A T A A C A G C A C C G C C G C C C A G C A T A
    5170                5180                5190
                LYS ASN ASP PRO ASP VAL SER PHE PRO LYS A
                A A A T G A C C C T G A T G T G T C T T T T C C C A A A C
                    5200                5210                5220

RG  ALA VAL ASP VAL LYS PRO GLU THR SER
G A G C G G T T G A T G T C A A A C C T G A A A C T T C C A
    5230                5240                5250
                ASN THR ASN GLU TYR GLY PHE ARG TYR GLN H
                A T A C C A A T G A A T A C G G C T T T C G C T A T C A G C
                    5260                5270                5280

IS  PRO TRP GLY ASP ILE GLU MET SER MET
A C C C T T G G G G G A T A T T G A G A T G A G C A T G T
    5290                5300                5310
                PHE LYS SER ARG TYR LYS ASP MET LEU ASP L
                T C A A A A G C C G T T A C A A G G A C A T G T T A G A T A
                    5320                5330                5340
```

FIG.4D'

```
YS  ALA ILE PRO ASN LEU THR LYS ALA GLN
A A G C C A T A C C G A A C C T A A C C A A A G C C C A G C
            5350                    5360                 5370
                         GLN GLU TYR CYS LYS ALA HIS LEU ASP SER A
                         A A G A G T A T T G T A A G G C T C A T T T G G A T T C C A
                                     5380                    5390                 5400

SN  GLU CYS VAL GLY ASN PRO PRO THR PRO
A T G A A T G T G T T G G T A A T C C C C A C G C C C A
            5410                    5420                 5430
                         LYS THR SER ASP GLU VAL PHE ALA ASN LEU T
                         A A C C A G T G A T G A G G T A T T T G C C A A C T T A T
                                     5440                    5450                 5460

YR  ASN ALA THR ILE LYS GLY VAL SER VAL
A T A A T G C C A C C A T C A A A G G G G T G A G T G T C A
            5470                    5480                 5490
                         LYS GLY LYS GLN LEU ASP LEU HIS ALA MET THR S
                         A A G G C A A A C T G G A T T T G C A T G C C A T G A C A T
                                     5500                    5510                 5520
```

FIG.4E'

```
ER  LYS LEU PRO ASP GLY LEU GLU MET THR
C A A A A C T G C C A G A T G G T C T T G A A A T G A C C T
                    5530                5540                5550
    LEU GLY TYR GLY HIS THR LYS LEU GLY LYS P
    T G G G T T A T G G T C A T A C C A A A T T G G G A A A T
            5560                5570                5580

HE  ASP TYR ILE ALA PRO LYS ASP ALA ASP
T T G A T T A C A T T G C A C C C A A A G A T G C C G A T G
                    5590                5600                5610
    GLY TRP TYR GLN ALA ARG PRO ALA PHE TRP A
    G T T G G T A T C A G G C C T C G C C C T G C T T T T G G G
            5620                5630                5640

SP  ALA ILE THR PRO ALA ARG TYR VAL VAL
A T G C C A T C A C C C C A G C G C G C T A T G T G G T C G
                    5650                5660                5670
    GLY LEU ASN TYR ASP HIS PRO SER GLN VAL T
    G T C T A A A C T A T G A C C A C C C A G T C A A G T A T
            5680                5690                5700
```

FIG.4F'

```
RP  GLY ILE GLY THR THR LEU THR HIS SER
GGGGCATTGGCACAACTTTAACGCACAGCA
    5710              5720              5730
                                    LYS GLN LYS ASP GLU ASN GLU LEU SER ALA L
                                    AACAAAAAGATGAAAATGAGCTAAGTGCCC
                                            5740              5750              5760

EU  ARG ILE ARG ASN GLY LYS ARG GLU ILE
TTAGAATCCGAAATGGCAAAAGAGAAATAC
    5770              5780              5790
                                    GLN THR LEU THR HIS THR ILE PRO LYS ALA T
                                    AAACCTTAACGCACACAAATACCCAAAGCCT
                                            5800              5810              5820

YR  THR LEU LEU ASP MET THR GLY TYR TYR
ATACCTTACTGGACATGACAGGCTATTATA
    5830              5840              5850
                                    SER PRO THR GLU SER ILE THR ALA ARG LEU G
                                    GCCCAACTGAGAGCATCACCGCTCGTCTTG
                                            5860              5870              5880
```

FIG.4G'

```
LY  ILE ASN ASN VAL LEU ASN THR ARG TYR
GTATCAACAATGTATTAAACACCCGCTA
          5890                 5900
                                    THR THR TRP GLU ALA ALA ARG GLN LEU PRO S
                                    CACCACATGGGAAGCGGCACGCCAACTGCCCA
                                          5910              5920              5930              5940

ER  GLU ALA ALA SER SER THR GLN SER THR
GCGAAGCTGCAAGCAGTACCCAATCAACCC
          5950                 5960                 5970
                                    ARG TYR ILE ALA PRO GLY ARG SER TYR PHE A
                                    GTTACATTGCACCAGGTCGCAGTTACTTTG
                                          5980              5990              6000
                                                            ORF 3
                                                                  MET THR
LA  SER LEU GLU MET LYS PHE ***       LYS THR ASN PRO ALA LEU LYS
CCAGTCTCTTGAAATGAAGTTTTAATATGACC
          6010                 6020                 6030
                                    CYS LEU PRO LYS THR ASN PRO ALA LEU LYS
                                    TGTTTACCAAAGACCAACCCTGCTTTAAAA
                                          6040              6050              6060
```

FIG.4H'

```
VAL LYS HIS ARG PHE LEU LYS GLN VAL LEU
GTCAAGCACACAGATTTTAAAGCAGGTGCTG
        6070              6080              6090
                                  LEU LEU CYS VAL ASP THR LEU THR ALA
                                  TTATTGCTTTGTGTTGATACATTAACAGCA
                                          6100              6110              6120

GLN ALA TYR ALA HIS SER HIS HIS THR PRO
CAGGCGTACGCCCACAGCCATCATACGCCC
        6130              6140              6150
                                  ILE HIS THR PRO THR HIS GLU LEU SER SER
                                  ATTCATACACCCACGCATGAGCTGTCATCT
                                          6160              6170              6180

ALA ASP ALA LEU SER ASP GLU GLY LEU GLY
GCTGATGCTTTATCAGATGAAGGCTTGGGT
        6190              6200              6210
                                  LYS ASP LEU GLY SER LEU ASP SER PRO ASP
                                  AAGGATTTGGGCAGTTTGGACAGCCCAGAT
                                          6220              6230              6240
```

FIG. 4I'

```
GLY LEU GLY ASP GLY LEU GLY ASP GLY LEU
G G T T T G G G T G A T G G T T T A G G C G A T G G T T T G
            6250                  6260                  6270
                        GLY ASP GLY LEU LYS SER ASP LYS THR PRO
                        G G T G A T G G C T T A A A A A G T G A T A A A A C C C C T
                                    6280                  6290                  6300

LEU PRO ILE ASN ALA LEU THR VAL ASN GLN
T T A C C C A T C A A C G C C T T G A C C G T T A A T C A G
            6310                  6320                  6330
                        SER ASN GLU SER GLN PRO ALA PRO PRO SER
                        A G C A A T G A G A G C C A G C C T G C C C C A C C G A G C
                                    6340                  6350                  6360

VAL ASP VAL ASN PHE LEU ALA GLN PRO
G T A G A T G T C A A T T T T T T A C T T G C C C A G C C A
            6370                  6380                  6390
                        GLU ALA PHE TYR HIS VAL PHE HIS GLN ALA
                        G A G G C A T T T T A T C A T G T C T T T C A T C A A G C G
                                    6400                  6410                  6420
```

FIG.4J'

```
ILE VAL GLN ASP ASP VAL ALA THR LEU ARG
ATTGTGCAAGATGATGATGTGGCAACATTACGC
        6430              6440          6450
                                              LEU LEU PRO PHE TYR ASP ARG LEU PRO
                                              TTGTTATTGCCATTTTATGACCGCCT
                                                   6460           6470          6480

ASP ASP TYR GLN ASP ASP VAL LEU LEU LEU
GATGATTATCAAGATGATGTTTTGTTA
        6490              6500          6510
                                              PHE ALA GLN SER LYS LEU ALA LEU SER ASP
                                              TTTGCCCAAAGTAAACTTGCCCTAAGTGAT
                                                  6520           6530          6540

GLY ASN THR LYS LEU ALA LEU ASN LEU LEU
GGCAATACCAAATTGGCATTGAATCTGCTG
        6550              6560          6570
                                              THR ASP LEU SER ASN LYS GLU PRO THR LEU
                                              ACCGATTTGAGTAACAAAGAGCCAACACTT
                                                   6580           6590          6600
```

FIG.4K'

```
THR ALA VAL LYS LEU GLN LEU ALA SER LEU
ACGGCGGTAAAATTACAACTTGCTTCCTTG
                6610              6620              6630
                    LEU LEU THR ASN LYS HIS ASP LYS HIS ALA
                    TTGCTGACCAACAAGCACGATAAACACGCC
                        6640              6650              6660

GLN MET VAL LEU ASP GLU LEU LYS ASP ASP
CAAATGGTGCTAGATGAACTCAAAGATGAT
                6670              6680              6690
                    ALA HIS PHE LEU LYS LEU SER LYS LYS GLU
                    GCCCACTTTTTAAAATTAAGCAAAAAGAG
                        6700              6710              6720

GLN ARG TRP VAL LEU SER GLN SER ARG TYR
CAAAGATGGGTGCTATCGCAAAGTCGCTAT
                6730              6740              6750
                    LEU HIS LYS LYS TYR LYS MET GLY LEU ASP
                    TTACATAAAAAATATAAAATGGGCTTGGAT
                        6760              6770              6780
```

FIG.4L'

```
LEU GLY ILE ASN TYR LEU HIS LEU ASP ASN
TTG GGC ATC AAC TAT CTG CAT TTG GAT AAT
            6790                6800              6810

ILE ASN ALA ALA SER THR ILE THR GLN PRO
           ATC AAC GCC GCC TCC ACC ATC ACC CAG CCC
                    6820              6830              6840

ASN ILE LYS LYS ASP ALA PRO LYS PRO ALA
AAC ATT AAA AAA GAT GCC CCC AAA CCT GCT
            6850              6860              6870

HIS GLY LEU ALA LEU SER LEU GLY VAL ASN
           CAT GGG CTT GCC CTT ATC GCT TGG TGT GAA T
                    6880              6890              6900

LYS TYR THR PRO LEU SER HIS GLY MET SER
AAA TAC ACG CCG CTT AGT CAT GGC ATG AGT
            6910              6920              6930

ILE TYR THR ALA LEU ASP VAL ASP GLY LYS
           ATT TAT ACA GCC CTA GAT GTT GAT GGT AAA
                    6940              6950              6960
```

FIG. 4M'

```
PHE TYR ASP ASP LYS SER HIS ASN GLU LEU
TTTTATGATGACAAAAGCCACAATGAACTG
        6970              6980              6990
                                                ALA VAL PHE ALA HIS ALA GLY LEU ARG LYS
                                                GCGGTTTTTGCTCATGCTGGACTAAGAAAA
                                                        7000              7010              7020

ASP HIS GLN LYS GLY TYR VAL ASP VAL VAL
GATCACCAAAAGGTTATGTTGATGTCGTA
        7030              7040              7050
                                                PRO PHE VAL GLY ARG ILE PHE ALA THR ASN
                                                CCTTTTGTTGGGCGTATTTTTGCCACCAAT
                                                        7060              7070              7080

GLN GLN HIS GLY ARG LEU SER PRO ARG LYS
CAGCAGCATGGCAGATTATCCCCCAGAAAA
        7090              7100              7110
                                                ASP SER GLN GLY VAL ALA PHE GLY SER HIS
                                                GACAGTCAGGGCGTGGCGTTTGGCAGCCAT
                                                        7120              7130              7140
```

FIG.4N'

```
HIS ARG ILE ASN ASP LYS TRP GLN ASN ALA
CAT CGG GAT CAA TGA TAA ATG GCA AAA TGC G
                7150                    7160                    7170
                    PHE PHE ALA ARG MET GLU LYS GLY ASN TYR
                    TTT TTT GCA CGC ATG GAA AAA GGC AAT TAT
                        7180                    7190                    7200

THR GLU HIS TYR GLN GLY TYR ASP GLY LYS
ACC GAG CAT TAT CAA GGT TAT GAT GGC AAG
                7210                    7220                    7230
                    ARG TYR HIS VAL ASN ASP THR ILE LEU LEU
                    CGT TAT CAT GTG AAT GAC ACC ATT TTG TTG
                        7240                    7250                    7260

GLN ASP GLY PRO ASN ARG ARG TYR SER LEU
CAA GAT GGC CCA AAT CGT CGT TAC TCT TTG
                7270                    7280                    7290
                    GLY VAL GLY TYR GLN LEU SER HIS LEU GLN
                    GGC GTG GGG TAT CAG CTT AGC CAT CTG CAA
                        7300                    7310                    7320
```

FIG. 4O'

```
ASP ALA THR LYS SER SER HIS ALA THR LYS               ILE HIS PHE GLY VAL LEU GLN ARG LEU PRO
GATGCAACAAAAAGCAGTCATGCCACAAAG                        ATACATTTTGGGGTGTTGCAAAGATTGCCA
        7330                  7340           7350              7360              7370        7380

ASN GLY LEU THR VAL GLN GLY ARG VAL SER               ALA GLU ARG GLU ARG TYR HIS GLY LYS LEU
AATGGTCTGACCCGTGCAAGGTAGAGTGAGT                       GCTGAGCGTGAGCGTTATCATGGTAAATTA
        7390                  7400           7410              7420              7430        7440

LEU ARG LEU VAL ASN PRO ASP ASP VAL TYR               ARG THR ASP LYS THR LEU THR LEU GLN THR
TTGCGTCTGGTTAATCCTGATGATGTGTAT                        CGCACAGATAAAACCCTAACCCTACAAACC
        7450                  7460           7470              7480              7490        7500
```

FIG. 4P'

```
SER ILE TRP HIS LYS ASP ILE HIS TRP LEU
TCC ATT TGG CAC AAA GAC ATT CAC TGG CTT
            7510                    7520                 7530
                         GLY LEU THR PRO LYS LEU THR TYR ARG TYR
                         GGA TTA ACG CCA AAA GCT GAC TTA TCG TTA C
                              7540                 7550                 7560

SER LYS ASN ASN SER ASN LEU PRO ALA LEU
AGT AAA AAA TAA CAG TAA CTT ACC AGC ACT T
            7570                    7580                 7590
                         TYR SER HIS ASN LYS GLN ASN PHE TYR LEU
                         TAT AGC CAT AAC AAA CAA AAT TTT ATT TG
                              7600                 7610                 7620

GLU LEU GLY ARG SER PHE ***
GAG CTT GGT CGG TCG TTT TAA
            7630                    7640
```

FIG.6A
Alignment of Lbp2 proteins

```
           10         20         30         40         50         60
MSKSITKTQTPSVHTMTTHRLNLAIKAALF-GVAVLPLSWAQENTQTDANSDAKDTKTPV                    4223
..........................................................                   Q8
.N.KHGFQL.LTA------.VA..-.PSY.AN.------E.A.-P..AQ.QS---                        BNCV
.N.KHSFPL.LTA------...AT.-.PSY.ANS------E.A.----Q.QS---                        H44/76
.N.KHGFPL.LTA------...AT.-.PAY.AQA------GAA.-L..AQSQS---                       FA19

70         80         90        100
VVLDAITVIAAPSAPVSRFDIDVTGLGKTVKTADTLAKEQ                                       4223
.......................................                                      Q8
--.KEV..R..K---..G.RSKEA.....IA..SE..N...                                     BNCV
--.KEV..R..K---..G.RSKE......I...SE..N...                                     H44/76
--.KEV..R..K---..G.RSKEA.....I...SE..N...                                     FA19

110        120        130        140        150        160
VQGIRDLVRYETGVSVVEQGRGGSSGFAIHGVDKNRVGITVDGIAQIQSYKDESTKRAGA-                   4223
............................................................                 Q8
.L.....T..DP..A.....N.A.G.YS.R......AVS...V.....AFTVQGSLSGYGG                  BNCV
.L.....T..DP..A.....N.A.G.YS.R......AVS...V.....AFTVQGSLSGYGG                  H44/76
.L.....T..DP..A.....N.A.G.YS.R......AVS...V.....AFTVQGSLSGYGG                  FA19

170        180        190        200
--GSGAMNEIEIENLAAVAINKGGNALFAGSGALGGSVAFHT                                     4223
--.......................................                                    Q8
RG....I...Y...ST.E.D..AGSSDH.........A...R.                                   BNCV
RG....I...Y...ST.E.D..AGSSDH.........A...R.                                   H44/76
RG....I...Y...ST.E.D..AGSSDH.........A...R.                                   FA19
```

FIG.6B

```
        210       220       230       240       250       260
KDVSDVLKSGKNLGAQSKITYNSKNDHFSQTLAAAGKTERVEAMQYTYRKGEKNKAHSDL                    4223
.........N..................................................                   Q8
.EAA.LISD..SW.I.A..A.G....RQ.MKS.G.GFSKDGW.GLLIR.E.Q.R.THP.G.I                  BNCV
.EAA.LISD..SW.I.A..A.G....RQ.MKS.G.GFSKDGW.GLLIR.E.Q.R.TRP.G.I                  H44/76
.EAA.LISD..SW.I.A..A.G....RQ.MKS.G.GFSKDGW.GLLIR.E.Q.R.TRP.G.I                  FA19

270       280       290       300
-NGINQSLYRLGAWQQKYDL-RKFNELFAGTSYTTESCLAS
-...................-...................
AD.VAYGIN..D.FR.T.GI-K..S.GGEYFLAEG..E.KP
AD.VAYGID..D.FR.T...I-Q.QNKKAEYFLAEG..E.KP
AD.VAYGID..D.FR.T..IK..TT.P.--FLAEG.NT.KP 310       320       330       340       350       360
DDPKSCVQPYVYTKARPDGIGNRNFSELSDAEKAQYLASTHPHEVVSAKDYTGIYRLLPD                    4223
............................................T...............                   Q8
VAKVAGNGNYILNQIN.WKERIEQNQP..AE.E.MVREAQAR..NL..QA...GG.I...                    BNCV
AAKLAGNGNYILNQIN.WEERKNNQS..AE.E.MVREAQAR..NL..QA...GG.I...                     H44/76
VAKLAGYGIYINRQLN.WKERIEQNQP..AE.E..VREAQAR..NL..QA...GG.I...                    FA19

370       380       390       400
PMDYRSDSYLARLNIKITPNLVSKLLEDTKQTYNIRDM                                          4223
.....................................                                          Q8
.....G.W...K.GYRFGGRHYVGGVF.....R.D...                                          BNCV
.....G.W...K.GYRFGGRHYVGGVF.....R.D...                                          H44/76
.....G.W...K.GYRFGGRHYVGGVF.....R.D...                                          FA19
```

FIG. 6C

```
          410       420       430       440       450       460
RHCSYHGARLGNDGKPANGGSIVLCDDYQEYLNANDASQALFRPGANDAPIPKLAYARSSV                        4223
..............S.............................................                        Q8
TEKQ.Y.TDEAKFRDKS.--VYDG..FRDG.YFVPNIEE-WKGDQKLIRGIG.K.S.TK-                         BNCV
TEKQ.Y.TDEATKFSDKS.--VYDG..FRDG.YFVPNIEE-WKGDK.LVKGIG.K.S.TK-                        H44/76
TEKQ.Y.TDEAEKFRDKS.--VYDG..FRDG.YFVPNIEE-WKGDK.LVKGIG.K.S.TK-                        FA19

470       480       490       500
          FNQEHGKTRY-GLSFEF---KPDTPMFKQAKLNLHQQNIQIIN                                 4223
          .................G..........................                               Q8
          .ID..HRR..RM..LYRYENE.YSIN.ADK.V..SFDK.GVAID.                               BNCV
          .ID..HRR..RM..LYRYENFAYSIN.ADK.V..SFDK.GVAID.                               H44/76
          .ID..HRR..RM..LYRYENE.YSIN.ADK.V..SFDK.GVAID.                               FA19

510       520       530       540       550       560
HDIKKSCSQYPKVDLNCGISEIGHYEYQ---NNYRYKEGRASLTGKLDFNFDL-LGQHDLTVLAG                    4223
.........................T..................................                        Q8
NTL.IN.AV..A..KS.RA.ADKP.S.DSSDRFH.R.QHNV.NASFEKSLKNKWTK.H..LGF.                     BNCV
NTL.IN.AV..A..KA.RA.ADKP.S.DSSDRFH.R.QHNV.NALFEKSLKNKWTK.H..LGF.                     H44/76
NTL.IN.AV..A..KA.RA.ADKP.S.DSSDRFH.R.QHNV.NASFEKSLKNKWTK.H..LGF.                     FA19

570       580       590       600
ADKVKSQFRANNPRRTIIDTTQGDALIDESTLTAQEQAK                                              4223
......................................                                              Q8
Y.ASNAIS..PEQLSHNAARISEYSDYT.KGD------                                               BNCV
Y.AS.AIS..PEQLSHNAARISEFSDYA.DGKY------                                              H44/76
Y.AS.AIS..PEQLSHNAARISE-STGF..KNQD-----                                              FA19
```

FIG.6D

```
              610        620        630        640        650
     FKQSGAAMIVKNRLGRLEEKDA--CGNANECERAP-----IHGSNQYVGINNLYTPNDYVD    4223
     ...........................................................    Q8
     ------YL..KP.WEGSV..YIETLRSRKCVPRK.N...IHISL.DRFSIGK.F.          BNCV
     ------YL..KP.WEGSV..YIETLRSRKCVPRK.N...IHISL.DRFSIGK.F.          H44/76
     ------Y...KP.WEGSV..YIETLRSRKCVPRK.N...IHISL.DRFSIGK.F.          FA19

660        670        680        690        700
     LSFGGRLDKQRIHSTDSNIISKTYTNKSYNFGAAVHLTPDFSLLYK                    4223
     .............................................                    Q8
     F.L...Y.RKNFTTSEELVR.GR.VDR.W.S.IVFKPNRH...S.R.                   BNCV
     F.L...Y.RQNFTTSEELVR.GR.DR.W.S.IVFKPSRHL..S.R.                    H44/76
     F.L...Y.RKNFTTSEELVR.GR.ADR.W.S.IVFKPNRH..VS.R.                   FA19

710        720        730        740        750        760
     TAKGFRTPSFYELYNYNSTAAQHKNDPDVSFPKRAVDVKPETSNINEVGFRYQHPMGIDVEM    4223
     ............................................I..                 Q8
     ASS........Q..FGIDIYH------YPKGMQRPAL.S.KAANR.I.LQWKGDF.FL.I     BNCV
     ASS........Q..FGIDIYH------YPKGMQRPAL.S.KAANR.I.LQWKGDF.FL.I     H44/76
     ASS........Q..FGIDIYH------YPKGMQRPAL.S.KAANR.I.LQWKGDF.FL.I     FA19

770        780        790        800
     SMFKSRYKDMLDKAIPNLIKAQ-QEYCKAHLDSNECVGNP                          4223
     .......................................                          Q8
     .S.RN..T...IAV.DHK-..LPN.AGQLTEI.IRDYY----                        BNCV
     .S.RN..T...IAV.DHK-..LPN.AGRLTEI.IRDYY----                        H44/76
     .S.RN..T...IAV.DQK-..LPDSAGRLTEI.IRDYY----                        FA19
```

FIG.6E

```
        810       820       830       840       850       860
PTPKTSDEVFANLYNATIKGVSVKGKLDLHAMTSKLPDGLEMTLGYGHIKLGKFDYIAPKD
------.AQ.MSLQ..NIL..I.WNGVYG....E..YT..A.NRI------.S
------.AQ.MSLQ..NIL..I.WNGVYG....E..YT..A.NRI------.S
------.AQ.MSLQ..INIL..I.WNGVYG....E..YT..A.NRI------.S 870       880       890       900
        ADGWYQA--RPAFWDAITPARYVWGLNYDHPSQWGIGITL               BNCV
        ..........VSNRPGLSL.SYAL..VQ.S...L.FG..Q.E

FIG. 7A

Alignment of M. catarrhalis Lbp2 proteins

```
         10        20        30        40        50        60
MSTVKTPHIFYQKRTLSLAIASIFAALVMTGCRSDDISVNAPNVTQLPGIVSPTPNTGH        Q8
.....P......................................................    4223
.....V......................................................    VH19

DNANNTNNQGNNIDNSTSTTDPNGDNNQLTQAQKTAAAAG
                                                   70        80        90       100
                                     ...T...................................    Q8
                                     ..T....................................    4223
                                                                                 VH19

110       120       130       140       150
FFVMGKIRDTISEKNDPDYSDDLKQQW----LGKLYVGIDAHRPDGIGKKNLRQPITAND      Q8
.....P........N.V....-Q..........T..........................     4223
.........TK..QGSVHTAGQ.LQ.L.TKEP....T.T........D.............    VH19
                       160       170       180       190       200
                    IKPLYFNKFPALSDLHLDSERHRFDPQKINTIKVYGYGNLTTPS
                                K.L..............................    Q8
                    ...T.....D..KI.....ENSE.V..AK.A.N..I.....A.SS.A  4223
                                                                     VH19

210       220       230       240       250       260
NNNTHINHQQADNKKNNKPVDPYENIRFGYLELQGSSLTQKNADNQNEQDR-IPKPMPILF     Q8
K...Y........................................P.DK..-............ 4223
K.P.YM.Y..EQ.I.K..G.D.Q......M..RELD.NK.G....SDKN.A.IFTT.T..     VH19
                      270       280       290       300
                    YHGENASSQLPSAGKFNYTGMLYLSDVKKRPALSASDER          Q8
                    ........................D..................    4223
                    ....TH.K...D.E.......T......F.DKT.DK             VH19
```

FIG. 7B

```
          310       320       330       340       350       360
          VGVYLNASGKANEGDVVSAAHIYLNGFQYKHTPATYQVDFDINSLTGKLSYYDNPNQQNN
                  S.                                                          Q8
          ..T.F.STR.S....L..........S.K..........S...Q.T.K.........K.TA      4223
                                                                        TA    VH19

370       380       390       400
          KGEYLKSQFDITKKVNETDVYQIDAKINGNRFVGTAKSLV
          Q.K.I.................................                            Q8
          D.R.IR....D....A..E.......T......I                                4223
                                                                             VH19

410       420       430       440       450       460
          NEKTQTAPFIKELFSKKANPNNPNSDTLEGGFYGESGDELAGKFLSNDNASYVFGGK
          ..N.E................................................             Q8
          DDN.N...V........D...................................             4223
                                                                              VH19

470       480       490       500
          RDKITKPVAIKTIVYFSAGFEKPSTSFVDNETIGGIIDRKG
                   TF............................R..NS.K                    Q8
          ....D..................................                            4223
          .......E.............T............G..E..S....G..                   VH19

510       520       530       540       550
          LN----NHINEDEIIP-SDDSYYGYIWGKPEKQFTKKVSSSTQVVPAYFGQHDKFYFNEN
          ..DAVNEK.DNGD.PT-..ER.DEFP..EKKAE..........A...............        Q8
          ..DEVN.Q.-...TV.V.NKE..E.NY.R.N......INA.V.KN...............       4223
                                                                              VH19

560       570       580       590       600
          YDDLSASRVDKLAPADAVKANQSIKEKYPNATLNKINQVTAIVLQ.......
          ...........S................................                       Q8
          .......KEAN..GVSQDTST.K..LA...D.KVST.K..K....                       4223
                                                                              VH19
```

FIG. 7C

```
     610       620       630       640       650       660
EAKINKPYTAIRAKSYQHISFGETLYNDANQTPTRSYFVQGGRADTSTILPQAGKFTYNG           Q8
Q...-.....H...D......V....NKGN..........Q.V.Q.S..........K..          4223
                                          LK.I.TAEAD-I..T..AR.T.       VH19
                                                                       H44/76

670       680       690       700
LWAGYLTQKDKGYSDNAETIKEKGHPGYLLTENFTPEDD
.........I...N.E...K..QD....D........
........KDED...Q..LKD.I..KD.I.Q..
T.EARISKPIQMDNHADKKAA-----------------

710       720       730       740       750
DDD---LTASDDSQDDINTHGDDDLIASDDSQDDDADGDDSDDLGDGADDAAGKVYHA
.........................DA.........A................
...DDS................................T..............
_____

760       770       780       790       800
GNIRPEFENKYLPINEPTHEKTFALDGKNKAKEVDENINSLIG           Q8
...........................D__D.........           4223
...........................D.N.D.........           VH19
.....................E.D...GEK.IS.                  H44/76
```

FIG. 7D

```
          810       820       830       840       850
KINDERGDIV-FDIKNGKIDGTGFTAKADVPNYREEV-GNNQGGGFLYNIKDIDVKG
..........................................................
..........................................................
T.TEKN.VQPA.H.E..V.E.N..H.T.RTRDNGINLS..DSTNPPSFKANNLL.T.
                          RDNGINLS..GSTNPPSFKADNLL.T.

860       870       880
QFFGTNGEELAGQLHHDKGD--GINDTAEKA----------------            Q8
    QY...........................T.............            4223
R...................                                       VH19
G.Y.PKA...G.IIFNND.KSL..TEGT.NKVE-ADVDVDVDVD               BNCV
G.Y.PQA...G.IIFNND.KSL..TEDT.NEAE-AEVENEAGVG--             H44/76
G.Y.PQAA..G.IIFNND.KSL..TEDI.NEVENEADVG--                  FA19

890
     --GAVEGAVKD----K*                                      Q8
     -----------.*                                          4223
     -----------.*                                          VH19
ADADVEQLKPEVKPQF.V....K..NKEVE.*                           BNCV
----EQLKPEAKPQF.V....K..NKEVE.*                            H44/76
-------EQLEPEVKPQF.V....K..NKEVE.*                         FA19
```

FIG.8A  *M. catarrhalis strain 4223 Tbp2/Lbp2 comparison*

```
           MKHIPLT--TLCVAISA----VLLTACGGSGGS-NPPAPT------PIPNASGSGNTG    Tbp2
MSTVKTP..FYQKR..SL..ASIFAALVM.G.RSDDI.V.A.NV.QLPQGTVS....TGHD-...N    Lbp2
    *       ** ******        *      *    *  *      *       *

NTGNAGG-TDNTANAGNTGGTNSGTGSANTPEPKYQDVPTEKNEKDKVSSIQEPAMG-----YGM    Tbp2
..N.Q.NN...STSTTDPN.D.NQLTQ.QKTAAAAGFFVMG.I-R.TSPKNDPDYSNDLVQQWQG    Lbp2
  * * **  ****** **  **  *    ***    *** *  **  **    *       *

ALSKINLNHNRQDTPLDEKNIITLDGKKQVAEGKKSPLPFSLDVENKLLDGYIAKMNVADKNAIGD    Tbp2
K.YVGIDAH.P.GIGTG..LRQPITANDIKPLYFNKF.ALS.L--------HL.SERHRF       Lbp2
 *       *  * **   *  **   *   *  *  **  *          *   *  *

RIKKGNKEISDEELAKQIKEAVRKSHEFQQVLSSLENKIFHSNDGTTKATTRDLKYVDYGYYLAN    Tbp2
DP..L.TIKVYGYGNLTTPSKNNTYINH..ADNKKN..PVDPYENIRFGYLELQGSSLTQKNADT    Lbp2
 *  *        *     * *   ***   ** *      *  **  *      *  *  *

DGNYLTVKTDKLMWNLGPVGGVFYNGTTTAKELPTQDAVKYKGHWDFMTDVANRRNRFSEVKENSQ    Tbp2
PNDKDRIPK------.MPIL..H.ENASSQ...SAGKFN.T.N.LYLS..KK.PALSASDDRV--    Lbp2
  * *           * ** ** ** *     ** ** * * ****  **  *  ***

AGWYYGASSKDEYNRLLTKEDSAPDGHSGEYGHSSEFTVNFKEKKLTGKL----------F      Tbp2
-.V.LN..G.SNEGDVVSAAHIYLN.FQYKHTPAT-YQ.D.DTNS.....SYYDNPNQQTAQGKY   Lbp2
   * **  * *  **  *  *   * * ***       ***       * *****

SNLQDRHKGNVTKTERYDIDANIHGNRFRGSATA-----SNKNDTSKHPFTSDAN-------NR   Tbp2
IKS.FDTTKK.NE.DV.Q...K.N....V.T.KSLVNENTETAPFI.EL.SKK..PNNPNPNSDT   Lbp2
 *    **  *  **  *   * *    * *        * * ***** **  **        *
```

FIG.8B

```
LEGGFYGPKGEELAGKFLTNDNKLFGVFGAKRESKAEEKTEAILDAYALGTFNTSNATTFTPFTE    Tbp2
.......ES.D........S.....ASYV...G..DKTDKPVATKTVFS.AFEKP-----------    Lbp2
* ******              *  *********  *

KQLDNFGNAKKLVLGSTVIDLVPTDATKNEFTKDKPESATNEAGETLMVNDEVSVKTYGKNFEYL    Tbp2
-----------------------------------------------------------------    Lbp2

KFGELSIGGSHSVFLQGERTATTGEKAVPTTGTAKYLGNWVGYITGKDTGTGKSFTDAQDVAD      Tbp2
-----------------------------------------------------------------    Lbp2

FDIDFGNKSVSGKLITKGRQDPVFSITGQIAGNGWTGTASTTKADAGGYKIDSSSTGKSIAIKDA    Tbp2
..........................................IKNG....GTGFTAKADVPNY-    Lbp2
                                            *  *     * ****  *

------NVTGGFYGPNAN-EMGGSFTHN------ADDS----------KASVVFGTKRQQEVK*    Tbp2
REEVGN.QG...LYNIKDIDVK.Q.FGTNGEEL.GQLQYDKGDGINDTAE..GA...AVKD---.*   Lbp2
     *  **                *        *          *** * ***** *      *
```

FIG.9A Alignment of M. catarrhalis Lbp3 sequences

```
                10        20        30        40        50
MTCLPKTNPALKVKHRFLKQVLLLLCVDTLTAQAYAHSHHTPIHTPTHEL.....    4223
..................................................         Q8

60        70        80        90       100
PSADALSDEGLGKDLGSLDSLDSPDGLGDGLGDGLKSDKAPLPINA.......       4223
.............................................T.....        Q8

110       120       130       140       150
LTAHQTNESQPAPPSVDVNFLLAQPEAFYHVFHQAIVQDDVATLRLLLPF...       4223
..VN.S..............................................        Q8

160       170       180       190       200
YDRLPDDYQDDVLLLFAQSKLLALSDGNTKLALNLLTDLSNKEPTLTAVKL..       4223
....................................................        Q8

210       220       230       240       250
QLASLLLTNKHDKHAQMVLDELKDDAHFLKLSKKEQRWVLSQSRYLHKKY..        4223
....................................................        Q8

260       270       280       290       300
KMGLDLGINYLHLDNINAASTITQPNIKKDAPKPAHGLALSLGVNKYTPL..        4223
....................................................        Q8

310       320       330       340       350
SHGMSIYTALDVDGKFYDDKSHNELAVFAHAGLRKDHQKGYVDVVPFVGR..        4223
....................................................        Q8
```

FIG.9B

```
         360        370        380        390        400
          .          .          .          .          .
IFATNQQHGRLSPRKDSQGVAFGSHHRINDKWQNAFFARMEKGNYTERYQ    4223
                                               H..   Q8

410        420        430        440        450
          .          .          .          .          .
GYDGKRYHVNDTILLQDGPNRRYSLGVGYQLSHLQDATKSSHATKIHFGV    4223
.................................................   Q8

460        470        480        490        500
          .          .          .          .          .
LQRLPNGLTVQGRVSAERERYHGKLLRLVNPDDVYRTDKTLTLQTSIWHK    4223
.................................................   Q8

510        520        530        540
          .          .          .          .
DIHWLGLTPKLTYRYSKNNSNLPALYSHNKQNFYLELGRSF*            4223
                                        **            Q8
```

EXPRESSION OF Q8 AND 4223 rLbp 1 PROTEINS.

Q8 rLbp1 rLbp1

Purification scheme for rLbp1 expressed from E.coli

Purification of Q8 rLbp1 from *E. coli*

1. *E. coli* whole cells
2. Soluble proteins in 50 mM Tris/ NaCl extraction
3. Soluble proteins in Tris/ Triton X-100 extraction
4. Soluble proteins in Tris/ octylglucoside extraction
5. rLbp1 inclusion bodies
6. rLbp1

FIG. 16A

Nucleotide and deduced amino acid sequence of the VH19 lbpB gene.

```
MET SER THR VAL LYS VAL PRL HIS ILE PHE
ATG AGT ACT GTC AAA GTC CCC ACA TTT TC
                  10              20          30

TYR GLN LYS ARG THR LEU SER LEU ALA ILE
TAC CAA AAA CGC ACC CTT AGC CTT GCC ATC
                  40              50          60

ALA SER ILE PHE ALA ALA VAL VAL MET THR
GCC AGT ATT TTT GCT GCC GTG GTG ATG ACA
                  70              80          90

GLY CYS ARG SER ASP ASP ILE SER VAL ASN
GGC TGC CGC TCT GAT GAC ATC AGC GTC AAT
                  100             110        120

ALA PRO ASN VAL THR GLN LEU PRO GLN GLY
GCA CCC AAT GTT ACC CAA CTG CCC CAA GGC
                  130             140        150

THR VAL SER PRO ILE PRO ASN THR GLY HIS
ACG GTT TCA CCA ATA CCG AAC ACA GGT CAT
                  160             170        180
```

FIG.16B

```
ASP ASN THR ASN ASN THR ASN ASN GLN GLY
GACAACACCAACAATAACCACCAATCAGGGC
            190              200              210
       ASN ASN THR ASP ASN SER THR SER THR THR
       AACAACACGGATAACAGCACCAGCACAACT
                220              230              240

ASP PRO ASN GLY ASP ASN ASN GLN LEU THR
GACCCAAATGGCGATAACAACCAAACTGACA
            250              260              270
       GLN ALA GLN LYS THR ALA ALA ALA GLY
       CAAGCACAAAAAACTGCCGCCGCCCAGGG
                280              290              300

PHE PHE VAL MET GLY LYS ILE ARG ASP THR
TTTTTTGTGATGGGTAAAATTCGTGATACC
            310              320              330
       SER GLU LYS ASN ASP PRO ASP TYR THR LYS
       AGCGAAAAAAATGACCCAGATTATACCAAAA
                340              350              360
```

FIG. 16C

```
ASP LEU GLN GLY SER VAL HIS THR ALA GLY
GATTTACAAGGCAGCGTACATACAGCAGGG
         370                    380                    390
                               GLN GLY LEU GLN TYR LEU GLY THR LYS GLU
                               CAAGGCTTACAGTACTTAGGCACCAAAGAG
                                        400                    410                    420

PRO ARG PRO ASP GLY THR GLY LYS
CCTCGGCCAGATGGCACAGGTAAA
         430                    440                    450
                               ASN LEU ARG GLN PRO ILE THR ALA ASP ASP
                               AACTTACGCCAGCCCATCACAGCTGATGAC
                                        460                    470                    480

ILE THR PRO LEU TYR PHE ASP LYS PHE PRO
ATTACACCACTTTATTTTGATAAATTCCCC
         490                    500                    510
                               LYS ILE SER ASP LEU HIS LEU GLU ALS SER
                               AAAATATCCGATCTGCACCTAGAAAACAGC
                                        520                    530                    540
```

FIG.16D

```
GLU HIS VAL PHE ASP ALA LYS LYS ALA ASN
GAGCATGTGTTTGATGCTAAAAAGCAAAT
         550              560          570
                       ASN ILE LYS ILE TYR GLY TYR SLY ALA LEU
                       AACATCAAAATATATGGTTATGGTGCATTG
                              580           590           600

SER SER PRO ALA LYS ASN PRO THR TYR MET
TCATCACCTGCCAAAAACCCAACCTACATG
         610              620         630
                       ASN TYR GLN GLN GLU GLN ASN ILE LYS ASN
                       AATTATCAAGAACAAGAAACATCAAAAAC
                              640           650           660

LYS LYS PRO GLY ASP ASP TYR GLN ASN ILE
AAAAAACCAGGCGATGATTATCAAAACATT
         670              680         690
                       ARG PHE GLY TYR MET GLU LEU ARG GLU LEU
                       CGTTTTGGCTATATGGAGCTAAGAGAGCTTG
                              700           710           720
```

FIG.16E

ASP LEU ASN LYS LYS GLY ALA ASP THR GLN
GACCTAAATAAAAAAGGTGCAGACACCCAG
         730              740         750

SER ASP LYS ASN ARG ALA ILE ILE PHE THR
AGCGACAAGAACCGTGCCATCATTTTCACC
         760              770         780

THR PRO THR LEU PHE TYR HIS GLY GLN ASN
ACACCTACTCTTTATTTTATCATGGTGAGAAT
         790              800         810

ALA SER THR HIS LEU PRO LYS ALA GLY LYS
GCCAGCACCCATCTGCCAAAGGCGGGTAAA
         820              830         840

PHE THR ASP ASP LYS VAL GLY THR TYR PHE
TTTGACTATGAGGGCAATTGGTTGTATCTG
         850              860         870

ASN SER THR ARG LYS SER ASN GLU GLY ASP
ACCGATGTCAAAAAACGCCCATTTTTAGAT
         880              890         900

FIG.16F

```
LYS THR ASP ASP LYS VAL GLY THR TYR PHE
AAAACAGACGATAAAGTAGGCACTTATTTT
     910              920         930
                    ASN SER THR ARG LYS SER ASN GLU GLY ASP
                    AACTCAACCAGAAAATCAAATGAAGGCGAT
                       940           950           960

LEU VAL SER ALA ALA HIS ILE TYR LEU ASN
TTGGTGAGTGCAGCACACATTTATCTAAAC
    970           980           990
                    SER PHE LYS TYR LYS HIS THR PRO ALA THR
                    AGCTTTAAATATAAACACACCCCGGCCACT
                       1000          1010          1020

TYR SER VAL ASP PHE ASP GLN ASN THR LEU
TATAGCGTGGACTTTGATCAAAATACCCTA
    1030          1040          1050
                    LYS GLY LYS LEU SER TYR TYR ASP ASN PRO
                    AAAGGCAAATTGTCTTATTATGACAACCCA
                       1060          1070          1080
```

FIG.16G

```
ASN LYS GLN THR ALA ASP GLY ARG TYR ILE
AACAAGCAAACAGCCGATGGGCGTTATATC
         1090                    1100                   1110
                    ARG SER GLN PHE ASP THR ASP LYS LYS VAL
                    AGAAGTCAGTTTGATACCGACAAAAGGTC
                              1120                  1130                  1140

ASN GLU ALA ASP VAL TYR GLU ILE ASP ALA
AATGAAGCCGATGTCTATGAGATTGACGCC
         1150                    1160                  1170
                    LYS ILE ASN GLY ASN ARG PHE THR GLY THR
                    AAGATTAATGGCAACCGCTTTACTGGCACA
                              1180                  1190                  1200

ALA LYS SER LEU ILE ASP ASP ASN THR ASN
GCCAAATCTTTGATTGATGATAACACCAAT
         1210                    1220                  1230
                    THR ALA PRO PHE VAL LYS GLU LEU PHE SER
                    ACCGCACCTTTTGTTAAAGAGCTGTTCTCC
                              1240                  1250                  1260
```

FIG.16H

```
LYS LYS ALA ASN PRO ASN ASN PRO ASP PRO
AAAAAGCCAATCCCAACAACCCAGACCCC
                1270              1280              1290

ASN SER ASP THR LEU GLU GLY GLY PHE TYR
                    AACTCAGATACGCTAGAAGGCGGGTTTTAT
                              1300              1310              1320

GLY GLU SER GLY ASP GLU LEU ALA GLY LYS
GGTGAGTCGGGCGATGAGCTGGCGGGTAAA
                1330              1340              1350

PHE LEU SER ASN ASP ASN ALA THR PHE VAL
                    TTTTTATCCAATGACAACGCAACTTTTGTG
                              1360              1370              1380

VAL PHE GLY GLY LYS ARG ASP LYS THR THR
GTCTTTGGTGGCAAACGAGACAAAACGACC
                1390              1400              1410

GLU PRO VAL ALA THR LYS THR VAL THR PHE
                    GAACCTGTCGCCACAAAAACGGTGTATTTT
                              1420              1430              1440
```

FIG.16I

```
SER THR GLY PHE GLU LYS POE SER THR SER
AGTACAGGATTTGAAAAACCCAGCACCAGC
        1450              1460              1470
                    PHE VAL GLY ASN GLU GLU ILE GLY SER ILE
                    TTTGTTGGCAATGAAGAGATTGGTAGCATT
                              1480              1490              1500

ILE ASP GLY LYS LYS LEU ASN ASP GLU VAL
ATTGACGGTAAAAAGTTAAATGATGAAGTC
        1510              1520              1530
                    ASN ASN GLN ILE GLU ASP GLU THR VAL PRO
                    AATAATCAAATTGAAGATGAAACTGTCCCT
                              1540              1550              1560

VAL SER ASN LYS GLU TYR TYR GLU TYR ASN
GTCAGTAATAAAGAATATTATGAATATAAT
        1570              1580              1590
                    TYR GLY ARG PRO ASN LYS GLN PHE THR LYS
                    TATGGACGACCCAACAAACAATTCACCAAA
                              1600              1610              1620
```

FIG. 16J

```
LYS ILE ASN ALA SER VAL GLN LYS ASN PRO
AAAATAAACGCCAGCGTCCAAAAAACCCT
       1630                1640            1650
                    ALA TYR PHE GLY GLN HIS ASP LYS PHE TYR
                    GCTTATTTTGGTCAGCATGATAAGTTTTAT
                           1660            1670           1680

PHE ASN GLY ASN TYR TYR ASP LEU SER ALA
TTTAATGGTAACTATTATGACTTATCAGCC
       1690            1700           1710
                    LYS GLU ALA ASN LYS LEU GLY VAL THR ASP
                    AAAGAAGCAAACAAGCTTGGTGTCTCCCAA
                           1720           1730            1740

ASP THR SER THR ASN LYS SER ILE LEU ALA
GATACCAGCACCAATAAGAGTATTTTGGCT
       1750           1760            1770
                    LYS TYR PRO ASP ALA LYS VAL SER THR ASP
                    AAATACCCAGATGCCAAAGTAAGCACAGAC
                           1780            1790           1800
```

FIG. 16K

ASN LYS VAL THR LYS ILE VAL LEU GLN GLN
A A T A A A G T T A C C A A A A T C G T T C T A C A A C A A
          1810                            1820                       1830
                                   ALA LYS ASP LYS PRO TYR THR ALA ILE HIS
                                   G C C A A A G A T A A G C C G T A T A C C G C C A T T C A T
                                           1840                            1850                      1860

ALA LYS SER TYR ASP HIS ILE SER PHE GLY
G C C A A A A G C T A T G A C C A C A T C A G T T T T G G T
          1870                            1880                       1890
                                 GLU VAL LEU TYR ASN ASP ASN LYS GLY ASN
                                 G A A G T A T T G T A T A A T G A T A A C A A A G G C A A C
                                         1900                         1910                      1920

PRO THR ARG SER TYR PHE VAL GLN GLY GLY
C C A A C A C G C A G T T A T T T T G T G C A A G G C G G T
          1930                            1940                       1950
                                 GLN ALA ASP VAL SER THR GLN LEU PRO SER
                                 C A A G C G G A T G T C A G T A C T C A G C T G C C C A G T
                                         1960                         1970                      1980

FIG.16L

ALA GLY LYS PHE THR TYR ASN GLY LEU TRP
GCAGGTAAATTCACCTATAATGGTCTTTGG
　　　　1990　　　　　　　　2000　　　　　　　　2010

ALA GLY TYR LEU THR GLN LYS LYS ASP LYS
GCAGGCTACCTGACCCAGAAAAAGACAAA
　　　　2020　　　　　　　　2030　　　　　　　　2040

GLY TYR SER LYS ASP GLU ASP THR ILE LYS
GGTTATAGCAAAGATGAGGATACCATCAAG
　　　　2050　　　　　　　　2060　　　　　　　　2070

GLN LYS GLY LEU LYS ASP TYR ILE LEU THR
CAAAAAGGTCTTAAAGATTATATATTGACC
　　　　2080　　　　　　　　2090　　　　　　　　2100

LYS ASP PHE ILE PRO GLN ASP ASP ASP
AAAGACTTTATCCCACAAGATGACGATGAC
　　　　2110　　　　　　　　2120　　　　　　　　2130

ASP ASP SER LEU THR ALA SER ASP ASP
GATGACGATAGTTTGACCGCATCTGATGAT
　　　　2140　　　　　　　　2150　　　　　　　　2160

FIG.16M

```
SER GLN ASP ASP ASN THR HIS GLY ASP ASP
TCACAAGATGATAATACACATGGCGATGAT
                 2170              2180              2190
                                                      ASP LEU ILE ALA SER ASP ASP SER GLN ASP
                                                      GATTTGATTGCATCTGATGATTCACAAGAT
                                        2200              2210              2220

ASP ASP THR ASP GLY ASP ASP ASP SER ASP
GATGACACAGATGGCGATGACGATTCAGAT
                 2230              2240              2250
                                                      ASP LEU GLY ASP GLY ALA ASP ASP ALS
                                                      GATTTGGGTGATGGTGCAGATGATGACGCC
                                        2260              2270              2280

ALA GLY LYS VAL TYR HIS ALA GLY ASN ILE
GCAGGCAAAGTGTATCATGCAGGTAATATT
                 2290              2300              2310
                                                      ARG PRO GLU PHE GLU ASN LYS TYR LEU PRO
                                                      CGCCCCTGAATTTGAAAACAAATACTTGCCC
                                        2320              2330              2340
```

FIG.16N

```
ILE ASN GLU PRO THR HIS GLU LYS THR PHE
ATTAATGAGCCTACTCATGAAAAACCTTT
            2350              2360              2370
                    ALA LEU ASP GLY LYS ASN LYS ALA LYS PHE
                    GCCCTAGATGGTAAAAATAAGGCTAAGTTT
                      2380              2390              2400

ASP VAL ASN PHE ASP THR ASN SER LEU THR
GATGTAAACTTTGACACCAACAGCCTAACT
            2410              2420              2430
                    GLY LYS LEU ASN ASP GLU ARG GLY ASP ILE
                    GGTAAATTAAACGATGAGAGAGGTGATATC
                      2440              2450              2460

VAL PHE ASP ILE LYS ASN GLY LYS ILE ASP
GTCTTTGATATCAAAAATGGCAAAATTGAT
            2470              2480              2490
                    GLY THR GLY PHE THR ALA LYS ALA ASP VAL
                    GGCACAGGATTTACCGCCAAAGCCGATGTG
                      2500              2510              2520
```

FIG.16O

```
PRO ASN TYR ARG GLU GLU VAL GLY ASN ASN
CCAAACTATCGTGAAGAAGTGGGTAACAAC
           2530                2540            2550
                                         GLN GLY GLY GLY PHE LEU TYR ASN ILE LYS
                                         CAAGGTGGCGGTTTCTTATACAACATCAAA
                                                2560            2570           2580

ASP ILE ASP VAL LYS GLY GLN PHE PHE GLY
GATATTGATGTTAAGGGGCAATTTTTTGGC
          2590            2600           2610
                                         THR ASN GLY GLU GLU LEU ALA GLY ARG LEU
                                         ACAAATGGCGAAGAGTTGGCAGGACGGTTA
                                                2620           2630            2640

HIS HIS ASP LYS GLY ASP GLY ILE THR ASP
CATCATGACAAAGGCGATGGCATCACTGAC
          2650            2660           2670
                                         THR ALA GLU LYS ALA GLY ALA VAL PHE GLY
                                         ACCGCCGAAAAAGCAGGGGCTGTCTTTGGG
                                                2680            2690           2700

ALA VAL LYS ASP LYS ***
GCTGTTAAAGATAAATAA
           2710
```

LACTOFERRIN RECEPTOR GENES OF MORAXELLA

REFERENCE TO RELATED APPLICATION

This application is a continuation-in-part of U.S. Patent application No. 08/867,941 filed Jun. 3, 1997 now U.S. Pat. Ser. No. 5,977,337.

FIELD OF INVENTION

The present invention relates to the molecular cloning of genes encoding lactoferrin receptor (LfR) proteins and, in particular, to the cloning of lactoferrin binding protein genes (lbp genes) from *Moraxella* (*Branhamella*) *catarrhalis*.

BACKGROUND OF THE INVENTION

*Moraxella* (*Branhamella*) *catarrhalis* bacteria are Gram-negative diplococcal pathogens which are carried asymptomatically in the healthy human respiratory tract. However, in recent years, *M. catarrhalis* has been recognized as an important causative agent of otitis media. In addition, *M. catarrhalis* has been associated with sinusitis, conjunctivitis, and urogenital infections, as well as with a number of inflammatory diseases of the lower respiratory tract in children and adults, including pneumonia, chronic bronchitis, tracheitis, and emphysema (refs. 1 to 8). (Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Occasionally, *M. catarrhalis* invades to cause septicaemia, arthritis, endocarditis, and meningitis (refs. 9 to 13).

*M. catarrhalis* colonizes the human upper respiratory tract and is an important cause of otitis media in infants and children as well as lower respiratory tract infections in adults with chronic obstructive pulmonary disease.

Otitis media is one of the most common illnesses of early childhood and approximately 80% of all children suffer at least one middle ear infection before the age of three (ref. 14). Chronic otitis media has been associated with auditory and speech impairment in children, and in some cases, has been associated with learning disabilities. Conventional treatments for otitis media include antibiotic administration and surgical procedures, including tonsillectomies, adenoidectomies, and tympanocentesis. In the United States, treatment costs for otitis media are estimated to be between one and two billion dollars per year.

In otitis media cases, *M. catarrhalis* is commonly co-isolated from middle ear fluid along with *Streptococcus pneumoniae* and non-typable *Haemophilus influenzae*, which are believed to be responsible for 50% and 30% of otitis media infections, respectively. *M. catarrhalis* is believed to be responsible for approximately 20% of otitis media infections (ref. 15). Epidemiological reports indicate that the number of cases of otitis media attributable to *M. catarrhalis* is increasing, along with the number of antibiotic-resistant isolates of *M. catarrhalis*. Thus, prior to 1970, no β-lactamase-producing *M. catarrhalis* isolates had been reported, but since the mid-seventies, an increasing number of β-lactamase-expressing isolates have been detected. Recent surveys suggest that up to 80 to 85% of clinical isolates produce β-lactamase (ref. 16, 22, 23).

Iron-restriction is a general host defence mechanism against microbial pathogens. A number of bacterial species including *Neisseria meningitidis* (ref. 17, 24), *N. gonorrhoeae* (ref. 25) and *M. catarrhalis* (ref. 17), express outer membrane proteins which specifically bind human lactoferrin.

*M. catarrhalis* infection may lead to serious disease. It would be advantageous to provide a recombinant source of lactoferrin binding proteins as antigens in immunogenic preparations including vaccines, carriers for other antigens and immunogens and the generation of diagnostic reagents. The genes encoding lactoferrin binding proteins and fragments thereof are particularly desirable and useful in the specific identification and diagnosis of Moraxella and for immunization against disease caused by *M. catarrhalis* and for the generation of diagnostic reagents.

SUMMARY OF THE INVENTION

The present invention is directed towards the provision of purified and isolated nucleic acid molecules encoding a lactoferrin receptor protein of a strain of Moraxella or a fragment or an analog of the lactoferrin receptor protein. The nucleic acid molecules and isolated and purified lactoferrin binding proteins provided herein are useful for the specific detection of strains of Moraxella and for diagnosis of infection by Moraxella. The purified and isolated nucleic acid molecules provided herein, such as DNA, are also useful for expressing the lbp genes by recombinant DNA means for providing, in an economical manner, purified and isolated lactoferrin receptor proteins free of other Moraxella proteins, as well as subunits, fragments or analogs thereof.

The lactoferrin receptor, subunits or fragments thereof or analogs thereof, as well as nucleic acid molecules encoding the same and vectors containing such nucleic acid molecules, are useful in immunogenic compositions for vaccinating against diseases caused by Moraxella, the diagnosis of infection by Moraxella, and as tools for the generation of immunological reagents.

Monoclonal antibodies or mono-specific antisera (antibodies) raised against the lactoferrin receptor protein produced in accordance with aspects of the present invention are useful for the diagnosis of infection by Moraxella, the specific detection of Moraxella (in, for example, in vitro and in vivo assays) and for the treatment of diseases caused by Moraxella.

In accordance with one aspect of the present invention, there is provided a purified and isolated nucleic acid molecule encoding a lactoferrin receptor protein of a strain of Moraxella, more particularly a strain of *M. catarrhalis*, specifically *M. catarrhalis* strain 4223, Q8 or VH19 or a fragment or an analog of the lactoferrin receptor protein. A fragment of the lactoferrin receptor protein is a portion of the protein which retains the immunological properties of the protein.

In one preferred embodiment of the invention, the nucleic acid molecule may encode only the Lbp1 protein of the Moraxella strain or only the Lbp2 protein of the Moraxella strain or only the ORF3 protein of the Moraxella strain. In another preferred embodiment of the invention, the nucleic acid may encode a fragment of the lactoferrin receptor protein of a strain of Moraxella having a conserved amino acid sequence.

In a further aspect of the present invention, there is provided an isolated and purified nucleic acid molecule encoding at least one lactoferrin binding protein of Moraxella having a restriction map as shown in FIG. 3 for *M. catarrhalis* 4223, FIG. 5 for *M. catarrhalis* Q8 or FIG. 17 for *M. catarrhalis* VH19 or the equivalent map from other strains of Moraxella.

In another aspect of the present invention, there is provided a purified and isolated nucleic acid molecule having a DNA sequence selected from the group consisting of (a) a DNA sequence as set out in FIG. 2 or 4 (SEQ ID Nos. 1, 2, 3, 4, 5, 6, 7, 8, 9, 10, 69) or the complementary DNA sequence thereto; (b) a DNA sequence encoding an amino acid sequence as set out in FIG. 2 or 4 (SEQ ID Nos. 11, 12, 13, 14, 15, 16,17, 18, 70) or the complementary DNA sequence thereto; and (c) a DNA sequence encoding a functional lactoferrin receptor protein of Moraxella, which may be a. DNA sequence which hybridizes under stringent conditions to any one of the DNA sequences defined in (a) or (b). The DNA sequence defined in (c) may have at least about 90% sequence identity with any one of the DNA sequences defined in (a) or (b). Stringent conditions of hybridization are described below. Sequence identity is determined in the manner described below.

In an additional aspect, the present invention includes a vector adapted for transformation of a host, comprising a nucleic acid molecule as provided herein and may have the characteristics of a nucleotide sequence contained within vectors pLD3, pLDW3, PLD1-8 and pLDW1.

The vector may be adapted for expression of the encoded lactoferrin receptor protein, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the lactoferrin receptor protein or the fragment or analog of the lactoferrin receptor protein.

In specific embodiments of this aspect of the invention, the nucleic acid molecule may encode substantially all the lactoferrin receptor protein, only the Lbp1 protein of the Moraxella strain, only the Lbp2 protein of the Moraxella strain, only the ORF3 protein of the Moraxella strain, or fragments of the Lbp1, Lbp2 or ORF3 proteins.

The expression means may include a nucleic acid portion encoding a leader sequence for secretion from the host of the lactoferrin receptor protein or the fragment or the analog of the lactoferrin receptor protein. The expression means also may include a nucleic acid portion encoding a lipidation signal for expression from the host of a lipidated form of the lactoferrin receptor protein or the fragment or the analog of the lactoferrin receptor protein. The host may be selected from, for example, *Escherichia coli*, Bacillus, Bordetella, Haemophilus, Moraxella, fungi, yeast or baculovirus and Semliki Forest virus expression system may be used. In a particular embodiment, the plasmid adapted for expression or Lbp2 is pRD2A, pRD2B, pQW2A or pQW2B; the plasmid adapted for expression of Lbp1 is pRD1A, pRD1B, PQ1A or pQ1B; and the plasmid adapted for expression of ORF3 is pLRD3 or pLQW3.

In an additional aspect of the invention, there is provided a transformed host containing an expression vector as provided herein. The invention further includes a recombinant lactoferrin receptor protein or fragment or analog thereof of a strain of Moraxella producible by the transformed host.

Such recombinant lactoferrin receptor protein may be provided in substantially pure form according to a further aspect of the invention, which provides a method of forming a substantially pure recombinant lactoferrin receptor protein, which comprises growing the transformed host provided herein and isolating and purifying the lactoferrin receptor protein, analog or fragment thereof. The lactoferrin receptor protein may be expressed in inclusion bodies, which may be purified free from cellular material and soluble proteins and lactoferrin receptor protein solubilized from the purified inclusion bodies, and the lactoferrin receptor protein purified free from other solubilized materials. The substantially pure recombinant lactoferrin receptor protein may comprise Lbp1 alone, Lbp2 alone, ORF3 or a mixture of two or more of such proteins. The recombinant protein is generally at least about 70% pure, preferably at least about 90% pure.

Further aspects of the present invention, therefore, provide recombinantly-produced Lbp1 protein (or a fragment or analog thereof) of a strain of Moraxella devoid of the Lbp2 and ORF3 proteins of the Moraxella strain and any other protein of the Moraxella strain, recombinantly-produced Lbp2 protein (or a fragment or analog thereof) of a strain of Moraxella devoid of the Lbp1 and ORF3 proteins of the Moraxella strain and any other protein of the Moraxella strain, and recombinantly-produced ORF3 protein (or a fragment or analog thereof) of a strain of Moraxella devoid of the Lbp1 and Lbp2 proteins of the Moraxella strain and any other protein of the Moraxella strain. The Moraxella strain may be *M. catarrhalis* 4223, Q8 or VH19 strain.

The invention further includes, in an additional aspect, an open reading frame protein 3 (ORF3) of a Moraxella strain or a fragment or analog of the lactoferrin binding protein which is encoded by region downstream from the genes encoding Lbp2 and Lbp1 proteins of the Moraxella strain. The ORF3 may be from a strain of *M. catarrhalis*, which may be strain 4223 or Q8. The Lbp3 may have a molecular mass of about 60 kDa.

In accordance with another aspect of the invention, an immunogenic composition is provided which comprises at least one active component selected from at least one nucleic acid molecule as provided herein, at least one recombinant protein as provided herein or at least one novel protein as provided herein, and a pharmaceutically acceptable carrier therefor or vector therefor. The at least one active component produces an immune response when administered to a host.

The immunogenic compositions provided herein may be formulated as a vaccine for in vivo administration to a host to provide protection against disease caused by *M. catarrhalis*. For such purpose, the compositions may be formulated as a microparticle, capsule, ISCOM or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine.

Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants to induce a TH1 response. Advantageous combination of adjuvants are described in copending U.S. patent applications Ser. No. 08/261,194 filed Jun. 16, 1994 and Ser. No. 08/483,856 filed Jun. 7, 1995, assigned to the assignee hereof and the disclosure of which is incorporated herein by reference (WO 95/34308, published Nov. 21, 1995).

In accordance with another aspect of the invention, there is provided a method for generating an immune response in a host, comprising the step of administering to a susceptible host, such as a human, an effective amount of the immunogenic composition as recited above. The immune response may be humoral or a cell-mediated immune response and may provide protection against disease caused by Moraxella. Hosts in which protection against disease may be conferred include primates, including humans.

In a further aspect, there is provided a live vector for delivery of lactoferrin receptor to a host, comprising a vector containing the nucleic acid molecule as described above. The vector may be selected from *Salmonella, Mycobacterium bovis*, BCG, adenovirus, poxvirus, vaccinia and poliovirus.

The nucleic acid molecules provided herein are useful in diagnostic applications. Accordingly, in a further aspect of the invention, there is provided a method of determining the presence, in a sample, of nucleic acid encoding a lactoferrin receptor protein of a strain of Moraxella, comprising the steps of:

a) contacting the sample with a nucleic acid molecule as provided herein to produce duplexes comprising the nucleic acid molecule and any nucleic acid molecule encoding the lactoferrin receptor protein of a strain of Moraxella present in the sample and specifically hybridizable therewith; and b) determining the production of the duplexes.

In addition, the present invention provides a diagnostic kit for determining the presence, in a sample, of nucleic acid encoding a lactoferrin receptor protein of a strain of Moraxella, comprising:

a) a nucleic acid molecule as provided herein;

b) means for contacting the nucleic acid molecule with the sample to produce duplexes comprising the nucleic acid molecule and any such nucleic acid present in the sample and hybridizable with the nucleic acid present in the sample and hydridizable with the nucleic acid molecule; and c) means for determining production of the duplexes.

The invention further includes the use of the nucleic acid molecules and proteins provided herein as medicines. The invention additionally includes the use of the nucleic acid molecules and proteins provided herein in the manufacture of medicaments for protection against disease caused by strains of Moraxella.

Advantages of the present invention include:

an isolated and purified nucleic acid molecule encoding a lactoferrin receptor protein of a strain of Moraxella or a fragment or an analog of the lactoferrin receptor protein;

recombinantly-produced lactoferrin receptor proteins, including Lbp1, Lbp2 and ORF3 and fragments and analogs thereof free from each other and other Moraxella proteins;

open reading frame protein 3; and diagnostic kits and immunological reagents for specific identification of Moraxella.

BRIEF DESCRIPTION OF DRAWINGS

The present invention will be further understood from the following description with reference to the drawings, in which:

FIG. 1 shows partial sequence of the 2.2 kb PCR amplified fragments of the lbpA genes from *M. catarrhalis* 4223 or Q8, which were used to probe the phage libraries. In the figure, Tbp1 is the deduced 4223 Tbp1 sequence (as described in U.S. patent application Ser. No. 08/613,009 filed Mar. 8, 1996, assigned to the assignee hereof and the disclosure of which is incorporated herein by reference) (SEQ ID No: 19), Lbp1 is the deduced full-length 4223 Lbp1 sequence (SEQ ID No: 3) used here solely for aligning the PCR fragments, PCR4 is the 4223 PCR fragment (SEQ ID No: 20), and PCR5 is a partial sequence of the Q8 PCR fragment (SEQ ID No: 21). Only single strand sequence was obtained for the PCR fragments and "X" has been inserted where there was a doubtful sequence. Dashes have been used for maximum alignment. The underlined sequence in Lbp1 (MVQYTYRKGKENKAH—SEQ ID No: 22) represents the position of a CNBr peptide used to generate the 5'-PCR primer.

FIG. 2 shows the nucleotide (SEQ ID No: 1, full sequence; SEQ ID No: 2, Lbp2 coding sequence; SEQ ID No: 3, Lbp1 coding sequence, first methionine; SEQ ID No: 4, Lbp1 coding sequence, second methionine; SEQ ID No: 5, ORF3 coding sequence) and deduced amino acid sequences (SEQ ID No: 11, Lbp2; SEQ ID No: 12, Lbp1, first methionine; SEQ ID No: 13, Lbp1, second methionine; SEQ ID No: 14, ORF3) of the putative lfr locus from *M. catarrhalis* 4223. There are three tandem genes in the putative lfr locus identified as lbpB, lbpA and orf3. Potential promoter elements found upstream of the lbpB and lbpA genes are indicated by underlining.

FIG. 4 shows the nucleotide (SEQ ID No: 6, full sequence; SEQ ID No: 7, Lbp2 coding sequence; SEQ ID No: 8, Lbp1 coding sequence, first methionine; SEQ ID No: 9, Lbp2, second methionine; SEQ ID No: 10, ORF3 coding sequence) and deduced amino acid sequences (SEQ ID No: 15, Lbp2; SEQ ID No: 16, Lbp1, first methionine; SEQ ID No: 17, Lbp1, second methionine; SEQ ID No: 18, Lbp3) of the putative lfr locus from *M. catarrhalis* Q8. There are three tandem genes in the putative lfr locus identified as lbpB, lbpA and orf3. Potential promoter elements found upstream of the lbpB and lbpA genes are indicated by underlining.

FIG. 6 shows a comparison of the amino acid sequences of Lbp1 from *M. catarrhalis* strains 4223 (SEQ ID No: 12) and Q8 (SEQ ID No: 16), *N. meningitidis* strains BNCV (SEQ ID No: 23) and H44/76 (SEQ ID No: 75), and *N. gonorrhoeae* strain FA19 (SEQ ID No: 24). Dots indicate identical residues and dashes have been introduced to achieve maximum sequence alignment.

FIG. 7 shows a comparison of the amino acid sequences of Lbp2 from *M. catarrhalis* strains 4223 (SEQ ID No: 11), Q8 (SEQ ID No: 15) and VH19 (SEQ ID No: 70). "Also shown is the partial carboxy terminal sequence of Lbp2 from *N. meningitidis* strains BNCV (SEQ ID No: 76) and H44/76 (SEQ ID No: 77) and *N. gonorrhoease* strain FA19 (SEQ ID No: 78)." Dots indicate identical residues. The arrow indicates the lipidated cysteine of a potential mature Lbp2 lipoprotein. The residues conserved with Tbp2 proteins are underlined and the RGD sequence is italicized.

FIG. 8 shows a comparison of the amino acid sequences of Tbp2 (USPA No: 08/613,009) (SEQ ID No: 25) and Lbp2 from *M. catarrhalis* strain 4223 (SEQ ID No: 11). Dots indicate identical residues and dashes have been inserted to achieve maximum sequence alignment. The asterisks indicate conserved residues and the putative site of lipidation for both proteins is indicated by the arrow.

FIG. 9 shows a comparison of the amino acid sequences of ORF3 from *M. catarrhalis* strains 422 (SEQ ID No: 14) and Q8 (SEQ ID No: 18). Dots indicate identical residues and dashes have been introduced for maximum alignment.

FIG. 16 shows the nucleotide sequence (SEQ ID No: 69) of the *M. catarrhalis* strain VH19 lbpB gene and the deduced amino acid sequence (SEQ ID No: 70) of the corresponding Lbp2 protein.

GENERAL DESCRIPTION OF THE INVENTION

Figure 3A:
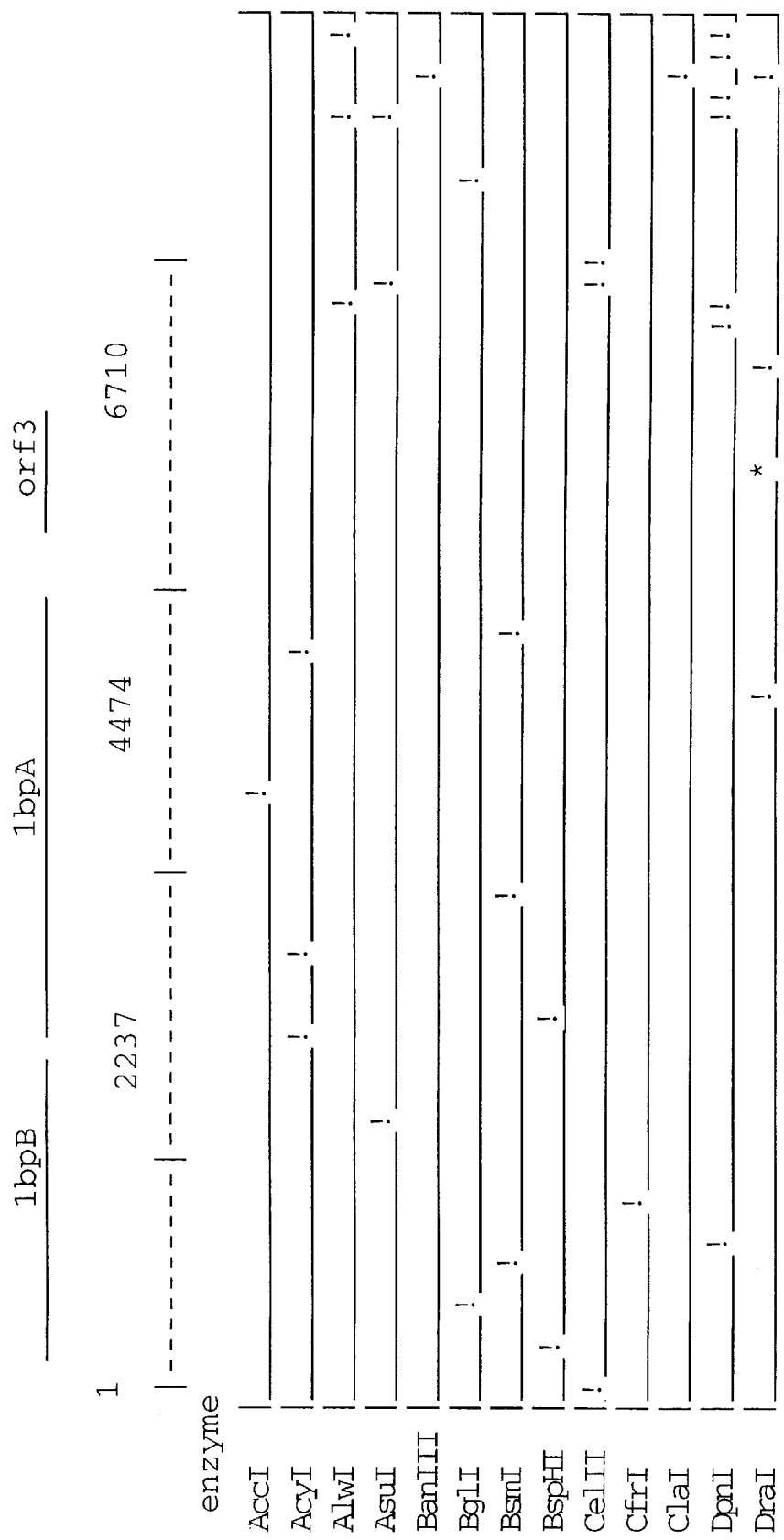
FIG. 3 shows a restriction map of clone pLD1-8 containing the lbpA, lbpB, and orf3 genes from *M. catarrhalis* isolate 4223.

Any Moraxella strain may be conveniently used to provide the purified and isolated nucleic acid, which may be in the form of DNA molecules, comprising at least a portion of the nucleic acid coding for a lactoferrin receptor as typified by embodiments of the present invention. Such strains are generally available from clinical sources and from bacterial culture collections, such as the American Type culture Collection.

In this application, the terms "lactoferrin receptor" (LfR) and "lactoferrin binding proteins" (Lbp) are used to define a family of Lbp1, Lbp2 and/or ORF3 proteins which includes those having variations in their amino acid sequences including those naturally occurring in various strains of, for example, Moraxella. The purified and isolated DNA molecules comprising at least a portion coding for lactoferrin receptor of the present invention also includes those encoding functional analogs of lactoferrin receptor proteins Lbp1, Lbp2 and/or Lbp3 of Moraxella. In this application, a first protein is an "analog" of a second protein if the first protein is immunologically related to and/or has the same function as the second protein. The analog may be, for example, a substitution, addition or deletion mutant thereof.

Lactoferrin receptor proteins were purified from *M. catarrhalis* membrane preparations by affinity chromatography on biotinylated human lactoferrin. Cyanogen bromide fragments were generated and amino acid sequence analysis of a 13 kDa fragment provided an internal Lbp1 sequence of MVQYTYRKGKENKAH (SEQ ID No: 22) underlined in FIG. 6. The C-terminus of *M. catarrhalis* Tbp1 (United States Patent Application No. 08/613,009), *N. meningitidis* Tbp1 (ref. 27) and *H. influenzae* Tbp1 (ref. 31) has a conserved LEMKF (SEQ ID No: 26) sequence. Oligonucleotide primers were generated based upon these two sequences and used to PCR amplify an approximately 2.2 kb fragment of the lbpA gene from *M. catarrhalis* strains 4223, Q8 and VH19. Partial sequence analysis demonstrated that the amplified genes were lbpA and not tbpA (see FIG. 1). The 2.2 kb PCR fragments were used to screen genomic libraries.

Chromosomal DNA from 4223, Q8 and VH19 was partially digested with Sau3A I and 15 to 2:3 kb fragments were purified before cloning into BamH I arms of the lambda vector EMBL3. The libraries were screened with the PCR fragment and positive clones were subjected to three rounds of plaque purification. Phage clone 4223LfR.17 containing an approximately 16 kb insert from 4223 and phage clone Q8LfR.13 containing an approximately 16 kb insert from Q8 were selected for further analysis.

Restriction enzyme and Southern blot analyses revealed that an internal Hind III fragment of approximately 9 kb contained at least a portion of the lbpA gene for both phage clones. The approximately 9 kb Hind III fragments were subcloned into pUC or pBluescript-based plasmids and sequenced. In each case, they contained the complete lbpA gene as well as an upstream gene identified as lbpB, and a downstream gene designated as orf3. The lbpB-lbpA gene arrangement is the same as present for Neisseria strains, but there has been no identification of a third gene for these organisms.

The gene arrangement is different than that observed for the *M. catarrhalis* tfr operon which was tbpA-orf-tbpB (United States Patent Application No. 08/613,009). There are promoter elements found upstream of both the lbpB and lbpA genes from strains 4223 and Q8. The third ORF is located immediately downstream of lbpA, separated by a single nucleotide.

By analogy with the *N. meningitidis* and *N. gonorrhoeae* transferrin receptor operons (ref. 26, 27, 28), the lactoferrin receptor operon was presurred to consist of two genes encoding lactoferrin binding proteins 1 and 2 (Lbp1 and Lbp2) (ref. 29). However, we report here that, for *M. catarrhalis*, there also appears to be a third gene located immediately downstream of lbpA encoding a potential lactoferrin binding protein 3 (ORF3).

The *M. catarrhalis* 4223 and Q8 lbpA genes encode proteins of molecular mass about 110 kDa and that are highly conserved with only seven residues difference between them. The N-terminal sequence of the native Lbp protein is unknown and there are two possible ATG start codons at positions 1 or 16. The first of these is adjacent to consensus sequences for promoter elements and the second is followed by a putative signal sequence. The exact peptide sequence used to design the PCR amplification primers was not found. When compared with other known Lbp1 sequences from *N. meningitidis* (refs. 31, 24) or *N. gonorrhoeae* (ref. 25) there is about 32% sequence identity and about. 50% sequence homology between the *M. catarrhalis* and the Neisseria proteins. There is some homology between the *M. catarrhalis* Lbp1 and Tbp1 proteins as shown in FIG. 1, but it is very scattered.

The *M. catarrhalis* 4223, Q8 and VH19 lbpB genes encode 898, 894 and 906 amino acid proteins, respectively. The *M. catarrhalis* Lbp2 proteins from strains 4223 and Q8 are 92% identical and 95% homologous while that from VH19 is 77% identical and 84% similar to the 4223 and Q8 Lbp2 proteins (FIG. 7). There is a consensus sequence for lipidation at the $Cys^{32}$ residue, suggesting that Lbp2 is a lipoprotein like Tbp2. There is little homology between the *M. catarrhalis* Lbp2 and Tbp2 proteins (FIG. 8) with the exception of a previously identified peptide sequence (LEGGFY (SEQ ID No: 27)) that is also found in *N. meningitidis* and *H. influenzae* Tbp2 (ref. 30).

The sequence of the proposed *M. catarrhalis* lfr-related downstream orf3 is conserved between strains 4223 and Q8. The encoded 4223 and Q8 ORF3 proteins when compared to the PIR and Swiss Prot protein databases were found to be previously unknown. The ORF3 protein may bind lactoferrin itself or may be an associated or regulatory protein for Lbp1 and/or Lbp2.

Expression vectors have been assembled from the lbpA and lbpB genes and recombinant Lbp1 and Lbp2 proteins isolated and purified, as described in detail in the Examples below.

Results shown in Table 1 below illustrate the ability of anti-Lbp1 guinea pig antiserum, produced by immunization with affinity purified Lbp1, to lyre *M. catarrhalis*. The results show that the antisera produced by immunization with Lbp1 protein isolated from *M. catarrhalis* isolate 4223 was bactericidal against a homologous non-clumping *M. catarrhalis* strain RH408 (a strain previously deposited in connection with United States Patent Application No. 08/328,589, assigned to the assignee hereof (WO 96/12733 published May 2, 1996)) derived from isolate 4223. In addition, antisera produced by immunization with Lbp1 protein isolated from *M. catarrhalis* 4223 were bactericidal against the heterologous non-clumping strain Q8. The results in Table 3 show that similarly-produced anti-Lbp2 guinea pig antiserum was bactericidal for the homologous strain and for three of five hetrologous strains. The ability of isolated and purified lactoferrin binding protein to generate bactericidal antibodies is in vivo evidence of utility of these proteins as vaccines to protect against disease caused by Moraxella.

Thus, in accordance with another aspect of the present invention, there is provided a vaccine against Moraxella comprising an immunogenically-effective amount of lactoferrin binding protein or fragment or analog thereof, or a nucleic acid molecule (DNA or RNA) encoding the lactoferrin binding protein or fragment or analog thereof, and a physiologically-acceptable carrier therefor. The lactoferrin binding protein or fragment or analog thereof provided herein may also be used as a carrier protein for haptens, polysaccharide or peptides to make conjugate vaccines against antigenic determinants unrelated to lactoferrin binding proteins.

In additional embodiments of the present invention, therefore, the lactoferrin binding protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial 842 pathogens may include, for example, *Haemophilus influenzae, Streptococcus pneumoniae, Escherichia coli, Neisseria meningitidis, Salmonella typhi, Streptococcus mutans, Cryptococcus neoformans, Klebsiella, Staphylococcus aureus* and *Pseudomonas aeruginosa*. Particular antigens which can be conjugated to lactoferrin binding protein and methods to achieve such conjugations are described in U.S. patent application No. 08/433,522 filed Nov. 23, 1993 (WO 94/12641), assigned to the assignee hereof and the disclosure of which is hereby incorporated by reference thereto.

In another embodiment, the carrier function of lactoferrin binding protein may be used, for example, to induce an immune response against abnormal polysaccharides of tumour cells, or to produce anti-tumour antibodies that can be conjugated to chemotherapeutic or bioactive agents.

The lactoferrin binding protein provided herein is useful as a diagnostic reagent, as an antigen or for the generation of anti-lactoferrin protein binding antibodies, antigen for vaccination against disease caused by species of Moraxella and for detecting infection by Moraxella and other such bacteria.

The invention extends to lactoferrin binding proteins or fragments or analogs thereof or nucleic acid molecules encoding the same from *Moraxella catarrhalis* for use as an active ingredient in a vaccine against disease caused by infection with Moraxella. The invention also extends to a pharmaceutical vaccinal composition containing lactoferrin binding proteins or fragments or analogs thereof or nucleic acid molecules encoding the same from *Moraxella catarrhalis* and optionally, a pharmaceutically acceptable carrier and/or diluent.

In a further aspect the invention provides the use of lactoferrin binding proteins or fragments or analogs thereof or nucleic acid molecules encoding the same for the preparation of a pharmaceutical vaccinal composition for immunization against disease caused by infection with Moraxella.

It is clearly apparent to one skilled in the art, that the various embodiments of the present invention have many applications in the fields of vaccination, diagnosis, treatment of, for example, Moraxella infections and the generation of immunological and other diagnostic reagents. A further non-limiting discussion of such uses is further presented below.

1. Vaccine Preparation and Use

Immunogenic compositions, suitable to be used as vaccines, may be prepared from immunogenic lactoferrin receptor proteins, analogs and fragments thereof encoded by the nucleic acid molecules as well as the nucleic acid molecules disclosed herein. The vaccine elicits an immune response which produces antibodies, including anti-lactoferrin receptor antibodies and antibodies that are opsonizing or bactericidal. Should the vaccinated subject be challenged by Moraxella, the antibodies bind to the lactoferrin receptor and thereby prevent access of the bacteria to an iron source which is required for viability. Furthermore, opsonizing or bactericidal anti-lactoferrin receptor antibodies may also provide protection by alternative mechanisms.

Immunogenic compositions, including vaccines, may be prepared as injectables, as liquid solutions or emulsions. The lactoferrin receptor proteins, analogs and fragments thereof and encoding nucleic acid molecules as well as the nucleic acid molecules described herein may be mixed with pharmaceutically acceptable excipients which are compatible with the lactoferrin receptor proteins, fragments, analogs or nucleic acid molecules. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants, to enhance the effectiveness of the vaccines. Immunogenic compositions and vaccines may be administered parenterally, by injection subcutaneously, intradermally or intramuscularly. Alternatively, the immunogenic compositions provided according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration, including suppositories and oral formulations, may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions may take the form of solutions, suspensions, tablets, pills, capsules, sustained release formulations or powders and contain about 1 to 95% of the lactoferrin receptor proteins, fragments, analogs and/or nucleic acid molecules.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and, if needed, to produce a cell-mediated immune response. Precise amounts of active ingredient required to be administered depend on the judgement of the practitioner. However, suitable dosage ranges are readily determinable by one skilled in the art and may be of the order of micrograms of the lactoferrin receptor proteins, analogs and fragments thereof and/or nucleic acid molecules. Suitable regimes for initial administration and booster doses are also variable, but may include an initial administration followed by subsequent administrations. The dosage of the vaccine may also depend on the route of administration and will vary according to the size of the host.

The nucleic acid molecules encoding the lactoferrin receptor of Moraxella may be used directly for immunization by administration of the DNA directly, for example, by injection for genetic immunization or by constructing a live vector, such as Salmonella, BCG, adenovirus, poxvirus, vaccinia or poliovirus containing the nucleic acid molecules. A discussion of some live vectors that have been used to carry heterologous antigens to the immune system is contained in, for example, O'Hagan (ref. 18). Processes for the direct injection of DNA into test subjects for genetic immunization are described in, for example, Ulmer et al. (ref. 19).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and an HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in Long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989, which is incorporated herein by reference thereto, teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 20) reported that N-glycolipid analogs displaying structural similarities to the naturally-occurring glycolipids, such as glycophospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, (ref. 21) reported that octadecyl esters of aromatic amino acids complexed with a recombinant hepatitis B surface antigen, enhanced the host immune responses against hepatitis B virus.

2. Immunoassays

The lactoferrin receptor proteins, analogs and/or fragments thereof of the present invention are useful as immunogens, as antigens in immunoassays including enzyme-linked immunosorbent assays (ELISA), RIAs and other non-enzyme linked antibody binding assays or procedures known in the art for the detection of anti-Moraxella, lactoferrin receptor protein antibodies. In ELISA assays, the lactoferrin receptor protein, analogs and/or fragments corresponding to portions of Lfr protein, are immobilized onto a selected surface, for example, a surface capable of binding proteins or peptides such as the wells of a polystyrene microtiter plate. After washing to remove incompletely adsorbed lactoferrin receptor, analogs and/or fragments, a non-specific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by non-specific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween or a borate buffer.

Following formation of specific immunocomplexes between the test sample and the bound lactoferrin receptor protein, analogs and/or fragments and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a spectrophotometer.

3. Use of Sequences as Hybridization Probes

The nucleotide sequences of the present invention, comprising the sequence of the lactoferrin receptor gene, now allow for the identification and cloning of the lactoferrin receptor genes from any species of Moraxella.

The nucleotide sequences comprising the sequence of the lactoferrin receptor genes of the present invention are useful for their ability to selectively form duplex molecules with complementary stretches of other lfr genes. Depending on the application, a variety of hybridization conditions may be employed to achieve varying degrees of selectivity of the probe toward the other lfr genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

Such hybridization conditions may be employed to determine DNA sequences which encode a functional lactoferrin receptor of Moraxella and which hybridize under stringent conditions to any one of the DNA sequences (a) or (b), described above.

In a clinical diagnostic embodiment, the nucleic acid sequences of the lfr genes of the present invention may be used in combination with an appropriate means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing lfr gene sequences.

The nucleic acid sequences of lfr genes of the present invention are useful as hybridization probes in is solution hybridizations and in embodiments employing solid-phase procedures. In embodiments involving solid-phase procedures, the test DNA (or RNA) from samples, such as clinical samples, including exudates, body fluids (e. g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the lfr genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Moraxella. The selected probe may be at least 18 bp and may be in the range of about 30 to 90 bp.

4. Expression of the Lactoferrin Receptor Genes

Plasmid vectors containing replicon and control sequences which are derived from species compatible with the host cell may be used for the expression of the lactoferrin receptor genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™–11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the lactoferrin receptor genes, fragments or analogs thereof, may include *E. coli*, Bacillus species, Haemophilus, fungi, yeast, Moraxella, Bordetella, or the baculovirus expression system may be used.

In accordance with this invention, it is preferred to produce the lactoferrin receptor protein, fragment or analog thereof, by recombinant methods, particularly since the naturally occurring LfR protein as purified from a culture of a species of Moraxella may include trace amounts of toxic materials or other contaminants. This problem can be avoided by using recombinantly produced LfR protein in heterologous systems which can be isolated from the host in a manner to minimize contaminants, including other proteins of the Moraxella strain, in the purified material. Particularly desirable hosts for expression in this regard include Gram positive bacteria which do not have LPS and are, therefore, endotoxin free. Such hosts include species of Bacillus and may be particularly useful for the production of non-pyrogenic lactoferrin receptor proteins, fragments or analogs thereof. Furthermore, recombinant methods of production permit the manufacture of Lbp1 or Lbp2 or ORF3 or respective analogs or fragments thereof, separate from one another which is distinct from the normal combined proteins present in Moraxella.

Sequence Alignment and Analysis

Sequence alignments were performed using the ALIGN (Trademark) or GENALIGN (Trademark) computer programs (Inteligenetics Suite 5.4, Oxford Molecular). ALIGN® uses the Needleman-Wunsch algorithm (ref. 35) and its later modifications to locate regions of similarity between two sequences. Finding regions of maximum similarity between two sequences can be solved in a rigorous manner using the iterative matrix calculation of the Needleman and Wunsch 1997 algorithm. The analysis is restricted to regions with no internal deletions or insertions, joined by a minimum number of loop-outs or deletions. Sellers (ref. 36) developed a true metric measure of the "distance" between sequences and Waterman (ref. 37) extended this algorithm to include insertions and deletions of arbitrary length. Smith (ref. 38) improved the early algorithms to find the subsequences of maximum similarity. The algorithm has been used to analyze sequences as long as 5000 bases by dividing these sequences into segments of 200 to 400 bases, and then reassembling them into a final best match. This method of dividing the sequence and then reassembling it has proven quite robust. The algorithm permits the size of the segment to be specified which the program searches for similarities. The program then assembles the segments after checking overlaps of adjacent subsequences. The weighting of deletions and the relative size of overlaps may be controlled. The program displays the results to show the differences in closely related sequences.

GENALIGN® is a multiple alignment program. Up to 99 sequences using the Martinez/Regions (ref. 39) or Needleman-Wunsch (ref. 35) method may be analyzed for alignment. GENALIGN places the sequences in an order that puts the most closely aligned sequence pairs adjacent to each other. A consensus sequence is displayed under the multiple sequence alignments. The sequences used in developing the consensus sequence file for use in other programs. GENALIGN allows the parameters of the search to be changed so that alternate alignments of the sequences can be formed.

These programs are used employing their default settings. The default settings are as follows:

| FastDB | |
|---|---|
| AMINO-Res-length | = 2 |
| DELetion-weight | = 5.00 |
| LEngth-factor | = 0 |
| Matching-weight | = 1.00 |
| NUCLEIC-Res-length | = 4 |
| SPread-factor | = 50 |
| Findseq | |
| Search Parameters: | |
| Similarity matrix | Unitary |
| K-tuple | 4 |
| Mismatch penalty | 1 |
| Joining Penalty | 30 |

-continued

| | |
|---|---|
| Randomization group length | 0 |
| Cutoff score | 5 |
| Alignment Parameters: | |
| Window size | 32 |
| Gap penalty | 1.00 |
| Gap size penalty | 0.33 |

Such procedures may be used to determine DNA sequences which encode a functional lactoferrin receptor of Moraxella and which may have at least about 90% sequence identity with any one of the DNA sequences (a) or (b), described above.

Biological Deposits

Certain vectors that contain at least a portion coding for a lactoferrin receptor protein from strains of Moraxella catarrhalis strain 4223 and Q8 and a strain of *M. catarrhalis* RH408 that are described and referred to herein have been deposited with the American Type Culture Collection (ATCC) located at 10801 University Boulevard, Manassas, Va., 20110-2209, USA, pursuant to the Methods of molecular genetics, protein biochemistry and immunology used but not explicitly described in this disclosure and these Examples are amply reported in the scientific literature and are well within the ability of those skilled in the art.

Example 1

This Example illustrates the generator of oligonucleotide primers for PCR amplification of *M. catarrhalis* lbpA.

Native Lbp1 was purified by affinity chromatography using high stringency conditions as described in U.S. patent application Ser. No. 08/552,232, assigned to the assignee hereof and the disclosure of which is incorporated herein by reference, and in ref. 40.

The purified Lbp1 protein was digested overnight with cyanogen bromide, then fragments separated by SDS PAGE and submitted to sequence analysis on an AB1 model 477A. A 13 kDa protein fragment was found to have the N-terminal sequence MVQYTYRKGKENKAH (SEQ ID No: 22). A degenerate oligonucleotide primer (4393.RD) was prepared based upon this sequence:

```
                                   (SEQ ID No: 28)
     Q   Y   T   R   K   G   E   N   K   A
5'                                           3'
```

```
                                              (SEQ ID No: 29)
CAA TAT ACI CGT AAA GGT GAA AAT AAA GC
                                              (SEQ ID No: 30)
CAA TAT ACI CGT AAA GGC GAA AAC AAA GC
                                              (SEQ ID No: 31)
CAA TAT ACI CGT AAA GGT GAA AAC AAA Gd
                                              (SEQ ID No: 32)
CAA TAT ACI CGT AAA GGC GAA AAT AAA GC
                                              (SEQ ID No: 33)
CAA TAT ACI CGC AAA GGC GAA AAC AAA GC
                                              (SEQ ID No: 34)
CAA TAT ACI CGC AAA GGC GAA AAT AAA GC
                                              (SEQ ID No: 35)
CAA TAT ACI CGC AAA GGT GAA AAT AAA GC
                                              (SEQ ID No: 36)
CAA TAT ACI CGC AAA GGT GAA AAC AAA GC
```

Budapest Treaty and prior to the filing of this application. Samples of the deposited vectors and bacterial strain will become available to the public and the restrictions imposed on access to the deposits will be removed upon grant of a patent based upon this United States patent application. In addition, the deposit will be replaced if viable samples cannot be dispensed by the Depository. The invention described and claimed herein is not to be limited in scope by the biological materials deposited, since the deposited embodiment is intended only as an illustration of the invention. Any equivalent or similar vectors or strains that encode similar or equivalent antigens as described in this application are within the scope of the invention.

Deposit Summary

| Deposit | ATCC Designation | Date deposited |
|---|---|---|
| Plasmid pLD1-8 | 97,997 | April 23, 1997 |
| Plasmid pLDW1 | 97,998 | April 23, 1997 |
| Strain RH408 | 55,637 | Dec. 9, 1994 |

EXAMPLE

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. The $Y^6$ and $K^{10}$ residues were omitted from the sequence analysis report for the N-terminal sequence and the oligonucleotides used to PCR amplify the 2.2 kb fragment were incorrect, but nevertheless were successful.

There is a conserved C-terminal pentapeptide found in all known Lbp1 and Tbp1 protein sequences: LEMKF (SEQ ID No. 26). An oligonucleotide primer (4572.RD) was prepared based upon the complementary DNA sequence encoding this pentapeptide:

```
     L    E    M    K    F    *
                                              (SEQ ID No: 37)
5'  CTT  GAA  ATG  AAG  TTT  TAA  3'
                                              (SEQ ID No: 38)
3'  GAA  CTT  TAC  TTC  AAA  ATT  5'  4572.RD
```

Example 2

This Example illustrates the preparation of chromosomal DNA from *M. catarrhalis* strains 4223 and Q8.

*M. catarrhalis* isolate 4223 was inoculated into 100 ml of BHI broth, and incubated for 18 hr at 37° C. with shaking. The cells were harvested by centrifugation at 10,000×g for 20 min. The pellet was used for extraction of *M. catarrhalis* 4223 chromosomal DNA.

The cell pellet was resuspended in 20 ml of 1.0 MM Tris-HCl (pH 7.5)–1.0 mM EDTA (TE). Pronase and SDS were added to final concentrations of 500 µg/ml and 1.0%, respectively, and the suspension was incubated at 37° C. for 2 hr. After several sequential extractions with phenol, phenol:chloroform (1:1), and chloroform:isoamyl alcohol (24:1), the aqueous extract was dialysed, at 4° C., against 1.0 M NaCl for 4 hr, and against TE (pH 7.5) for a further 48 hr with three buffer changes. Two volumes of ethanol were added to the dialysate, and the DNA was spooled onto a glass rod. The DNA was allowed to air-dry, and was dissolved in 3.0 ml of water. Concentration was estimated, by UV spectrophotometry, to be about 290 µg/ml.

*M. catarrhalis* strain Q8 was grown in BHI broth. Cells were pelleted from 50 ml of culture by centrifugation at 5000 rpm for 20 minutes, at 4° C. The cell pellet was resuspended in 10 ml of TE (10 mM Tris-HC1, 1 mM EDTA, pH 7.5) and proteinase K and SDS were added to final concentrations of 500 µg/ml and 1%, respectively. The sample was incubated at 37° C. for 4 hours until a clear lysate was obtained. The lysate was extracted twice with Tris-saturated phenol/chloroform (1:1), and twice with chloroform. The final aqueous phase was dialysed for 24 hours against 2×1000 ml of 1 M NaCl at 4° C., changing the buffer once, and for 24 hours against 2×1000 ml of TE at 4°, changing the buffer once. The final dialysate was precipitated with two volume of 100% ethanol. The DNA was spooled, dried and resuspended in 5 to 10 ml of TE buffer.

Example 3

This Example illustrates the PCR amplification of a fragment of *M. catarrhalis* lbpA and the generation of probes for screening libraries.

PCR amplification was performed on chromosomaL DNA isolated in Example 2 using primers 4393.RD and 4572.RD under the following cycling conditions: 25 cycles of 94° C. for 1 min, 47° C. for 30 sec and 72° C. for 1 min. PCR4 is the amplification of the 4223 lbpA fragment and PCR5 is the amplification of the Q8 lbpA fragment. A specific band of about 2.2 kb was amplified and partial sequence analysis was performed to ensure that the gene product was related to lbpA and was not tbpA. The derived amino acid sequences are shown in FIG. 1 and have been aligned with the complete 4223 Lbp1 sequence to show their placement and the 4223 Tbp1 sequence (USAN 08/613,009) to indicate their uniqueness.

The full-length 2.2 kb gene fragment was randomly labeled with $^{32}$P and used to probe genomic libraries.

Example 4

This Example illustrates the generation and screening of the EMBL 3 libraries.

Chromosomal DNA was prepared as described in Example 2. A series of Sau3AI restriction digests of chromosomal DNA, in final volumes of 10 µL each, were carried out in order to optimize the conditions necessary to generate maximal amounts of restriction fragments within a 15 to 23 kb size range. Using the optimized digestion conditions, a large-scale digestion was set up in a 100 µL volume, containing the following: 50 µL of chromosomal DNA (290 µg/ml), 33 µL water, 10 µL 10×Sau3A buffer (New England Biolabs), 1.0 µL BSA (10 mg/ml, New England Biolabs), and 6.3 µL Sau3A (0.04 U/µL). Following a 15 min. incubation at 37° C., the digestion was terminated by the addition of 10 µL of 100 mM Tris-HCl (pH 8.0)–10 mM EDTA-0.1% bromophenol blue-50% glycerol (loading buffer). Digested DNA was electrophoresed through a 0.5% agarose gel in 40 mM Tris acetate-2 mM $Na_2EDTA.2H_2O$ (pH 8.5)(TAE buffer) at 50 V for 6 hr. The region containing restriction fragments within a 15 to 23 kb molecular size range was excised from the gel, and placed into dialysis tubing containing 3.0 ml of TAE buffer. DNA was electroeluted from the gel fragment by applying a field strength of 1.0 V/cm for 18 hr. Electroeluted DNA was extracted once each with phenol and phenol:chloroform (1:1), and precipitated with ethanol. The dried DNA was dissolved in 5.0 µL water.

Size-fractionated chromosomal DNA was ligated with BamHI-digested EMBL3 arms (Promega), using T4 DNA ligase in a final volume of 9 µL. The entire ligation mixture was packaged into lambda phage using a commercial packaging kit (Amersham), following manufacturer's instructions.

The packaged DNA library was amplified on solid media. 0.1 ml aliquots of *Escherichia coli* strain NM539 in 10 mM $MgSO_4$ ($OD_{260}$ =0.5) were incubated at 37° C. for 15 min. with 15 to 25 µL of the packaged DNA library. Samples were mixed with 3 ml of 0.6% agarose containing 1.0% BBL trypticase peptone-0.5% NaCl (BBL top agarose), and mixtures were plated onto 1.5% agar plates containing 1.0% BBL trypticase peptone-0.5% NaCl, and incubated at 37° C. for 18 hr. 3 ml quantities of 50 mM Tris-HCl (pH 7.5)–4 8 mM magnesium sulfate heptahydrate-100 mM NaCl-0.01% (w/v) gelatin (SM buffer) were added to each plate, and plates were left at 4° C. for 7 hr. SM buffer containing phage was collected from the plates, pooled together, and stored in a screwcap tube at 4° C., with chloroform.

Ten µL aliquots of phage stock were combined each with 100 µL of *E. coli* strain LE392 in 10 mM MgSO4 ($OD_{260}$= 0.5) (plating cells), and incubated at 37° C. for 15 min. The samples were mixed with 3 ml each of BBL top agarose, and the mixtures were poured onto 1.5% agarose plates containing 1% bacto tryptone-0.5% bacto yeast extract-0.05% NaCl (LB agarose; Difco) and supplemented with 200 µM EDDA. The plates were incubated at 37° C. for 18 hr. Plaques were lifted onto nitrocellulose filters (Amersham Hybond-C Extra) which were hybridized with the 32P-labelled 2.2 kb PCR fragment. Several putative phage clones were obtained from each library and clones 4223LfR.17 and Q8LfR.13 were chosen for further analysis.

Example 5

This Example illustrates the subcloning of the phage clones containing *M. catarrhalis* lfr genes.

Restriction enzyme analysis and Southern blotting using the screening probes, indicated that at least a portion of lbpA was localized to an about 9 kb Hind III fragment from each phage clone. The about 9 kb Hind III fragment from 4223LfR.17 was subcloned into pUC 18, generating clone pLD1-8. The about 9 kb Hind III fragment from Q8LfR.13 was subcloned into pBluescript, generating plasmid pLDW1. Internal about 5.5 kb EcoR V fragments were subcloned generating plasmids pLD3 and pLDW3 for the 4223 and Q8 genes, respectively.

Example 6

This Example illustrates the sequence analysis of clones containing the *M. catarrhalis* lfr genes from strains 4223 and Q8 .

Figure 3B:
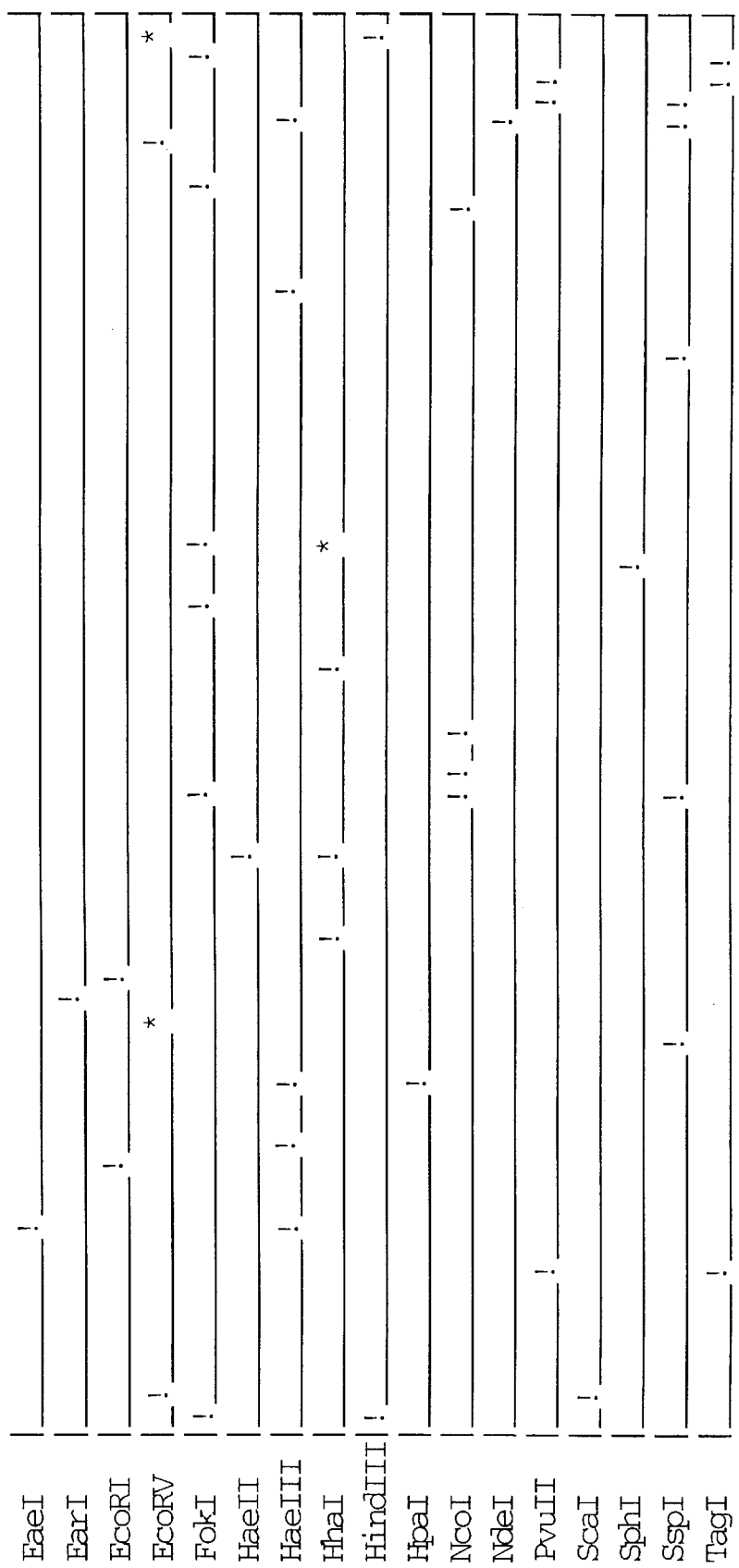
Figure 5A:
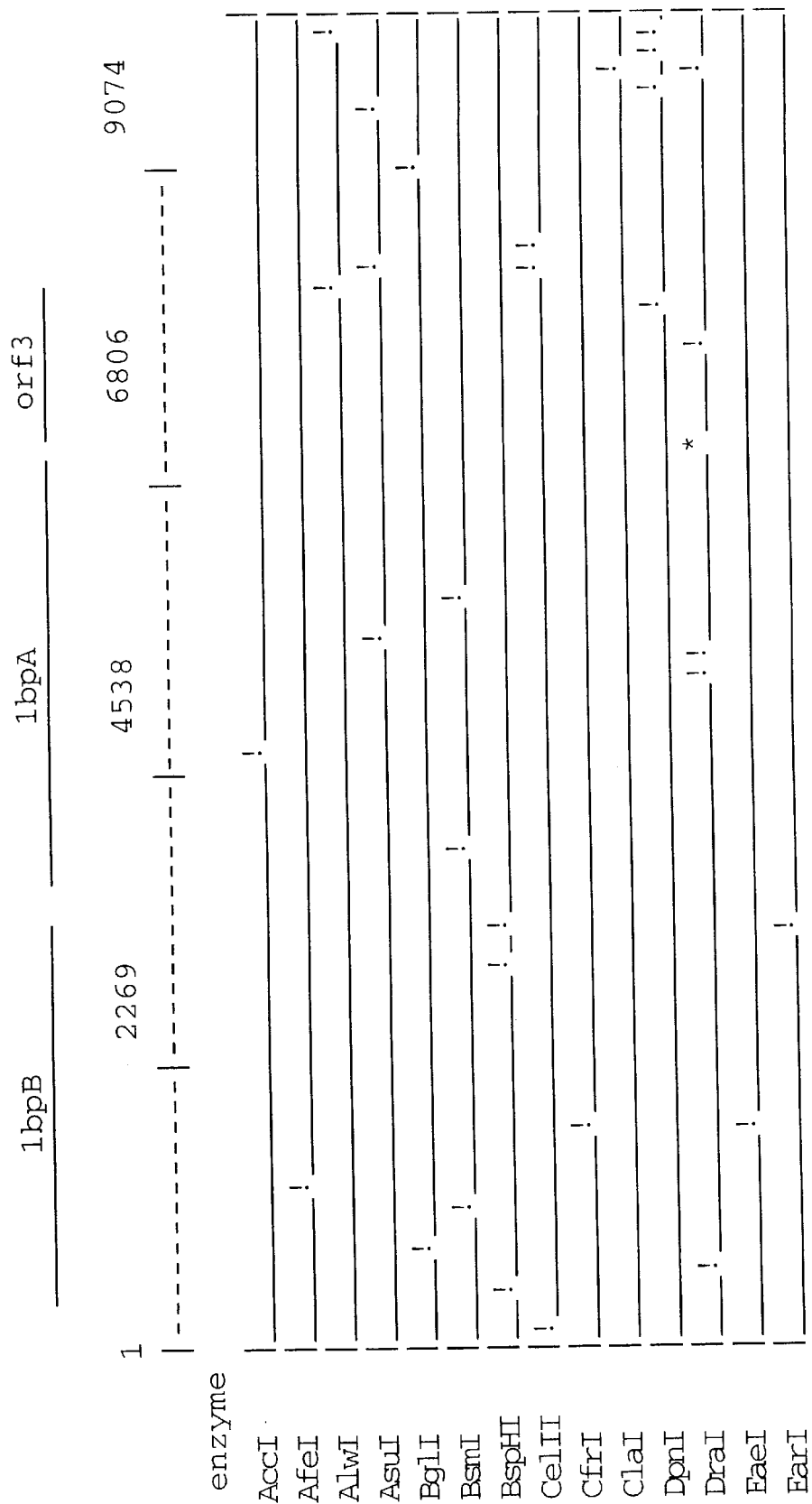
FIG. 5 shows a restriction map of clone pLDW1 containing the lbpA, lbpB and orf3 genes from *M. catarrhalis* isolate Q8.
Figure 5B:
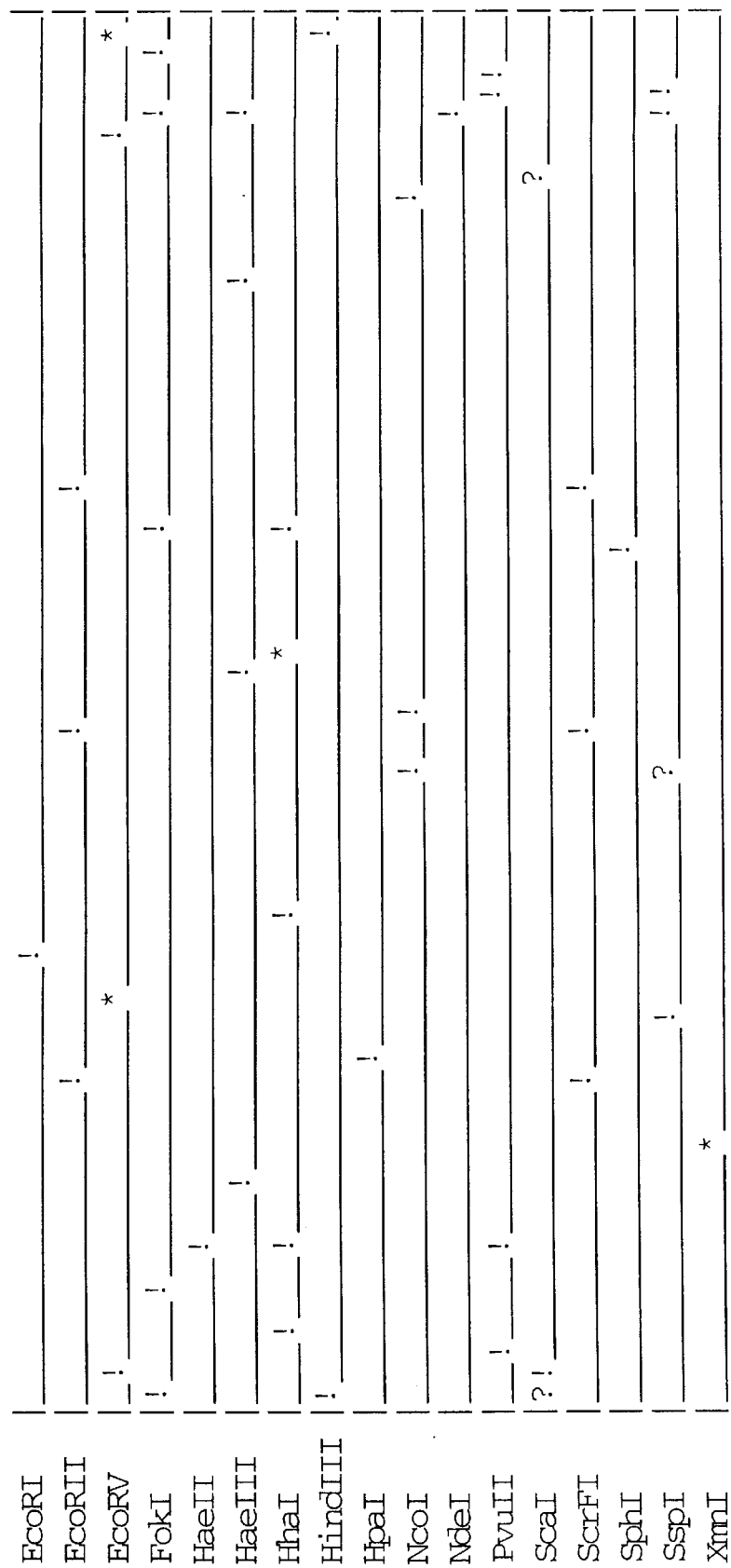

Sequence analysis of the 5.5 kb EcoR V fragments from pLD3 and pLDW3, revealed that they each contained the 3'-end of lbpB, the complete lbpA gene, and a third complete gene designated orf3. The remainder of the lbpB genes was found on the about 9 kb Hind III fragments from pLD1-8 and pLDW1. Partial restriction enzyme analysis of the 4223 lbpA, lbpB, and orf3 genes, based upon the nucleotide sequences is shown in FIG. 3. Partial restriction enzyme analysis of the Q8 lbpA, lbpB, and orf3 genes, based upon the nucleotide sequences is shown in FIG. 5. The complete sequences of the lbpB, lbpA, and orf3 genes comprising the putative lfr locus from *M. catarrhalis* 4223 and Q8 is shown in FIGS. 2 and 4, respectively. The intergenic distance between the lbpB and lbpA genes is 184 nucleotides, while a single nucleotide separates the lbpA and orf3 genes. A putative promoter and ribosome binding site is indicated by underlining upstream of both lbpb and lbpA. A fourth potential gene was cloned on the approximately 9 kb Hind III fragments.

The N-terminal sequence of the native Lbp1 protein is unknown. Examination of the deduced amino acid sequence of the lbpA gene indicates that there are two possible ATG start codons at positions 1 and 16. The first position is downstream of strong promoter elements found in the lbpB-lbpA intergenic region and the second position is followed by a putative signal sequence. The *M. catarrhalis* 4223 and Q8 Lbp1 proteins (from the first ATG) have molecular mass value3 of about 110 kDa and are 99% identical. The deduced Lbp1 protein sequences from *M. catarrhalis* strains 4223 and Q8 are compared in FIG. 6. They are also compared with the iroA/lbpA gene from *N. meningitidis* strain BNCV (ref. 24) and the lbpA gene from *N. gonorrhoeae* strain FA19 (ref. 25). The *M. catarrhalis* proteins are found to be about 32% identical and about 50% similar to the Neisseria proteins. As shown in FIG. 1, there is very limited sequence homology between the *M. catarrhalis* Tbp1 and Lbp1 sequences.

The deduced Lbp2 protein sequences from *M. catarrhalis* strains 4223 and Q8 are compared in FIG. 7. The 4223 and Q8 Lbp2 proteins both have molecular masses of about 99 kDa and are 92% identical and 95% similar to each other. A comparison to the *M. catarrhalis* Tbp2 proteins shows very little homology except the LEGGFY (SEQ ID No: 27) epitope previously identified in *H. influenzae* and *N. men-*

*ingitidis* Tbp2 proteins (FIG. 8). A cysteine residue at position 32 is preceded by a consensus sequence for lipoproteins suggesting that Lbp2, like Tbp2, is a lipoprotein. An unusual feature of the Lbp2 proteins is the high combined aspartic acid and asparagine content which is nearly 20%. In addition, the 4223 Lbp2 amino acid composition from residues 698 to 751 is about 52% aspartic acid.

The 4223 and Q8 lfr orf3 genes would encode proteins of molecular mass about 60 kDa, respectively. A notable feature of the ORF3 protein is a potential signal sequence, a terminal phenylalanine which is often associated with membrane anchored proteins, an internal repeat sequence of DGLG (SEQ ID No: 39), and a high leucine content of 15%. The deduced Lbp3 protein sequences are compared in FIG. 9. These proteins are 98% identical and 99% similar.

Example 7

This Example illustrates the construction of vectors to express *M. catarrhalis* Lbp1 from the first methionine in *E. coli*.

Figure 10:
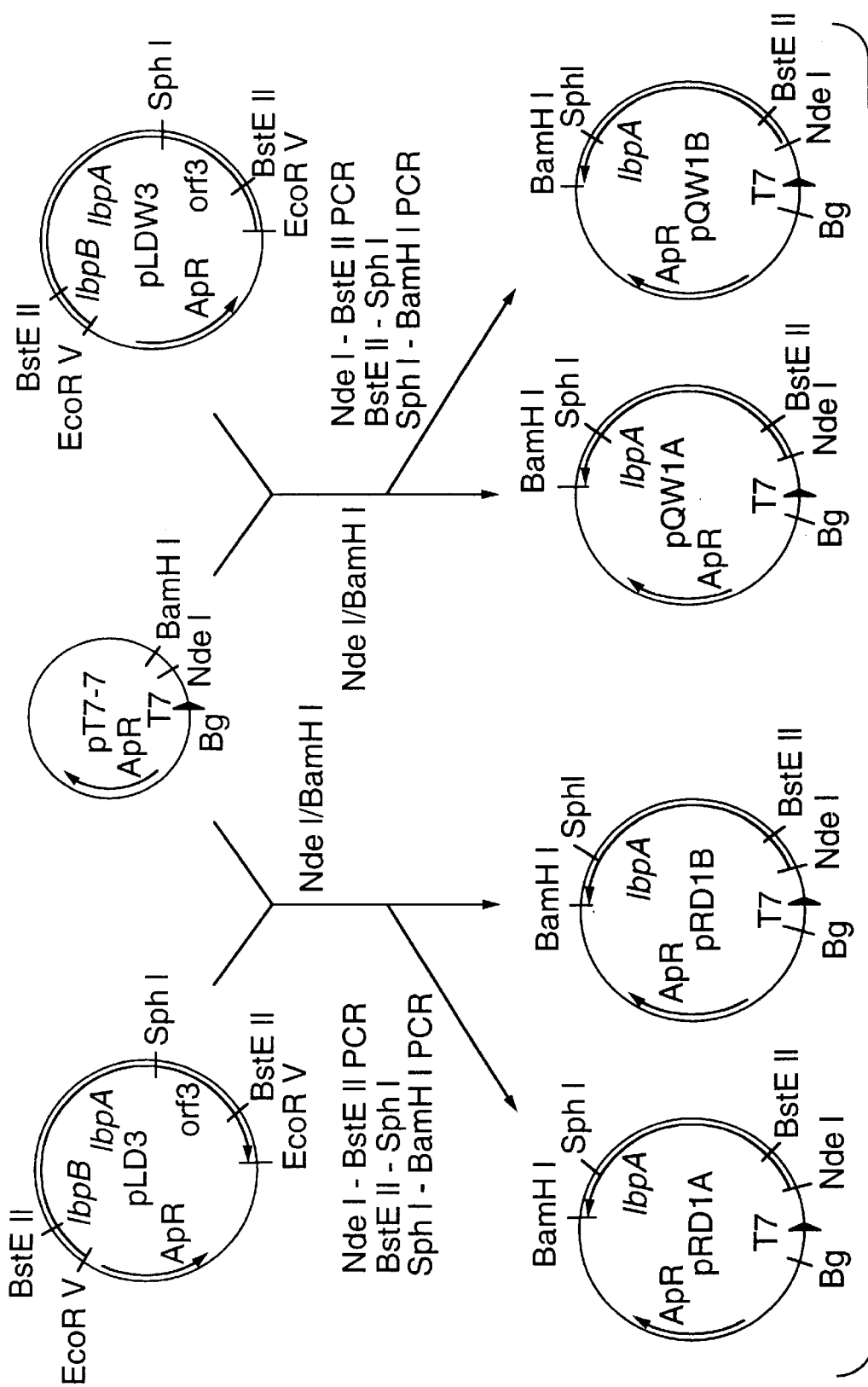
FIG. 10 shows the construction of plasmids for expression of recombinant Lbp1 protein from *E. coli*. Plasmids pRD1A and pRD1B express 4223 Lbp1 from the first or second methionine residues, respectively. Plasmids pQW1A and pQW1B express Q8 Lbp1 from the first or second methionine residues, respectively.

There are two possible start codons at the beginning of the lbpA gene and hence two expression constructs were made. The construction scheme for 4223 or Q8 lbpA expressed from the first methionine is shown in FIG. 10. An approximately 200 bp fragment of the 5'-end of lbpA from the ATG to a BstE II site was PCR amplified using primers 5405.RD and 5407.RD. An Nde I site was engineered at the 5'-end to facilitate cloning into the pT7-7 vector.

```
NdeI
              M    S    K    S    I    T              (SEQ ID No: 40)

5'   GGAATTCCAT ATG  TCA  AAA  TCT  ATC  ACA  AA 3'  5405.RD    (SEQ ID No: 41)

BstE II

L    D    A    I    T    V    T    A    A         (SEQ ID No: 42)

5'   T  TTA  GAT  GCC  ATC  ACGGTA ACC  GCC  GCC  CC 3'         (SEQ ID No: 43)

3'   A  AAT  CTA  CGG  TAG  TGC  CAT  TGG  CGG  CGG  GG 5'  5407.RD  (SEQ ID No: 44)
```

In order to subclone the lbpA gene into pT7-7, a approximately 515 bp fragment of the 3'-end of the gene from an Sph I site to the stop codon was PCR amplified using primers 5281.RD and 5282.RD and a EamH1 site was engineered at 3'-end.

```
                              Sph I
         G    K    L    D    L    H    A    M    T    S         (SEQ ID No: 45)

5'   GGC  AAA  CTG  GAT  TTG CAT GCC  ATG  ACA  TCA    3'  5281.RD  (SEQ ID No: 46)

S    L    E    M    K    F    *                        (SEQ ID No: 47)

5'   AGT  CTT  GAA  ATG  AAG  TTT  TAA              3'          (SEQ ID No: 48)

3'   TCA  GAA  CTT  TAC  TTC  AAA  ATT  GCC CTA GGG C 5'  5282.RD  (SEQ ID No: 49)
                                          BamH I
```

Figure 11A:
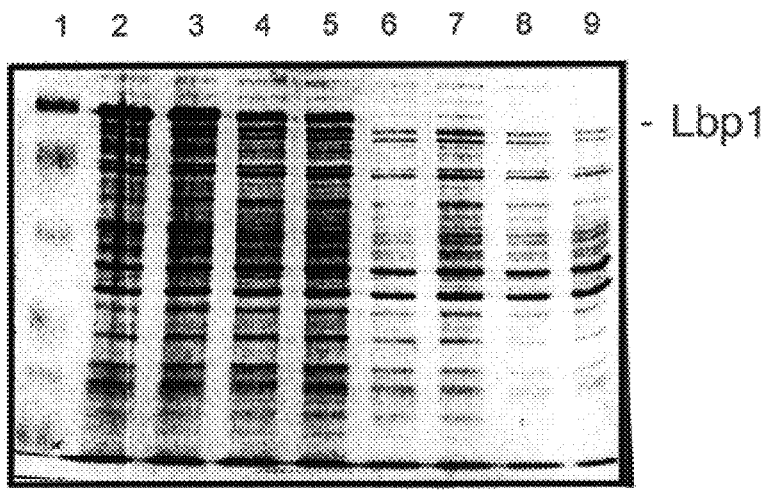
FIG. 11, comprising panels A and B, shows the expression of recombinant Lbp1 (rLbp1) proteins from *E. coli*. Panel A shows the expression of the QE8 Lbp1 proteins and panel B shows the expression of the 4223 Lbp1 proteins. Lane 1, molecular weight marker. Lanes 2 and 3 demonstrate the induced expression of the longer Lbp1 starting from the first methionine residues and lanes 4 and 5 illustrate the expression of the shorter Lbp1 proteins starting from the second methionine residues. Lanes 6, 7, 8 and 9 are uninduced samples.
Figure 11B:
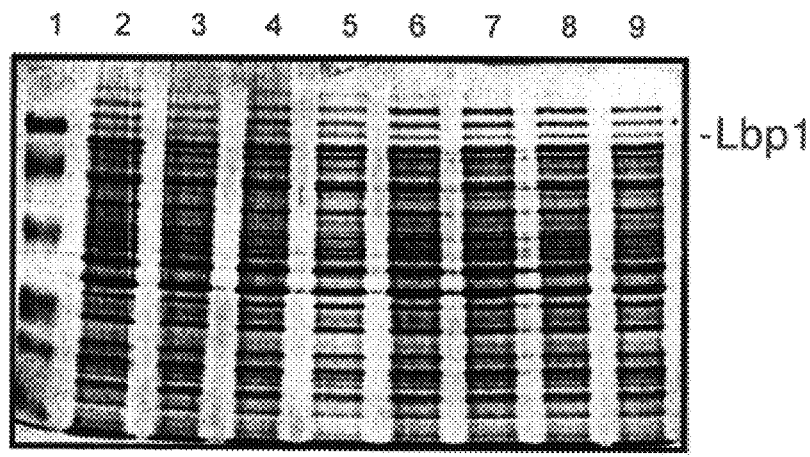

For the Q8 subclone, plasmid pLDW3, prepared as described in Example 5, was digested with BstE II and Sph I generating a 2.3kb fragment of lbpA which was ligated with the Nde I-BstE II and SphI-BamH I PCR fragments and cloned into pT7-7 digested with NdeI and BamH I. The resulting plasmid pQW1A thus contains the full-length Q8 lbpA gene from the first methionine, under the control of the T7 promoter. DNA from pQW1A was purified and transformed by electroporation into electrocompetent BL21 (DE3) cells to generate strain QW1A which was grown and induced using IPTG. Expressed proteins were resolved by SDS-PAGE and the induced Lbp1 protein was visualized by Coomassie blue staining (FIG. 11).

Figure 15:
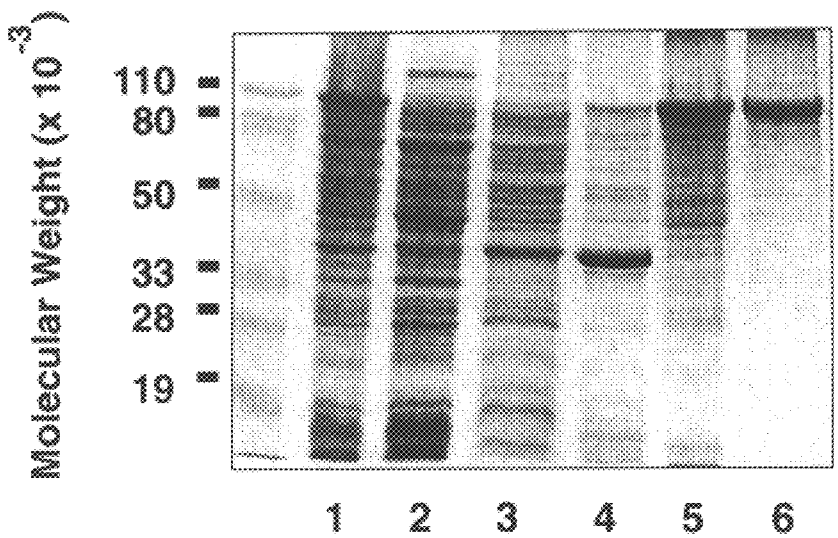
FIG. 15 shows an SDS PAGE gel of the purification of Q8 Lbp1 from *E. coli*. Lane 1, BL21(DE3) lysate; lane 2, soluble proteins after 50 mM Tris/5 mM AEBSF/0.5 M NaCl, pH 8.0 extraction; lane 3, soluble proteins after 50 mM Tris/0.5% Triton X-100/10 mM EDTA, pH 8.0 extraction; lane 4, soluble proteins after 50 mM Tris-HCl/1% octylglucoside, pH 8.0 extraction; lane 5, solubilized inclusion bodies; lane 6, purified Lbp1.

For the 4223 subclone, plasmid pLD3, prepared as described in Example 5 was digested with BstEII and SphI, generating a 2.3 kb fragment of lbpA, which was ligated with the Nde I-BstE II and SphI-BamH I PCR fragments and cloned into pT7-7 digested with NdeI and BamH I. The resulting plasmid pRD1A thus contains the full-length 4223 lbpA gene from the first possible methionine under the control of the T7 promoter. DNA from pRD1A was purified and transformed by electroporation into electrocompetent BL21(DE3) cells to generate strain RD1A which was grown and induced using IPTG. Expressed proteins were resolved was further purified on a Superdex 200 gel filtration column equilibrated in 50 mM Tris-HCl, pH 8.0, containing 2 M guanidine and 5 mM DTT. The fractions were analysed by SDS-PAGE and those containing purified rLbp1 were pooled. Triton X-100 was added to the pooled rLbp1 fraction to a final concentration of 0.1%. The fraction was dialysed overnight at 4° C. against PBS, and then centrifuged at 20,000×g for 30 min. The purified rLbp1 was stored at −20° C. Samples from the purification were analyzed by SDS-PAGE (FIG. 15).

Example 9

This Example illustrates the construction of vectors to express *M. catarrhalis* Lbp1 from the second methionine in *E. coli*.

The construction scheme for 4223 or Q8 lbpA expressed from the second methionine is shown in FIG. 10. An approximately 200 bp fragment of the 5'-end of lbpA from the ATG to a BstE II site was PCR amplified using primers 5406.RD and 5407.RD. An Nde I site was engineered at the 5'-end to facilitate cloning into the pT7-7 vector.

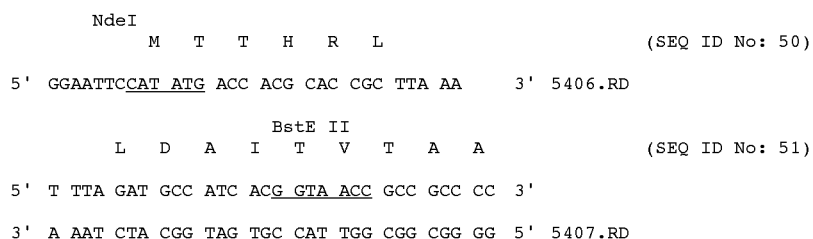

by SDS-PAGE and the induced Lbp1 protein was visualized by Coomassie blue staining (FIG. 11).

The Q8 Lbp1 protein was expressed at very high levels but the 4223 Lbp1 protein was expressed at substantially lower levels.

Example 8

Figure 14:
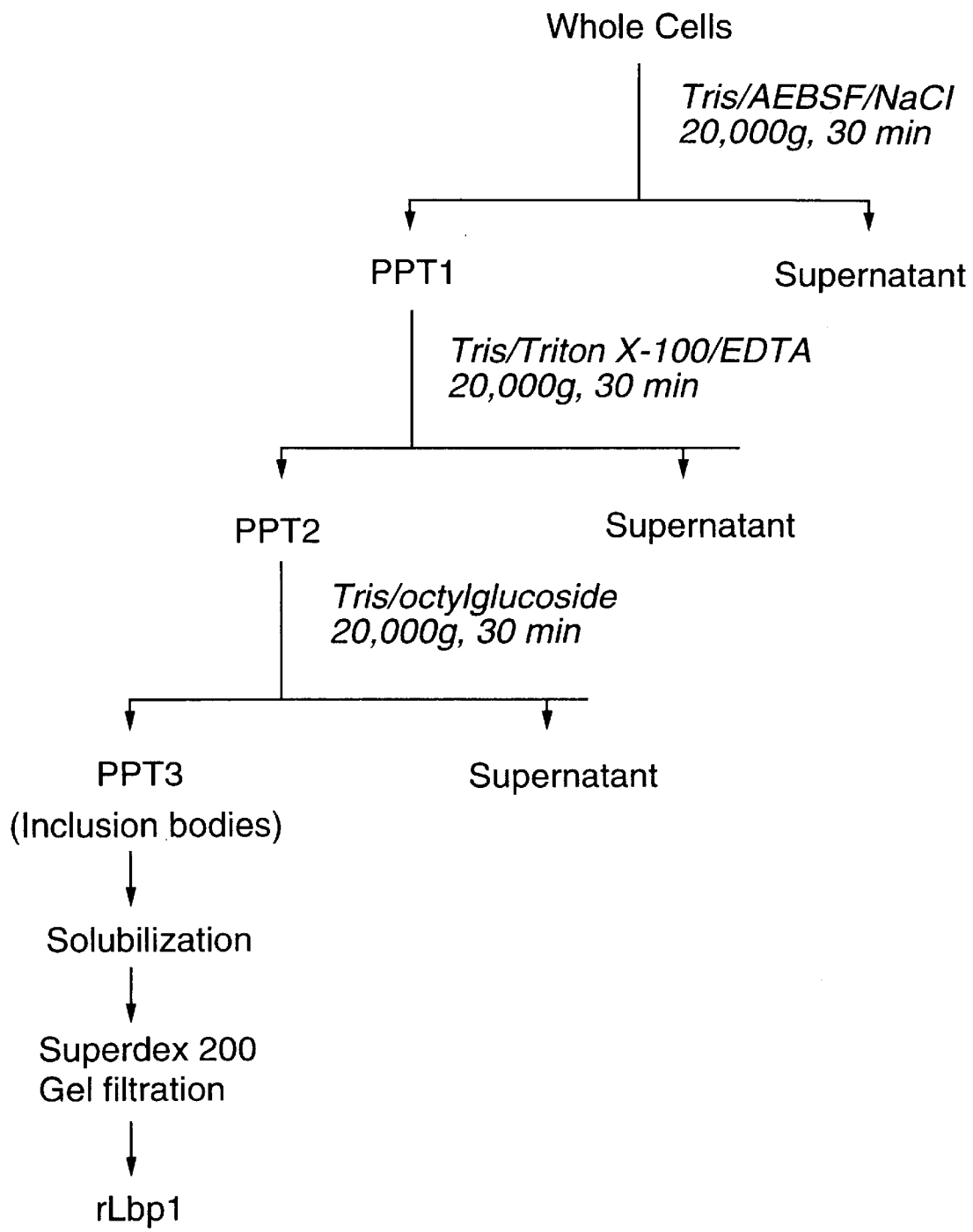
FIG. 14 shows a purification scheme for rLbp1 expressed from *E. coli*.

This Example illustrates the extraction and purification of rLbp1 from *E. coli*. The procedure is illustrated generally in FIG. 14.

*E. coli* cells from a 500 ml culture, prepared as described in Example 7, were resuspended in 40 ml of 50 mM Tris-HCl, pH 8.0 containing 5 mM AEBSF (protease inhibitor) and 0.1 M NaCl, and disrupted by sonication (3×10 min, 70% duty circle). The extract was centrifuged at 20,000×g for 30 min and the resultant supernatant, which contained greater than 95% of the soluble proteins from *E. coli*, was discarded. The remaining pellet (FIG. 14, PPT1) was further extracted in 40 ml of 50 mM Tris, pH 8.0 containing 0.5% Triton X-100 and 10 mM EDTA. The mixture was stirred at 4° C. for at least 1 hour and then centrifuged at 20,000×g for 30 min and the supernatant containing residual soluble proteins and the majority of the membrane proteins was discarded. The resultant pellet (FIG. 14, PPT2) was further extracted in 40 ml of 50 mM Tris, pH 8.0 containing 1% octylglucoside. The mixture was stirred at 4° C. for at least 1 hour and then centrifuged at 20,000×g for 30 min. The supernatant containing residual contaminating proteins was discarded. The resultant pellet (FIG. 14, PPT3) obtained after the above extractions contained the Lbp1 protein as inclusion bodies.

The rLbp1 protein was solubilized from the inclusion bodies in 50 mM Tris, pH 8.0, containing 6 M guanidine and 5 mM DTT. After centrifugation, the resultant supernatant The 3'-end of the lbpA gene was PCR amplified from the SphI restriction site to the stop codon using primers 5281.RD and 5282.RD as described in Example 8. The 2.3 kb BstE II-Sph I fragments described in Example 8 were ligated to the Nde I-BstE II and Sph I-BamH I PCR fragments and cloned into pT7-7 that had been digested with NdeI and BamH I. Plasmid pQW1B thus contains a full-length Q8 lbpA gene from the second methionine and plasmid pRD1B contains a full-length 4223 lbpA gene from the second methionine under the direction of the T7 promoter. DNA was purified and transformed by electroporation into electrocompetent BL21(DE3) cells to generate recombinant strains which were grown and induced using IPTG. Expressed proteins were resolved by SDS-PAGE and the induced Lbp1 proteins were visible by Coomassie blue staining (FIG. 11).

As seen for the longer protein in Example 8, the shorter Lbp1 from Q8 was expressed to much higher levels than the corresponding 4223 protein.

Example 10

This Example illustrates the construction of vectors to express *M. catarrhalis* Lbp2 with a leader sequence from *E. coli*.

Figure 12:
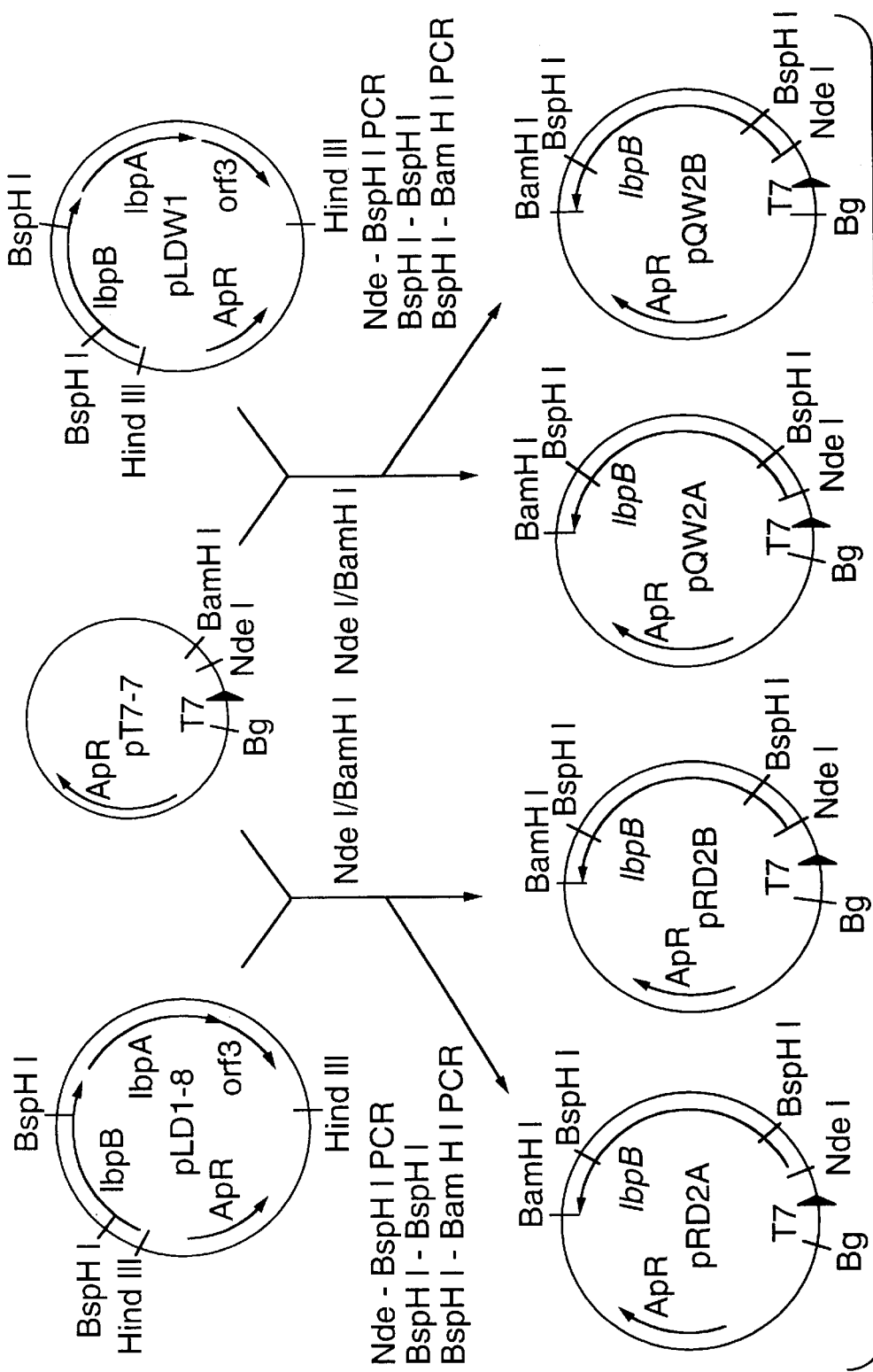
FIG. 12 shows the construction of plasmids for expression of recombinant Lbp2 (rLbp2) protein from *E. coli*. Plasmids pRD2A and pRD2B express 4223 Lbp2 with or without the native leader sequence, respectively. Plasmids pQW2A and pQW2B express Q8 Lbp2 with or without the native leader sequence, respectively.

The construction scheme is illustrated in FIG. 12. There are two BspH I sites within the lbpB genes of strains 4223 and Q8. The 5'-end of the lbpB gene was PCR amplified from the ATG start codon through the first BspH I site generating an approximately 201 bp fragment. An NdeI site was engineered at the ATG to facilitate cloning into the pT7-7 expression vector. The oligonucleotides used for amplification are illustrated below:

```
         NdeI
              M    S    T    V    K    T    P    H              (SEQ ID No: 52)

5' GGAATTCCAT ATG AGT ACT GTC AAA ACC CCC CAC A 3'  5533.RD     (SEQ ID No: 53)

BSpH I

I    P    N    T    G    H    D    N    T    N        (SEQ ID No: 54)

5'       A ATA CCG AAC ACA GGT CAT GAC AAC ACC AAT 3'           (SEQ ID No: 55)

T TAT GGC TTG TGT CCA GTA CTG TTG TGG TTA 5'  5534.RD  (SEQ ID No: 56)
```

The 3'-end of the lbpB gene was PCR amplified from the second BspH I site to the TAA stop codon generating a 381 bp fragment. A BamH I site was introduced after the stop codon for cloning purposes. The oligonucleotides used for amplification are illustrated below:

the lbpB gene, a sense PCR primer is designed that includes an NdeI site for subsequent cloning and an ATG start codon for initiation of translation followed immediately by the Cys$^{32}$ residue. The antisense primer is the same as that described in Example 9 (5534.RD) and includes the BspH I

```
      N    E    P    T    H    E    K    T    F    A            (SEQ ID No: 57)

5' AAT GAG CCT ACT CAT GAA AAA ACC TTT GCC 3'         5535.RD   (SEQ ID No: 58)

G    A    V    F    G    A    V    K    D    K    *          (SEQ ID No: 59)

5' GG GCT GTC TTT GGG GCT GTT AAA GAT AAA TAA 3'                (SEQ ID No: 60)

CC CGA CAG AAA CCC CGA CAA TTT CTA TTT ATT CCTAGGGC 5' 5536.RD (SEQ ID No. 61)
                                              Bam H I
```

Plasmids pLD1-8 or pLDW1, prepared as described in Example 4, were digested with BspH I to release a 2.1 kb cloning site. The amplified fragment is ~112 bp long. The oligonucleotides are illustrated below:

```
             NdeI
                  M    C    R    S    D    D    I    S    V    N    (SEQ ID No: 62)

5' GGAATT CAT ATG TGC CGC TCT GAT GAC ATC AGC GTC AAT 3'    .RD (SEQ ID No: 63)

BspH I

I    P    N    T    G    H    D    N    T    N         (SEQ ID No: 54)

5'     A ATA CCG AAC ACA GGT CAT GAC AAC ACC AAT 3'        (SEQ ID No: 55)

3'     T TAT GGC TTG TGT CCA GTA CTG TTG TGG TTA 5'   5534.RD (SEQ ID No: 56)
``` internal fragment of the lbpb gene which was ligated with the 5'- and 3'-PCR fragments and cloned into pT7-7 that had been digested with NdeI and BamH I. The resulting plasmids, pLD2A and pLDW2A, contain the full-length 4223 and Q8 lbpb genes under the control of the T7 promoter, respectively.

Example 11

This Example illustrates the construction of vectors to express the mature *M. catarrhalis* Lbp2 proteins from *E. coli*.

The construction scheme is illustrated in FIG. 12. The putative mature Lbp2 lipoproteins start at the Cys$^{32}$ residue. A scheme similar to that described in Example 10 can be used to generate expression clones. To amplify the 5'-end of The BspH I-BamH I 3'-end of the lbpb gene is PCR amplified as in Example 9 and the plasmid expressing mature Lbp2 is constructed by ligating the 5'- and 3'-PCR fragments with the 2.1 kb BspH I fragment and vector pT7-7 digested with NdeI and BamH I. The resulting plasmids, pLD2B and pLDW2B, contain the lbpB gene encoding the mature Lbp2 proteins from strains 4223 and Q8 under the direction of the T7 promoter, respectively.

Example 12

This Example illustrates the construction of a vector to express the *M. catarrhalis* lfr Lbp3 from *E. coli*.

Figure 13:
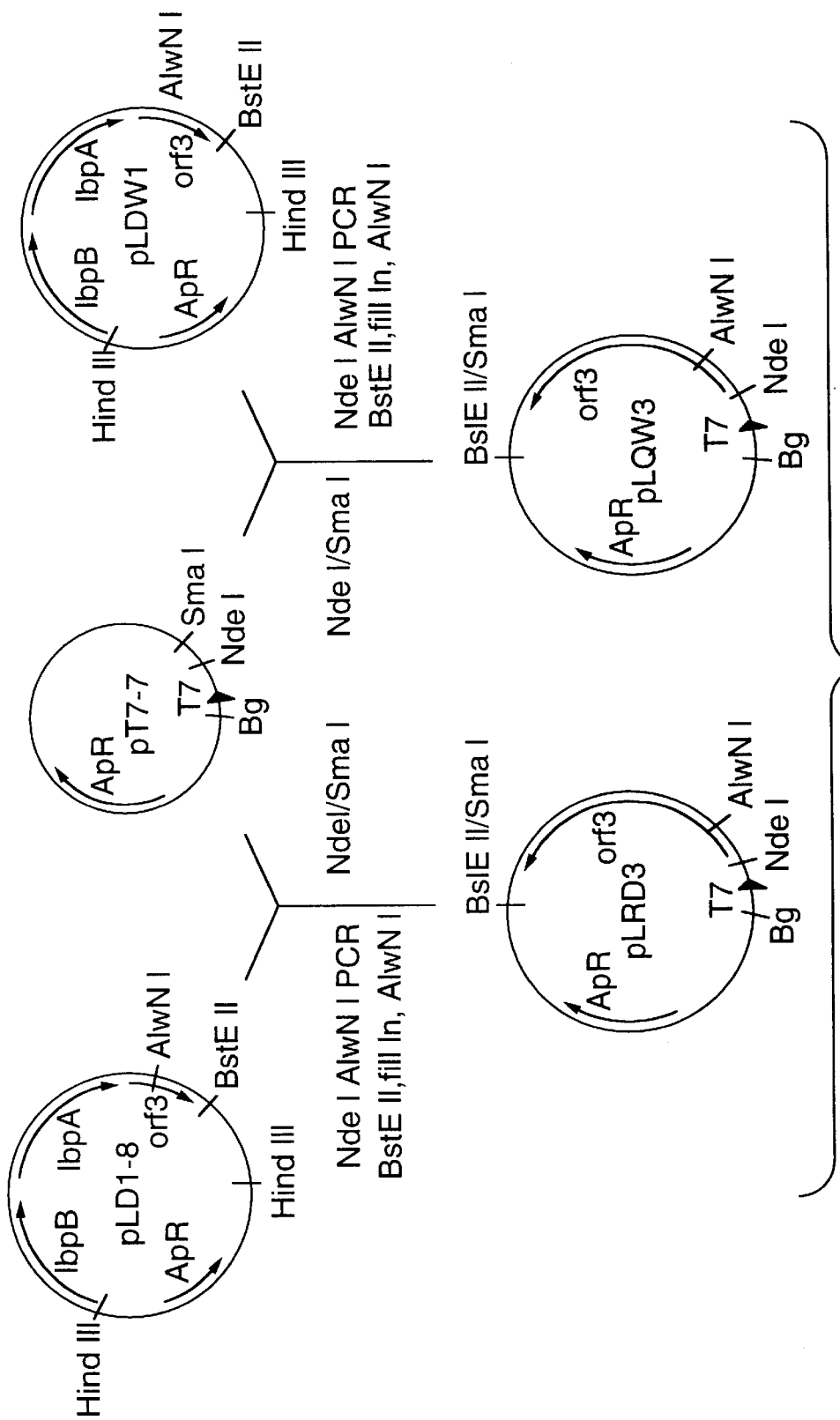
FIG. 13 shows the construction of a plasmid for expression of recombinant ORF3 (rORF3) proteins from *E. coli*.

The construction scheme is illustrated in FIG. 13. Oligonucleotides were used to generate the 5'-end of the orf3 gene from the ATG start codon to an AlwN I site. An NdeI site was engineered at the 5'-end for subsequent cloning into pT7-7. The oligonucleotides are shown below:

```
NdeI

M   T   C   L   P   K   T   N   P   A   L   K   V   K   H   R

5'  T ATG ACC TGT TTA CCA AAG ACC AAC CCT GCT TTA AAA GTC AAG CAC AGA

3'    AC TGG ACA AAT GGT TTC TGG TTG GGA CGA AAT TTT CAG TTC GTG TCT

AlwN I

F   L   K   Q   V                        (SEQ ID No: 64)

TTT TTA AAG CAG GTG      3'   5532.RD     (SEQ ID No: 65)

AAA AAT TTC GTC          5'   5457.RD     (SEQ ID No: 66)
```

The pLD1-8 or PLDW1 plasmid, prepared as described in Example 5, was digested with BstE II generating a 4.6 kb fragment which was filled in with Klenow polymerase before being digested with AlwNI. The resultant 1.8 kb fragment was ligated with the annealed NdeI-AlwN I oligonucleotides and cloned into pT7-7 that had been digested with NdeI and SmaI. The resulting plasmids, pLRD3 and pLQW3, contain the full-length orf3 genes from strains 4223 and Q8 under the direction of the T7 promoter, respectively.

Example 13

This Example describes the cloning and sequencing of the lbpB gene from *M. catarrhalis* strain VH19.

Chromosomal DNA was prepared from *M. catarrhalis* strain VH19, as described previously in Example 2. Oligonucleotide primers were designed based upon the flanking sequence of the 4223 lbpB gene. The sense primer was 5' AAGCTTAGCATGATGGCATCGGCT 3' (SEQ ID No: 67) and the antisense primer was 5' TTAGCCCAAG-GCAAATCTGGTGCA 3' (SEQ ID No: 68). PCR was performed in buffer containing 10mM Tris-HCl (pH 8.3), 50 mM potassium chloride and 1.5 mM magnesium chloride. Each 100 μl reaction mixture contained 1 μg chromosomal DNA, 0.1 μ each primer, 2.5 units amplitaq DNA polymerase (Perkin Elmer Cetus, Foster City, Calif.) and 10 mM of each dNTP (Perkin Elmer Cetus). The cycling conditions were 24 cycles of 94° C. for 1 min, 47° C. for 30 sec and 72° C. for 1 min. Specific 2.9 kb fragments were amplified from two independent reactions and subcloned into pCR II (Invitrogen, Carlsbad, Calif.), generating plasmids pVH19pcr1 and pVH19pcr2 for sequence analysis. A third PCR amplification was performed without subcloning the resultant DNA. Plasmid DNA from pVH19pcr1 and pVH19pcr2 was prepared from 50 ml overnight cultures using the Qiagen Plasmid Midi kit (Qiagen Inc, Chatsworth, Calif.). PCR amplified DNA was purified for direct sequencing using a Qiagen PCR purification kit. DNA samples were sequenced on an ABI model 373A DNA sequencer using dye terminator chemistry. Oligonucleotide primers 17 to 25 bases in length were used to sequence both strands of the DNA.

Figure 17A:
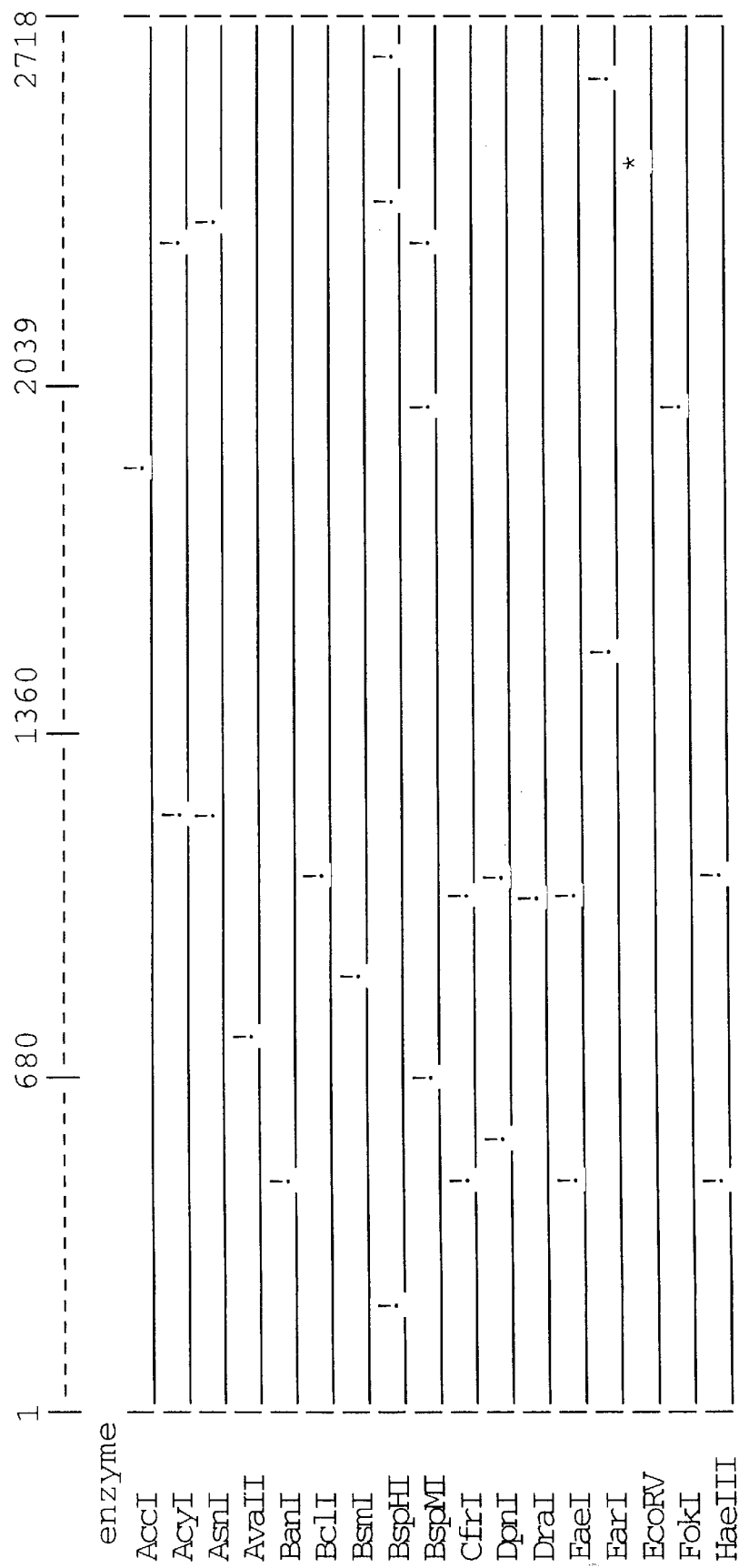
FIG. 17 shows a partial restriction map of the *M. catarrhalis* strain VH19 lbpB gene.
Figure 17B:
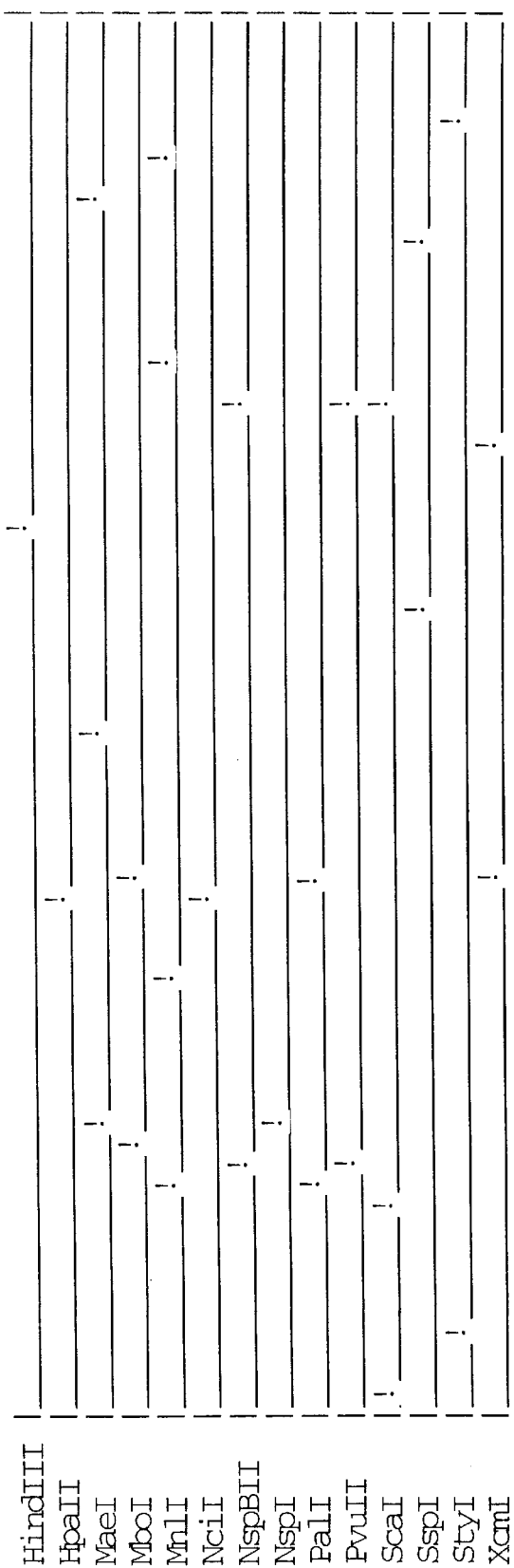

The nucleotide sequence (SEQ ID No: 69) of the VH19 lbpB gene and the deduced amino acid sequence of the corresponding Lbp2 protein (SEQ ID No: 70) are shown in FIG. 16. The encoded VH19 Lbp2 protein is 906 amino acids and is 77% identical and 84% similar to the 4223 and Q8 Lbp2 proteins. There is a putative lipoprotein signal sequence which is very similar to the 4223 and Q8 signal sequences. The high Asp and Asn content found in the 4223 and Q8 Lbp2 proteins is also present in the VH19 LbpB protein, as is the RGD sequence. A partial restriction map of the VH19 lbpb gene is shown in FIG. 17.

An alignment of the Lbp2 proteins from *M. catarrhalis* strains 4223, Q8 and VH19 is shown in FIG. 7. The *M. catarrhalis* Lbp2 proteins are also compared with partial Lbp2 sequences from *N. meningitis* strains BNCV (ref. 31) and H44/76 (ref. 24) and *N. gonorrhoeae* strain FA19 (ref. 25). There are small scattered regions of sequence homology to the known bacterial Tbp2 proteins (ref. 32). Residues that are conserved among the Tbp2 proteins and the *M. catarrhalis* Lbp2 proteins are underlined in FIG. 7 and include the LEGGFYG (SEQ ID No: 71) motif.

Example 14

This Example describes the construction of vectors for expression of the *M. catarrhalis* Lbp2 protein.

By analogy with Tbp2 proteins, Lbp2 was assumed to be a lipoprotein and constructs were designed for expression of Lbp2 with or without a lipopeptide signal sequence. There is a unique Bgl I site in lbpb. To express the full-length Lbp2 protein with leader sequence (construct A), an approximately 429 bp 5'-fragment from the Met$^1$ start codon to the Bgl I site was PCR amplified and to express the mature protein (construct B), an approximately 329 bp 5'-fragment from the putative Cys$^{32}$ start to the Bgl I site was PCR amplified. The following sense primers were used:

```
                  Nde I

M   S   T   V   K   T   P   H                (SEQ ID No: 52)

5' GGAATTCCAT ATG AGT ACT GTC AAA ACC CCC CAC A 3'           (SEQ ID No: 53)

for construct A or

Nde I
```

```
                    -continued
         M   C   R   S   D   D   I   S   V   N       (SEQ ID No: 62)

5' GGAATTCCAT ATG TGC CGC TCT GAT GAC ATC AGC GTC AAT 3'   (SEQ ID No: 63)

for construct B and the anti-sense primer was:

G   K   N   L   R   G   P   I               (SEQ ID No: 72)

5' GGT AAA AAC TTG CGT CAG CCC ATC 3'            (SEQ ID No: 73)

3' CCA TTT TTG AAC GCA GTC GGG TAG 5'            (SEQ ID No: 74)
                              Bgl I
```

Figure 18A:
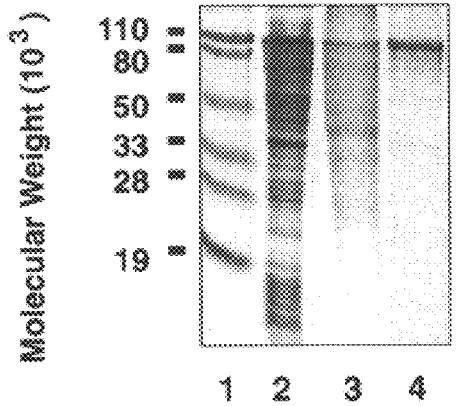
FIG. 18, comprising panels A, B and C, shows SDS-PAGE gels of the purification of recombinant Lbp proteins. Panel A shows an SDS-PAGE gel of the purification of Q8 rLbp1. Panels B and C show the purification of Q8 rLbp2 and 4223 rLbp2, respectively. Lane 1, molecular weight markers; lane 2, whole cell lysates; lane 3, inclusion bodies; lane 4, purified protein.
Figure 18B:
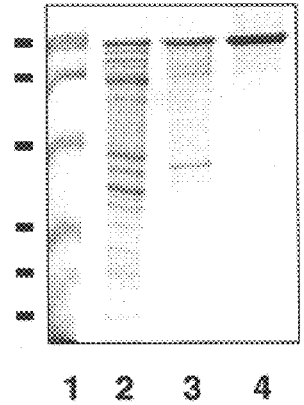
Figure 18C:
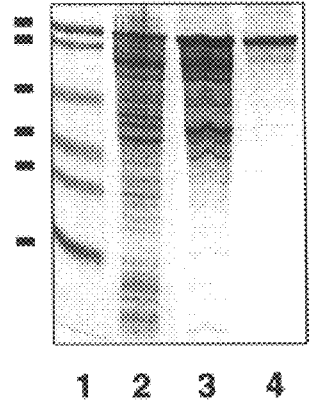

The Q8 lfr-containing plasmid, pLDW1 (Example 5), was digested with Bgl I and EcoR I to release a 2.3 kb lbpB fragment which was ligated with the Nde I-Bgl I PCR fragment and cloned into pT7-7 that had been digested with Nde I and EcoR I. The resulting plasmids, pQW2A and pQW2B, thus contain the Q8 lbpB gene encoding the full-length or mature Lbp2 proteins under the direction of the T7 promoter. The plasmids expressing the 4223 full-length or mature Lbp2 proteins were constructed in a similar manner and designated pRD2A and pRD2B. There was no measurable expression of rLbp2 from constructs containing the signal sequence, however the mature rLbp2 proteins were expressed at 5 to 10% of total proteins as inclusion bodies and were purified by the same process as that described for rLbp1 in Example 8. Samples from the purification were analyzed by SDS-PAGE (FIG. 18).

Example 15

This Example describes the functional characterization of the recombinant lactoferrin binding proteins.

Figure 19A:
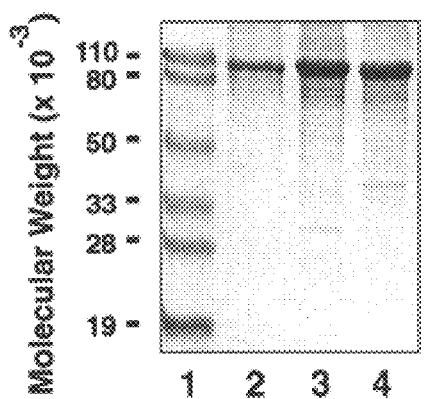
FIG. 19, comprising panels A and B, shows binding of recombinant Lbp proteins to lactoferrin. Panel A shows an SDS PAGE gel of purified recombinant proteins. Panel B shows the binding of recombinant proteins to human lactoferrin. Lane 1, molecular weight markers; lane 2, Q8 rLbp1; lane 3, Q8 rLbp2; lane 4, 4223 rLbp2.
Figure 19B:
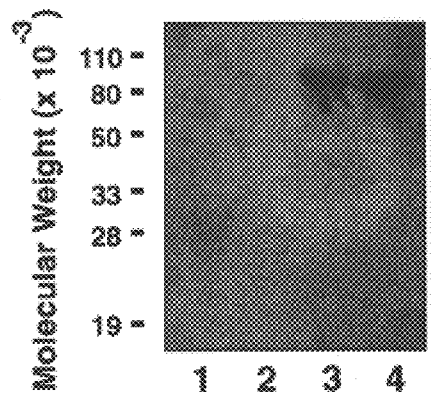
Figure 20A:
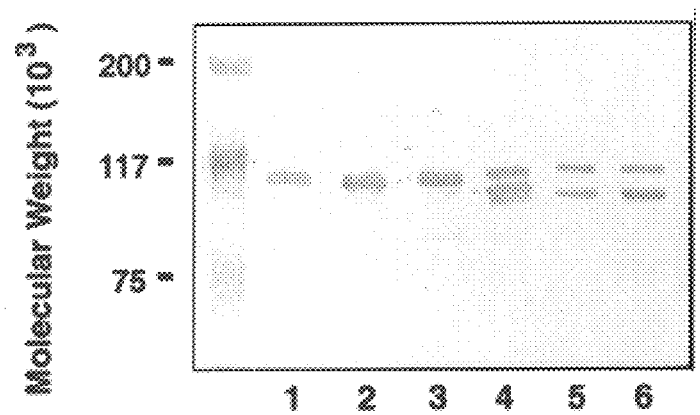
FIG. 20, comprising panels A, B and C, shows an immunoblot of *M. catarrhalis* strains reacted with anti-rLbp1 and anti-rLbp2 antibodies. Panel A: whole cell lysates probed with anti-Q8 rLbp1+anti-Q8 rLbp2 antisera. All cells were grown in the presence of EDDA. Panel B: whole cell lystaes probed with anti-Q8 rLbp1 antibody. Panel C: whole cell lysates probed with anti-Q8 rLbp2 antibody. Lane 1, strain Q8; lane 2, strain 4223; lane 3, strain VH19; lane 4, strain LES-1; lane 5, strain H-04; lane 6, strain 3. + indicates growth in the presence of EDDA and − indicates growth in the absence of EDDA.
Figure 20B:
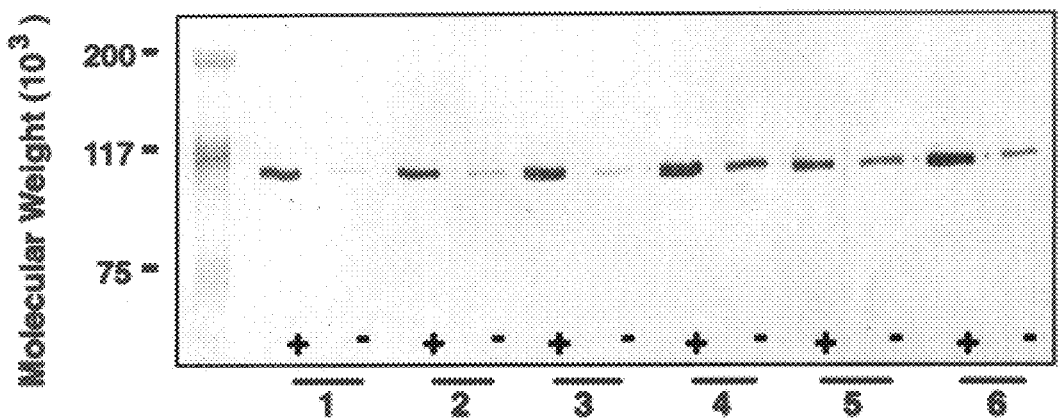
Figure 20C:
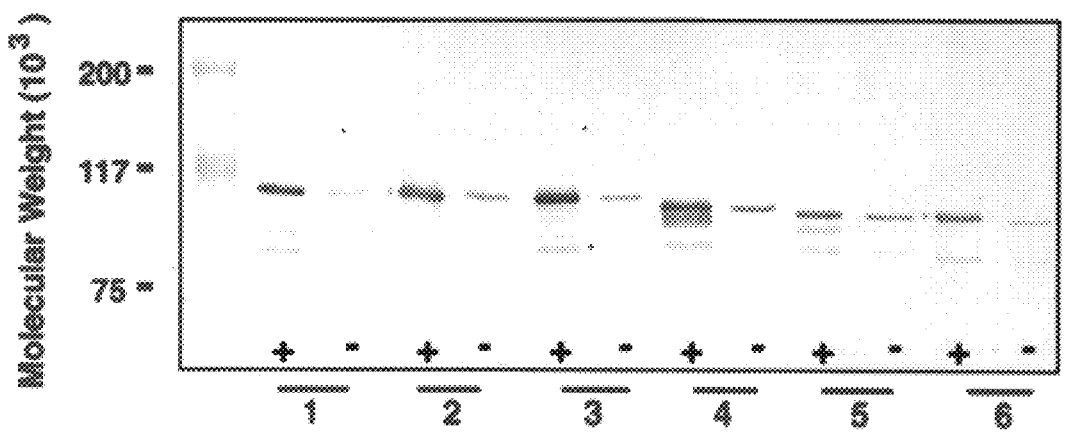

Human lactoferrin (Sigma) was conjugated to horseradish peroxidase using an EZ-Link maleimide activated horseradish peroxidase (HRP) kit (Pierce, Rockford, Illinois) according to the manufacturer's instructions. The lactoferrin binding activity of rLbp1 or rLbp2 was assessed by modifying the procedure described for transferrin binding proteins (ref. 17). Briefly, purified rLbp1 or rLbp2 was subjected to discontinuous electrophoresis through a 12.5% SDS PAGE gel. The proteins were electrophoretically transferred to a polyvinylidene difluoride (PVDF) membrane (Millipore, Bedford, Massachusetts) and incubated with horseradish peroxidase-conjugated human lactoferrin (1:20 dilution) at 4° C. overnight. LumiGLO substrate (Kirkegaard and Perry Laboratories, Inc., Gaithersburg, Maryland) was used for chemiluminescent detection of HRP activity according to the manufacturer's instructions. The Q8 rLbp1 protein did not bind human lactoferrin under these conditions, but the 4223 rLbp2 and Q8 rLbp2 proteins did (FIG. 19).

Example 16

This Example describes the immunization of animals and immunoassays.

Groups of two guinea pigs (Hartley outbred, Charles River, Quebec) were immunized intramuscularly (i.m.) with 5 µg doses of purified rLbp1 or rLbp2 protein emulsified in CFA or IFA. Anti-Lbp antibody titers in guinea pig immune sera were determined by antigen-specific ELISA. Microtiter wells (Nunc-MAXISORB, Nunc, Denmark) were coated with 50 µl of protein (0.5 µg ml$^{-1}$). The reactive titer of an antiserum was defined as the reciprocal of the highest dilution consistently showing a two-fold increase in absorbance at 450 nm over that obtained with the pre-immune serum samples. The recombinant proteins elicited high titer antibodies as shown in Tables 1 and 2.

Example 17

This Example describes the antigenic conservation of Lbp1 and Lbp2 in M. catarrhalis strains.

To demonstrate the iron-dependent expression of the lbpA and lbpB genes, representative M. catarrhalis strains were grown in BHI±25 mM EDDA. Whole cell lysates were separated by SDS PAGE and electrophoretically transferred to nitrocellulose membrane. Guinea pig anti-Q8 rLbp1, anti-Q8 rLbp2 and anti-4223 rLbp2 antisera were used as first antibodies and horseradish peroxidase-conjugated protein G (ZYMED) was used as secondary antibody. To assess antigenic conservation, approximately 90 M. catarrhalis strains, obtained from North America or Finland were grown in BHI +25 mM EDDA, and immunoblots were probed with guinea pig anti-4223 rLbp2 antibody, as above. All strains showed a protein band reactive with anti-rLbp2 antibody. There was very little size heterogeneity for the Lbp2 proteins from the 90 M. catarrhalis strains, ranging from approximately 100 kDa to 105 kDa. Representative immunoblots are illustrated in FIG. 19.

Example 18

This Example describes the assay used to determine the bactericidal antibody activity of anti-Lbp antibodies.

The assay was performed as described by ref. 33. Briefly, the M. catarrhalis strains were grown to an OD$_{578}$ of 0.5 in BHI medium containing 25 mM EDDA. The bacteria were diluted so that the pre-bleed control plates contained 100 to 300 cfu. Guinea pig anti-rLbp1 or anti-rLbp2 antisera and pre-bleed controls, were heated to 56° C. for 30 min to inactivate endogenous complement and were diluted 1:64 with veronal buffer containing 0.1% BSA (VBS). Guinea pig complement (Biowhittaker, Walkersville, Maryland) was diluted 1:10 in VBS. Twenty-five µl each of diluted antiserum, bacteria and complement were added to duplicate wells of a 96 well microtiter plate (Nunc). The plates were incubated at 37° C. for 60 min, gently shaking at 70 rpm on a rotary platform. Fifty µl of each reaction mixture were plated onto Mueller Hinton agar plates (Becton-Dickinson, Cockeysville, Maryland) which were incubated at 37° C. for 24 h, then room temperature for 24 h, before the bacteria were counted. Antisera were determined to be bactericidal if ≧50% of bacteria were killed compared with negative controls.

Six strains of different geographical and anatomical origins were tested. The data in Table 3 illustrates that anti-4223 rLbp2 antibody was bactericidal for the homologous strain and three of five heterologous strains.

SUMMARY OF THE DISCLOSURE

In summary of this disclosure, the present invention provides purified and isolated DNA molecules containing lactoferrin receptor genes from *Moraxella catarrhalis*, the sequences of these lactoferrin receptor genes, and the derived amino acid sequences thereof. The genes and DNA sequences are useful for diagnosis, immunization, and the generation of diagnostic and immunological reagents. Immunogenic compositions, including vaccines, based upon expressed recombinant Lbp1 and/or Lbp2 and/or ORF3, portions thereof, or analogs thereof, can be prepared for prevention of diseases caused by Moraxetlla. Modifications are possible within the scope of this invention.

TABLE 1

Bactericidal antibody titres for anti-native Lbp1

| Antibody | Bactericidal titre - RH408 | | Bactericidal titre - Q8 | |
|---|---|---|---|---|
| | Pre-immune | Immune | Pre-immune | Immune |
| Anti-4223 Lbp1 | <8 | 114–330 | <8 | 128–512 |

Bactericidal titres are expressed as the reciprocal dilution of antiserum capable of killing 50% of *M. catarrhalis* cells

TABLE 2

ELISA titers for guinea pig anti-Lbp antibodies raised against recombinant lactoferrin binding proteins

| Coated antigen | Anti-Q8 rLbp1 | Anti-Q8 rLbp2 | Anti-4223 rLbp2 |
|---|---|---|---|
| Q8 rLbp1 | 3,200 25,600 | — | — |
| Q8 rLbp2 | — | 1,638,400 1,638,400 | 409,600 409,600 |
| 4223 rLbp2 | — | 409,600 409,600 | 819,200 819,200 |

TABLE 3

Bactericidal antibody activity of guinea pig anti-rLbp2 antibodies

| | | | | Bactericidial antibody activity[3] | |
|---|---|---|---|---|---|
| Strain | locale[1] | source[2] | Lbp2 size | Anti-4223 rLbp2 | Anti-Q8 rLbp2 |
| 4223 | New York | MEF | 105 kDa | ++ | — |
| Q8 | Quebec | sputum | 105 kDa | ± | — |
| VH19 | Texas | MEF | 105 kDa | + | NT[4] |
| LES-1 | Finland | MEF | 102 kDa | − | NT |
| H-04 | Nova Scotia | MEF | 100 kDa | + | NT |
| 3 | New York | sputum | 100 kDa | ++ | NT |

[1]geographic locale where strain was isolated
[2]anatomical source of clinical isolate. MEF is middle ear fluid from otitis media patients
[3]killing by antiserum diluted 1:64, compared to negative controls: − indicates 0–25% killing; ± indicates 26–49% killing; + indicates 50–75% killing; ++ indicates 76–100% killing.
[4]NT = not tested

REFERENCES

1. Brorson, J-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
2. Catlin, B. W., 1990. *Branhamella catarrhalis*: an organism gaining respect as a pathogen. Clin. Microbiol. Rev. 3: 293–320.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder. 1986. Bronchopulmonary infection due to *M. catarrhalis*. Clinical features and therapeutic response. Drugs 31(Suppl.3):109–112.
5. Nicotra, B., M. Rivera, J. I. Luman, and R. J. Wallace. 1986. *Branhamella catarrhalis* as a lower respiratory tract pathogen in patients with chronic lung disease. Arch.Intern.Med. 146:890–893.
6. Ninane, G., J. Joly, and M. Kraytman. 1978. Bronchopulmonary infection due to *Branhamella catarrhalis* 11 cases assessed by transtracheal puncture. Br.Med.Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am. Rev. Respir. Dis. 123:553–555.
8. West, M., S. L. Berk, and J. K. Smith. 1982. *Branhamella catarrhalis* pneumonia., South. Med. J. 75:1021–1023.
9. Christensen, J. J., and B. Bruun. 1985. Bacteremia caused by a beta-lactamase producing strain of *Branhamella catarrhalis*. Acta. Pathol. Microbiol. Immunol. Scand. Sect. B 93:273–275.
10. Craig, D. B., and P. A. Wehrle. 1983. *Branhamella catarrhalis* septic arthritis. J. Rheumatol. 10:985–986.
11. Guthrie, R., K. Bakenhaster, R. Nelson, and R. Woskobnick. 1988. *Branhamella catarrhalis* sepsis: a case report and review of the literature. J. Infect. Dis. 158:907–908.
12. Hiroshi, S., E. J. Anaissie, N. Khardori, and G. P. Bodey. 1988. *Branhamella catarrhalis* septicemia in patients with leukemia. Cancer 61:2315–2317.
13. O'Neill, J. H., and P. W. Mathieson. 1987. Meningitis due to *Branhamella catarrhalis*. Aust. N. Z. J. Med. 17:241–242.
14. Murphy, T. F. 1989. The surface of *Branhamella catarrhalis*: a systematic approach to the surface antigens of an emerging pathogen. Pediatr. Infect. Dis. J. 8:S75–S77.
15. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16–27.
16. Jorgensen, J. H., Doern, G. V., Maher, L. A., Howell, A. W., and Redding, J. S., 1990 Antimicrobial resistance among respiratory isolates of *Haemophilus influenza, Moraxella catarrhalis*, and *Streptococcus pneumoniae* in the United States. Antibicrob. Agents Chemother. 34: 2075–2080.
17. Schryvers, A. B. and Lee, B. C. (1988) Comparative analysis of the transferrin and lactoferrin binding proteins in the family Neisseriaceae. Can. J. Microbiol. 35, 409–415.
18. O'Hagan, D T. 1992. Oral deleivery of vaccines. Formulation and clinical pharmaco kinetic considerations. Clin. Pharmacokinet 22(t): 1–10.
19. Ulmer et al. 1993. Curr. Opinion Invest. Drugs 2:983–989.
20. Lockhoff, O., 1991. Glycolipids as immunomodulators: Synthesis and properties.
21. Nixon-George A., et al., 1990. The adjuvant effect of stearyl tyrosine on a recombinant subunit hepatitis B surface antigen. J Immunol 144 (12): 4798–4802.
22. Wallace, R. J. et al., 1990. Antibiotic susceptibiles and drug resistance in *Moraxella* (*Branhaemella*) *catarrhalis*. Am. J. Med. 88(5A): 465–505.

23. Nissinen A, et al., 1995. Development of beta-lactamase-mediated resistance to penicillin in middle-ear isolates of *Moraxella catarrhalis* in Finnish children, 1978–1993. Clin Infect Dis 21 (5): 1193–1196.
24. Pettersson, A., et al., 1994. Identification of iroa Gene Product of *Neisseria meningitides* as a Lactoferrin Receptor. J. Bacteriol. 176(6): 1764–1766.
25. Biswas G D, Sparring P F. 1995. Characterization of lbpa, the structural gene for a lactoferrin receptor in *Neisseria gonorrhoeae*. Infect Initnun 63 (8): 2958–2967.
26. Legrain M, et al. 1993. Cloning and characterization of *Neisseria meningitides* genes encoding the transferrin-binding proteins Tbp1 and Tbp2. Gene 130 (1): 73–80.
27. Cornelissen C N, Biswas G D, Sparling P. F. 1993. Expression of gonococcal transferrin-binding rotein 1 causes *Escherichia coli* to bind human transferrin. J Bacteriol 175 (8): 2448–2450.
28. Anderson J E, Sparling P F, Cornelissen C N. 1994. Gonococcal transferrin-binding protein 2 facilitates but is not essential for transferrin utilization. J Bacteriol 176 (11): 31623170.
29. Ogunnariwo J A, Schryvers A B. 1996. Rapid identification and cloning of bacterial transferrin and lactoferrin receptor protein genes. J Bacteriol 178 (24): 7326–7328.
30. Loosmore S M, et al. 1996. Cloning and expression of the *Haemophilus influenzae* transferrin receptor genes. Mol Microbiol 19 (3): 575–586.
31. Pettersson, A. et al. 1993. Molecular Characterization of the 98-Kilodallon Iron-Regulated Outer membrane Protein of *Neisseria meningitides*. Infect. Immun. 61 (ti): 4724473.
32. Ogunnariwo, J. A., Woo, T. K. W., Lo, R. Y. C. , Gonzalez, G. C. , and Schryvers, A. B. (1997) Characterization of the *Pasteurella haemolytica* transferrin receptor genes and the recombinant receptor proteins. Microbial Pathog 23:273–284.
33. Yang, Y. P., Myers, L. E., McGuinness, U., Chong, P., Kwok, Y., Klein, M. H., and Harkness, R. E. (1997) The outer membrane protein, CD, extracted from *Moraxella* (*Branhamella*) *catarrhalis* is a potential vaccine antigen that induces bactericidal antibodies. FEMS Immun Med Microbiol 17:187–199.
34. Pettersson, A., Klarenbeek, V., van Deurzen, J., Poolman, J. T., and Tommassen, J. (1994a) Molecular characterization of the structural gene for the lactoferrin receptor of the meningococcal strain H44/76. Microb Pathog 17:395–408.
35. Needleman, S. B., and Wunsch, C. D. 1970, J. Mol Biol. 48:443–453.
36. Sellers, P. H. 1974 On the theory and computation of evolutionary distances. J. Appl. Math(Siam) 26:787–793.
37. Waterman, M. S., Smith, T. F., and Beyer, W. A. 1976. Advan. Math. 20:367–387.
38. Smith, T. F., and Waterman, M. S. 1981 Identification of common molecular subsequences. J. Mol. Biol. 147:195–197.
39. Sobel, E. and Martinez, H. M. 1985 A Multiple Sequence Alignment Program. Nucleic Acid Res. 14:363–374.
40. Bonnat, R. A., Yu, R. H. and Schryvers, A. B. 1995, Biochemical Analysis of Lactoferrin Receptors in the Neisseriaceae: Identification of a Second Lactoferrin Receptor Protein. Microb. Pathog. 19:285–297.

SEQUENCE LISTING (1) GENERAL INFORMATION:

(iii) NUMBER OF SEQUENCES: 78

(2) INFORMATION FOR SEQ ID NO:1:

(i) SEQUENCE CHARACTERISTICS:
      (A) LENGTH: 7650 base pairs
      (B) TYPE: nucleic acid
      (C) STRANDEDNESS: single
      (D) TOPOLOGY: linear (xi) SEQUENCE DESCRIPTION: SEQ ID NO:1:

```
AAGCTTAGCA TGATGGCATC GGCTGATTGT CTTTTTGCCT TGTTGTGTGT TTGTGGGAGT      60

TGATTGTACT TACCTTAGTG GTGGATGCTT GGGCTGATTT AATAAAGCGG TCTTCACAAC     120

ACACCAAACG AGATATCACC ATGAGTACTG TCAAAACCCC CCACATTTTC TACCAAAAAC     180

GCACCCTTAG CCTTGCCATC GCCAGTATTT TTGCTGCCTT GGTGATGACA GGCTGCCGCT     240

CTGATGACAT CAGCGTCAAT GCACCCAATG TTACCCAACT GCCCCAAGGC ACGGTTTCAC     300

CAATACCGAA CACAGGTCAT GACAACACCA ATAACACCAA CAATCAGGGC AACAACACGG     360

ATAACAGCAC CAGCACAACT GACCCAAATG GCGATAACAA CCAACTGACA CAAGCACAAA     420

AGACCGCCGC TGCCGCAGGG TTTTTTGTGA TGGGTAAAAT TCGTGATACC AGCCCAAAAA     480

ATGACCCAGA TTATAGCAAT GATTTAGTAC AGCAGTGGCA AGGCAAATTA TATGTTGGTA     540

TTGATGCCCA TCGCCCAGAT GGCATCGGCA CAGGTAAAAA CTTGCGTCAG CCCATCACCG     600

CCAATGACAT CAAACCCTTG TATTTTAACA AATTCCCTGC ATTGTCTGAT TTGCATTTAG     660
```

| | |
|---|---|
| ACAGTGAACG CCACCGTTTT GACCCCAAAA AGCTAAACAC CATTAAAGTG TATGGTTATG | 720 |
| GCAACTTAAC AACACCCTCT AAAAACAACA CTTACATCAA TCATCAGCAA GCTGATAATA | 780 |
| AGAAAAATAA CAAGCCTGTT GACCCTTATG AAAATATCCG TTTTGGGTAT CTTGAACTAC | 840 |
| AAGGAAGCAG TCTGACCCAA AAAAATGCCG ATACTCCAAA TGACAAAGAC CGCATTCCCA | 900 |
| AACCCATGCC CATTTTGTTT TATCACGGAG AAAACGCCAG CAGCCAGCTG CCCAGTGCTG | 960 |
| GTAAATTTAA CTACACAGGC AACTGGCTGT ACCTAAGTGA TGTCAAAAAA CGCCCTGCAC | 1020 |
| TTTCAGCATC AGATGATCGA GTGGGGGTCT ATCTCAATGC CAGTGGCAAA TCCAATGAGG | 1080 |
| GCGATGTCGT CAGTGCCGCC CACATTTATC TAAACGGCTT TCAATATAAG CACACGCCTG | 1140 |
| CCACTTATCA GGTGGATTTT GACACAAACT CATTAACAGG CAAGCTGTCT TATTATGACA | 1200 |
| ATCCCAACCA GCAAACTGCC CAAGGCAAAT ACATCAAAAG CCAATTTGAC ACTACCAAAA | 1260 |
| AAGTCAATGA AACCGATGTG TATCAAATTG ATGCCAAAAT CAACGGCAAC CGCTTCGTCG | 1320 |
| GTACGGCCAA ATCTTTGGTT AATGAGAACA CAGAAACCGC ACCTTTTATC AAAGAGCTGT | 1380 |
| TCTCCAAAAA AGCCAATCCC AATAACCCAA ACCCTAATTC AGACACGCTA GAAGGCGGGT | 1440 |
| TTTATGGTGA GTCGGGCGAT GAGCTGGCGG GTAAATTTTT ATCCAATGAC AACGCATCTT | 1500 |
| ATGTGGTCTT TGGTGGTAAA CGAGACAAAA CAGACAAACC TGTCGCCACA AAACGGTGT | 1560 |
| ATTTTAGTGC AGGCTTTGAA AAACCTAGCA CCAGTTTTGT GGATAATGAA ACGATTGGCA | 1620 |
| GAATTATTAA CAGCAAAAAG TTAAATGATG CGGTGAATGA GAAAATTGAT AATGGTGATA | 1680 |
| TTCCTACCAG TGATGAACGC TATGATGAAT TTCCTTGGGG CGAAAAAAAA GCAGAATTCA | 1740 |
| CCAAAAAAGT CAGCAGCAGC ACCCAAGCCG TGCCAGCTTA TTTTGGGCAA CATGATAAAT | 1800 |
| TTTATTTTAA TGGCAACTAT TATGACCTAT CAGCCAGCAG TGTTGATAAA TTGGCCCCTG | 1860 |
| CCGATGCTGT CAAAGCCAAC CAATCCATTA AGAAAAAATA CCCTAATGCC ACACTAAATA | 1920 |
| AGGACAACCA AGTTACCGCC ATCGTGCTAC AAGAAGCCAA AGATAATAAG CCTTATACCG | 1980 |
| CCATTCGTGC CAAAAGCTAT CAGCACATCA GTTTTGGCGA GACGCTGTAT AACGATGCCA | 2040 |
| ACCAAACCCC AACACGCAGT TATTTTGTGC AAGGCGGTAG GGCAGATACC AGCACCACGC | 2100 |
| TGCCCAAGGC AGGTAAATTC ACTTACAACG GTCTTTGGGC AGGCTATCTT ATCCAAAAAA | 2160 |
| AGGACAAAGG TTATAGCAAT AATGAAGAAA CCATCAAGAA AAAAGGCCAT CAAGATTATC | 2220 |
| TGTTAACCGA AGACTTCACC CCAGAAGATG ATGACGATGA TTTGACCGCA TCTGATGATT | 2280 |
| CACAAGATGA TGATGCACAT GGCGATGATG ATTTGATTGC ATCTGATGAT TCACAAGATG | 2340 |
| ATGACGCAGA TGGCGATGAC GATTCAGATG ATTTGGGTGA TGGTGCAGAT GACGCCGCCG | 2400 |
| CAGGCAAAGT GTATCATGCA GGTAATATTC GCCCTGAATT TGAAAACAAA TACTTGCCCA | 2460 |
| TTAATGAGCC TACTCATGAA AAAACCTTTG CCCTAGATGG TAAAAATAAA GCTAAGTTTG | 2520 |
| ATGTGGATTT TGACACCAAC AGCCTAACTG GTAAATTAAA CGATGAGAGA GGTGATATCG | 2580 |
| TCTTTGATAT CAAAAATGGC AAAATTGATG GCACAGGCTT TACCGCCAAA GCCGATGTGC | 2640 |
| CAAACTATCG TGAAGAAGTG GGTAACAACC AAGGTGGCGG TTTCTTATAC AACATCAAAG | 2700 |
| ATATTGATGT CAAGGGGCAA TTTTTTGGCA CAAATGGCGA AGAGTTGGCA GGGCAGTTAC | 2760 |
| AGTACGACAA AGGCGATGGC ATCAATGACA CCGCCGAAAA AGCAGGGGCT GTCTTTGGGG | 2820 |
| CTGTTAAAGA TAAATAAAGC CCCCTTCATC ATCGTTTAGT CGCTTGACCG ACAGTTGATG | 2880 |
| ACGCCCTTGG CAATGTCTTA AAACAGCACT TTGAAACAGT GCCTTGGGCG AATTCTTGGA | 2940 |
| TAAATGCACC AGATTTGCCT TGGGCTAATA TCTTGATAAA ACATCGCCAT AAAATAGAAA | 3000 |

```
ATAAAGTTTA GGATTTTTTT ATGTCAAAAT CTATCACAAA AACACAAACA CCATCAGTCC    3060

ATACCATGAC CACGCACCGC TTAAACCTTG CCATCAAAGC GGCGTTATTT GGTGTGGCAG    3120

TTTTACCCCT ATCCGTCTGG GCGCAAGAGA ACACTCAGAC AGATGCCAAC TCTGATGCCA    3180

AAGACACAAA AACCCCTGTC GTCTATTTAG ATGCCATCAC GGTAACCGCC GCCCCATCTG    3240

CCCCTGTTTC TCGGTTTGAC ACCGATGTAA CAGGGCTTGG CAAAACGGTC AAAACCGCTG    3300

ACACGCTGGC AAAAGAACAA GTGCAGGGCA TTCGTGATTT GGTGCGTTAT GAAACTGGGG    3360

TGAGTGTGGT TGAGCAGGGG CGTGGTGGCA GCAGCGGATT TGCCATTCAT GGCGTGGATA    3420

AAAACCGAGT GGGCATTACC GTAGATGGCA TTGCCCAAAT TCAATCCTAC AAAGATGAAT    3480

CCACCAAACG AGCTGGTGCA GGCTCTGGGG CGATGAATGA GATAGAGATT GAAAACATTG    3540

CCGCCGTTGC CATCAATAAA GGTGGTAATG CCCTAGAAGC AGGCTCTGGT GCGTTGGGCG    3600

GTTCGGTGGC GTTTCATACC AAAGATGTGA GCGATGTCTT AAAATCTGGT AAAAATCTTG    3660

GCGCTCAAAG CAAAACCACT TATAACAGCA AAAATGACCA TTTTAGTCAG ACGCTGGCAG    3720

CGGCAGGTAA AACCGAGCGT GTGGAAGCGA TGGTGCAATA TACCTACCGT AAAGGCAAAG    3780

AAAACAAAGC ACACAGCGAC CTAAATGGCA TCAACCAAAG CCTATATCGC TTGGGTGCAT    3840

GGCAACAAAA ATATGATTTA AGAAAGCCCA ATGAACTGTT TGCAGGCACA AGCTACATCA    3900

CCGAAAGCTG TTTGGCAAGT GATGACCCAA AAAGCTGCGT ACAATACCCT TATGTCTACA    3960

CCAAAGCCCG ACCAGATGGC ATCGGCAATC GCAATTTTTC TGAGTTAAGC GATGCTGAAA    4020

AAGCACAATA TTTGGCATCC ACGCACCCCC ATGAGGTTGT CTCTGCCAAA GATTATACAG    4080

GCATTTATCG GTTGTTACCT GACCCCATGG ACTATCGTTC AGACTCGTAT TTGGCACGCC    4140

TTAACATCAA AATCACCCCA AATCTGGTCA GTAAACTGTT ATTAGAAGAC ACCAAGCAAA    4200

CATACAACAT TCGTGATATG CGTCATTGTA GTTACCATGG GGCAAGATTG GGCAATGATG    4260

GTAAGCCTGC CAATGGTGGC TCCATTGTTC TTTGCGATGA TTATCAAGAG TATCTAAACG    4320

CCAATGACGC ATCACAAGCA TTATTTAGAC CAGGTGCTAA TGATGCCCCC ATTCCAAAAC    4380

TGGCTTATGC CAGAAGCAGT GTGTTTAACC AAGAGCATGG CAAAACTCGC TATGGGTTAA    4440

GTTTTGAGTT TAAGCCTGAC ACGCCATGGT TTAAGCAAGC AAAATTAAAC CTACACCAAC    4500

AAAATATCCA AATCATTAAC CATGACATTA AAAAATCGTG CAGCCAATAT CCTAAGGTGG    4560

ATTTAAATTG TGGCATCAGT GAAATTGGGC ATTATGAATA TCAAAATAAT TACCGTTATA    4620

AAGAAGGGCG TGCCAGCTTG ACAGGCAAAC TTGATTTTAA TTTTGACCTG CTGGGTCAGC    4680

ACGATTTGAC GGTGTTGGCT GGTGCAGATA AAGTTAAAAG CCAATTTCGT GCCAACAACC    4740

CCAGACGCAC AATCATTGAC ACCACCCAAG GCGATGCCAT CATTGATGAA AGCACGCTGA    4800

CAGCACAGGA GCAAGCCAAA TTTAAGCAAT CGGGGGCGGC ATGGATTGTC AAAAATCGCC    4860

TTGGACGCTT AGAAGAAAAA GACGCCTGTG GCAATGCCAA TGAATGTGAA CGCGCCCCCA    4920

TTCATGGCAG TAACCAATAT GTGGGCATTA ACAACCTTTA TACACCAAAT GATTATGTGG    4980

ATTTAAGTTT TGGTGGACGC TTGGATAAAC AACGCATTCA CAGCACCGAT TCAAACATCA    5040

TCAGCAAAAC TTACACCAAC AAAAGCTATA ATTTTGGAGC GGCGGTTCAT CTGACACCTG    5100

ATTTTAGCCT GTTGTATAAA ACTGCCAAAG GCTTTCGTAC GCCAAGTTTT TATGAACTGT    5160

ACAACTATAA CAGCACCGCC GCCCAGCATA AAAATGACCC TGATGTGTCT TTTCCCAAAC    5220

GAGCGGTTGA TGTCAAACCT GAAACTTCCA ATACCAATGA ATACGGCTTT CGCTATCAGC    5280

ACCCTTGGGG GGATGTTGAG ATGAGCATGT TCAAAAGCCG TTACAAGGAC ATGTTAGATA    5340

AAGCCATACC GAACCTAACC AAAGCCCAAC AAGAGTATTG TAAGGCTCAT TTGGATTCCA    5400
```

```
ATGAATGTGT TGGCAATCCG CCCACGCCCA AAACCAGTGA TGAGGTATTT GCCAACTTAT    5460

ATAATGCCAC CATCAAAGGG GTGAGTGTCA AAGGCAAACT GGATTTGCAT GCCATGACAT    5520

CAAAACTGCC AGATGGTCTT GAAATGACCT TGGGTTATGG TCATACCAAA TTGGGGAAAT    5580

TTGATTACAT TGCACCCAAA GATGCCGATG GTTGGTATCA GGCTCGCCCT GCTTTTTGGG    5640

ATGCCATCAC CCCAGCGCGC TATGTGGTCG GTCTAAACTA TGACCACCCC AGTCAAGTAT    5700

GGGGCATTGG CACAACTTTA ACGCACAGCA AACAAAAAGA TGAAAATGAG CTAAGTGCCC    5760

TTAGAATCCG AAATGGCAAA AGAGAAACAC AAACCTTAAC GCACACAATA CCCAAAGCCT    5820

ATACCTTACT GGACATGACA GGCTATTATA GCCCAACTGA GAGCATCACC GCTCGTCTTG    5880

GTATCAACAA TGTATTAAAC ACCCGCTACA CCACATGGGA AGCGGCACGC CAACTGCCCA    5940

GCGAAGCTGC AAGCAGTACC CAATCAACCC GTTACATTGC ACCAGGTCGC AGTTACTTTG    6000

CCAGTCTTGA AATGAAGTTT TAATATGACC TGTTTACCAA AGACCAACCC TGCTTTAAAA    6060

GTCAAGCACA GATTTTTAAA GCAGGTGCTG TTATTGCTTT GTGTTGATAC ATTAACAGCA    6120

CAGGCGTACG CCCACAGCCA TCATACGCCC ATTCATACAC CCACGCATGA GCTGCCATCT    6180

GCTGATGCTT TATCAGATGA AGGCTTGGGT AAGGATTTGG GCAGTTTGGA CAGTTTGGAT    6240

AGCCCAGATG GTTGGGTGA TGGTTTAGGC GATGGTTTGG GTGATGGCTT AAAAAGTGAT    6300

AAAGCCCCTT TACCCATCAA CGCCTTGACC GCCCATCAGA CCAATGAGAG CCAGCCTGCC    6360

CCACCGAGCG TAGATGTCAA TTTTTTACTT GCCCAGCCAG AGGCATTTTA TCATGTCTTT    6420

CATCAAGCGA TTGTGCAAGA TGATGTGGCA ACATTACGCT TGTTATTGCC ATTTTATGAC    6480

CGCCTGCCTG ATGATTATCA AGATGATGTT TTGTTGTTAT TTGCCCAAAG TAAACTTGCC    6540

CTAAGTGATG GCAATACCAA ATTGGCATTG AATCTGCTGA CCGATTTGAG TAACAAAGAG    6600

CCAACACTTA CGGCGGTAAA ATTACAACTT GCTTCCTTGT TGCTGACCAA CAAGCACGAT    6660

AAACACGCCC AAATGGTGCT AGATGAACTC AAAGATGATG CCCACTTTTT AAAATTAAGC    6720

AAAAAAGAGC AAAGATGGGT GCTATCGCAA AGTCGCTATT TACATAAAAA ATATAAAATG    6780

GGCTTGGATT TGGGCATCAA CTATCTGCAT TTGGATAATA TCAACGCCGC CTCCACCATC    6840

ACCCAGCCCA ATATTAAAAA AGATGCCCCA AAACCTGCTC ATGGGCTTGC CTTATCGCTT    6900

GGTGTGAATA AATACACGCC GCTTAGTCAT GGCATGAGTA TTTATACAGC CCTAGATGTT    6960

GATGGTAAAT TTTATGATGA CAAAAGCCAC AATGAACTGG CGGTTTTTGC TCATGCTGGA    7020

CTAAGAAAAG ATCACCAAAA AGGTTATGTT GATGTCGTAC CTTTTGTTGG GCGTATTTTT    7080

GCCACCAATC AGCAGCATGG CAGATTATCC CCCAGAAAAG ACAGTCAGGG CGTGGCGTTT    7140

GGCAGCCATC ATCGGATCAA TGATAAATGG CAAAATGCGT TTTTTGCACG CATGGAAAAA    7200

GGCAATTATA CCGAGCGTTA TCAAGGTTAT GATGGCAAGC GTTATCATGT GAATGACACC    7260

ATTTTGTTGC AAGATGGCCC AAATCGTCGT TACTCTTTGG GCGTGGGGTA TCAGCTTAGC    7320

CATCTGCAAG ATGCAACAAA AAGCAGTCAT GCCACAAAGA TACATTTTGG GGTGTTGCAA    7380

AGATTGCCAA ATGGTCTGAC CGTGCAAGGT AGAGTGAGTG CTGAGCGTGA GCGTTATCAT    7440

GGTAAATTAT TGCGTCTGGT TAATCCTGAT GATGTGTATC GCACAGATAA AACCCTAACC    7500

CTACAAACCT CCATTTGGCA CAAAGACATT CACTGGCTTG GATTAACGCC AAAGCTGACT    7560

TATCGTTACA GTAAAAATAA CAGTAACTTA CCAGCACTTT ATAGCCATAA CAAACAAAAT    7620

TTTTATTTGG AGCTTGGTCG GTCGTTTTAA                                    7650
```

(2) INFORMATION FOR SEQ ID NO:2:

(i) SEQUENCE CHARACTERISTICS:
    (A) LENGTH: 2694 base pairs
    (B) TYPE: nucleic acid
    (C) STRANDEDNESS: single
    (D) TOPOLOGY: linear (xi) SEQUENCE DESCRIPTION: SEQ ID NO:2:

```
ATGAGTACTG TCAAAACCCC CCACATTTTC TACCAAAAAC GCACCCTTAG CCTTGCCATC     60

GCCAGTATTT TTGCTGCCTT GGTGATGACA GGCTGCCGCT CTGATGACAT CAGCGTCAAT    120

GCACCCAATG TTACCCAACT GCCCCAAGGC ACGGTTTCAC AATACCGAA CACAGGTCAT     180

GACAACACCA ATAACACCAA CAATCAGGGC AACAACACGG ATAACAGCAC CAGCACAACT    240

GACCCAAATG GCGATAACAA CCAACTGACA CAAGCACAAA AGACCGCCGC TGCCGCAGGG    300

TTTTTTGTGA TGGGTAAAAT TCGTGATACC AGCCCAAAAA ATGACCCAGA TTATAGCAAT    360

GATTTAGTAC AGCAGTGGCA AGGCAAATTA TATGTTGGTA TTGATGCCCA TCGCCCAGAT    420

GGCATCGGCA CAGGTAAAAA CTTGCGTCAG CCCATCACCG CCAATGACAT CAAACCCTTG    480

TATTTTAACA AATTCCCTGC ATTGTCTGAT TTGCATTTAG ACAGTGAACG CCACCGTTTT    540

GACCCCAAAA AGCTAAACAC CATTAAAGTG TATGGTTATG CAACTTAAC AACACCCTCT     600

AAAAACAACA CTTACATCAA TCATCAGCAA GCTGATAATA AGAAAAATAA CAAGCCTGTT    660

GACCCTTATG AAAATATCCG TTTTGGGTAT CTTGAACTAC AAGGAAGCAG TCTGACCCAA    720

AAAAATGCCG ATACTCCAAA TGACAAAGAC CGCATTCCCA AACCCATGCC CATTTTGTTT    780

TATCACGGAG AAAACGCCAG CAGCCAGCTG CCCAGTGCTG GTAAATTTAA CTACACAGGC    840

AACTGGCTGT ACCTAAGTGA TGTCAAAAAA CGCCCTGCAC TTTCAGCATC AGATGATCGA    900

GTGGGGGTCT ATCTCAATGC CAGTGGCAAA TCCAATGAGG GCGATGTCGT CAGTGCCGCC    960

CACATTTATC TAAACGGCTT TCAATATAAG CACACGCCTG CCACTTATCA GGTGGATTTT   1020

GACACAAACT CATTAACAGG CAAGCTGTCT TATTATGACA ATCCCAACCA GCAAACTGCC   1080

CAAGGCAAAT ACATCAAAAG CCAATTTGAC ACTACCAAAA AAGTCAATGA AACCGATGTG   1140

TATCAAATTG ATGCCAAAAT CAACGGCAAC CGCTTCGTCG GTACGGCCAA ATCTTTGGTT   1200

AATGAGAACA CAGAAACCGC ACCTTTTATC AAAGAGCTGT TCTCCAAAAA AGCCAATCCC   1260

AATAACCCAA ACCCTAATTC AGACACGCTA GAAGGCGGGT TTTATGGTGA GTCGGGCGAT   1320

GAGCTGGCGG GTAAATTTTT ATCCAATGAC AACGCATCTT ATGTGGTCTT TGGTGGTAAA   1380

CGAGACAAAA CAGACAAACC TGTCGCCACA AAAACGGTGT ATTTTAGTGC AGGCTTTGAA   1440

AAACCTAGCA CCAGTTTTGT GGATAATGAA ACGATTGGCA GAATTATTAA CAGCAAAAAG   1500

TTAAATGATG CGGTGAATGA GAAAATTGAT AATGGTGATA TTCCTACCAG TGATGAACGC   1560

TATGATGAAT TCCTTGGGG CGAAAAAAAA GCAGAATTCA CCAAAAAAGT CAGCAGCAGC   1620

ACCCAAGCCG TGCCAGCTTA TTTTGGGCAA CATGATAAAT TTTATTTTAA TGGCAACTAT   1680

TATGACCTAT CAGCCAGCAG TGTTGATAAA TTGGCCCCTG CCGATGCTGT CAAAGCCAAC   1740

CAATCCATTA AGAAAAAATA CCCTAATGCC ACACTAAATA AGGACAACCA AGTTACCGCC   1800

ATCGTGCTAC AAGAAGCCAA AGATAATAAG CCTTATACCG CCATTCGTGC CAAAAGCTAT   1860

CAGCACATCA GTTTTGGCGA GACGCTGTAT AACGATGCCA ACCAAACCCC AACACGCAGT   1920

TATTTTGTGC AAGGCGGTAG GGCAGATACC AGCACCACGC TGCCCAAGGC AGGTAAATTC   1980

ACTTACAACG GTCTTTGGGC AGGCTATCTT ATCCAAAAAA AGGACAAAGG TTATAGCAAT   2040

AATGAAGAAA CCATCAAGAA AAAAGGCCAT CAAGATTATC TGTTAACCGA AGACTTCACC   2100
```

```
CCAGAAGATG ATGACGATGA TTTGACCGCA TCTGATGATT CACAAGATGA TGATGCACAT    2160

GGCGATGATG ATTTGATTGC ATCTGATGAT TCACAAGATG ATGACGCAGA TGGCGATGAC    2220

GATTCAGATG ATTTGGGTGA TGGTGCAGAT GACGCCGCCG CAGGCAAAGT GTATCATGCA    2280

GGTAATATTC GCCCTGAATT TGAAAACAAA TACTTGCCCA TTAATGAGCC TACTCATGAA    2340

AAAACCTTTG CCCTAGATGG TAAAAATAAA GCTAAGTTTG ATGTGGATTT TGACACCAAC    2400

AGCCTAACTG GTAAATTAAA CGATGAGAGA GGTGATATCG TCTTTGATAT CAAAAATGGC    2460

AAAATTGATG GCACAGGCTT TACCGCCAAA GCCGATGTGC CAAACTATCG TGAAGAAGTG    2520

GGTAACAACC AAGGTGGCGG TTTCTTATAC AACATCAAAG ATATTGATGT CAAGGGGCAA    2580

TTTTTTGGCA CAAATGGCGA AGAGTTGGCA GGGCAGTTAC AGTACGACAA AGGCGATGGC    2640

ATCAATGACA CCGCCGAAAA AGCAGGGGCT GTCTTTGGGG CTGTTAAAGA TAAA          2694

(2) INFORMATION FOR SEQ ID NO:3:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (xi) SEQUENCE DESCRIPTION: SEQ ID NO:3:

ATGTCAAAAT CTATCACAAA AACACAAACA CCATCAGTCC ATACCATGAC CACGCACCGC      60

TTAAACCTTG CCATCAAAGC GGCGTTATTT GGTGTGGCAG TTTTACCCCT ATCCGTCTGG    120

GCGCAAGAGA ACACTCAGAC AGATGCCAAC TCTGATGCCA AAGACACAAA AACCCCTGTC    180

GTCTATTTAG ATGCCATCAC GGTAACCGCC GCCCCATCTG CCCCTGTTTC TCGGTTTGAC    240

ACCGATGTAA CAGGGCTTGG CAAAACGGTC AAAACCGCTG ACACGCTGGC AAAAGAACAA    300

GTGCAGGGCA TTCGTGATTT GGTGCGTTAT GAAACTGGGG TGAGTGTGGT TGAGCAGGGG    360

CGTGGTGGCA GCAGCGGATT TGCCATTCAT GGCGTGGATA AAAACCGAGT GGGCATTACC    420

GTAGATGGCA TTGCCCAAAT TCAATCCTAC AAAGATGAAT CCACCAAACG AGCTGGTGCA    480

GGCTCTGGGG CGATGAATGA GATAGAGATT GAAAACATTG CCGCCGTTGC CATCAATAAA    540

GGTGGTAATG CCCTAGAAGC AGGCTCTGGT GCGTTGGGCG GTTCGGTGGC GTTTCATACC    600

AAAGATGTGA GCGATGTCTT AAAATCTGGT AAAAATCTTG GCGCTCAAAG CAAAACCACT    660

TATAACAGCA AAAATGACCA TTTTAGTCAG ACGCTGGCAG CGGCAGGTAA AACCGAGCGT    720

GTGGAAGCGA TGGTGCAATA TACCTACCGT AAAGGCAAAG AAAACAAAGC ACACAGCGAC    780

CTAAATGGCA TCAACCAAAG CCTATATCGC TTGGGTGCAT GGCAACAAAA ATATGATTTA    840

AGAAAGCCCA ATGAACTGTT TGCAGGCACA AGCTACATCA CCGAAAGCTG TTTGGCAAGT    900

GATGACCCAA AAAGCTGCGT ACAATACCCT TATGTCTACA CCAAAGCCCG ACCAGATGGC    960

ATCGGCAATC GCAATTTTTC TGAGTTAAGC GATGCTGAAA AAGCACAATA TTTGGCATCC   1020

ACGCACCCCC ATGAGGTTGT CTCTGCCAAA GATTATACAG GCATTTATCG GTTGTTACCT   1080

GACCCCATGG ACTATCGTTC AGACTCGTAT TTGGCACGCC TTAACATCAA AATCACCCCA   1140

AATCTGGTCA GTAAACTGTT ATTAGAAGAC ACCAAGCAAA CATACAACAT TCGTGATATG   1200

CGTCATTGTA GTTACCATGG GGCAAGATTG GGCAATGATG GTAAGCCTGC AATGGTGGC    1260

TCCATTGTTC TTTGCGATGA TTATCAAGAG TATCTAAACG CCAATGACGC ATCACAAGCA   1320

TTATTTAGAC CAGGTGCTAA TGATGCCCCC ATTCCAAAAC TGGCTTATGC CAGAAGCAGT   1380

GTGTTTAACC AAGAGCATGG CAAAACTCGC TATGGGTTAA GTTTTGAGTT TAAGCCTGAC   1440
```

```
ACGCCATGGT TTAAGCAAGC AAAATTAAAC CTACACCAAC AAAATATCCA AATCATTAAC   1500

CATGACATTA AAAAATCGTG CAGCCAATAT CCTAAGGTGG ATTTAAATTG TGGCATCAGT   1560

GAAATTGGGC ATTATGAATA TCAAAATAAT TACCGTTATA AAGAAGGGCG TGCCAGCTTG   1620

ACAGGCAAAC TTGATTTTAA TTTTGACCTG CTGGGTCAGC ACGATTTGAC GGTGTTGGCT   1680

GGTGCAGATA AAGTTAAAAG CCAATTTCGT GCCAACAACC CCAGACGCAC AATCATTGAC   1740

ACCACCCAAG GCGATGCCAT CATTGATGAA AGCACGCTGA CAGCACAGGA GCAAGCCAAA   1800

TTTAAGCAAT CGGGGGCGGC ATGGATTGTC AAAAATCGCC TTGGACGCTT AGAAGAAAAA   1860

GACGCCTGTG GCAATGCCAA TGAATGTGAA CGCGCCCCCA TTCATGGCAG TAACCAATAT   1920

GTGGGCATTA CAACCTTTA TACACCAAAT GATTATGTGG ATTTAAGTTT TGGTGGACGC     1980

TTGGATAAAC AACGCATTCA CAGCACCGAT TCAAACATCA TCAGCAAAAC TTACACCAAC   2040

AAAAGCTATA ATTTTGGAGC GGCGGTTCAT CTGACACCTG ATTTTAGCCT GTTGTATAAA   2100

ACTGCCAAAG GCTTTCGTAC GCCAAGTTTT TATGAACTGT ACAACTATAA CAGCACCGCC   2160

GCCCAGCATA AAAATGACCC TGATGTGTCT TTTCCCAAAC GAGCGGTTGA TGTCAAACCT   2220

GAAACTTCCA ATACCAATGA ATACGGCTTT CGCTATCAGC ACCCTTGGGG GGATGTTGAG   2280

ATGAGCATGT TCAAAAGCCG TTACAAGGAC ATGTTAGATA AAGCCATACC GAACCTAACC   2340

AAAGCCCAAC AAGAGTATTG TAAGGCTCAT TTGGATTCCA ATGAATGTGT TGGCAATCCG   2400

CCCACGCCCA AAACCAGTGA TGAGGTATTT GCCAACTTAT ATAATGCCAC CATCAAAGGG   2460

GTGAGTGTCA AAGGCAAACT GGATTTGCAT GCCATGACAT CAAAACTGCC AGATGGTCTT   2520

GAAATGACCT TGGGTTATGG TCATACCAAA TTGGGGAAAT TTGATTACAT TGCACCCAAA   2580

GATGCCGATG GTTGGTATCA GGCTCGCCCT GCTTTTTGGG ATGCCATCAC CCCAGCGCGC   2640

TATGTGGTCG GTCTAAACTA TGACCACCCC AGTCAAGTAT GGGGCATTGG CACAACTTTA   2700

ACGCACAGCA AACAAAAAGA TGAAAATGAG CTAAGTGCCC TTAGAATCCG AAATGGCAAA   2760

AGAGAAACAC AAACCTTAAC GCACACAATA CCCAAAGCCT ATACCTTACT GGACATGACA   2820

GGCTATTATA GCCCAACTGA GAGCATCACC GCTCGTCTTG GTATCAACAA TGTATTAAAC   2880

ACCCGCTACA CCACATGGGA AGCGGCACGC CAACTGCCCA GCGAAGCTGC AAGCAGTACC   2940

CAATCAACCC GTTACATTGC ACCAGGTCGC AGTTACTTTG CCAGTCTTGA AATGAAGTTT   3000

(2) INFORMATION FOR SEQ ID NO:4:

(i) SEQUENCE CHARACTERISTICS:
        (A) LENGTH: 2955 base pairs
        (B) TYPE: nucleic acid
        (C) STRANDEDNESS: single
        (D) TOPOLOGY: linear (xi) SEQUENCE DESCRIPTION: SEQ ID NO:4:

ATGACCACGC ACCGCTTAAA CCTTGCCATC AAAGCGGCGT TATTTGGTGT GGCAGTTTTA     60

CCCCTATCCG TCTGGGCGCA AGAGAACACT CAGACAGATG CCAACTCTGA TGCCAAAGAC   120

ACAAAAACCC CTGTCGTCTA TTTAGATGCC ATCACGGTAA CCGCCGCCCC ATCTGCCCCT   180

GTTTCTCGGT TTGACACCGA TGTAACAGGG CTTGGCAAAA CGGTCAAAAC CGCTGACACG   240

CTGGCAAAAG AACAAGTGCA GGGCATTCGT GATTTGGTGC GTTATGAAAC TGGGGTGAGT   300

GTGGTTGAGC AGGGGCGTGG TGGCAGCAGC GGATTTGCCA TTCATGGCGT GGATAAAAAC   360

CGAGTGGGCA TTACCGTAGA TGGCATTGCC CAAATTCAAT CCTACAAAGA TGAATCCACC   420

AAACGAGCTG GTGCAGGCTC TGGGGCGATG AATGAGATAG AGATTGAAAA CATTGCCGCC   480
```

-continued

```
GTTGCCATCA ATAAAGGTGG TAATGCCCTA GAAGCAGGCT CTGGTGCGTT GGGCGGTTCG    540

GTGGCGTTTC ATACCAAAGA TGTGAGCGAT GTCTTAAAAT CTGGTAAAAA TCTTGGCGCT    600

CAAAGCAAAA CCACTTATAA CAGCAAAAAT GACCATTTTA GTCAGACGCT GGCAGCGGCA    660

GGTAAAACCG AGCGTGTGGA AGCGATGGTG CAATATACCT ACCGTAAAGG CAAAGAAAAC    720

AAAGCACACA GCGACCTAAA TGGCATCAAC CAAAGCCTAT ATCGCTTGGG TGCATGGCAA    780

CAAAAATATG ATTTAAGAAA GCCCAATGAA CTGTTTGCAG GCACAAGCTA CATCACCGAA    840

AGCTGTTTGG CAAGTGATGA CCCAAAAAGC TGCGTACAAT ACCCTTATGT CTACACCAAA    900

GCCCGACCAG ATGGCATCGG CAATCGCAAT TTTTCTGAGT TAAGCGATGC TGAAAAAGCA    960

CAATATTTGG CATCCACGCA CCCCCATGAG GTTGTCTCTG CCAAAGATTA TACAGGCATT   1020

TATCGGTTGT TACCTGACCC CATGGACTAT CGTTCAGACT CGTATTTGGC ACGCCTTAAC   1080

ATCAAAATCA CCCCAAATCT GGTCAGTAAA CTGTTATTAG AAGACACCAA GCAAACATAC   1140

AACATTCGTG ATATGCGTCA TTGTAGTTAC CATGGGGCAA GATTGGGCAA TGATGGTAAG   1200

CCTGCCAATG GTGGCTCCAT TGTTCTTTGC GATGATTATC AAGAGTATCT AAACGCCAAT   1260

GACGCATCAC AAGCATTATT TAGACCAGGT GCTAATGATG CCCCCATTCC AAAACTGGCT   1320

TATGCCAGAA GCAGTGTGTT TAACCAAGAG CATGGCAAAA CTCGCTATGG GTTAAGTTTT   1380

GAGTTTAAGC CTGACACGCC ATGGTTTAAG CAAGCAAAAT TAAACCTACA CCAACAAAAT   1440

ATCCAAATCA TTAACCATGA CATTAAAAAA TCGTGCAGCC AATATCCTAA GGTGGATTTA   1500

AATTGTGGCA TCAGTGAAAT TGGGCATTAT GAATATCAAA ATAATTACCG TTATAAAGAA   1560

GGGCGTGCCA GCTTGACAGG CAAACTTGAT TTTAATTTTG ACCTGCTGGG TCAGCACGAT   1620

TTGACGGTGT TGGCTGGTGC AGATAAAGTT AAAAGCCAAT TCGTGCCAA CAACCCCAGA   1680

CGCACAATCA TTGACACCAC CCAAGGCGAT GCCATCATTG ATGAAAGCAC GCTGACAGCA   1740

CAGGAGCAAG CCAAATTTAA GCAATCGGGG GCGGCATGGA TTGTCAAAAA TCGCCTTGGA   1800

CGCTTAGAAG AAAAAGACGC CTGTGGCAAT GCCAATGAAT GTGAACGCGC CCCCATTCAT   1860

GGCAGTAACC AATATGTGGG CATTAACAAC CTTTATACAC AAATGATTA TGTGGATTTA    1920

AGTTTTGGTG GACGCTTGGA TAAACAACGC ATTCACAGCA CCGATTCAAA CATCATCAGC   1980

AAAACTTACA CCAACAAAAG CTATAATTTT GGAGCGGCGG TTCATCTGAC ACCTGATTTT   2040

AGCCTGTTGT ATAAAACTGC CAAAGGCTTT CGTACGCCAA GTTTTATGA ACTGTACAAC    2100

TATAACAGCA CCGCCGCCCA GCATAAAAAT GACCCTGATG TGTCTTTTCC CAAACGAGCG   2160

GTTGATGTCA AACCTGAAAC TTCCAATACC AATGAATACG GCTTTCGCTA TCAGCACCCT   2220

TGGGGGATG TTGAGATGAG CATGTTCAAA AGCCGTTACA AGGACATGTT AGATAAAGCC    2280

ATACCGAACC TAACCAAAGC CCAACAAGAG TATTGTAAGG CTCATTTGGA TTCCAATGAA   2340

TGTGTTGGCA ATCCGCCCAC GCCCAAAACC AGTGATGAGG TATTTGCCAA CTTATATAAT   2400

GCCACCATCA AAGGGGTGAG TGTCAAAGGC AAACTGGATT TGCATGCCAT GACATCAAAA   2460

CTGCCAGATG GTCTTGAAAT GACCTTGGGT TATGGTCATA CCAAATTGGG GAAATTTGAT   2520

TACATTGCAC CCAAAGATGC CGATGGTTGG TATCAGGCTC GCCCTGCTTT TGGGATGCC    2580

ATCACCCCAG CGCGCTATGT GGTCGGTCTA AACTATGACC ACCCCAGTCA AGTATGGGGC   2640

ATTGGCACAA CTTTAACGCA CAGCAAACAA AAAGATGAAA ATGAGCTAAG TGCCCTTAGA   2700

ATCCGAAATG GCAAAAGAGA AACACAAACC TTAACGCACA CAATACCCAA AGCCTATACC   2760

TTACTGGACA TGACAGGCTA TTATAGCCCA ACTGAGAGCA TCACCGCTCG TCTTGGTATC   2820

AACAATGTAT TAAACACCCG CTACACCACA TGGGAAGCGG CACGCCAACT GCCCAGCGAA   2880
```

| | |
|---|---|
| GCTGCAAGCA GTACCCAATC AACCCGTTAC ATTGCACCAG GTCGCAGTTA CTTTGCCAGT | 2940 |
| CTTGAAATGA AGTTT | 2955 |

(2) INFORMATION FOR SEQ ID NO:5:

(i) SEQUENCE CHARACTERISTICS:
        (A) LENGTH: 1623 base pairs
        (B) TYPE: nucleic acid
        (C) STRANDEDNESS: single
        (D) TOPOLOGY: linear (xi) SEQUENCE DESCRIPTION: SEQ ID NO:5:

| | |
|---|---|
| ATGACCTGTT TACCAAAGAC CAACCCTGCT TTAAAAGTCA AGCACAGATT TTTAAAGCAG | 60 |
| GTGCTGTTAT TGCTTTGTGT TGATACATTA ACAGCACAGG CGTACGCCCA CAGCCATCAT | 120 |
| ACGCCCATTC ATACACCCAC GCATGAGCTG CCATCTGCTG ATGCTTTATC AGATGAAGGC | 180 |
| TTGGGTAAGG ATTTGGGCAG TTTGGACAGT TTGGATAGCC CAGATGGTTT GGGTGATGGT | 240 |
| TTAGGCGATG GTTTGGGTGA TGGCTTAAAA AGTGATAAAG CCCCTTTACC CATCAACGCC | 300 |
| TTGACCGCCC ATCAGACCAA TGAGAGCCAG CCTGCCCCAC CGAGCGTAGA TGTCAATTTT | 360 |
| TTACTTGCCC AGCCAGAGGC ATTTTATCAT GTCTTTCATC AAGCGATTGT GCAAGATGAT | 420 |
| GTGGCAACAT TACGCTTGTT ATTGCCATTT TATGACCGCC TGCCTGATGA TTATCAAGAT | 480 |
| GATGTTTTGT TGTTATTTGC CCAAAGTAAA CTTGCCCTAA GTGATGGCAA TACCAAATTG | 540 |
| GCATTGAATC TGCTGACCGA TTTGAGTAAC AAAGAGCCAA CACTTACGGC GGTAAAATTA | 600 |
| CAACTTGCTT CCTTGTTGCT GACCAACAAG CACGATAAAC ACGCCCAAAT GGTGCTAGAT | 660 |
| GAACTCAAAG ATGATGCCCA CTTTTTAAAA TTAAGCAAAA AAGAGCAAAG ATGGGTGCTA | 720 |
| TCGCAAAGTC GCTATTTACA TAAAAAATAT AAAATGGGCT TGGATTTGGG CATCAACTAT | 780 |
| CTGCATTTGG ATAATATCAA CGCCGCCTCC ACCATCACCC AGCCCAATAT TAAAAAAGAT | 840 |
| GCCCCAAAAC CTGCTCATGG GCTTGCCTTA TCGCTTGGTG TGAATAAATA CACGCCGCTT | 900 |
| AGTCATGGCA TGAGTATTTA TACAGCCCTA GATGTTGATG GTAAATTTTA TGATGACAAA | 960 |
| AGCCACAATG AACTGGCGGT TTTTGCTCAT GCTGGACTAA GAAAAGATCA CCAAAAAGGT | 1020 |
| TATGTTGATG TCGTACCTTT TGTTGGGCGT ATTTTTGCCA CCAATCAGCA GCATGGCAGA | 1080 |
| TTATCCCCCA GAAAAGACAG TCAGGGCGTG GCGTTTGGCA GCCATCATCG GATCAATGAT | 1140 |
| AAATGGCAAA ATGCGTTTTT TGCACGCATG GAAAAAGGCA ATTATACCGA GCGTTATCAA | 1200 |
| GGTTATGATG GCAAGCGTTA TCATGTGAAT GACACCATTT TGTTGCAAGA TGGCCCAAAT | 1260 |
| CGTCGTTACT CTTTGGGCGT GGGGTATCAG CTTAGCCATC TGCAAGATGC AACAAAAAGC | 1320 |
| AGTCATGCCA CAAAGATACA TTTTGGGGTG TTGCAAAGAT TGCCAAATGG TCTGACCGTG | 1380 |
| CAAGGTAGAG TGAGTGCTGA GCGTGAGCGT TATCATGGTA AATTATTGCG TCTGGTTAAT | 1440 |
| CCTGATGATG TGTATCGCAC AGATAAAACC CTAACCCTAC AAACCTCCAT TTGGCACAAA | 1500 |
| GACATTCACT GGCTTGGATT AACGCCAAAG CTGACTTATC GTTACAGTAA AAATAACAGT | 1560 |
| AACTTACCAG CACTTTATAG CCATAACAAA CAAAATTTTT ATTTGGAGCT TGGTCGGTCG | 1620 |
| TTT | 1623 |

(2) INFORMATION FOR SEQ ID NO:6:

(i) SEQUENCE CHARACTERISTICS:
        (A) LENGTH: 7641 base pairs
        (B) TYPE: nucleic acid
        (C) STRANDEDNESS: single (D) TOPOLOGY: linear (xi) SEQUENCE DESCRIPTION: SEQ ID NO:6:

```
AAGCTTAGCA TGATGGCATC GGCTGATTGT CTTTTTGCCT TGTTGTGTGT TTGTGGGAGT      60
TGATTGTACT TACCTTAGTG GTGGATGCTT GGGCTGATTT AATTAAATTT AATCAAAGCG     120
GTCTTCACAA CACACCAAAC GAGATATCAC CATGAGTACT GTCAAAACCC CCATATTTT     180
CTACCAAAAA CGCACCCTTA GCCTTGCCAT CGCCAGTATT TTTGCTGCCT TGGTGATGAC     240
AGGCTGCCGC TCTGATGACA TCAGCGTCAA TGCACCCAAT GTTACCCAGC TGCCCCAAGG     300
CACGGTTTCA CCAACGCCGA ACACAGGTCA TGACAACGCC AATAACACCA ACAATCAGGG     360
CAACAACACG GATAACAGCA CCAGCACAAC TGACCCAAAT GGCGATAACA ACCAACTGAC     420
ACAAGCGCAA AAAACTGCCG CCGCCGCAGG GTTTTTTGTG ATGGGTAAAA TTCGTGATAC     480
CAGCGAAAAA AATGACCCAG ATTATAGTGA TGATTTAAAA CAGCAGTGGC TGGGCAAATT     540
ATATGTTGGT ATTGATGCCC ATCGCCCAGA TGGCATCGGA AAAGGTAAAA ACTTGCGTCA     600
GCCCATCACC GCCAATGACA TCAAACCCTT GTATTTTAAC AAATTCCCTG CATTGTCTGA     660
TTTGCACTTA GACAGTGAAC GCCATCGTTT TGACCCCCAA AAGATAAACA CCATTAAAGT     720
GTATGGTTAT GGTAACTTAA CAACACCATC CAACAACAAC ACTCACATCA ATCATCAGCA     780
AGCTGATAAT AAGAAAAATA ACAAGCCTGT TGACCCTTAT GAAAATATCC GTTTTGGGTA     840
TCTTGAACTA CAAGGAAGCA GCCTGACCCA AAAAAATGCC GATAATCAAA ATGAGCAAGA     900
CCGCATTCCC AAACCCATGC CCATTTTGTT TTATCATGGA GAAAACGCCA GCAGCCAGCT     960
GCCCAGCGCT GGTAAATTTA ACTACACAGG CAACTGGCTG TACCTAAGTG ATGTCAAAAA    1020
ACGCCCTGCC CTTTCAGCAT CAGATGAGCG AGTGGGGGTC TATCTCAATG CCAGTGGCAA    1080
AGCCAACGAG GGCGATGTCG TCAGTGCCGC CCACATTTAT CTAAACGGCT TCAATATAA     1140
GCACACGCCT GCCACTTATC AGGTGGATTT TGACACAAAC TCATTAACAG GCAAGCTGTC    1200
CTATTATGAC AATCCCAATC AGCAAAATAA TAAAGGCGAA TATCTCAAAA GCCAATTTGA    1260
CACTACCAAA AAAGTCAATG AAACCGATGT GTATCAAATT GATGCCAAAA TCAACGGTAA    1320
CCGCTTTGTC GGTACGGCCA AATCTTTGGT TAATGAGAAA ACACAAACCG CACCTTTTAT    1380
CAAAGAGCTG TTCTCCAAAA AAGCCAACCC CAATAACCCA AACCCTAATT CAGACACGCT    1440
AGAAGGCGGA TTTTATGGTG AGTCGGGCGA TGAGCTGGCG GGTAAATTTT TATCCAATGA    1500
CAACGCATCT TATGTGGTCT TTGGTGGCAA ACGAGACAAA ACGACTAAAC CTGTCGCCAC    1560
AAAAACGGTG TATTTAGTG CAGGCTTTGA AAAACCCAGC ACCAGTTTTG TGGATAATGA    1620
AACGATTGGT GGAATTATTG ACCGTAAAGG GTTAAATAAT CACATTAATG AAGATGAAAT    1680
TATTCCCAGT GATGATAGTT ATTATGGATA TACTTGGGGC AAGCCAGAGA AGCAGTTCAC    1740
CAAAAAAGTC AGCAGCAGCA CCCAAGTCGT GCCAGCTTAT TTTGGGCAAC ATGATAAATT    1800
TTATTTTAAT GGCAACTATT ATGACCTATC AGCCAGTCGT GTTGATAAAT TAGCCCCTGC    1860
CGATGCTGTC AAAGCCAACC AATCCATTAA AGAAAAATAC CCTAATGCCA CACTAAATAA    1920
GGACAACCAA GTTACCGCCA TCGTGCTACA AGAAGCCAAA GATAATAAGC CTTATACCGC    1980
CATTCGTGCC AAAAGCTATC AGCACATCAG TTTTGGCGAG ACGCTGTATA ACGATGCCAA    2040
CCAAACCCCA ACACGCAGTT ATTTTGTGCA AGGCGGTAGG GCAGATACCA GCACAACTTT    2100
GCCCCAGGCA GGTAAATTCA CTTACAACGG TCTTTGGGCA GGCTACCTGA CCCAAAAAAA    2160
GGACAAAGGT TATAGCGATA ATGCAGAAAC CATCAAGGAA AAAGGTCATC CAGGTTATCT    2220
GTTAACCGAA AACTTCACCC CAGAAGATGA TGACGATGAT TTGACCGCAT CTGATGATTC    2280
```

-continued

```
ACAAGATGAT AATACACATG GCGATGATGA TTTGATTGCA TCTGATGATT CACAAGATGA    2340

TGACGCAGAT GGAGATGACG ATTCAGATGA TTTGGGTGAT GGTGCAGATG ATGACGCCGC    2400

AGGCAAAGTG TATCATGCAG GTAATATTCG CCCTGAATTT GAAAACAAAT ACTTGCCCAT    2460

TAATGAGCCT ACTCATGAAA AAACCTTTGC CCTAGATGGT AAAAATAAAG CTAAGTTTGA    2520

AGTGGATTTT AACACCAACA GCCTAACTGG TAAATTAAAC GATGAGAGAG GTGATATCGT    2580

CTTTGATATC AAAAATGGCA AAATTGATGG CACAGGATTT ACCGCCAAAG CCGATGTGCC    2640

AAACTATCGT GAAGAAGTGG GTAACAACCA AGGTGGCGGT TTCTTATACA ACATCAAAGA    2700

TATTGATGTT AAGGGGCAAT TTTTTGGCAC AAATGGCGAA GAGTTGGCAG ACAGTTACA     2760

TCATGACAAA GGCGATGGCA TCAATGACAC CGCCGAAAAA GCAGGGCTG TCTTTGGGGC     2820

TGTTAAAGAT AAATAAAGCC CCCCTTCATC ATCGTTTAGT CGCTTGACCG ACAGTTGATG    2880

ACGCCCTTGG CAATGTCTTA AAACAGCACT TTGAAACAGT GCCTTGGGCG AATTCTTGGA    2940

TAAATGCACC AGATTTGCCT TGGGCTAATA TCTTGATAAA ACATCGCCAT AAAATAGAAA    3000

ATAAAGTTTA GGATTTTTTT ATGTCAAAAT CTATACACAA AACACAAACA CCATCAGTCC    3060

ATACCATGAC CACGCACCGC TTAAACCTTG CCATCAAAGC GGCGTTATTT GGTGTGGCAG    3120

TTTTACCCCT ATCCGTCTGG GCGCAAGAGA ACACTCAGAC AGATGCCAAC TCTGATGCCA    3180

AAGCACAAAA AACCCCTGTC GTCTATTTAG ATGCCATCAC GGTAACCGCC GCCCCATCTG    3240

CCCCTGTTTC TCGGTTTGAC ACCGATGTAA CAGGGCTTGG CAAAACCGTC AAAACCGCTG    3300

ACACGCTGGC AAAAGAACAA GTACAGGGCA TTCGTGATTT GGTGCGTTAT GAAACTGGGG    3360

TGAGTGTGGT TGAGCAGGGG CGTGGTGGCA GCAGCGGATT TGCCATTCAT GGCGTGGATA    3420

AAAACCGAGT GGGCATTACC GTAGATGGCA TTGCCCAAAT TCAATCCTAC AAAGACGAAT    3480

CCACTAAGCG AGCTGGGGCA GGCTCTGGGG CGATGAACGA GATAGAGATT GAAAACATTG    3540

CCGCCGTTGC CATCAATAAA GGCGGTAATG CCTTAGAAGC AGGCTCTGGT GCGTTGGGTG    3600

GTTCGGTGGC GTTTCATACC AAAGATGTGA GCGATGTCTT AAAATCTGGT AACAATCTTG    3660

GTGCTCAAAG CAAAACCACT TATAACAGCA AAAATGACCA TTTTAGTCAG ACGCTGGCAG    3720

CGGCAGGTAA AACCGAGCGT GTGGAAGCGA TGGTGCAATA TACCTACCGT AAAGGCAAAG    3780

AAAACAAAGC ACACAGCGAC CTAAATGGCA TCAACCAAAG CCTATATCGC TTGGGTGCAT    3840

GGCAACAAAA ATATGATTTA AGAAAGCCTA ACGAACTGTT TGCAGGCACA AGCTATATCA    3900

CCGAAAGCTG TTTGGCAAGT GATGACCCAA AAAGCTGCGT ACAATACCCT TATGTCTACA    3960

CCAAAGCCCG ACCAGATGGT ATCGGCAATC GCAATTTTTC TGAGTTAAGC GATGCTGAAA    4020

AAGCACAATA TTTGGCGTCC ACGCACCCCC ATGAGGTTGT CTCTGCCAAA GATTATACAG    4080

GCACTTATCG GTTGTTACCT GACCCCATGG ACTATCGTTC AGACTCGTAT TTGGCACGCC    4140

TTAACATCAA AATCACCCCA AATTTGGTCA GTAAACTGTT ATTAGAAGAC ACCAAGCAAA    4200

CATACAACAT TCGTGATATG CGTCATTGTA GTTATCATGG GGCAAGATTG GGCAATGACG    4260

GTAAGCCTGC CAATGGCGGC TCCATTGTCC TTTGCGATGA TTATCAAGAG TATCTAAATG    4320

CCAATGACGC ATCACAAGCA TCATTTAGAC CAGGGGCTAA TGACGCCCCC ATTCCAAAAC    4380

TGGCTTATGC CAGAAGCAGT GTGTTTAACC AAGAGCATGG CAAAACTCGC TATGGGTTAG    4440

GTTTTGAGTT TAAGCCTGAC ACGCCATGGT TTAAACAAGC AAAATTAAAC CTACATCAAC    4500

AAAATATCCA AATCATTAAC CATGACATTA AAAAATCGTG CAGCCAATAT CCCAAGGTGG    4560

ATTTAAATTG TGGCATCAGT GAAATTGGGC ATTATGAATA TCAAAACAAT TACCGTTATA    4620
```

-continued

```
AAGAAGGGCG TACCAGTTTG ACAGGCAAAC TTGATTTTAA TTTTGACCTG CTGGGCCAGC    4680

ACGATTTGAC GGTGTTGGCT GGTGCAGATA AAGTTAAAAG CCAATTTCGT GCCAACAACC    4740

CCAGACGCAC AATCATTGAC ACCACCCAAG GCGATGCCAT CATTGATGAA AGCACGCTGA    4800

CAGCACAGGA GCAAGCCAAA TTTAAGCAAT CAGGGGCAGC ATGGATTGTC AAAAATCGCT    4860

TAGGACGCTT AGAAGAAAAA GACGCCTGTG GCAATGCCAA TGAATGTGAA CGCGCGCCCA    4920

TTCATGGCAG TAACCAATAT GTGGGCATTA ACAACCTTTA TACACCAAAT GATTATGTGG    4980

ATTTAAGTTT TGGTGGACGC TTGGATAAAC AACGCATTCA CAGCACCGAT TCAAACATCA    5040

TCAGCAAAAC TTACACCAAC AAAAGCTATA ATTTTGGAGC GGCGGTTCAT CTGACACCTG    5100

ATTTTAGCCT GTTGTATAAA ACTGCCAAAG GCTTTCGTAC GCCAAGTTTT TATGAACTGT    5160

ACAACTATAA CAGCACCGCC GCCCAGCATA AAAATGACCC TGATGTGTCT TTTCCCAAAC    5220

GAGCGGTTGA TGTCAAACCT GAAACTTCCA ATACCAATGA ATACGGCTTT CGCTATCAGC    5280

ACCCTTGGGG GGATATTGAG ATGAGCATGT TCAAAAGCCG TTACAAGGAC ATGTTAGATA    5340

AAGCCATACC GAACCTAACC AAAGCCCAGC AAGAGTATTG TAAGGCTCAT TTGGATTCCA    5400

ATGAATGTGT TGGTAATCCA CCCACGCCCA AAACCAGTGA TGAGGTATTT GCCAACTTAT    5460

ATAATGCCAC CATCAAAGGG GTGAGTGTCA AAGGCAAACT GGATTTGCAT GCCATGACAT    5520

CAAAACTGCC AGATGGTCTT GAAATGACCT TGGGTTATGG TCATACCAAA TTGGGGAAAT    5580

TTGATTACAT TGCACCCAAA GATGCCGATG GTTGGTATCA GGCTCGCCCT GCTTTTTGGG    5640

ATGCCATCAC CCCAGCGCGC TATGTGGTCG GTCTAAACTA TGACCACCCC AGTCAAGTAT    5700

GGGGCATTGG CACAACTTTA ACGCACAGCA AACAAAAAGA TGAAAATGAG CTAAGTGCCC    5760

TTAGAATCCG AAATGGCAAA AGAGAAATAC AAACCTTAAC GCACACAATA CCCAAAGCCT    5820

ATACCTTACT GGACATGACA GGCTATTATA GCCCAACTGA GAGCATCACC GCTCGTCTTG    5880

GTATCAACAA TGTATTAAAC ACCCGCTACA CCACATGGGA AGCGGCACGC CAACTGCCCA    5940

GCGAAGCTGC AAGCAGTACC CAATCAACCC GTTACATTGC ACCAGGTCGC AGTTACTTTG    6000

CCAGTCTTGA AATGAAGTTT TAATATGACC TGTTTACCAA AGACCAACCC TGCTTTAAAA    6060

GTCAAGCACA GATTTTTAAA GCAGGTGCTG TTATTGCTTT GTGTTGATAC ATTAACAGCA    6120

CAGGCGTACG CCCACAGCCA TCATACGCCC ATTCATACAC CCACGCATGA GCTGTCATCT    6180

GCTGATGCTT TATCAGATGA AGGCTTGGGT AAGGATTTGG GCAGTTTGGA CAGCCCAGAT    6240

GGTTTGGGTG ATGGTTTAGG CGATGGTTTG GGTGATGGCT TAAAAAGTGA TAAAACCCCT    6300

TTACCCATCA ACGCCTTGAC CGTTAATCAG AGCAATGAGA GCCAGCCTGC CCCACCGAGC    6360

GTAGATGTCA ATTTTTTACT TGCCCAGCCA GAGGCATTTT ATCATGTCTT TCATCAAGCG    6420

ATTGTGCAAG ATGATGTGGC AACATTACGC TTGTTATTGC CATTTATGA CCGCCTGCCT    6480

GATGATTATC AAGATGATGT TTTGTTGTTA TTTGCCCAAA GTAAACTTGC CCTAAGTGAT    6540

GGCAATACCA AATTGGCATT GAATCTGCTG ACCGATTTGA GTAACAAAGA GCCAACACTT    6600

ACGGCGGTAA AATTACAACT TGCTTCCTTG TTGCTGACCA ACAAGCACGA TAAACACGCC    6660

CAAATGGTGC TAGATGAACT CAAAGATGAT GCCCACTTTT TAAAATTAAG CAAAAAAGAG    6720

CAAAGATGGG TGCTATCGCA AAGTCGCTAT TTACATAAAA AATATAAAAT GGGCTTGGAT    6780

TTGGGCATCA ACTATCTGCA TTTGGATAAT ATCAACGCCG CCTCCACCAT CACCCAGCCC    6840

AACATTAAAA AAGATGCCCC AAAACCTGCT CATGGGCTTG CCTTATCGCT TGGTGTGAAT    6900

AAATACACGC CGCTTAGTCA TGGCATGAGT ATTTATACAG CCCTAGATGT TGATGGTAAA    6960

TTTTATGATG ACAAAAGCCA CAATGAACTG GCGGTTTTTG CTCATGCTGG ACTAAGAAAA    7020
```

-continued

```
GATCACCAAA AAGGTTATGT TGATGTCGTA CCTTTTGTTG GGCGTATTTT TGCCACCAAT      7080

CAGCAGCATG GCAGATTATC CCCCAGAAAA GACAGTCAGG GCGTGGCGTT TGGCAGCCAT      7140

CATCGGATCA ATGATAAATG GCAAAATGCG TTTTTTGCAC GCATGGAAAA AGGCAATTAT      7200

ACCGAGCATT ATCAAGGTTA TGATGGCAAG CGTTATCATG TGAATGACAC CATTTTGTTG      7260

CAAGATGGCC CAAATCGTCG TTACTCTTTG GGCGTGGGGT ATCAGCTTAG CCATCTGCAA      7320

GATGCAACAA AAAGCAGTCA TGCCACAAAG ATACATTTTG GGTGTTGCA AAGATTGCCA       7380

AATGGTCTGA CCGTGCAAGG TAGAGTGAGT GCTGAGCGTG AGCGTTATCA TGGTAAATTA     7440

TTGCGTCTGG TTAATCCTGA TGATGTGTAT CGCACAGATA AAACCCTAAC CCTACAAACC     7500

TCCATTTGGC ACAAAGACAT TCACTGGCTT GGATTAACGC CAAAGCTGAC TTATCGTTAC     7560

AGTAAAAATA ACAGTAACTT ACCAGCACTT TATAGCCATA ACAAACAAAA TTTTTATTTG     7620

GAGCTTGGTC GGTCGTTTTA A                                              7641
```

(2) INFORMATION FOR SEQ ID NO:7:

(i) SEQUENCE CHARACTERISTICS:
        (A) LENGTH: 2682 base pairs
        (B) TYPE: nucleic acid
        (C) STRANDEDNESS: single
        (D) TOPOLOGY: linear (xi) SEQUENCE DESCRIPTION: SEQ ID NO:7:

```
ATGAGTACTG TCAAAACCCC CCATATTTTC TACCAAAAAC GCACCCTTAG CCTTGCCATC       60

GCCAGTATTT TTGCTGCCTT GGTGATGACA GGCTGCCGCT CTGATGACAT CAGCGTCAAT      120

GCACCCAATG TTACCCAGCT GCCCCAAGGC ACGGTTTCAC CAACGCCGAA CACAGGTCAT      180

GACAACGCCA ATAACACCAA CAATCAGGGC AACAACACGG ATAACAGCAC CAGCACAACT     240

GACCCAAATG GCGATAACAA CCAACTGACA CAAGCGCAAA AAACTGCCGC CGCCGCAGGG     300

TTTTTTGTGA TGGGTAAAAT TCGTGATACC AGCGAAAAAA ATGACCCAGA TTATAGTGAT     360

GATTTAAAAC AGCAGTGGCT GGGCAAATTA TATGTTGGTA TTGATGCCCA TCGCCCAGAT     420

GGCATCGGAA AAGGTAAAAA CTTGCGTCAG CCCATCACCG CCAATGACAT CAAACCCTTG     480

TATTTTAACA AATTCCCTGC ATTGTCTGAT TTGCACTTAG ACAGTGAACG CCATCGTTTT     540

GACCCCCAAA AGATAAACAC CATTAAAGTG TATGGTTATG GTAACTTAAC AACACCATCC     600

AACAACAACA CTCACATCAA TCATCAGCAA GCTGATAATA AGAAAAATAA CAAGCCTGTT     660

GACCCTTATG AAAATATCCG TTTTGGGTAT CTTGAACTAC AAGGAAGCAG CCTGACCCAA     720

AAAAATGCCG ATAATCAAAA TGAGCAAGAC CGCATTCCCA AACCCATGCC CATTTTGTTT     780

TATCATGGAG AAAACGCCAG CAGCCAGCTG CCCAGCGCTG GTAAATTTAA CTACACAGGC     840

AACTGGCTGT ACCTAAGTGA TGTCAAAAAA CGCCCTGCCC TTTCAGCATC AGATGAGCGA     900

GTGGGGGTCT ATCTCAATGC CAGTGGCAAA GCCAACGAGG GCGATGTCGT CAGTGCCGCC     960

CACATTTATC TAAACGGCTT TCAATATAAG CACACGCCTG CCACTTATCA GGTGGATTTT    1020

GACACAAACT CATTAACAGG CAAGCTGTCC TATTATGACA ATCCCAATCA GCAAAATAAT    1080

AAAGGCGAAT ATCTCAAAAG CCAATTTGAC ACTACCAAAA AAGTCAATGA AACCGATGTG    1140

TATCAAATTG ATGCCAAAAT CAACGGTAAC CGCTTTGTCG GTACGGCCAA ATCTTTGGTT    1200

AATGAGAAAA CACAAACCGC ACCTTTTATC AAAGAGCTGT TCTCCAAAAA AGCCAACCCC    1260

AATAACCCAA ACCCTAATTC AGACACGCTA GAAGGCGGAT TTTATGGTGA GTCGGGCGAT    1320

GAGCTGGCGG GTAAATTTTT ATCCAATGAC AACGCATCTT ATGTGGTCTT TGGTGGCAAA    1380
```

```
CGAGACAAAA CGACTAAACC TGTCGCCACA AAAACGGTGT ATTTTAGTGC AGGCTTTGAA    1440

AAACCCAGCA CCAGTTTTGT GGATAATGAA ACGATTGGTG GAATTATTGA CCGTAAAGGG    1500

TTAAATAATC ACATTAATGA AGATGAAATT ATTCCCAGTG ATGATAGTTA TTATGGATAT    1560

ACTTGGGGCA AGCCAGAGAA GCAGTTCACC AAAAAAGTCA GCAGCAGCAC CCAAGTCGTG    1620

CCAGCTTATT TTGGGCAACA TGATAAATTT TATTTTAATG GCAACTATTA TGACCTATCA    1680

GCCAGTCGTG TTGATAAATT AGCCCCTGCC GATGCTGTCA AAGCCAACCA ATCCATTAAA    1740

GAAAAATACC CTAATGCCAC ACTAAATAAG GACAACCAAG TTACCGCCAT CGTGCTACAA    1800

GAAGCCAAAG ATAATAAGCC TTATACCGCC ATTCGTGCCA AAAGCTATCA GCACATCAGT    1860

TTTGGCGAGA CGCTGTATAA CGATGCCAAC CAAACCCCAA CACGCAGTTA TTTTGTGCAA    1920

GGCGGTAGGG CAGATACCAG CACAACTTTG CCCCAGGCAG GTAAATTCAC TTACAACGGT    1980

CTTTGGGCAG GCTACCTGAC CCAAAAAAAG GACAAAGGTT ATAGCGATAA TGCAGAAACC    2040

ATCAAGGAAA AAGGTCATCC AGGTTATCTG TTAACCGAAA ACTTCACCCC AGAAGATGAT    2100

GACGATGATT TGACCGCATC TGATGATTCA CAAGATGATA ATACACATGG CGATGATGAT    2160

TTGATTGCAT CTGATGATTC ACAAGATGAT GACGCAGATG GAGATGACGA TTCAGATGAT    2220

TTGGGTGATG GTGCAGATGA TGACGCCGCA GGCAAAGTGT ATCATGCAGG TAATATTCGC    2280

CCTGAATTTG AAAACAAATA CTTGCCCATT AATGAGCCTA CTCATGAAAA AACCTTTGCC    2340

CTAGATGGTA AAAATAAAGC TAAGTTTGAA GTGGATTTTA ACACCAACAG CCTAACTGGT    2400

AAATTAAACG ATGAGAGAGG TGATATCGTC TTTGATATCA AAAATGGCAA AATTGATGGC    2460

ACAGGATTTA CCGCCAAAGC CGATGTGCCA AACTATCGTG AAGAAGTGGG TAACAACCAA    2520

GGTGGCGGTT TCTTATACAA CATCAAAGAT ATTGATGTTA AGGGGCAATT TTTTGGCACA    2580

AATGGCGAAG AGTTGGCAGG ACAGTTACAT CATGACAAAG GCGATGGCAT CAATGACACC    2640

GCCGAAAAAG CAGGGGCTGT CTTTGGGGCT GTTAAAGATA AA                       2682

(2) INFORMATION FOR SEQ ID NO:8:
        (i) SEQUENCE CHARACTERISTICS:
            (A) LENGTH: 3000 base pairs
            (B) TYPE: nucleic acid
            (C) STRANDEDNESS: single
            (D) TOPOLOGY: linear (xi) SEQUENCE DESCRIPTION: SEQ ID NO:8:

ATGTCAAAAT CTATCACAAA AACACAAACA CCATCAGTCC ATACCATGAC CACGCACCGC      60

TTAAACCTTG CCATCAAAGC GGCGTTATTT GGTGTGGCAG TTTTACCCCT ATCCGTCTGG     120

GCGCAAGAGA ACACTCAGAC AGATGCCAAC TCTGATGCCA AGACACAAA  AACCCCTGTC     180

GTCTATTTAG ATGCCATCAC GGTAACCGCC GCCCCATCTG CCCCTGTTTC TCGGTTTGAC     240

ACCGATGTAA CAGGGCTTGG CAAAACCGTC AAAACCGCTG ACACGCTGGC AAAAGAACAA     300

GTACAGGGCA TTCGTGATTT GGTGCGTTAT GAAACTGGGG TGAGTGTGGT TGAGCAGGGG     360

CGTGGTGGCA GCAGCGGATT TGCCATTCAT GGCGTGGATA AAAACCGAGT GGGCATTACC     420

GTAGATGGCA TTGCCCAAAT TCAATCCTAC AAAGACGAAT CCACTAAGCG AGCTGGGGCA     480

GGCTCTGGGG CGATGAACGA GATAGAGATT GAAAACATTG CCGCCGTTGC CATCAATAAA     540

GGCGGTAATG CCTTAGAAGC AGGCTCTGGT GCGTTGGGTG GTTCGGTGGC GTTTCATACC     600

AAAGATGTGA GCGATGTCTT AAAATCTGGT AACAATCTTG GTGCTCAAAG CAAAACCACT     660

TATAACAGCA AAAATGACCA TTTTAGTCAG ACGCTGGCAG CGGCAGGTAA AACCGAGCGT     720
```

```
GTGGAAGCGA TGGTGCAATA TACCTACCGT AAAGGCAAAG AAAACAAAGC ACACAGCGAC      780

CTAAATGGCA TCAACCAAAG CCTATATCGC TTGGGTGCAT GGCAACAAAA ATATGATTTA      840

AGAAAGCCTA ACGAACTGTT TGCAGGCACA AGCTATATCA CCGAAAGCTG TTTGGCAAGT      900

GATGACCCAA AAAGCTGCGT ACAATACCCT TATGTCTACA CCAAAGCCCG ACCAGATGGT      960

ATCGGCAATC GCAATTTTTC TGAGTTAAGC GATGCTGAAA AGCACAATA TTTGGCGTCC      1020

ACGCACCCCC ATGAGGTTGT CTCTGCCAAA GATTATACAG GCACTTATCG GTTGTTACCT      1080

GACCCCATGG ACTATCGTTC AGACTCGTAT TTGGCACGCC TTAACATCAA AATCACCCCA      1140

AATTTGGTCA GTAAACTGTT ATTAGAAGAC ACCAAGCAAA CATACAACAT TCGTGATATG      1200

CGTCATTGTA GTTATCATGG GGCAAGATTG GGCAATGACG GTAAGCCTGC CAATGGCGGC      1260

TCCATTGTCC TTTGCGATGA TTATCAAGAG TATCTAAATG CCAATGACGC ATCACAAGCA      1320

TCATTTAGAC CAGGGGCTAA TGACGCCCCC ATTCCAAAAC TGGCTTATGC CAGAAGCAGT      1380

GTGTTTAACC AAGAGCATGG CAAAACTCGC TATGGGTTAG GTTTTGAGTT TAAGCCTGAC      1440

ACGCCATGGT TTAAACAAGC AAAATTAAAC CTACATCAAC AAAATATCCA AATCATTAAC      1500

CATGACATTA AAAATCGTG CAGCCAATAT CCCAAGGTGG ATTTAAATTG TGGCATCAGT      1560

GAAATTGGGC ATTATGAATA TCAAAACAAT TACCGTTATA AGAAGGGCG TACCAGTTTG      1620

ACAGGCAAAC TTGATTTTAA TTTTGACCTG CTGGGCCAGC ACGATTTGAC GGTGTTGGCT      1680

GGTGCAGATA AAGTTAAAAG CCAATTTCGT GCCAACAACC CCAGACGCAC AATCATTGAC      1740

ACCACCCAAG GCGATGCCAT CATTGATGAA AGCACGCTGA CAGCACAGGA GCAAGCCAAA      1800

TTTAAGCAAT CAGGGGCAGC ATGGATTGTC AAAAATCGCT TAGGACGCTT AGAAGAAAAA      1860

GACGCCTGTG GCAATGCCAA TGAATGTGAA CGCGCGCCCA TTCATGGCAG TAACCAATAT      1920

GTGGGCATTA CAACCTTTA TACACCAAAT GATTATGTGG ATTTAAGTTT TGGTGGACGC      1980

TTGGATAAAC AACGCATTCA CAGCACCGAT TCAAACATCA TCAGCAAAAC TTACACCAAC      2040

AAAAGCTATA ATTTTGGAGC GGCGGTTCAT CTGACACCTG ATTTTAGCCT GTTGTATAAA      2100

ACTGCCAAAG GCTTTCGTAC GCCAAGTTTT TATGAACTGT ACAACTATAA CAGCACCGCC      2160

GCCCAGCATA AAAATGACCC TGATGTGTCT TTTCCCAAAC GAGCGGTTGA TGTCAAACCT      2220

GAAACTTCCA ATACCAATGA ATACGGCTTT CGCTATCAGC ACCCTTGGGG GGATATTGAG      2280

ATGAGCATGT TCAAAAGCCG TTACAAGGAC ATGTTAGATA AGCCATACC GAACCTAACC      2340

AAAGCCCAGC AAGAGTATTG TAAGGCTCAT TTGGATTCCA ATGAATGTGT TGGTAATCCA      2400

CCCACGCCCA AAACCAGTGA TGAGGTATTT GCCAACTTAT ATAATGCCAC CATCAAAGGG      2460

GTGAGTGTCA AAGGCAAACT GGATTTGCAT GCCATGACAT CAAAACTGCC AGATGGTCTT      2520

GAAATGACCT TGGGTTATGG TCATACCAAA TTGGGGAAAT TTGATTACAT TGCACCCAAA      2580

GATGCCGATG GTTGGTATCA GGCTCGCCCT GCTTTTTGGG ATGCCATCAC CCCAGCGCGC      2640

TATGTGGTCG GTCTAAACTA TGACCACCCC AGTCAAGTAT GGGGCATTGG CACAACTTTA      2700

ACGCACAGCA AACAAAAAGA TGAAAATGAG CTAAGTGCCC TTAGAATCCG AAATGGCAAA      2760

AGAGAAATAC AAACCTTAAC GCACACAATA CCCAAAGCCT ATACCTTACT GGACATGACA      2820

GGCTATTATA GCCCAACTGA GAGCATCACC GCTCGTCTTG GTATCAACAA TGTATTAAAC      2880

ACCCGCTACA CCACATGGGA AGCGGCACGC CAACTGCCCA GCGAAGCTGC AAGCAGTACC      2940

CAATCAACCC GTTACATTGC ACCAGGTCGC AGTTACTTTG CCAGTCTTGA AATGAAGTTT      3000
```

(2) INFORMATION FOR SEQ ID NO:9:

(i) SEQUENCE CHARACTERISTICS:
    (A) LENGTH: 2955 base pairs
    (B) TYPE: nucleic acid
    (C) STRANDEDNESS: single
    (D) TOPOLOGY: linear (xi) SEQUENCE DESCRIPTION: SEQ ID NO:9:

| | | | | | |
|---|---|---|---|---|---|
| ATGACCACGC | ACCGCTTAAA | CCTTGCCATC | AAAGCGGCGT | TATTTGGTGT | GGCAGTTTTA | 60 |
| CCCCTATCCG | TCTGGGCGCA | AGAGAACACT | CAGACAGATG | CCAACTCTGA | TGCCAAAGAC | 120 |
| ACAAAAACCC | CTGTCGTCTA | TTTAGATGCC | ATCACGGTAA | CCGCCGCCCC | ATCTGCCCCT | 180 |
| GTTTCTCGGT | TTGACACCGA | TGTAACAGGG | CTTGGCAAAA | CCGTCAAAAC | CGCTGACACG | 240 |
| CTGGCAAAAG | AACAAGTACA | GGGCATTCGT | GATTTGGTGC | GTTATGAAAC | TGGGGTGAGT | 300 |
| GTGGTTGAGC | AGGGGCGTGG | TGGCAGCAGC | GGATTTGCCA | TTCATGGCGT | GGATAAAAAC | 360 |
| CGAGTGGGCA | TTACCGTAGA | TGGCATTGCC | CAAATTCAAT | CCTACAAAGA | CGAATCCACT | 420 |
| AAGCGAGCTG | GGGCAGGCTC | TGGGGCGATG | AACGAGATAG | AGATTGAAAA | CATTGCCGCC | 480 |
| GTTGCCATCA | ATAAAGGCGG | TAATGCCTTA | GAAGCAGGCT | CTGGTGCGTT | GGGTGGTTCG | 540 |
| GTGGCGTTTC | ATACCAAAGA | TGTGAGCGAT | GTCTTAAAAT | CTGGTAACAA | TCTTGGTGCT | 600 |
| CAAAGCAAAA | CCACTTATAA | CAGCAAAAAT | GACCATTTTA | GTCAGACGCT | GGCAGCGGCA | 660 |
| GGTAAAACCG | AGCGTGTGGA | AGCGATGGTG | CAATATACCT | ACCGTAAAGG | CAAAGAAAAC | 720 |
| AAAGCACACA | GCGACCTAAA | TGGCATCAAC | CAAAGCCTAT | ATCGCTTGGG | TGCATGGCAA | 780 |
| CAAAAATATG | ATTTAAGAAA | GCCTAACGAA | CTGTTTGCAG | GCACAAGCTA | TATCACCGAA | 840 |
| AGCTGTTTGG | CAAGTGATGA | CCCAAAAAGC | TGCGTACAAT | ACCCTTATGT | CTACACCAAA | 900 |
| GCCCGACCAG | ATGGTATCGG | CAATCGCAAT | TTTTCTGAGT | TAAGCGATGC | TGAAAAAGCA | 960 |
| CAATATTTGG | CGTCCACGCA | CCCCCATGAG | GTTGTCTCTG | CCAAAGATTA | TACAGGCACT | 1020 |
| TATCGGTTGT | TACCTGACCC | CATGGACTAT | CGTTCAGACT | CGTATTTGGC | ACGCCTTAAC | 1080 |
| ATCAAAATCA | CCCCAAATTT | GGTCAGTAAA | CTGTTATTAG | AAGACACCAA | GCAAACATAC | 1140 |
| AACATTCGTG | ATATGCGTCA | TTGTAGTTAT | CATGGGGCAA | GATTGGGCAA | TGACGGTAAG | 1200 |
| CCTGCCAATG | GCGGCTCCAT | TGTCCTTTGC | GATGATTATC | AAGAGTATCT | AAATGCCAAT | 1260 |
| GACGCATCAC | AAGCATCATT | TAGACCAGGG | GCTAATGACG | CCCCCATTCC | AAAACTGGCT | 1320 |
| TATGCCAGAA | GCAGTGTGTT | TAACCAAGAG | CATGGCAAAA | CTCGCTATGG | GTTAGGTTTT | 1380 |
| GAGTTTAAGC | CTGACACGCC | ATGGTTTAAA | CAAGCAAAAT | TAAACCTACA | TCAACAAAAT | 1440 |
| ATCCAAATCA | TTAACCATGA | CATTAAAAAA | TCGTGCAGCC | AATATCCCAA | GGTGGATTTA | 1500 |
| AATTGTGGCA | TCAGTGAAAT | TGGGCATTAT | GAATATCAAA | ACAATTACCG | TTATAAAGAA | 1560 |
| GGGCGTACCA | GTTTGACAGG | CAAACTTGAT | TTTAATTTTG | ACCTGCTGGG | CCAGCACGAT | 1620 |
| TTGACGGTGT | TGGCTGGTGC | AGATAAAGTT | AAAAGCCAAT | TCGTGCCAA | CAACCCCAGA | 1680 |
| CGCACAATCA | TTGACACCAC | CCAAGGCGAT | GCCATCATTG | ATGAAAGCAC | GCTGACAGCA | 1740 |
| CAGGAGCAAG | CCAAATTTAA | GCAATCAGGG | GCAGCATGGA | TTGTCAAAAA | TCGCTTAGGA | 1800 |
| CGCTTAGAAG | AAAAAGACGC | CTGTGGCAAT | GCCAATGAAT | GTGAACGCGC | GCCCATTCAT | 1860 |
| GGCAGTAACC | AATATGTGGG | CATTAACAAC | CTTTATACAC | AAATGATTA | TGTGGATTTA | 1920 |
| AGTTTTGGTG | GACGCTTGGA | TAAACAACGC | ATTCACAGCA | CCGATTCAAA | CATCATCAGC | 1980 |
| AAAACTTACA | CCAACAAAAG | CTATAATTTT | GGAGCGGCGG | TTCATCTGAC | ACCTGATTTT | 2040 |
| AGCCTGTTGT | ATAAAACTGC | CAAAGGCTTT | CGTACGCCAA | GTTTTTATGA | ACTGTACAAC | 2100 |

-continued

```
TATAACAGCA CCGCCGCCCA GCATAAAAAT GACCCTGATG TGTCTTTTCC CAAACGAGCG    2160

GTTGATGTCA AACCTGAAAC TTCCAATACC AATGAATACG GCTTTCGCTA TCAGCACCCT    2220

TGGGGGATA TTGAGATGAG CATGTTCAAA AGCCGTTACA AGGACATGTT AGATAAAGCC     2280

ATACCGAACC TAACCAAAGC CCAGCAAGAG TATTGTAAGG CTCATTTGGA TTCCAATGAA    2340

TGTGTTGGTA ATCCACCCAC GCCCAAAACC AGTGATGAGG TATTTGCCAA CTTATATAAT    2400

GCCACCATCA AAGGGGTGAG TGTCAAAGGC AAACTGGATT TGCATGCCAT GACATCAAAA   2460

CTGCCAGATG GTCTTGAAAT GACCTTGGGT TATGGTCATA CCAAATTGGG GAAATTTGAT   2520

TACATTGCAC CCAAAGATGC CGATGGTTGG TATCAGGCTC GCCCTGCTTT TTGGGATGCC   2580

ATCACCCCAG CGCGCTATGT GGTCGGTCTA AACTATGACC ACCCCAGTCA AGTATGGGGC   2640

ATTGGCACAA CTTTAACGCA CAGCAAACAA AAAGATGAAA ATGAGCTAAG TGCCCTTAGA   2700

ATCCGAAATG GCAAAAGAGA AATACAAACC TTAACGCACA CAATACCCAA AGCCTATACC   2760

TTACTGGACA TGACAGGCTA TTATAGCCCA ACTGAGAGCA TCACCGCTCG TCTTGGTATC   2820

AACAATGTAT TAAACACCCG CTACACCACA TGGGAAGCGG CACGCCAACT GCCCAGCGAA   2880

GCTGCAAGCA GTACCCAATC AACCCGTTAC ATTGCACCAG GTCGCAGTTA CTTTGCCAGT   2940

CTTGAAATGA AGTTT                                                    2955
```

(2) INFORMATION FOR SEQ ID NO:10:

(i) SEQUENCE CHARACTERISTICS:
        (A) LENGTH: 1614 base pairs
        (B) TYPE: nucleic acid
        (C) STRANDEDNESS: single
        (D) TOPOLOGY: linear (xi) SEQUENCE DESCRIPTION: SEQ ID NO:10:

```
ATGACCTGTT TACCAAAGAC CAACCCTGCT TTAAAAGTCA AGCACAGATT TTTAAAGCAG      60

GTGCTGTTAT TGCTTTGTGT TGATACATTA ACAGCACAGG CGTACGCCCA CAGCCATCAT    120

ACGCCCATTC ATACACCCAC GCATGAGCTG TCATCTGCTG ATGCTTTATC AGATGAAGGC    180

TTGGGTAAGG ATTTGGGCAG TTTGGACAGC CCAGATGGTT TGGGTGATGG TTTAGGCGAT    240

GGTTTGGGTG ATGGCTTAAA AAGTGATAAA ACCCCTTTAC CCATCAACGC CTTGACCGTT    300

AATCAGAGCA ATGAGAGCCA GCCTGCCCCA CCGAGCGTAG ATGTCAATTT TTTACTTGCC    360

CAGCCAGAGG CATTTTATCA TGTCTTTCAT CAAGCGATTG TGCAAGATGA TGTGGCAACA    420

TTACGCTTGT TATTGCCATT TTATGACCGC CTGCCTGATG ATTATCAAGA TGATGTTTTG    480

TTGTTATTTG CCCAAAGTAA ACTTGCCCTA AGTGATGGCA ATACCAAATT GGCATTGAAT    540

CTGCTGACCG ATTTGAGTAA CAAAGAGCCA ACACTTACGG CGGTAAAATT ACAACTTGCT    600

TCCTTGTTGC TGACCAACAA GCACGATAAA CACGCCCAAA TGGTGCTAGA TGAACTCAAA    660

GATGATGCCC ACTTTTTAAA ATTAAGCAAA AAAGAGCAAA GATGGGTGCT ATCGCAAAGT    720

CGCTATTTAC ATAAAAAATA TAAAATGGGC TTGGATTTGG GCATCAACTA TCTGCATTTG    780

GATAATATCA ACGCCGCCTC CACCATCACC CAGCCCAACA TTAAAAAAGA TGCCCCAAAA    840

CCTGCTCATG GGCTTGCCTT ATCGCTTGGT GTGAATAAAT ACACGCCGCT TAGTCATGGC    900

ATGAGTATTT ATACAGCCCT AGATGTTGAT GGTAAATTTT ATGATGACAA AGCCACAAT    960

GAACTGGCGG TTTTTGCTCA TGCTGGACTA AGAAAGATC ACCAAAAAGG TTATGTTGAT   1020

GTCGTACCTT TGTTGGGCG TATTTTTGCC ACCAATCAGC AGCATGGCAG ATTATCCCCC   1080

AGAAAAGACA GTCAGGGCGT GGCGTTTGGC AGCCATCATC GGATCAATGA TAAATGGCAA   1140
```

-continued

```
AATGCGTTTT TTGCACGCAT GGAAAAAGGC AATTATACCG AGCATTATCA AGGTTATGAT    1200

GGCAAGCGTT ATCATGTGAA TGACACCATT TTGTTGCAAG ATGGCCCAAA TCGTCGTTAC    1260

TCTTTGGGCG TGGGGTATCA GCTTAGCCAT CTGCAAGATG CAACAAAAAG CAGTCATGCC    1320

ACAAAGATAC ATTTTGGGGT GTTGCAAAGA TTGCCAAATG GTCTGACCGT GCAAGGTAGA    1380

GTGAGTGCTG AGCGTGAGCG TTATCATGGT AAATTATTGC GTCTGGTTAA TCCTGATGAT    1440

GTGTATCGCA CAGATAAAAC CCTAACCCTA CAAACCTCCA TTTGGCACAA AGACATTCAC    1500

TGGCTTGGAT TAACGCCAAA GCTGACTTAT CGTTACAGTA AAAATAACAG TAACTTACCA    1560

GCACTTTATA GCCATAACAA ACAAAATTTT TATTTGGAGC TTGGTCGGTC GTTT         1614
```

(2) INFORMATION FOR SEQ ID NO:11:

(i) SEQUENCE CHARACTERISTICS:
  (A) LENGTH: 2439 amino acids
  (B) TYPE: amino acid
  (C) STRANDEDNESS: single
  (D) TOPOLOGY: linear (xi) SEQUENCE DESCRIPTION: SEQ ID NO:11:

```
Met Ser Thr Val Lys Thr Pro His Ile Phe Tyr Gln Lys Arg Thr Leu
1               5                   10                  15

Ser Leu Ala Ile Ala Ser Ile Phe Ala Ala Leu Val Met Thr Gly Cys
            20                  25                  30

Arg Ser Asp Asp Ile Ser Val Asn Ala Pro Asn Val Thr Gln Leu Pro
        35                  40                  45

Gln Gly Thr Val Ser Pro Ile Pro Asn Thr Gly His Asp Asn Thr Asn
    50                  55                  60

Asn Thr Asn Asn Gln Gly Asn Asn Thr Asp Asn Ser Thr Ser Thr Thr
65                  70                  75                  80

Asp Pro Asn Gly Asp Asn Asn Gln Leu Thr Gln Ala Gln Lys Thr Ala
                85                  90                  95

Ala Ala Ala Gly Phe Phe Val Met Gly Lys Ile Arg Asp Thr Ser Pro
            100                 105                 110

Lys Asn Asp Pro Asp Tyr Ser Asn Asp Leu Val Gln Gln Trp Gln Gly
        115                 120                 125

Lys Leu Tyr Val Gly Ile Asp Ala His Arg Pro Asp Gly Ile Gly Thr
    130                 135                 140

Gly Lys Asn Leu Arg Gln Pro Ile Thr Ala Asn Asp Ile Lys Pro Leu
145                 150                 155                 160

Tyr Phe Asn Lys Phe Pro Ala Leu Ser Asp Leu His Leu Asp Ser Glu
                165                 170                 175

Arg His Arg Phe Asp Pro Lys Lys Leu Asn Thr Ile Lys Val Tyr Gly
            180                 185                 190

Tyr Gly Asn Leu Thr Thr Pro Ser Lys Asn Asn Thr Tyr Ile Asn His
        195                 200                 205

Gln Gln Ala Asp Asn Lys Lys Asn Asn Lys Pro Val Asp Pro Tyr Glu
    210                 215                 220

Asn Ile Arg Phe Gly Tyr Leu Glu Leu Gln Gly Ser Ser Leu Thr Gln
225                 230                 235                 240

Lys Asn Ala Asp Thr Pro Asn Asp Lys Asp Arg Ile Pro Lys Pro Met
                245                 250                 255

Pro Ile Leu Phe Tyr His Gly Glu Asn Ala Ser Ser Gln Leu Pro Ser
            260                 265                 270

Ala Gly Lys Phe Asn Tyr Thr Gly Asn Trp Leu Tyr Leu Ser Asp Val
```

-continued

```
                275                 280                 285
Lys Lys Arg Pro Ala Leu Ser Ala Ser Asp Asp Arg Val Gly Val Tyr
    290                 295                 300

Leu Asn Ala Ser Gly Lys Ser Asn Glu Gly Asp Val Val Ser Ala Ala
305                 310                 315                 320

His Ile Tyr Leu Asn Gly Phe Gln Tyr Lys His Thr Pro Ala Thr Tyr
                325                 330                 335

Gln Val Asp Phe Asp Thr Asn Ser Leu Thr Gly Lys Leu Ser Tyr Tyr
            340                 345                 350

Asp Asn Pro Asn Gln Gln Thr Ala Gln Gly Lys Tyr Ile Lys Ser Gln
            355                 360                 365

Phe Asp Thr Thr Lys Lys Val Asn Glu Thr Asp Val Tyr Gln Ile Asp
    370                 375                 380

Ala Lys Ile Asn Gly Asn Arg Phe Val Gly Thr Ala Lys Ser Leu Val
385                 390                 395                 400

Asn Glu Asn Thr Glu Thr Ala Pro Phe Ile Lys Glu Leu Phe Ser Lys
                405                 410                 415

Lys Ala Asn Pro Asn Asn Pro Asn Ser Asp Thr Leu Glu Gly
            420                 425                 430  Gly

Gly Phe Tyr Gly Glu Ser Gly Asp Glu Leu Ala Gly Lys Phe Leu Ser
            435                 440                 445

Asn Asp Asn Ala Ser Tyr Val Val Phe Gly Gly Lys Arg Asp Lys Thr
450                 455                 460

Asp Lys Pro Val Ala Thr Lys Thr Val Tyr Phe Ser Ala Gly Phe Glu
465                 470                 475                 480

Lys Pro Ser Thr Ser Phe Val Asp Asn Glu Thr Ile Gly Arg Ile Ile
                485                 490                 495

Asn Ser Lys Lys Leu Asn Asp Ala Val Asn Glu Lys Ile Asp Asn Gly
            500                 505                 510

Asp Ile Pro Thr Ser Asp Glu Arg Tyr Asp Glu Phe Pro Trp Gly Glu
            515                 520                 525

Lys Lys Ala Glu Phe Thr Lys Lys Val Ser Ser Ser Thr Gln Ala Val
    530                 535                 540

Pro Ala Tyr Phe Gly Gln His Asp Lys Phe Tyr Phe Asn Gly Asn Tyr
545                 550                 555                 560

Tyr Asp Leu Ser Ala Ser Ser Val Asp Lys Leu Ala Pro Ala Asp Ala
                565                 570                 575

Val Lys Ala Asn Gln Ser Ile Lys Glu Lys Tyr Pro Asn Ala Thr Leu
            580                 585                 590

Asn Lys Asp Asn Gln Val Thr Ala Ile Val Leu Gln Glu Ala Lys Asp
            595                 600                 605

Asn Lys Pro Tyr Thr Ala Ile Arg Ala Lys Ser Tyr Gln His Ile Ser
    610                 615                 620

Phe Gly Glu Thr Leu Tyr Asn Asp Ala Asn Gln Thr Pro Thr Arg Ser
625                 630                 635                 640

Tyr Phe Val Gln Gly Gly Arg Ala Asp Thr Ser Thr Leu Pro Lys
                645                 650                 655

Ala Gly Lys Phe Thr Tyr Asn Gly Leu Trp Ala Gly Tyr Leu Ile Gln
            660                 665                 670

Lys Lys Asp Lys Gly Tyr Ser Asn Asn Glu Glu Thr Ile Lys Lys Lys
            675                 680                 685

Gly His Gln Asp Tyr Leu Leu Thr Glu Asp Phe Thr Pro Glu Asp Asp
    690                 695                 700
```

```
Asp Asp Asp Leu Thr Ala Ser Asp Asp Ser Gln Asp Asp Ala His
705                 710                 715                 720

Gly Asp Asp Leu Ile Ala Ser Asp Asp Ser Gln Asp Asp Ala
                725                 730                 735

Asp Gly Asp Asp Asp Ser Asp Asp Leu Gly Asp Gly Ala Asp Asp Ala
            740                 745                 750

Ala Ala Gly Lys Val Tyr His Ala Gly Asn Ile Arg Pro Glu Phe Glu
            755                 760                 765

Asn Lys Tyr Leu Pro Ile Asn Glu Pro Thr His Glu Lys Thr Phe Ala
770                 775                 780

Leu Asp Gly Lys Asn Lys Ala Lys Phe Asp Val Asp Phe Asp Thr Asn
785                 790                 795                 800

Ser Leu Thr Gly Lys Leu Asn Asp Glu Arg Gly Asp Ile Val Phe Asp
                805                 810                 815

Ile Lys Asn Gly Lys Ile Asp Gly Thr Gly Phe Thr Ala Lys Ala Asp
                820                 825                 830

Val Pro Asn Tyr Arg Glu Glu Val Gly Asn Asn Gln Gly Gly Gly Phe
                835                 840                 845

Leu Tyr Asn Ile Lys Asp Ile Asp Val Lys Gly Gln Phe Phe Gly Thr
850                 855                 860

Asn Gly Glu Glu Leu Ala Gly Gln Leu Gln Tyr Asp Lys Gly Asp Gly
865                 870                 875                 880

Ile Asn Asp Thr Ala Glu Lys Ala Gly Ala Val Phe Gly Ala Val Lys
                885                 890                 895

Asp Lys Met Ser Lys Ser Ile Thr Lys Thr Gln Thr Pro Ser Val His
                900                 905                 910

Thr Met Thr Thr His Arg Leu Asn Leu Ala Ile Lys Ala Ala Leu Phe
                915                 920                 925

Gly Val Ala Val Leu Pro Leu Ser Val Trp Ala Gln Glu Asn Thr Gln
                930                 935                 940

Thr Asp Ala Asn Ser Asp Ala Lys Asp Thr Lys Thr Pro Val Val Tyr
945                 950                 955                 960

Leu Asp Ala Ile Thr Val Thr Ala Ala Pro Ser Ala Pro Val Ser Arg
                965                 970                 975

Phe Asp Thr Asp Val Thr Gly Leu Gly Lys Thr Val Lys Thr Ala Asp
                980                 985                 990

Thr Leu Ala Lys Glu Gln Val Gln Gly Ile Arg Asp Leu Val Arg Tyr
                995                 1000                1005

Glu Thr Gly Val Ser Val Glu Gln Gly Arg Gly Gly Ser Ser Gly
    1010                1015                1020

Phe Ala Ile His Gly Val Asp Lys Asn Arg Val Gly Ile Thr Val Asp
1025                1030                1035                1040

Gly Ile Ala Gln Ile Gln Ser Tyr Lys Asp Glu Ser Thr Lys Arg Ala
                1045                1050                1055

Gly Ala Gly Ser Gly Ala Met Asn Glu Ile Glu Ile Glu Asn Ile Ala
                1060                1065                1070

Ala Val Ala Ile Asn Lys Gly Gly Asn Ala Leu Glu Ala Gly Ser Gly
                1075                1080                1085

Ala Leu Gly Gly Ser Val Ala Phe His Thr Lys Asp Val Ser Asp Val
                1090                1095                1100

Leu Lys Ser Gly Lys Asn Leu Gly Ala Gln Ser Lys Thr Thr Tyr Asn
1105                1110                1115                1120
```

-continued

```
Ser Lys Asn Asp His Phe Ser Gln Thr Leu Ala Ala Gly Lys Thr
            1125                1130                1135

Glu Arg Val Glu Ala Met Val Gln Tyr Thr Tyr Arg Lys Gly Lys Glu
        1140                1145                1150

Asn Lys Ala His Ser Asp Leu Asn Gly Ile Asn Gln Ser Leu Tyr Arg
            1155                1160                1165

Leu Gly Ala Trp Gln Gln Lys Tyr Asp Leu Arg Lys Pro Asn Glu Leu
    1170                1175                1180

Phe Ala Gly Thr Ser Tyr Ile Thr Glu Ser Cys Leu Ala Ser Asp Asp
1185                1190                1195                1200

Pro Lys Ser Cys Val Gln Tyr Pro Tyr Val Tyr Thr Lys Ala Arg Pro
            1205                1210                1215

Asp Gly Ile Gly Asn Arg Asn Phe Ser Glu Leu Ser Asp Ala Glu Lys
            1220                1225                1230

Ala Gln Tyr Leu Ala Ser Thr His Pro His Glu Val Val Ser Ala Lys
            1235                1240                1245

Asp Tyr Thr Gly Ile Tyr Arg Leu Leu Pro Asp Pro Met Asp Tyr Arg
        1250                1255                1260

Ser Asp Ser Tyr Leu Ala Arg Leu Asn Ile Lys Ile Thr Pro Asn Leu
1265                1270                1275                1280

Val Ser Lys Leu Leu Leu Glu Asp Thr Lys Gln Thr Tyr Asn Ile Arg
            1285                1290                1295

Asp Met Arg His Cys Ser Tyr His Gly Ala Arg Leu Gly Asn Asp Gly
        1300                1305                1310

Lys Pro Ala Asn Gly Gly Ser Ile Val Leu Cys Asp Asp Tyr Gln Glu
            1315                1320                1325

Tyr Leu Asn Ala Asn Asp Ala Ser Gln Ala Leu Phe Arg Pro Gly Ala
    1330                1335                1340

Asn Asp Ala Pro Ile Pro Lys Leu Ala Tyr Ala Arg Ser Ser Val Phe
1345                1350                1355                1360

Asn Gln Glu His Gly Lys Thr Arg Tyr Gly Leu Ser Phe Glu Phe Lys
            1365                1370                1375

Pro Asp Thr Pro Trp Phe Lys Gln Ala Lys Leu Asn Leu His Gln Gln
            1380                1385                1390

Asn Ile Gln Ile Ile Asn His Asp Ile Lys Lys Ser Cys Ser Gln Tyr
            1395                1400                1405

Pro Lys Val Asp Leu Asn Cys Gly Ile Ser Glu Ile Gly His Tyr Glu
    1410                1415                1420

Tyr Gln Asn Asn Tyr Arg Tyr Lys Glu Gly Arg Ala Ser Leu Thr Gly
1425                1430                1435                1440

Lys Leu Asp Phe Asn Phe Asp Leu Leu Gly Gln His Asp Leu Thr Val
            1445                1450                1455

Leu Ala Gly Ala Asp Lys Val Lys Ser Gln Phe Arg Ala Asn Asn Pro
            1460                1465                1470

Arg Arg Thr Ile Ile Asp Thr Thr Gln Gly Asp Ala Ile Ile Asp Glu
            1475                1480                1485

Ser Thr Leu Thr Ala Gln Glu Gln Ala Lys Phe Lys Gln Ser Gly Ala
    1490                1495                1500

Ala Trp Ile Val Lys Asn Arg Leu Gly Arg Leu Glu Glu Lys Asp Ala
1505                1510                1515                1520

Cys Gly Asn Ala Asn Glu Cys Glu Arg Ala Pro Ile His Gly Ser Asn
            1525                1530                1535

Gln Tyr Val Gly Ile Asn Asn Leu Tyr Thr Pro Asn Asp Tyr Val Asp
```

-continued

```
                  1540                1545                1550

Leu Ser Phe Gly Gly Arg Leu Asp Lys Gln Arg Ile His Ser Thr Asp
            1555                1560                1565

Ser Asn Ile Ile Ser Lys Thr Tyr Thr Asn Lys Ser Tyr Asn Phe Gly
    1570                1575                1580

Ala Ala Val His Leu Thr Pro Asp Phe Ser Leu Leu Tyr Lys Thr Ala
1585                1590                1595                1600

Lys Gly Phe Arg Thr Pro Ser Phe Tyr Glu Leu Tyr Asn Tyr Asn Ser
                1605                1610                1615

Thr Ala Ala Gln His Lys Asn Asp Pro Asp Val Ser Phe Pro Lys Arg
            1620                1625                1630

Ala Val Asp Val Lys Pro Glu Thr Ser Asn Thr Asn Glu Tyr Gly Phe
        1635                1640                1645

Arg Tyr Gln His Pro Trp Gly Asp Val Glu Met Ser Met Phe Lys Ser
    1650                1655                1660

Arg Tyr Lys Asp Met Leu Asp Lys Ala Ile Pro Asn Leu Thr Lys Ala
1665                1670                1675                1680

Gln Gln Glu Tyr Cys Lys Ala His Leu Asp Ser Asn Glu Cys Val Gly
                1685                1690                1695

Asn Pro Pro Thr Pro Lys Thr Ser Asp Glu Val Phe Ala Asn Leu Tyr
            1700                1705                1710

Asn Ala Thr Ile Lys Gly Val Ser Val Lys Gly Lys Leu Asp Leu His
        1715                1720                1725

Ala Met Thr Ser Lys Leu Pro Asp Gly Leu Glu Met Thr Leu Gly Tyr
    1730                1735                1740

Gly His Thr Lys Leu Gly Lys Phe Asp Tyr Ile Ala Pro Lys Asp Ala
1745                1750                1755                1760

Asp Gly Trp Tyr Gln Ala Arg Pro Ala Phe Trp Asp Ala Ile Thr Pro
                1765                1770                1775

Ala Arg Tyr Val Val Gly Leu Asn Tyr Asp His Pro Ser Gln Val Trp
            1780                1785                1790

Gly Ile Gly Thr Thr Leu Thr His Ser Lys Gln Lys Asp Glu Asn Glu
        1795                1800                1805

Leu Ser Ala Leu Arg Ile Arg Asn Gly Lys Arg Glu Thr Gln Thr Leu
    1810                1815                1820

Thr His Thr Ile Pro Lys Ala Tyr Thr Leu Leu Asp Met Thr Gly Tyr
1825                1830                1835                1840

Tyr Ser Pro Thr Glu Ser Ile Thr Ala Arg Leu Gly Ile Asn Asn Val
                1845                1850                1855

Leu Asn Thr Arg Tyr Thr Thr Trp Glu Ala Ala Arg Gln Leu Pro Ser
            1860                1865                1870

Glu Ala Ala Ser Ser Thr Gln Ser Thr Arg Tyr Ile Ala Pro Gly Arg
        1875                1880                1885

Ser Tyr Phe Ala Ser Leu Glu Met Lys Phe Met Thr Cys Leu Pro Lys
    1890                1895                1900

Thr Asn Pro Ala Leu Lys Val Lys His Arg Phe Leu Lys Gln Val Leu
1905                1910                1915                1920

Leu Leu Leu Cys Val Asp Thr Leu Thr Ala Gln Ala Tyr Ala His Ser
                1925                1930                1935

His His Thr Pro Ile His Thr Pro Thr His Glu Leu Pro Ser Ala Asp
            1940                1945                1950

Ala Leu Ser Asp Glu Gly Leu Gly Lys Asp Leu Gly Ser Leu Asp Ser
        1955                1960                1965
```

-continued

```
Leu Asp Ser Pro Asp Gly Leu Gly Asp Gly Leu Asp Gly Leu Gly
    1970                1975                1980
Asp Gly Leu Lys Ser Asp Lys Ala Pro Leu Pro Ile Asn Ala Leu Thr
1985                1990                1995                2000
Ala His Gln Thr Asn Glu Ser Gln Pro Ala Pro Pro Ser Val Asp Val
            2005                2010                2015
Asn Phe Leu Leu Ala Gln Pro Glu Ala Phe Tyr His Val Phe His Gln
            2020                2025                2030
Ala Ile Val Gln Asp Asp Val Ala Thr Leu Arg Leu Leu Leu Pro Phe
        2035                2040                2045
Tyr Asp Arg Leu Pro Asp Asp Tyr Gln Asp Asp Val Leu Leu Leu Phe
    2050                2055                2060
Ala Gln Ser Lys Leu Ala Leu Ser Asp Gly Asn Thr Lys Leu Ala Leu
2065                2070                2075                2080
Asn Leu Leu Thr Asp Leu Ser Asn Lys Glu Pro Thr Leu Thr Ala Val
            2085                2090                2095
Lys Leu Gln Leu Ala Ser Leu Leu Leu Thr Asn Lys His Asp Lys His
            2100                2105                2110
Ala Gln Met Val Leu Asp Glu Leu Lys Asp Asp Ala His Phe Leu Lys
            2115                2120                2125
Leu Ser Lys Lys Glu Gln Arg Trp Val Leu Ser Gln Ser Arg Tyr Leu
    2130                2135                2140
His Lys Lys Tyr Lys Met Gly Leu Asp Leu Gly Ile Asn Tyr Leu His
2145                2150                2155                2160
Leu Asp Asn Ile Asn Ala Ala Ser Thr Ile Thr Gln Pro Asn Ile Lys
            2165                2170                2175
Lys Asp Ala Pro Lys Pro Ala His Gly Leu Ala Leu Ser Leu Gly Val
            2180                2185                2190
Asn Lys Tyr Thr Pro Leu Ser His Gly Met Ser Ile Tyr Thr Ala Leu
            2195                2200                2205
Asp Val Asp Gly Lys Phe Tyr Asp Asp Lys Ser His Asn Glu Leu Ala
        2210                2215                2220
Val Phe Ala His Ala Gly Leu Arg Lys Asp His Gln Lys Gly Tyr Val
2225                2230                2235                2240
Asp Val Val Pro Phe Val Gly Arg Ile Phe Ala Thr Asn Gln Gln His
            2245                2250                2255
Gly Arg Leu Ser Pro Arg Lys Asp Ser Gln Gly Val Ala Phe Gly Ser
            2260                2265                2270
His His Arg Ile Asn Asp Lys Trp Gln Asn Ala Phe Phe Ala Arg Met
        2275                2280                2285
Glu Lys Gly Asn Tyr Thr Glu Arg Tyr Gln Gly Tyr Asp Gly Lys Arg
        2290                2295                2300
Tyr His Val Asn Asp Thr Ile Leu Leu Gln Asp Gly Pro Asn Arg Arg
2305                2310                2315                2320
Tyr Ser Leu Gly Val Gly Tyr Gln Leu Ser His Leu Gln Asp Ala Thr
            2325                2330                2335
Lys Ser Ser His Ala Thr Lys Ile His Phe Gly Val Leu Gln Arg Leu
            2340                2345                2350
Pro Asn Gly Leu Thr Val Gln Gly Arg Val Ser Ala Glu Arg Glu Arg
        2355                2360                2365
Tyr His Gly Lys Leu Leu Arg Leu Val Asn Pro Asp Asp Val Tyr Arg
    2370                2375                2380
```

```
Thr Asp Lys Thr Leu Thr Leu Gln Thr Ser Ile Trp His Lys Asp Ile
2385                2390                2395                2400

His Trp Leu Gly Leu Thr Pro Lys Leu Thr Tyr Arg Tyr Ser Lys Asn
            2405                2410                2415

Asn Ser Asn Leu Pro Ala Leu Tyr Ser His Asn Lys Gln Asn Phe Tyr
            2420                2425                2430

Leu Glu Leu Gly Arg Ser Phe
        2435
```

(2) INFORMATION FOR SEQ ID NO:12:

(i) SEQUENCE CHARACTERISTICS:
        (A) LENGTH: 1000 amino acids
        (B) TYPE: amino acid
        (C) STRANDEDNESS: single
        (D) TOPOLOGY: linear (xi) SEQUENCE DESCRIPTION: SEQ ID NO:12:

```
Met Ser Lys Ser Ile Thr Lys Thr Gln Thr Pro Ser Val His Thr Met
1               5                   10                  15

Thr Thr His Arg Leu Asn Leu Ala Ile Lys Ala Ala Leu Phe Gly Val
            20                  25                  30

Ala Val Leu Pro Leu Ser Val Trp Ala Gln Glu Asn Thr Gln Thr Asp
            35                  40                  45

Ala Asn Ser Asp Ala Lys Asp Thr Lys Thr Pro Val Val Tyr Leu Asp
50                  55                  60

Ala Ile Thr Val Thr Ala Ala Pro Ser Ala Pro Val Ser Arg Phe Asp
65                  70                  75                  80

Thr Asp Val Thr Gly Leu Gly Lys Thr Val Lys Thr Ala Asp Thr Leu
                85                  90                  95

Ala Lys Glu Gln Val Gln Gly Ile Arg Asp Leu Val Arg Tyr Glu Thr
            100                 105                 110

Gly Val Ser Val Val Glu Gln Gly Arg Gly Ser Ser Gly Phe Ala
            115                 120                 125

Ile His Gly Val Asp Lys Asn Arg Val Gly Ile Thr Val Asp Gly Ile
    130                 135                 140

Ala Gln Ile Gln Ser Tyr Lys Asp Glu Ser Thr Lys Arg Ala Gly Ala
145                 150                 155                 160

Gly Ser Gly Ala Met Asn Glu Ile Glu Ile Glu Asn Ile Ala Ala Val
                165                 170                 175

Ala Ile Asn Lys Gly Gly Asn Ala Leu Glu Ala Gly Ser Gly Ala Leu
            180                 185                 190

Gly Gly Ser Val Ala Phe His Thr Lys Asp Val Ser Asp Val Leu Lys
        195                 200                 205

Ser Gly Lys Asn Leu Gly Ala Gln Ser Lys Thr Thr Tyr Asn Ser Lys
210                 215                 220

Asn Asp His Phe Ser Gln Thr Leu Ala Ala Ala Gly Lys Thr Glu Arg
225                 230                 235                 240

Val Glu Ala Met Val Gln Tyr Thr Tyr Arg Lys Gly Lys Glu Asn Lys
                245                 250                 255

Ala His Ser Asp Leu Asn Gly Ile Asn Gln Ser Leu Tyr Arg Leu Gly
            260                 265                 270

Ala Trp Gln Gln Lys Tyr Asp Leu Arg Lys Pro Asn Glu Leu Phe Ala
        275                 280                 285

Gly Thr Ser Tyr Ile Thr Glu Ser Cys Leu Ala Ser Asp Asp Pro Lys
        290                 295                 300
```

-continued

```
Ser Cys Val Gln Tyr Pro Tyr Val Tyr Thr Lys Ala Arg Pro Asp Gly
305                 310                 315                 320

Ile Gly Asn Arg Asn Phe Ser Glu Leu Ser Asp Ala Glu Lys Ala Gln
                325                 330                 335

Tyr Leu Ala Ser Thr His Pro His Glu Val Val Ser Ala Lys Asp Tyr
                340                 345                 350

Thr Gly Ile Tyr Arg Leu Leu Pro Asp Pro Met Asp Tyr Arg Ser Asp
            355                 360                 365

Ser Tyr Leu Ala Arg Leu Asn Ile Lys Ile Thr Pro Asn Leu Val Ser
370                 375                 380

Lys Leu Leu Glu Asp Thr Lys Gln Thr Tyr Asn Ile Arg Asp Met
385                 390                 395                 400

Arg His Cys Ser Tyr His Gly Ala Arg Leu Gly Asn Asp Gly Lys Pro
                405                 410                 415

Ala Asn Gly Gly Ser Ile Val Leu Cys Asp Asp Tyr Gln Glu Tyr Leu
                420                 425                 430

Asn Ala Asn Asp Ala Ser Gln Ala Leu Phe Arg Pro Gly Ala Asn Asp
                435                 440                 445

Ala Pro Ile Pro Lys Leu Ala Tyr Ala Arg Ser Ser Val Phe Asn Gln
450                 455                 460

Glu His Gly Lys Thr Arg Tyr Gly Leu Ser Phe Glu Phe Lys Pro Asp
465                 470                 475                 480

Thr Pro Trp Phe Lys Gln Ala Lys Leu Asn Leu His Gln Gln Asn Ile
                485                 490                 495

Gln Ile Ile Asn His Asp Ile Lys Lys Ser Cys Ser Gln Tyr Pro Lys
                500                 505                 510

Val Asp Leu Asn Cys Gly Ile Ser Glu Ile Gly His Tyr Glu Tyr Gln
            515                 520                 525

Asn Asn Tyr Arg Tyr Lys Glu Gly Arg Ala Ser Leu Thr Gly Lys Leu
530                 535                 540

Asp Phe Asn Phe Asp Leu Leu Gly Gln His Asp Leu Thr Val Leu Ala
545                 550                 555                 560

Gly Ala Asp Lys Val Lys Ser Gln Phe Arg Ala Asn Asn Pro Arg Arg
                565                 570                 575

Thr Ile Ile Asp Thr Thr Gln Gly Asp Ala Ile Ile Asp Glu Ser Thr
                580                 585                 590

Leu Thr Ala Gln Glu Gln Ala Lys Phe Lys Gln Ser Gly Ala Ala Trp
            595                 600                 605

Ile Val Lys Asn Arg Leu Gly Arg Leu Glu Glu Lys Asp Ala Cys Gly
610                 615                 620

Asn Ala Asn Glu Cys Glu Arg Ala Pro Ile His Gly Ser Asn Gln Tyr
625                 630                 635                 640

Val Gly Ile Asn Asn Leu Tyr Thr Pro Asn Asp Tyr Val Asp Leu Ser
                645                 650                 655

Phe Gly Gly Arg Leu Asp Lys Gln Arg Ile His Ser Thr Asp Ser Asn
                660                 665                 670

Ile Ile Ser Lys Thr Tyr Thr Asn Lys Ser Tyr Asn Phe Gly Ala Ala
                675                 680                 685

Val His Leu Thr Pro Asp Phe Ser Leu Leu Tyr Lys Thr Ala Lys Gly
            690                 695                 700

Phe Arg Thr Pro Ser Phe Tyr Glu Leu Tyr Asn Tyr Asn Ser Thr Ala
705                 710                 715                 720
```

-continued

```
Ala Gln His Lys Asn Asp Pro Asp Val Ser Phe Pro Lys Arg Ala Val
            725                 730                 735

Asp Val Lys Pro Glu Thr Ser Asn Thr Asn Glu Tyr Gly Phe Arg Tyr
            740                 745                 750

Gln His Pro Trp Gly Asp Val Glu Met Ser Met Phe Lys Ser Arg Tyr
            755                 760                 765

Lys Asp Met Leu Asp Lys Ala Ile Pro Asn Leu Thr Lys Ala Gln Gln
            770                 775                 780

Glu Tyr Cys Lys Ala His Leu Asp Ser Asn Glu Cys Val Gly Asn Pro
785                 790                 795                 800

Pro Thr Pro Lys Thr Ser Asp Glu Val Phe Ala Asn Leu Tyr Asn Ala
            805                 810                 815

Thr Ile Lys Gly Val Ser Val Lys Gly Lys Leu Asp Leu His Ala Met
            820                 825                 830

Thr Ser Lys Leu Pro Asp Gly Leu Glu Met Thr Leu Gly Tyr Gly His
            835                 840                 845

Thr Lys Leu Gly Lys Phe Asp Tyr Ile Ala Pro Lys Asp Ala Asp Gly
            850                 855                 860

Trp Tyr Gln Ala Arg Pro Ala Phe Trp Asp Ala Ile Thr Pro Ala Arg
865                 870                 875                 880

Tyr Val Val Gly Leu Asn Tyr Asp His Pro Ser Gln Val Trp Gly Ile
            885                 890                 895

Gly Thr Thr Leu Thr His Ser Lys Gln Lys Asp Glu Asn Glu Leu Ser
            900                 905                 910

Ala Leu Arg Ile Arg Asn Gly Lys Arg Glu Thr Gln Thr Leu Thr His
            915                 920                 925

Thr Ile Pro Lys Ala Tyr Thr Leu Leu Asp Met Thr Gly Tyr Tyr Ser
            930                 935                 940

Pro Thr Glu Ser Ile Thr Ala Arg Leu Gly Ile Asn Asn Val Leu Asn
945                 950                 955                 960

Thr Arg Tyr Thr Thr Trp Glu Ala Ala Arg Gln Leu Pro Ser Glu Ala
            965                 970                 975

Ala Ser Ser Thr Gln Ser Thr Arg Tyr Ile Ala Pro Gly Arg Ser Tyr
            980                 985                 990

Phe Ala Ser Leu Glu Met Lys Phe
            995                 1000

(2) INFORMATION FOR SEQ ID NO:13:

(i) SEQUENCE CHARACTERISTICS:
        (A) LENGTH: 985 amino acids
        (B) TYPE: amino acid
        (C) STRANDEDNESS: single
        (D) TOPOLOGY: linear (xi) SEQUENCE DESCRIPTION: SEQ ID NO:13:

Met Thr Thr His Arg Leu Asn Leu Ala Ile Lys Ala Ala Leu Phe Gly
1               5                   10                  15

Val Ala Val Leu Pro Leu Ser Val Trp Ala Gln Glu Asn Thr Gln Thr
            20                  25                  30

Asp Ala Asn Ser Asp Ala Lys Asp Thr Lys Thr Pro Val Val Tyr Leu
            35                  40                  45

Asp Ala Ile Thr Val Thr Ala Ala Pro Ser Ala Pro Val Ser Arg Phe
            50                  55                  60

Asp Thr Asp Val Thr Gly Leu Gly Lys Thr Val Lys Thr Ala Asp Thr
65                  70                  75                  80
```

-continued

```
Leu Ala Lys Glu Gln Val Gln Gly Ile Arg Asp Leu Val Arg Tyr Glu
                85                  90                  95
Thr Gly Val Ser Val Val Glu Gln Gly Arg Gly Gly Ser Ser Gly Phe
            100                 105                 110
Ala Ile His Gly Val Asp Lys Asn Arg Val Gly Ile Thr Val Asp Gly
            115                 120                 125
Ile Ala Gln Ile Gln Ser Tyr Lys Asp Glu Ser Thr Lys Arg Ala Gly
            130                 135                 140
Ala Gly Ser Gly Ala Met Asn Glu Ile Glu Ile Glu Asn Ile Ala Ala
145                 150                 155                 160
Val Ala Ile Asn Lys Gly Gly Asn Ala Leu Glu Ala Gly Ser Gly Ala
                165                 170                 175
Leu Gly Gly Ser Val Ala Phe His Thr Lys Asp Val Ser Asp Val Leu
            180                 185                 190
Lys Ser Gly Lys Asn Leu Gly Ala Gln Ser Lys Thr Thr Tyr Asn Ser
            195                 200                 205
Lys Asn Asp His Phe Ser Gln Thr Leu Ala Ala Gly Lys Thr Glu
            210                 215                 220
Arg Val Glu Ala Met Val Gln Tyr Thr Tyr Arg Lys Gly Lys Glu Asn
225                 230                 235                 240
Lys Ala His Ser Asp Leu Asn Gly Ile Asn Gln Ser Leu Tyr Arg Leu
                245                 250                 255
Gly Ala Trp Gln Gln Lys Tyr Asp Leu Arg Lys Pro Asn Glu Leu Phe
            260                 265                 270
Ala Gly Thr Ser Tyr Ile Thr Glu Ser Cys Leu Ala Ser Asp Asp Pro
            275                 280                 285
Lys Ser Cys Val Gln Tyr Pro Tyr Val Tyr Thr Lys Ala Arg Pro Asp
            290                 295                 300
Gly Ile Gly Asn Arg Asn Phe Ser Glu Leu Ser Asp Ala Glu Lys Ala
305                 310                 315                 320
Gln Tyr Leu Ala Ser Thr His Pro His Glu Val Val Ser Ala Lys Asp
                325                 330                 335
Tyr Thr Gly Ile Tyr Arg Leu Leu Pro Asp Pro Met Asp Tyr Arg Ser
            340                 345                 350
Asp Ser Tyr Leu Ala Arg Leu Asn Ile Lys Ile Thr Pro Asn Leu Val
            355                 360                 365
Ser Lys Leu Leu Leu Glu Asp Thr Lys Gln Thr Tyr Asn Ile Arg Asp
            370                 375                 380
Met Arg His Cys Ser Tyr His Gly Ala Arg Leu Gly Asn Asp Gly Lys
385                 390                 395                 400
Pro Ala Asn Gly Gly Ser Ile Val Leu Cys Asp Asp Tyr Gln Glu Tyr
                405                 410                 415
Leu Asn Ala Asn Asp Ala Ser Gln Ala Leu Phe Arg Pro Gly Ala Asn
            420                 425                 430
Asp Ala Pro Ile Pro Lys Leu Ala Tyr Ala Arg Ser Ser Val Phe Asn
            435                 440                 445
Gln Glu His Gly Lys Thr Arg Tyr Gly Leu Ser Phe Glu Phe Lys Pro
            450                 455                 460
Asp Thr Pro Trp Phe Lys Gln Ala Lys Leu Asn Leu His Gln Gln Asn
465                 470                 475                 480
Ile Gln Ile Ile Asn His Asp Ile Lys Lys Ser Cys Ser Gln Tyr Pro
                485                 490                 495
```

-continued

Lys Val Asp Leu Asn Cys Gly Ile Ser Glu Ile Gly His Tyr Glu Tyr
                500                 505                 510
Gln Asn Asn Tyr Arg Tyr Lys Glu Gly Arg Ala Ser Leu Thr Gly Lys
            515                 520                 525
Leu Asp Phe Asn Phe Asp Leu Leu Gly Gln His Asp Leu Thr Val Leu
        530                 535                 540
Ala Gly Ala Asp Lys Val Lys Ser Gln Phe Arg Ala Asn Asn Pro Arg
545                 550                 555                 560
Arg Thr Ile Ile Asp Thr Thr Gln Gly Asp Ala Ile Ile Asp Glu Ser
                565                 570                 575
Thr Leu Thr Ala Gln Glu Gln Ala Lys Phe Lys Gln Ser Gly Ala Ala
            580                 585                 590
Trp Ile Val Lys Asn Arg Leu Gly Arg Leu Glu Glu Lys Asp Ala Cys
        595                 600                 605
Gly Asn Ala Asn Glu Cys Glu Arg Ala Pro Ile His Gly Ser Asn Gln
610                 615                 620
Tyr Val Gly Ile Asn Asn Leu Tyr Thr Pro Asn Asp Tyr Val Asp Leu
625                 630                 635                 640
Ser Phe Gly Gly Arg Leu Asp Lys Gln Arg Ile His Ser Thr Asp Ser
                645                 650                 655
Asn Ile Ile Ser Lys Thr Tyr Thr Asn Lys Ser Tyr Asn Phe Gly Ala
            660                 665                 670
Ala Val His Leu Thr Pro Asp Phe Ser Leu Leu Tyr Lys Thr Ala Lys
        675                 680                 685
Gly Phe Arg Thr Pro Ser Phe Tyr Glu Leu Tyr Asn Tyr Asn Ser Thr
        690                 695                 700
Ala Ala Gln His Lys Asn Asp Pro Asp Val Ser Phe Pro Lys Arg Ala
705                 710                 715                 720
Val Asp Val Lys Pro Glu Thr Ser Asn Thr Asn Glu Tyr Gly Phe Arg
                725                 730                 735
Tyr Gln His Pro Trp Gly Asp Val Glu Met Ser Met Phe Lys Ser Arg
            740                 745                 750
Tyr Lys Asp Met Leu Asp Lys Ala Ile Pro Asn Leu Thr Lys Ala Gln
        755                 760                 765
Gln Glu Tyr Cys Lys Ala His Leu Asp Ser Asn Glu Cys Val Gly Asn
        770                 775                 780
Pro Pro Thr Pro Lys Thr Ser Asp Glu Val Phe Ala Asn Leu Tyr Asn
785                 790                 795                 800
Ala Thr Ile Lys Gly Val Ser Val Lys Gly Lys Leu Asp Leu His Ala
                805                 810                 815
Met Thr Ser Lys Leu Pro Asp Gly Leu Glu Met Thr Leu Gly Tyr Gly
            820                 825                 830
His Thr Lys Leu Gly Lys Phe Asp Tyr Ile Ala Pro Lys Asp Ala Asp
        835                 840                 845
Gly Trp Tyr Gln Ala Arg Pro Ala Phe Trp Asp Ala Ile Thr Pro Ala
        850                 855                 860
Arg Tyr Val Val Gly Leu Asn Tyr Asp His Pro Ser Gln Val Trp Gly
865                 870                 875                 880
Ile Gly Thr Thr Leu Thr His Ser Lys Gln Lys Asp Glu Asn Glu Leu
                885                 890                 895
Ser Ala Leu Arg Ile Arg Asn Gly Lys Arg Glu Thr Gln Thr Leu Thr
            900                 905                 910
His Thr Ile Pro Lys Ala Tyr Thr Leu Leu Asp Met Thr Gly Tyr Tyr

-continued

```
                915                 920                      925
Ser Pro Thr Glu Ser Ile Thr Ala Arg Leu Gly Ile Asn Asn Val Leu
    930                 935                 940

Asn Thr Arg Tyr Thr Thr Trp Glu Ala Ala Arg Gln Leu Pro Ser Glu
945                 950                 955                 960

Ala Ala Ser Ser Thr Gln Ser Thr Arg Tyr Ile Ala Pro Gly Arg Ser
                965                 970                 975

Tyr Phe Ala Ser Leu Glu Met Lys Phe
            980                 985
```

(2) INFORMATION FOR SEQ ID NO:14:

(i) SEQUENCE CHARACTERISTICS:
        (A) LENGTH: 541 amino acids
        (B) TYPE: amino acid
        (C) STRANDEDNESS: single
        (D) TOPOLOGY: linear (xi) SEQUENCE DESCRIPTION: SEQ ID NO:14:

```
Met Thr Cys Leu Pro Lys Thr Asn Pro Ala Leu Lys Val Lys His Arg
1               5                   10                  15

Phe Leu Lys Gln Val Leu Leu Leu Cys Val Asp Thr Leu Thr Ala
            20                  25                  30

Gln Ala Tyr Ala His Ser His His Thr Pro Ile His Thr Pro Thr His
        35                  40                  45

Glu Leu Pro Ser Ala Asp Ala Leu Ser Asp Glu Gly Leu Gly Lys Asp
    50                  55                  60

Leu Gly Ser Leu Asp Ser Leu Asp Ser Pro Asp Gly Leu Gly Asp Gly
65                  70                  75                  80

Leu Gly Asp Gly Leu Gly Asp Gly Leu Lys Ser Asp Lys Ala Pro Leu
                85                  90                  95

Pro Ile Asn Ala Leu Thr Ala His Gln Thr Asn Glu Ser Gln Pro Ala
                100                 105                 110

Pro Pro Ser Val Asp Val Asn Phe Leu Leu Ala Gln Pro Glu Ala Phe
            115                 120                 125

Tyr His Val Phe His Gln Ala Ile Val Gln Asp Asp Val Ala Thr Leu
        130                 135                 140

Arg Leu Leu Leu Pro Phe Tyr Asp Arg Leu Pro Asp Tyr Gln Asp
145                 150                 155                 160

Asp Val Leu Leu Leu Phe Ala Gln Ser Lys Leu Ala Leu Ser Asp Gly
                165                 170                 175

Asn Thr Lys Leu Ala Leu Asn Leu Leu Thr Asp Leu Ser Asn Lys Glu
            180                 185                 190

Pro Thr Leu Thr Ala Val Lys Leu Gln Leu Ala Ser Leu Leu Leu Thr
        195                 200                 205

Asn Lys His Asp Lys His Ala Gln Met Val Leu Asp Glu Leu Lys Asp
    210                 215                 220

Asp Ala His Phe Leu Lys Leu Ser Lys Lys Glu Gln Arg Trp Val Leu
225                 230                 235                 240

Ser Gln Ser Arg Tyr Leu His Lys Lys Tyr Lys Met Gly Leu Asp Leu
                245                 250                 255

Gly Ile Asn Tyr Leu His Leu Asp Asn Ile Asn Ala Ala Ser Thr Ile
            260                 265                 270

Thr Gln Pro Asn Ile Lys Lys Asp Ala Pro Lys Pro Ala His Gly Leu
        275                 280                 285
```

```
Ala Leu Ser Leu Gly Val Asn Lys Tyr Thr Pro Leu Ser His Gly Met
    290                 295                 300

Ser Ile Tyr Thr Ala Leu Asp Val Asp Gly Lys Phe Tyr Asp Asp Lys
305                 310                 315                 320

Ser His Asn Glu Leu Ala Val Phe Ala His Ala Gly Leu Arg Lys Asp
                325                 330                 335

His Gln Lys Gly Tyr Val Asp Val Pro Phe Val Gly Arg Ile Phe
            340                 345                 350

Ala Thr Asn Gln Gln His Gly Arg Leu Ser Pro Arg Lys Asp Ser Gln
        355                 360                 365

Gly Val Ala Phe Gly Ser His His Arg Ile Asn Asp Lys Trp Gln Asn
    370                 375                 380

Ala Phe Phe Ala Arg Met Glu Lys Gly Asn Tyr Thr Glu Arg Tyr Gln
385                 390                 395                 400

Gly Tyr Asp Gly Lys Arg Tyr His Val Asn Asp Thr Ile Leu Leu Gln
                405                 410                 415

Asp Gly Pro Asn Arg Arg Tyr Ser Leu Gly Val Gly Tyr Gln Leu Ser
            420                 425                 430

His Leu Gln Asp Ala Thr Lys Ser Ser His Ala Thr Lys Ile His Phe
        435                 440                 445

Gly Val Leu Gln Arg Leu Pro Asn Gly Leu Thr Val Gln Gly Arg Val
    450                 455                 460

Ser Ala Glu Arg Glu Arg Tyr His Gly Lys Leu Leu Arg Leu Val Asn
465                 470                 475                 480

Pro Asp Asp Val Tyr Arg Thr Asp Lys Thr Leu Thr Leu Gln Thr Ser
                485                 490                 495

Ile Trp His Lys Asp Ile His Trp Leu Gly Leu Thr Pro Lys Leu Thr
            500                 505                 510

Tyr Arg Tyr Ser Lys Asn Asn Ser Asn Leu Pro Ala Leu Tyr Ser His
        515                 520                 525

Asn Lys Gln Asn Phe Tyr Leu Glu Leu Gly Arg Ser Phe
    530                 535                 540

(2) INFORMATION FOR SEQ ID NO:15:

(i) SEQUENCE CHARACTERISTICS:
        (A) LENGTH: 2432 amino acids
        (B) TYPE: amino acid
        (C) STRANDEDNESS: single
        (D) TOPOLOGY: linear (xi) SEQUENCE DESCRIPTION: SEQ ID NO:15:

Met Ser Thr Val Lys Thr Pro His Ile Phe Tyr Gln Lys Arg Thr Leu
1               5                   10                  15

Ser Leu Ala Ile Ala Ser Ile Phe Ala Ala Leu Val Met Thr Gly Cys
            20                  25                  30

Arg Ser Asp Asp Ile Ser Val Asn Ala Pro Asn Val Thr Gln Leu Pro
        35                  40                  45

Gln Gly Thr Val Ser Pro Thr Pro Asn Thr Gly His Asp Asn Ala Asn
    50                  55                  60

Asn Thr Asn Asn Gln Gly Asn Asn Thr Asp Asn Ser Thr Ser Thr Thr
65                  70                  75                  80

Asp Pro Asn Gly Asp Asn Asn Gln Leu Thr Gln Ala Gln Lys Thr Ala
                85                  90                  95

Ala Ala Ala Gly Phe Phe Val Met Gly Lys Ile Arg Asp Thr Ser Glu
            100                 105                 110
```

-continued

```
Lys Asn Asp Pro Asp Tyr Ser Asp Asp Leu Lys Gln Gln Trp Leu Gly
        115                 120                 125
Lys Leu Tyr Val Gly Ile Asp Ala His Arg Pro Asp Gly Ile Gly Lys
        130                 135                 140
Gly Lys Asn Leu Arg Gln Pro Ile Thr Ala Asn Asp Ile Lys Pro Leu
145                 150                 155                 160
Tyr Phe Asn Lys Phe Pro Ala Leu Ser Asp Leu His Leu Asp Ser Glu
                165                 170                 175
Arg His Arg Phe Asp Pro Gln Lys Ile Asn Thr Ile Lys Val Tyr Gly
                180                 185                 190
Tyr Gly Asn Leu Thr Thr Pro Ser Asn Asn Thr His Ile Asn His
        195                 200                 205
Gln Gln Ala Asp Asn Lys Lys Asn Lys Pro Val Asp Pro Tyr Glu
        210                 215                 220
Asn Ile Arg Phe Gly Tyr Leu Glu Leu Gln Gly Ser Ser Leu Thr Gln
225                 230                 235                 240
Lys Asn Ala Asp Asn Gln Asn Glu Gln Asp Arg Ile Pro Lys Pro Met
                245                 250                 255
Pro Ile Leu Phe Tyr His Gly Glu Asn Ala Ser Ser Gln Leu Pro Ser
                260                 265                 270
Ala Gly Lys Phe Asn Tyr Thr Gly Asn Trp Leu Tyr Leu Ser Asp Val
        275                 280                 285
Lys Lys Arg Pro Ala Leu Ser Ala Ser Asp Glu Arg Val Gly Val Tyr
        290                 295                 300
Leu Asn Ala Ser Gly Lys Ala Asn Glu Gly Asp Val Val Ser Ala Ala
305                 310                 315                 320
His Ile Tyr Leu Asn Gly Phe Gln Tyr Lys His Thr Pro Ala Thr Tyr
                325                 330                 335
Gln Val Asp Phe Asp Thr Asn Ser Leu Thr Gly Lys Leu Ser Tyr Tyr
                340                 345                 350
Asp Asn Pro Asn Gln Gln Asn Asn Lys Gly Glu Tyr Leu Lys Ser Gln
                355                 360                 365
Phe Asp Thr Thr Lys Lys Val Asn Glu Thr Asp Val Tyr Gln Ile Asp
        370                 375                 380
Ala Lys Ile Asn Gly Asn Arg Phe Val Gly Thr Ala Lys Ser Leu Val
385                 390                 395                 400
Asn Glu Lys Thr Gln Thr Ala Pro Phe Ile Lys Glu Leu Phe Ser Lys
                405                 410                 415
Lys Ala Asn Pro Asn Asn Pro Asn Pro Asn Ser Asp Thr Leu Glu Gly
                420                 425                 430
Gly Phe Tyr Gly Glu Ser Gly Asp Glu Leu Ala Gly Lys Phe Leu Ser
        435                 440                 445
Asn Asp Asn Ala Ser Tyr Val Val Phe Gly Gly Lys Arg Asp Lys Thr
        450                 455                 460
Thr Lys Pro Val Ala Thr Lys Thr Val Tyr Phe Ser Ala Gly Phe Glu
465                 470                 475                 480
Lys Pro Ser Thr Ser Phe Val Asp Asn Glu Thr Ile Gly Gly Ile Ile
                485                 490                 495
Asp Arg Lys Gly Leu Asn Asn His Ile Asn Glu Asp Glu Ile Ile Pro
                500                 505                 510
Ser Asp Asp Ser Tyr Tyr Gly Tyr Thr Trp Gly Lys Pro Glu Lys Gln
                515                 520                 525
```

```
Phe Thr Lys Lys Val Ser Ser Thr Gln Val Pro Ala Tyr Phe
    530                 535                 540

Gly Gln His Asp Lys Phe Tyr Phe Asn Gly Asn Tyr Tyr Asp Leu Ser
545                 550                 555                 560

Ala Ser Arg Val Asp Lys Leu Ala Pro Ala Asp Ala Val Lys Ala Asn
                565                 570                 575

Gln Ser Ile Lys Glu Lys Tyr Pro Asn Ala Thr Leu Asn Lys Asp Asn
            580                 585                 590

Gln Val Thr Ala Ile Val Leu Gln Glu Ala Lys Asp Asn Lys Pro Tyr
        595                 600                 605

Thr Ala Ile Arg Ala Lys Ser Tyr Gln His Ile Ser Phe Gly Glu Thr
    610                 615                 620

Leu Tyr Asn Asp Ala Asn Gln Thr Pro Thr Arg Ser Tyr Phe Val Gln
625                 630                 635                 640

Gly Gly Arg Ala Asp Thr Ser Thr Thr Leu Pro Gln Ala Gly Lys Phe
                645                 650                 655

Thr Tyr Asn Gly Leu Trp Ala Gly Tyr Leu Thr Gln Lys Lys Asp Lys
            660                 665                 670

Gly Tyr Ser Asp Asn Ala Glu Thr Ile Lys Glu Lys Gly His Pro Gly
        675                 680                 685

Tyr Leu Leu Thr Glu Asn Phe Thr Pro Glu Asp Asp Asp Asp Asp Leu
    690                 695                 700

Thr Ala Ser Asp Asp Ser Gln Asp Asp Asn Thr His Gly Asp Asp Asp
705                 710                 715                 720

Leu Ile Ala Ser Asp Asp Ser Gln Asp Asp Asp Ala Asp Gly Asp Asp
                725                 730                 735

Asp Ser Asp Asp Leu Gly Asp Gly Ala Asp Asp Ala Ala Gly Lys
            740                 745                 750

Val Tyr His Ala Gly Asn Ile Arg Pro Glu Phe Glu Asn Lys Tyr Leu
        755                 760                 765

Pro Ile Asn Glu Pro Thr His Glu Lys Thr Phe Ala Leu Asp Gly Lys
    770                 775                 780

Asn Lys Ala Lys Phe Glu Val Asp Phe Asn Thr Asn Ser Leu Thr Gly
785                 790                 795                 800

Lys Leu Asn Asp Glu Arg Gly Asp Ile Val Phe Asp Ile Lys Asn Gly
                805                 810                 815

Lys Ile Asp Gly Thr Gly Phe Thr Ala Lys Ala Asp Val Pro Asn Tyr
            820                 825                 830

Arg Glu Glu Val Gly Asn Asn Gln Gly Gly Phe Leu Tyr Asn Ile
        835                 840                 845

Lys Asp Ile Asp Val Lys Gly Gln Phe Phe Gly Thr Asn Gly Glu Glu
    850                 855                 860

Leu Ala Gly Gln Leu His His Asp Lys Gly Asp Gly Ile Asn Asp Thr
865                 870                 875                 880

Ala Glu Lys Ala Gly Ala Val Phe Gly Ala Val Lys Asp Lys Met Ser
                885                 890                 895

Lys Ser Ile Thr Lys Thr Gln Thr Pro Ser Val His Thr Met Thr Thr
            900                 905                 910

His Arg Leu Asn Leu Ala Ile Lys Ala Ala Leu Phe Gly Val Ala Val
        915                 920                 925

Leu Pro Leu Ser Val Trp Ala Gln Glu Asn Thr Gln Thr Asp Ala Asn
    930                 935                 940

Ser Asp Ala Lys Asp Thr Lys Thr Pro Val Val Tyr Leu Asp Ala Ile
```

```
                945                 950                 955                 960
Thr Val Thr Ala Ala Pro Ser Ala Pro Val Ser Arg Phe Asp Thr Asp
                    965                 970                 975
Val Thr Gly Leu Gly Lys Thr Val Lys Thr Ala Asp Thr Leu Ala Lys
                    980                 985                 990
Glu Gln Val Gln Gly Ile Arg Asp Leu Val Arg Tyr Glu Thr Gly Val
                    995                1000                1005
Ser Val Val Glu Gln Gly Arg Gly Gly Ser Ser Gly Phe Ala Ile His
                   1010                1015                1020
Gly Val Asp Lys Asn Arg Val Gly Ile Thr Val Asp Gly Ile Ala Gln
1025                1030                1035                1040
Ile Gln Ser Tyr Lys Asp Glu Ser Thr Lys Arg Ala Gly Ala Gly Ser
                   1045                1050                1055
Gly Ala Met Asn Glu Ile Glu Ile Glu Asn Ile Ala Ala Val Ala Ile
                   1060                1065                1070
Asn Lys Gly Gly Asn Ala Leu Glu Ala Gly Ser Gly Ala Leu Gly Gly
                   1075                1080                1085
Ser Val Ala Phe His Thr Lys Asp Val Ser Asp Val Leu Lys Ser Gly
                   1090                1095                1100
Asn Asn Leu Gly Ala Gln Ser Lys Thr Thr Tyr Asn Ser Lys Asn Asp
1105                1110                1115                1120
His Phe Ser Gln Thr Leu Ala Ala Ala Gly Lys Thr Glu Arg Val Glu
                   1125                1130                1135
Ala Met Val Gln Tyr Thr Tyr Arg Lys Gly Lys Glu Asn Lys Ala His
                   1140                1145                1150
Ser Asp Leu Asn Gly Ile Asn Gln Ser Leu Tyr Arg Leu Gly Ala Trp
                   1155                1160                1165
Gln Gln Lys Tyr Asp Leu Arg Lys Pro Asn Glu Leu Phe Ala Gly Thr
                   1170                1175                1180
Ser Tyr Ile Thr Glu Ser Cys Leu Ala Ser Asp Pro Lys Ser Cys
1185                1190                1195                1200
Val Gln Tyr Pro Tyr Val Tyr Thr Lys Ala Arg Pro Asp Gly Ile Gly
                   1205                1210                1215
Asn Arg Asn Phe Ser Glu Leu Ser Asp Ala Glu Lys Ala Gln Tyr Leu
                   1220                1225                1230
Ala Ser Thr His Pro His Glu Val Val Ser Ala Lys Asp Tyr Thr Gly
                   1235                1240                1245
Thr Tyr Arg Leu Leu Pro Asp Pro Met Asp Tyr Arg Ser Asp Ser Tyr
                   1250                1255                1260
Leu Ala Arg Leu Asn Ile Lys Ile Thr Pro Asn Leu Val Ser Lys Leu
1265                1270                1275                1280
Leu Leu Glu Asp Thr Lys Gln Thr Tyr Asn Ile Arg Asp Met Arg His
                   1285                1290                1295
Cys Ser Tyr His Gly Ala Arg Leu Gly Asn Asp Gly Lys Pro Ala Asn
                   1300                1305                1310
Gly Gly Ser Ile Val Leu Cys Asp Asp Tyr Gln Glu Tyr Leu Asn Ala
                   1315                1320                1325
Asn Asp Ala Ser Gln Ala Ser Phe Arg Pro Gly Ala Asn Asp Ala Pro
                   1330                1335                1340
Ile Pro Lys Leu Ala Tyr Ala Arg Ser Ser Val Phe Asn Gln Glu His
1345                1350                1355                1360
Gly Lys Thr Arg Tyr Gly Leu Gly Phe Glu Phe Lys Pro Asp Thr Pro
                   1365                1370                1375
```

```
Trp Phe Lys Gln Ala Lys Leu Asn Leu His Gln Gln Asn Ile Gln Ile
            1380                1385                1390
Ile Asn His Asp Ile Lys Lys Ser Cys Ser Gln Tyr Pro Lys Val Asp
        1395                1400                1405
Leu Asn Cys Gly Ile Ser Glu Ile Gly His Tyr Glu Tyr Gln Asn Asn
    1410                1415                1420
Tyr Arg Tyr Lys Glu Gly Arg Thr Ser Leu Thr Gly Lys Leu Asp Phe
1425                1430                1435                1440
Asn Phe Asp Leu Leu Gly Gln His Asp Leu Thr Val Leu Ala Gly Ala
                1445                1450                1455
Asp Lys Val Lys Ser Gln Phe Arg Ala Asn Asn Pro Arg Arg Thr Ile
            1460                1465                1470
Ile Asp Thr Thr Gln Gly Asp Ala Ile Ile Asp Glu Ser Thr Leu Thr
        1475                1480                1485
Ala Gln Glu Gln Ala Lys Phe Lys Gln Ser Gly Ala Ala Trp Ile Val
    1490                1495                1500
Lys Asn Arg Leu Gly Arg Leu Glu Glu Lys Asp Ala Cys Gly Asn Ala
1505                1510                1515                1520
Asn Glu Cys Glu Arg Ala Pro Ile His Gly Ser Asn Gln Tyr Val Gly
                1525                1530                1535
Ile Asn Asn Leu Tyr Thr Pro Asn Asp Tyr Val Asp Leu Ser Phe Gly
            1540                1545                1550
Gly Arg Leu Asp Lys Gln Arg Ile His Ser Thr Asp Ser Asn Ile Ile
        1555                1560                1565
Ser Lys Thr Tyr Thr Asn Lys Ser Tyr Asn Phe Gly Ala Ala Val His
    1570                1575                1580
Leu Thr Pro Asp Phe Ser Leu Leu Tyr Lys Thr Ala Lys Gly Phe Arg
1585                1590                1595                1600
Thr Pro Ser Phe Tyr Glu Leu Tyr Asn Tyr Asn Ser Thr Ala Ala Gln
                1605                1610                1615
His Lys Asn Asp Pro Asp Val Ser Phe Pro Lys Arg Ala Val Asp Val
            1620                1625                1630
Lys Pro Glu Thr Ser Asn Thr Asn Glu Tyr Gly Phe Arg Tyr Gln His
        1635                1640                1645
Pro Trp Gly Asp Ile Glu Met Ser Met Phe Lys Ser Arg Tyr Lys Asp
    1650                1655                1660
Met Leu Asp Lys Ala Ile Pro Asn Leu Thr Lys Ala Gln Gln Glu Tyr
1665                1670                1675                1680
Cys Lys Ala His Leu Asp Ser Asn Glu Cys Val Gly Asn Pro Pro Thr
                1685                1690                1695
Pro Lys Thr Ser Asp Glu Val Phe Ala Asn Leu Tyr Asn Ala Thr Ile
            1700                1705                1710
Lys Gly Val Ser Val Lys Gly Lys Leu Asp Leu His Ala Met Thr Ser
        1715                1720                1725
Lys Leu Pro Asp Gly Leu Glu Met Thr Leu Gly Tyr Gly His Thr Lys
    1730                1735                1740
Leu Gly Lys Phe Asp Tyr Ile Ala Pro Lys Asp Ala Asp Gly Trp Tyr
1745                1750                1755                1760
Gln Ala Arg Pro Ala Phe Trp Asp Ala Ile Thr Pro Ala Arg Tyr Val
                1765                1770                1775
Val Gly Leu Asn Tyr Asp His Pro Ser Gln Val Trp Gly Ile Gly Thr
            1780                1785                1790
```

-continued

```
Thr Leu Thr His Ser Lys Gln Lys Asp Glu Asn Glu Leu Ser Ala Leu
        1795                1800                1805
Arg Ile Arg Asn Gly Lys Arg Glu Ile Gln Thr Leu Thr His Thr Ile
    1810                1815                1820
Pro Lys Ala Tyr Thr Leu Leu Asp Met Thr Gly Tyr Tyr Ser Pro Thr
1825                1830                1835                1840
Glu Ser Ile Thr Ala Arg Leu Gly Ile Asn Asn Val Leu Asn Thr Arg
                1845                1850                1855
Tyr Thr Thr Trp Glu Ala Ala Arg Gln Leu Pro Ser Glu Ala Ala Ser
            1860                1865                1870
Ser Thr Gln Ser Thr Arg Tyr Ile Ala Pro Gly Arg Ser Tyr Phe Ala
        1875                1880                1885
Ser Leu Glu Met Lys Phe Met Thr Cys Leu Pro Lys Thr Asn Pro Ala
    1890                1895                1900
Leu Lys Val Lys His Arg Phe Leu Lys Gln Val Leu Leu Leu Leu Cys
1905                1910                1915                1920
Val Asp Thr Leu Thr Ala Gln Ala Tyr Ala His Ser His Thr Pro
                1925                1930                1935
Ile His Thr Pro Thr His Glu Leu Ser Ser Ala Asp Ala Leu Ser Asp
            1940                1945                1950
Glu Gly Leu Gly Lys Asp Leu Gly Ser Leu Asp Ser Pro Asp Gly Leu
        1955                1960                1965
Gly Asp Gly Leu Gly Asp Gly Leu Gly Asp Gly Leu Lys Ser Asp Lys
    1970                1975                1980
Thr Pro Leu Pro Ile Asn Ala Leu Thr Val Asn Gln Ser Asn Glu Ser
1985                1990                1995                2000
Gln Pro Ala Pro Pro Ser Val Asp Val Asn Phe Leu Leu Ala Gln Pro
                2005                2010                2015
Glu Ala Phe Tyr His Val Phe Gln Ala Ile Val Gln Asp Asp Val
            2020                2025                2030
Ala Thr Leu Arg Leu Leu Leu Pro Phe Tyr Asp Arg Leu Pro Asp Asp
        2035                2040                2045
Tyr Gln Asp Asp Val Leu Leu Leu Phe Ala Gln Ser Lys Leu Ala Leu
    2050                2055                2060
Ser Asp Gly Asn Thr Lys Leu Ala Leu Asn Leu Leu Thr Asp Leu Ser
2065                2070                2075                2080
Asn Lys Glu Pro Thr Leu Thr Ala Val Lys Leu Gln Leu Ala Ser Leu
                2085                2090                2095
Leu Leu Thr Asn Lys His Asp Lys His Ala Gln Met Val Leu Asp Glu
            2100                2105                2110
Leu Lys Asp Asp Ala His Phe Leu Lys Leu Ser Lys Lys Glu Gln Arg
        2115                2120                2125
Trp Val Leu Ser Gln Ser Arg Tyr Leu His Lys Lys Tyr Lys Met Gly
    2130                2135                2140
Leu Asp Leu Gly Ile Asn Tyr Leu His Leu Asp Asn Ile Asn Ala Ala
2145                2150                2155                2160
Ser Thr Ile Thr Gln Pro Asn Ile Lys Lys Asp Ala Pro Lys Pro Ala
                2165                2170                2175
His Gly Leu Ala Leu Ser Leu Gly Val Asn Lys Tyr Thr Pro Leu Ser
            2180                2185                2190
His Gly Met Ser Ile Tyr Thr Ala Leu Asp Val Asp Gly Lys Phe Tyr
        2195                2200                2205
Asp Asp Lys Ser His Asn Glu Leu Ala Val Phe Ala His Ala Gly Leu
```

```
                2210                2215                2220
Arg Lys Asp His Gln Lys Gly Tyr Val Asp Val Pro Phe Val Gly
2225                2230                2235                2240

Arg Ile Phe Ala Thr Asn Gln Gln His Gly Arg Leu Ser Pro Arg Lys
                2245                2250                2255

Asp Ser Gln Gly Val Ala Phe Gly Ser His His Arg Ile Asn Asp Lys
                2260                2265                2270

Trp Gln Asn Ala Phe Phe Ala Arg Met Glu Lys Gly Asn Tyr Thr Glu
            2275                2280                2285

His Tyr Gln Gly Tyr Asp Gly Lys Arg Tyr His Val Asn Asp Thr Ile
            2290                2295                2300

Leu Leu Gln Asp Gly Pro Asn Arg Arg Tyr Ser Leu Gly Val Gly Tyr
2305                2310                2315                2320

Gln Leu Ser His Leu Gln Asp Ala Thr Lys Ser Ser His Ala Thr Lys
                2325                2330                2335

Ile His Phe Gly Val Leu Gln Arg Leu Pro Asn Gly Leu Thr Val Gln
                2340                2345                2350

Gly Arg Val Ser Ala Glu Arg Glu Arg Tyr His Gly Lys Leu Leu Arg
            2355                2360                2365

Leu Val Asn Pro Asp Asp Val Tyr Arg Thr Asp Lys Thr Leu Thr Leu
            2370                2375                2380

Gln Thr Ser Ile Trp His Lys Asp Ile His Trp Leu Gly Leu Thr Pro
2385                2390                2395                2400

Lys Leu Thr Tyr Arg Tyr Ser Lys Asn Asn Ser Asn Leu Pro Ala Leu
                2405                2410                2415

Tyr Ser His Asn Lys Gln Asn Phe Tyr Leu Glu Leu Gly Arg Ser Phe
                2420                2425                2430

(2) INFORMATION FOR SEQ ID NO:16:

(i) SEQUENCE CHARACTERISTICS:
        (A) LENGTH: 1000 amino acids
        (B) TYPE: amino acid
        (C) STRANDEDNESS: single
        (D) TOPOLOGY: linear (xi) SEQUENCE DESCRIPTION: SEQ ID NO:16:

Met Ser Lys Ser Ile Thr Lys Thr Gln Thr Pro Ser Val His Thr Met
1               5                   10                  15

Thr Thr His Arg Leu Asn Leu Ala Ile Lys Ala Ala Leu Phe Gly Val
                20                  25                  30

Ala Val Leu Pro Leu Ser Val Trp Ala Gln Glu Asn Thr Gln Thr Asp
            35                  40                  45

Ala Asn Ser Asp Ala Lys Asp Thr Lys Thr Pro Val Val Tyr Leu Asp
        50                  55                  60

Ala Ile Thr Val Thr Ala Ala Pro Ser Ala Pro Val Ser Arg Phe Asp
65                  70                  75                  80

Thr Asp Val Thr Gly Leu Gly Lys Thr Val Lys Thr Ala Asp Thr Leu
                85                  90                  95

Ala Lys Glu Gln Val Gln Gly Ile Arg Asp Leu Val Arg Tyr Glu Thr
            100                 105                 110

Gly Val Ser Val Val Glu Gln Gly Arg Gly Ser Ser Gly Phe Ala
            115                 120                 125

Ile His Gly Val Asp Lys Asn Arg Val Gly Ile Thr Val Asp Gly Ile
        130                 135                 140
```

-continued

```
Ala Gln Ile Gln Ser Tyr Lys Asp Glu Ser Thr Lys Arg Ala Gly Ala
145                 150                 155                 160

Gly Ser Gly Ala Met Asn Glu Ile Glu Ile Glu Asn Ile Ala Ala Val
                165                 170                 175

Ala Ile Asn Lys Gly Gly Asn Ala Leu Glu Ala Gly Ser Gly Ala Leu
            180                 185                 190

Gly Gly Ser Val Ala Phe His Thr Lys Asp Val Ser Asp Val Leu Lys
        195                 200                 205

Ser Gly Asn Asn Leu Gly Ala Gln Ser Lys Thr Thr Tyr Asn Ser Lys
    210                 215                 220

Asn Asp His Phe Ser Gln Thr Leu Ala Ala Gly Lys Thr Glu Arg
225                 230                 235                 240

Val Glu Ala Met Val Gln Tyr Thr Tyr Arg Lys Gly Lys Glu Asn Lys
                245                 250                 255

Ala His Ser Asp Leu Asn Gly Ile Asn Gln Ser Leu Tyr Arg Leu Gly
            260                 265                 270

Ala Trp Gln Gln Lys Tyr Asp Leu Arg Lys Pro Asn Glu Leu Phe Ala
        275                 280                 285

Gly Thr Ser Tyr Ile Thr Glu Ser Cys Leu Ala Ser Asp Pro Lys
    290                 295                 300

Ser Cys Val Gln Tyr Pro Tyr Val Tyr Thr Lys Ala Arg Pro Asp Gly
305                 310                 315                 320

Ile Gly Asn Arg Asn Phe Ser Glu Leu Ser Asp Ala Glu Lys Ala Gln
                325                 330                 335

Tyr Leu Ala Ser Thr His Pro His Glu Val Val Ser Ala Lys Asp Tyr
            340                 345                 350

Thr Gly Thr Tyr Arg Leu Leu Pro Asp Pro Met Asp Tyr Arg Ser Asp
        355                 360                 365

Ser Tyr Leu Ala Arg Leu Asn Ile Lys Ile Thr Pro Asn Leu Val Ser
    370                 375                 380

Lys Leu Leu Leu Glu Asp Thr Lys Gln Thr Tyr Asn Ile Arg Asp Met
385                 390                 395                 400

Arg His Cys Ser Tyr His Gly Ala Arg Leu Gly Asn Asp Gly Lys Pro
                405                 410                 415

Ala Asn Gly Gly Ser Ile Val Leu Cys Asp Asp Tyr Gln Glu Tyr Leu
            420                 425                 430

Asn Ala Asn Asp Ala Ser Gln Ala Ser Phe Arg Pro Gly Ala Asn Asp
        435                 440                 445

Ala Pro Ile Pro Lys Leu Ala Tyr Ala Arg Ser Ser Val Phe Asn Gln
450                 455                 460

Glu His Gly Lys Thr Arg Tyr Gly Leu Gly Phe Glu Phe Lys Pro Asp
465                 470                 475                 480

Thr Pro Trp Phe Lys Gln Ala Lys Leu Asn Leu His Gln Gln Asn Ile
                485                 490                 495

Gln Ile Ile Asn His Asp Ile Lys Lys Ser Cys Ser Gln Tyr Pro Lys
            500                 505                 510

Val Asp Leu Asn Cys Gly Ile Ser Glu Ile Gly His Tyr Glu Tyr Gln
        515                 520                 525

Asn Asn Tyr Arg Tyr Lys Glu Gly Arg Thr Ser Leu Thr Gly Lys Leu
    530                 535                 540

Asp Phe Asn Phe Asp Leu Leu Gly Gln His Asp Leu Thr Val Leu Ala
545                 550                 555                 560

Gly Ala Asp Lys Val Lys Ser Gln Phe Arg Ala Asn Asn Pro Arg Arg
```

-continued

```
                        565                 570                 575
Thr Ile Ile Asp Thr Thr Gln Gly Asp Ala Ile Ile Asp Glu Ser Thr
                    580                 585                 590
Leu Thr Ala Gln Glu Gln Ala Lys Phe Lys Gln Ser Gly Ala Ala Trp
                595                 600                 605
Ile Val Lys Asn Arg Leu Gly Arg Leu Glu Glu Lys Asp Ala Cys Gly
            610                 615                 620
Asn Ala Asn Glu Cys Glu Arg Ala Pro Ile His Gly Ser Asn Gln Tyr
625                 630                 635                 640
Val Gly Ile Asn Asn Leu Tyr Thr Pro Asn Asp Tyr Val Asp Leu Ser
                        645                 650                 655
Phe Gly Arg Leu Asp Lys Gln Arg Ile His Ser Thr Asp Ser Asn
                    660                 665                 670
Ile Ile Ser Lys Thr Tyr Thr Asn Lys Ser Tyr Asn Phe Gly Ala Ala
                675                 680                 685
Val His Leu Thr Pro Asp Phe Ser Leu Leu Tyr Lys Thr Ala Lys Gly
            690                 695                 700
Phe Arg Thr Pro Ser Phe Tyr Glu Leu Tyr Asn Tyr Asn Ser Thr Ala
705                 710                 715                 720
Ala Gln His Lys Asn Asp Pro Asp Val Ser Phe Pro Lys Arg Ala Val
                        725                 730                 735
Asp Val Lys Pro Glu Thr Ser Asn Thr Asn Glu Tyr Gly Phe Arg Tyr
                    740                 745                 750
Gln His Pro Trp Gly Asp Ile Glu Met Ser Met Phe Lys Ser Arg Tyr
                755                 760                 765
Lys Asp Met Leu Asp Lys Ala Ile Pro Asn Leu Thr Lys Ala Gln Gln
            770                 775                 780
Glu Tyr Cys Lys Ala His Leu Asp Ser Asn Glu Cys Val Gly Asn Pro
785                 790                 795                 800
Pro Thr Pro Lys Thr Ser Asp Glu Val Phe Ala Asn Leu Tyr Asn Ala
                        805                 810                 815
Thr Ile Lys Gly Val Ser Val Lys Gly Lys Leu Asp Leu His Ala Met
                    820                 825                 830
Thr Ser Lys Leu Pro Asp Gly Leu Glu Met Thr Leu Gly Tyr Gly His
                835                 840                 845
Thr Lys Leu Gly Lys Phe Asp Tyr Ile Ala Pro Lys Asp Ala Asp Gly
            850                 855                 860
Trp Tyr Gln Ala Arg Pro Ala Phe Trp Asp Ala Ile Thr Pro Ala Arg
865                 870                 875                 880
Tyr Val Val Gly Leu Asn Tyr Asp His Pro Ser Gln Val Trp Gly Ile
                        885                 890                 895
Gly Thr Thr Leu Thr His Ser Lys Gln Lys Asp Glu Asn Glu Leu Ser
                    900                 905                 910
Ala Leu Arg Ile Arg Asn Gly Lys Arg Glu Ile Gln Thr Leu Thr His
                915                 920                 925
Thr Ile Pro Lys Ala Tyr Thr Leu Leu Asp Met Thr Gly Tyr Tyr Ser
            930                 935                 940
Pro Thr Glu Ser Ile Thr Ala Arg Leu Gly Ile Asn Asn Val Leu Asn
945                 950                 955                 960
Thr Arg Tyr Thr Thr Trp Glu Ala Ala Arg Gln Leu Pro Ser Glu Ala
                        965                 970                 975
Ala Ser Ser Thr Gln Ser Thr Arg Tyr Ile Ala Pro Gly Arg Ser Tyr
                    980                 985                 990
```

```
Phe Ala Ser Leu Glu Met Lys Phe
        995                 1000

(2) INFORMATION FOR SEQ ID NO:17:

(i) SEQUENCE CHARACTERISTICS:
        (A) LENGTH: 985 amino acids
        (B) TYPE: amino acid
        (C) STRANDEDNESS: single
        (D) TOPOLOGY: linear (xi) SEQUENCE DESCRIPTION: SEQ ID NO:17:

Met Thr Thr His Arg Leu Asn Leu Ala Ile Lys Ala Ala Leu Phe Gly
1               5                   10                  15

Val Ala Val Leu Pro Leu Ser Val Trp Ala Gln Glu Asn Thr Gln Thr
            20                  25                  30

Asp Ala Asn Ser Asp Ala Lys Asp Thr Lys Thr Pro Val Val Tyr Leu
        35                  40                  45

Asp Ala Ile Thr Val Thr Ala Ala Pro Ser Ala Pro Val Ser Arg Phe
    50                  55                  60

Asp Thr Asp Val Thr Gly Leu Gly Lys Thr Val Lys Thr Ala Asp Thr
65                  70                  75                  80

Leu Ala Lys Glu Gln Val Gln Gly Ile Arg Asp Leu Val Arg Tyr Glu
                85                  90                  95

Thr Gly Val Ser Val Val Glu Gln Gly Arg Gly Gly Ser Ser Gly Phe
            100                 105                 110

Ala Ile His Gly Val Asp Lys Asn Arg Val Gly Ile Thr Val Asp Gly
        115                 120                 125

Ile Ala Gln Ile Gln Ser Tyr Lys Asp Glu Ser Thr Lys Arg Ala Gly
    130                 135                 140

Ala Gly Ser Gly Ala Met Asn Glu Ile Glu Ile Glu Asn Ile Ala Ala
145                 150                 155                 160

Val Ala Ile Asn Lys Gly Gly Asn Ala Leu Glu Ala Gly Ser Gly Ala
                165                 170                 175

Leu Gly Gly Ser Val Ala Phe His Thr Lys Asp Val Ser Asp Val Leu
            180                 185                 190

Lys Ser Gly Asn Asn Leu Gly Ala Gln Ser Lys Thr Thr Tyr Asn Ser
        195                 200                 205

Lys Asn Asp His Phe Ser Gln Thr Leu Ala Ala Gly Lys Thr Glu
    210                 215                 220

Arg Val Glu Ala Met Val Gln Tyr Thr Tyr Arg Lys Gly Lys Glu Asn
225                 230                 235                 240

Lys Ala His Ser Asp Leu Asn Gly Ile Asn Gln Ser Leu Tyr Arg Leu
                245                 250                 255

Gly Ala Trp Gln Gln Lys Tyr Asp Leu Arg Lys Pro Asn Glu Leu Phe
            260                 265                 270

Ala Gly Thr Ser Tyr Ile Thr Glu Ser Cys Leu Ala Ser Asp Asp Pro
        275                 280                 285

Lys Ser Cys Val Gln Tyr Pro Tyr Val Tyr Thr Lys Ala Arg Pro Asp
    290                 295                 300

Gly Ile Gly Asn Arg Asn Phe Ser Glu Leu Ser Asp Ala Glu Lys Ala
305                 310                 315                 320

Gln Tyr Leu Ala Ser Thr His Pro His Glu Val Val Ser Ala Lys Asp
                325                 330                 335

Tyr Thr Gly Thr Tyr Arg Leu Leu Pro Asp Pro Met Asp Tyr Arg Ser
```

-continued

```
                    340                 345                 350
    Asp Ser Tyr Leu Ala Arg Leu Asn Ile Lys Ile Thr Pro Asn Leu Val
                355                 360                 365
    Ser Lys Leu Leu Leu Glu Asp Thr Lys Gln Thr Tyr Asn Ile Arg Asp
                370                 375                 380
    Met Arg His Cys Ser Tyr His Gly Ala Arg Leu Gly Asn Asp Gly Lys
    385                 390                 395                 400
    Pro Ala Asn Gly Gly Ser Ile Val Leu Cys Asp Asp Tyr Gln Glu Tyr
                    405                 410                 415
    Leu Asn Ala Asn Asp Ala Ser Gln Ala Ser Phe Arg Pro Gly Ala Asn
                420                 425                 430
    Asp Ala Pro Ile Pro Lys Leu Ala Tyr Ala Arg Ser Ser Val Phe Asn
                435                 440                 445
    Gln Glu His Gly Lys Thr Arg Tyr Gly Leu Gly Phe Glu Phe Lys Pro
                450                 455                 460
    Asp Thr Pro Trp Phe Lys Gln Ala Lys Leu Asn Leu His Gln Gln Asn
    465                 470                 475                 480
    Ile Gln Ile Ile Asn His Asp Ile Lys Lys Ser Cys Ser Gln Tyr Pro
                    485                 490                 495
    Lys Val Asp Leu Asn Cys Gly Ile Ser Glu Ile Gly His Tyr Glu Tyr
                500                 505                 510
    Gln Asn Asn Tyr Arg Tyr Lys Glu Gly Arg Thr Ser Leu Thr Gly Lys
                515                 520                 525
    Leu Asp Phe Asn Phe Asp Leu Leu Gly Gln His Asp Leu Thr Val Leu
                530                 535                 540
    Ala Gly Ala Asp Lys Val Lys Ser Gln Phe Arg Ala Asn Asn Pro Arg
    545                 550                 555                 560
    Arg Thr Ile Ile Asp Thr Thr Gln Gly Asp Ala Ile Ile Asp Glu Ser
                    565                 570                 575
    Thr Leu Thr Ala Gln Glu Gln Ala Lys Phe Lys Gln Ser Gly Ala Ala
                580                 585                 590
    Trp Ile Val Lys Asn Arg Leu Gly Arg Leu Glu Glu Lys Asp Ala Cys
                595                 600                 605
    Gly Asn Ala Asn Glu Cys Glu Arg Ala Pro Ile His Gly Ser Asn Gln
                610                 615                 620
    Tyr Val Gly Ile Asn Asn Leu Tyr Thr Pro Asn Asp Tyr Val Asp Leu
    625                 630                 635                 640
    Ser Phe Gly Gly Arg Leu Asp Lys Gln Arg Ile His Ser Thr Asp Ser
                    645                 650                 655
    Asn Ile Ile Ser Lys Thr Tyr Thr Asn Lys Ser Tyr Asn Phe Gly Ala
                660                 665                 670
    Ala Val His Leu Thr Pro Asp Phe Ser Leu Leu Tyr Lys Thr Ala Lys
                675                 680                 685
    Gly Phe Arg Thr Pro Ser Phe Tyr Glu Leu Tyr Asn Tyr Asn Ser Thr
                690                 695                 700
    Ala Ala Gln His Lys Asn Asp Pro Asp Val Ser Phe Pro Lys Arg Ala
    705                 710                 715                 720
    Val Asp Val Lys Pro Glu Thr Ser Asn Thr Asn Glu Tyr Gly Phe Arg
                    725                 730                 735
    Tyr Gln His Pro Trp Gly Asp Ile Glu Met Ser Met Phe Lys Ser Arg
                740                 745                 750
    Tyr Lys Asp Met Leu Asp Lys Ala Ile Pro Asn Leu Thr Lys Ala Gln
                755                 760                 765
```

```
Gln Glu Tyr Cys Lys Ala His Leu Asp Ser Asn Glu Cys Val Gly Asn
    770                 775                 780
Pro Pro Thr Pro Lys Thr Ser Asp Glu Val Phe Ala Asn Leu Tyr Asn
785                 790                 795                 800
Ala Thr Ile Lys Gly Val Ser Val Lys Gly Lys Leu Asp Leu His Ala
                805                 810                 815
Met Thr Ser Lys Leu Pro Asp Gly Leu Glu Met Thr Leu Gly Tyr Gly
                820                 825                 830
His Thr Lys Leu Gly Lys Phe Asp Tyr Ile Ala Pro Lys Asp Ala Asp
                835                 840                 845
Gly Trp Tyr Gln Ala Arg Pro Ala Phe Trp Asp Ala Ile Thr Pro Ala
850                 855                 860
Arg Tyr Val Val Gly Leu Asn Tyr Asp His Pro Ser Gln Val Trp Gly
865                 870                 875                 880
Ile Gly Thr Thr Leu Thr His Ser Lys Gln Lys Asp Glu Asn Glu Leu
                885                 890                 895
Ser Ala Leu Arg Ile Arg Asn Gly Lys Arg Glu Ile Gln Thr Leu Thr
                900                 905                 910
His Thr Ile Pro Lys Ala Tyr Thr Leu Leu Asp Met Thr Gly Tyr Tyr
                915                 920                 925
Ser Pro Thr Glu Ser Ile Thr Ala Arg Leu Gly Ile Asn Asn Val Leu
                930                 935                 940
Asn Thr Arg Tyr Thr Thr Trp Glu Ala Ala Arg Gln Leu Pro Ser Glu
945                 950                 955                 960
Ala Ala Ser Ser Thr Gln Ser Thr Arg Tyr Ile Ala Pro Gly Arg Ser
                965                 970                 975
Tyr Phe Ala Ser Leu Glu Met Lys Phe
                980                 985

(2) INFORMATION FOR SEQ ID NO:18:

(i) SEQUENCE CHARACTERISTICS:
        (A) LENGTH: 538 amino acids
        (B) TYPE: amino acid
        (C) STRANDEDNESS: single
        (D) TOPOLOGY: linear (xi) SEQUENCE DESCRIPTION: SEQ ID NO:18:

Met Thr Cys Leu Pro Lys Thr Asn Pro Ala Leu Lys Val Lys His Arg
1               5                   10                  15
Phe Leu Lys Gln Val Leu Leu Leu Cys Val Asp Thr Leu Thr Ala
                20                  25                  30
Gln Ala Tyr Ala His Ser His His Thr Pro Ile His Thr Pro Thr His
                35                  40                  45
Glu Leu Ser Ser Ala Asp Ala Leu Ser Asp Glu Gly Leu Gly Lys Asp
    50                  55                  60
Leu Gly Ser Leu Asp Ser Pro Asp Gly Leu Gly Asp Gly Leu Gly Asp
65                  70                  75                  80
Gly Leu Gly Asp Gly Leu Lys Ser Asp Lys Thr Pro Leu Pro Ile Asn
                85                  90                  95
Ala Leu Thr Val Asn Gln Ser Asn Glu Ser Gln Pro Ala Pro Pro Ser
                100                 105                 110
Val Asp Val Asn Phe Leu Leu Ala Gln Pro Glu Ala Phe Tyr His Val
            115                 120                 125
Phe His Gln Ala Ile Val Gln Asp Asp Val Ala Thr Leu Arg Leu Leu
```

```
            130                 135                 140
Leu Pro Phe Tyr Asp Arg Leu Pro Asp Asp Tyr Gln Asp Asp Val Leu
145                 150                 155                 160
Leu Leu Phe Ala Gln Ser Lys Leu Ala Leu Ser Asp Gly Asn Thr Lys
                165                 170                 175
Leu Ala Leu Asn Leu Leu Thr Asp Leu Ser Asn Lys Glu Pro Thr Leu
            180                 185                 190
Thr Ala Val Lys Leu Gln Leu Ala Ser Leu Leu Thr Asn Lys His
        195                 200                 205
Asp Lys His Ala Gln Met Val Leu Asp Glu Leu Lys Asp Ala His
        210                 215                 220
Phe Leu Lys Leu Ser Lys Lys Glu Gln Arg Trp Val Leu Ser Gln Ser
225                 230                 235                 240
Arg Tyr Leu His Lys Lys Tyr Lys Met Gly Leu Asp Leu Gly Ile Asn
                245                 250                 255
Tyr Leu His Leu Asp Asn Ile Asn Ala Ala Ser Thr Ile Thr Gln Pro
            260                 265                 270
Asn Ile Lys Lys Asp Ala Pro Lys Pro Ala His Gly Leu Ala Leu Ser
        275                 280                 285
Leu Gly Val Asn Lys Tyr Thr Pro Leu Ser His Gly Met Ser Ile Tyr
    290                 295                 300
Thr Ala Leu Asp Val Asp Gly Lys Phe Tyr Asp Asp Lys Ser His Asn
305                 310                 315                 320
Glu Leu Ala Val Phe Ala His Ala Gly Leu Arg Lys Asp His Gln Lys
                325                 330                 335
Gly Tyr Val Asp Val Val Pro Phe Val Gly Arg Ile Phe Ala Thr Asn
            340                 345                 350
Gln Gln His Gly Arg Leu Ser Pro Arg Lys Asp Ser Gln Gly Val Ala
        355                 360                 365
Phe Gly Ser His His Arg Ile Asn Asp Lys Trp Gln Asn Ala Phe Phe
    370                 375                 380
Ala Arg Met Glu Lys Gly Asn Tyr Thr Glu His Tyr Gln Gly Tyr Asp
385                 390                 395                 400
Gly Lys Arg Tyr His Val Asn Asp Thr Ile Leu Leu Gln Asp Gly Pro
                405                 410                 415
Asn Arg Arg Tyr Ser Leu Gly Val Gly Tyr Gln Leu Ser His Leu Gln
            420                 425                 430
Asp Ala Thr Lys Ser Ser His Ala Thr Lys Ile His Phe Gly Val Leu
        435                 440                 445
Gln Arg Leu Pro Asn Gly Leu Thr Val Gln Gly Arg Val Ser Ala Glu
    450                 455                 460
Arg Glu Arg Tyr His Gly Lys Leu Leu Arg Leu Val Asn Pro Asp Asp
465                 470                 475                 480
Val Tyr Arg Thr Asp Lys Thr Leu Thr Leu Gln Thr Ser Ile Trp His
                485                 490                 495
Lys Asp Ile His Trp Leu Gly Leu Thr Pro Lys Leu Thr Tyr Arg Tyr
            500                 505                 510
Ser Lys Asn Asn Ser Asn Leu Pro Ala Leu Tyr Ser His Asn Lys Gln
        515                 520                 525
Asn Phe Tyr Leu Glu Leu Gly Arg Ser Phe
    530                 535
```

(2) INFORMATION FOR SEQ ID NO:19:

(i) SEQUENCE CHARACTERISTICS:
           (A) LENGTH: 1076 amino acids
           (B) TYPE: amino acid
           (C) STRANDEDNESS: single
           (D) TOPOLOGY: linear (xi) SEQUENCE DESCRIPTION: SEQ ID NO:19:

Met Asn Gln Ser Lys Gln Asn Asn Lys Ser Lys Ser Lys Gln Val
1               5                   10                  15

Leu Lys Leu Ser Ala Leu Ser Leu Gly Leu Leu Asn Ile Thr Gln Val
            20                  25                  30

Ala Leu Ala Asn Thr Thr Ala Asp Lys Ala Glu Ala Thr Asp Lys Thr
            35                  40                  45

Asn Leu Val Val Val Leu Asp Glu Thr Val Val Ala Lys Lys Asn
    50                  55                  60

Ala Pro Val Ser Arg Lys Ala Asn Glu Val Thr Gly Leu Gly Lys Val
65                  70                  75                  80

Val Lys Thr Ala Glu Thr Ile Asn Lys Glu Gln Val Leu Asn Ile Arg
                85                  90                  95

Asp Leu Thr Arg Tyr Asp Pro Gly Ile Ala Val Val Glu Gln Gly Arg
                100                 105                 110

Gly Ala Ser Ser Gly Tyr Ser Ile Arg Gly Met Asp Lys Asn Arg Val
                115                 120                 125

Ala Val Leu Val Asp Gly Ile Asn Gln Ala Gln His Tyr Gln Gly Pro
130                 135                 140

Val Ala Gly Lys Asn Tyr Ala Ala Gly Ala Ile Asn Glu Ile Glu
145                 150                 155                 160

Tyr Glu Asn Val Arg Ser Val Glu Ile Ser Lys Gly Ala Asn Ser Ser
                165                 170                 175

Glu Tyr Gly Ser Gly Ala Leu Ser Gly Ser Val Ala Phe Val Thr Lys
                180                 185                 190

Thr Ala Asp Asp Ile Ile Lys Asp Gly Lys Asp Trp Gly Val Gln Thr
                195                 200                 205

Lys Thr Ala Tyr Ala Ser Lys Asn Asn Ala Trp Val Asn Ser Val Ala
210                 215                 220

Ala Ala Gly Lys Ala Gly Ser Phe Ser Gly Leu Ile Ile Tyr Thr Asp
225                 230                 235                 240

Arg Arg Gly Gln Glu Tyr Lys Ala His Asp Asp Ala Tyr Gln Gly Ser
                245                 250                 255

Gln Ser Phe Asp Arg Ala Val Ala Thr Thr Asp Pro Asn Asn Arg Thr
                260                 265                 270

Phe Leu Ile Ala Asn Glu Cys Ala Asn Gly Asn Tyr Glu Ala Cys Ala
            275                 280                 285

Ala Gly Gly Gln Thr Lys Leu Gln Ala Lys Pro Thr Asn Val Arg Asp
            290                 295                 300

Lys Val Asn Val Lys Asp Tyr Thr Gly Pro Asn Arg Leu Ile Pro Asn
305                 310                 315                 320

Pro Leu Thr Gln Asp Ser Lys Ser Leu Leu Leu Arg Pro Gly Tyr Gln
                325                 330                 335

Leu Asn Asp Lys His Tyr Val Gly Val Tyr Glu Ile Thr Lys Gln
                340                 345                 350

Asn Tyr Ala Met Gln Asp Lys Thr Val Pro Ala Tyr Leu Ala Val His
            355                 360                 365

Asp Ile Glu Lys Ser Arg Leu Ser Asn His Ala Gln Ala Asn Gly Tyr

-continued

```
          370                 375                 380
Tyr Gln Gly Asn Asn Leu Gly Glu Arg Ile Arg Asp Thr Ile Gly Pro
385                 390                 395                 400
Asp Ser Gly Tyr Gly Ile Asn Tyr Ala His Gly Val Phe Tyr Asp Glu
                405                 410                 415
Lys His Gln Lys Asp Arg Leu Gly Leu Glu Tyr Val Tyr Asp Ser Lys
                420                 425                 430
Gly Glu Asn Lys Trp Phe Asp Asp Val Arg Val Ser Tyr Asp Lys Gln
                435                 440                 445
Asp Ile Thr Leu Arg Ser Gln Leu Thr Asn Thr His Cys Ser Thr Tyr
450                 455                 460
Pro His Ile Asp Lys Asn Cys Thr Pro Asp Val Asn Lys Pro Phe Ser
465                 470                 475                 480
Val Lys Glu Val Asp Asn Asn Ala Tyr Lys Glu Gln His Asn Leu Ile
                485                 490                 495
Lys Ala Val Phe Asn Lys Lys Met Ala Leu Gly Ser Thr His His His
                500                 505                 510
Ile Asn Leu Gln Val Gly Tyr Asp Lys Phe Asn Ser Ser Leu Ser Arg
                515                 520                 525
Val Glu Tyr Arg Leu Ala Thr His Gln Ser Tyr Gln Lys Leu Asp Tyr
530                 535                 540
Thr Pro Pro Ser Asn Pro Leu Pro Asp Lys Phe Lys Pro Ile Leu Gly
545                 550                 555                 560
Ser Asn Asn Lys Pro Ile Cys Leu Asp Ala Tyr Gly Tyr Gly His Asp
                565                 570                 575
His Pro Gln Ala Cys Asn Ala Lys Asn Ser Thr Tyr Gln Asn Phe Ala
                580                 585                 590
Ile Lys Lys Gly Ile Glu Gln Tyr Asn Gln Lys Thr Asn Thr Asp Lys
                595                 600                 605
Ile Asp Tyr Gln Ala Ile Ile Asp Gln Tyr Asp Lys Gln Asn Pro Asn
610                 615                 620
Ser Thr Leu Lys Pro Phe Glu Lys Ile Lys Gln Ser Leu Gly Gln Glu
625                 630                 635                 640
Lys Tyr Asn Lys Ile Asp Glu Leu Gly Phe Lys Ala Tyr Lys Asp Leu
                645                 650                 655
Arg Asn Glu Trp Ala Gly Trp Thr Asn Asp Asn Ser Gln Gln Asn Ala
                660                 665                 670
Asn Lys Gly Thr Asp Asn Ile Tyr Gln Pro Asn Gln Ala Thr Val Val
                675                 680                 685
Lys Asp Asp Lys Cys Lys Tyr Ser Glu Thr Asn Ser Tyr Ala Asp Cys
                690                 695                 700
Ser Thr Thr Pro Arg His Ile Ser Gly Asp Asn Tyr Phe Ile Ala Leu
705                 710                 715                 720
Lys Asp Asn Met Thr Ile Asn Lys Tyr Val Asp Leu Gly Leu Gly Ala
                725                 730                 735
Arg Tyr Asp Arg Ile Lys His Lys Ser Asp Val Pro Leu Val Asp Asn
                740                 745                 750
Ser Ala Ser Asn Gln Leu Ser Trp Asn Phe Gly Val Val Lys Pro
                755                 760                 765
Thr Asn Trp Leu Asp Ile Ala Tyr Arg Ser Ser Gln Gly Phe Arg Met
                770                 775                 780
Pro Ser Phe Ser Glu Met Tyr Gly Glu Arg Phe Gly Val Thr Ile Gly
785                 790                 795                 800
```

```
Lys Gly Thr Gln His Gly Cys Lys Gly Leu Tyr Tyr Ile Cys Gln Gln
                805                 810                 815

Thr Val His Gln Thr Lys Leu Lys Pro Glu Lys Ser Phe Asn Gln Glu
            820                 825                 830

Ile Gly Ala Thr Leu His Asn His Leu Gly Ser Leu Glu Val Ser Tyr
            835                 840                 845

Phe Lys Asn Arg Tyr Thr Asp Leu Ile Val Gly Lys Ser Glu Glu Ile
    850                 855                 860

Arg Thr Leu Thr Gln Gly Asp Asn Ala Gly Lys Gln Arg Gly Lys Gly
865                 870                 875                 880

Asp Leu Gly Phe His Asn Gly Gln Asp Ala Asp Leu Thr Gly Ile Asn
                885                 890                 895

Ile Leu Gly Arg Leu Asp Leu Asn Ala Ala Asn Ser Arg Leu Pro Tyr
                900                 905                 910

Gly Leu Tyr Ser Thr Leu Ala Tyr Asn Lys Val Asp Val Lys Gly Lys
            915                 920                 925

Thr Leu Asn Pro Thr Leu Ala Gly Thr Asn Ile Leu Phe Asp Ala Ile
            930                 935                 940

Gln Pro Ser Arg Tyr Val Val Gly Leu Gly Tyr Asp Ala Pro Ser Gln
945                 950                 955                 960

Lys Trp Gly Ala Asn Ala Ile Phe Thr His Ser Asp Ala Lys Asn Pro
                965                 970                 975

Ser Glu Leu Leu Ala Asp Lys Asn Leu Gly Asn Gly Asn Ile Gln Thr
            980                 985                 990

Lys Gln Ala Thr Lys Ala Lys Ser Thr Pro Trp Gln Thr Leu Asp Leu
            995                 1000                1005

Ser Gly Tyr Val Asn Ile Lys Asp Asn Phe Thr Leu Arg Ala Gly Val
        1010                1015                1020

Tyr Asn Val Phe Asn Thr Tyr Tyr Thr Trp Glu Ala Leu Arg Gln
1025                1030                1035                1040

Thr Ala Lys Gly Ala Val Asn Gln His Thr Gly Leu Ser Gln Asp Lys
                1045                1050                1055

His Tyr Gly Arg Tyr Ala Ala Pro Gly Arg Asn Tyr Gln Leu Ala Leu
            1060                1065                1070

Glu Met Lys Phe
        1075

(2) INFORMATION FOR SEQ ID NO:20:

(i) SEQUENCE CHARACTERISTICS:
          (A) LENGTH: 753 amino acids
          (B) TYPE: amino acid
          (C) STRANDEDNESS: single
          (D) TOPOLOGY: linear (xi) SEQUENCE DESCRIPTION: SEQ ID NO:20:

Gln Tyr Thr Arg Lys Gly Glu Asn Lys Ala His Ser Asp Leu Asn Gly
1               5                   10                  15

Ile Asn Gln Ser Leu Tyr Arg Leu Gly Ala Trp Gln Gln Lys Tyr Asp
            20                  25                  30

Leu Arg Lys Pro Asn Glu Leu Phe Ala Gly Thr Ser Tyr Ile Thr Glu
            35                  40                  45

Ser Cys Leu Ala Ser Asp Asp Pro Lys Ser Cys Val Gln Tyr Pro Tyr
        50                  55                  60

Val Tyr Thr Lys Ala Arg Pro Asp Gly Ile Gly Asn Arg Asn Phe Ser
```

-continued

```
               65                  70                  75                  80
Glu Leu Ser Asp Ala Glu Lys Ala Gln Tyr Leu Ala Ser Thr His Pro
                85                  90                  95
His Glu Val Val Ser Ala Lys Asp Tyr Thr Gly Ile Tyr Arg Leu Leu
            100                 105                 110
Pro Asp Pro Met Asp Tyr Arg Ser Asp Ser Tyr Leu Ala Arg Leu Asn
        115                 120                 125
Ile Lys Ile Thr Pro Asn Leu Val Xaa Lys Leu Leu Leu Glu Asp Thr
    130                 135                 140
Lys Gln Thr Tyr Asn Ile Arg Asp Met Arg His Cys Ser Tyr His Gly
145                 150                 155                 160
Ala Arg Leu Gly Asn Asp Gly Lys Pro Ala Asn Gly Gly Ser Ile Val
                165                 170                 175
Leu Cys Asp Asp Tyr Gln Glu Tyr Leu Asn Ala Asn Asp Ala Ser Gln
            180                 185                 190
Ala Leu Phe Arg Pro Gly Ala Asn Asp Ala Pro Ile Pro Lys Leu Ala
        195                 200                 205
Tyr Ala Arg Ser Ser Val Phe Asn Gln Glu His Gly Lys Thr Arg Tyr
    210                 215                 220
Gly Leu Ser Phe Glu Phe Lys Pro Asp Thr Pro Trp Phe Lys Gln Ala
225                 230                 235                 240
Lys Leu Asn Leu His Gln Gln Asn Ile Gln Ile Ile Asn His Asp Ile
                245                 250                 255
Lys Lys Ser Cys Ser Gln Tyr Pro Lys Val Asp Ser Asn Cys Gly Ile
            260                 265                 270
Ser Glu Ile Gly His Tyr Glu Tyr Gln Xaa Asn Tyr Arg Tyr Lys Glu
        275                 280                 285
Gly Arg Ala Ser Leu Thr Gly Lys Leu Asp Phe Asn Phe Asp Leu Leu
    290                 295                 300
Gly Gln His Asp Leu Thr Val Leu Ala Gly Thr Asp Lys Val Lys Ser
305                 310                 315                 320
Gln Phe Arg Ala Asn Asn Pro Arg Arg Thr Ile Ile Asp Thr Thr Gln
                325                 330                 335
Gly Asp Ala Ile Ile Asp Glu Ser Thr Leu Thr Ala Gln Glu Gln Ala
            340                 345                 350
Lys Phe Lys Gln Ser Gly Ala Ala Trp Ile Val Lys Asn Arg Leu Gly
        355                 360                 365
Arg Leu Glu Glu Lys Asp Ala Cys Gly Asn Ala Asn Glu Cys Glu Arg
    370                 375                 380
Ala Pro Ile His Gly Ser Asn Gln Tyr Val Gly Ile Asn Asn Leu Tyr
385                 390                 395                 400
Thr Pro Asn Asp Tyr Val Asp Xaa Ser Phe Gly Gly Arg Leu Asp Lys
                405                 410                 415
Gln Arg Ile His Ser Thr Asp Ser Asn Ile Ile Ser Lys Thr Tyr Thr
            420                 425                 430
Asn Lys Ser Tyr Asn Phe Gly Ala Val His Leu Thr Pro Asp Phe
        435                 440                 445
Ser Leu Leu Tyr Lys Thr Ala Lys Gly Phe Arg Thr Pro Ser Phe Tyr
    450                 455                 460
Glu Leu Tyr Asn Tyr Asn Ser Thr Ala Ala Gln His Lys Asn Asp Pro
465                 470                 475                 480
Asp Val Ser Phe Pro Lys Arg Ala Val Asp Val Lys Pro Glu Thr Ser
                485                 490                 495
```

```
Asn Thr Asn Glu Tyr Gly Phe Arg Tyr Gln His Pro Trp Gly Asp Val
            500                 505                 510
Glu Met Ser Met Phe Lys Ser Arg Tyr Lys Asp Met Leu Asp Lys Ala
            515                 520                 525
Ile Pro Asn Leu Thr Lys Ala Gln Gln Glu Tyr Cys Arg Ala His Leu
            530                 535                 540
Asp Ser Asn Glu Cys Val Gly Asn Pro Pro Thr Pro Lys Thr Ser Asp
545                 550                 555                 560
Glu Val Phe Ala Asn Leu Tyr Asn Ala Thr Ile Lys Gly Val Ser Val
                565                 570                 575
Lys Gly Lys Leu Asp Leu His Ala Met Thr Ser Lys Leu Pro Asp Gly
            580                 585                 590
Leu Glu Met Thr Leu Gly Tyr Gly His Thr Lys Leu Gly Lys Phe Xaa
            595                 600                 605
Tyr Ile Ala Pro Lys Asp Ala Asp Gly Trp Tyr Gln Ala Arg Pro Ala
            610                 615                 620
Phe Trp Asp Ala Ile Thr Pro Ala Arg Tyr Val Val Gly Leu Asn Tyr
625                 630                 635                 640
Asp His Pro Ser Gln Val Trp Gly Ile Gly Ala Thr Leu Thr His Ser
                645                 650                 655
Lys Gln Lys Asp Glu Asn Glu Leu Ser Ala Leu Arg Ile Arg Asn Gly
            660                 665                 670
Lys Arg Glu Thr Gln Thr Leu Thr His Thr Ile Pro Lys Ala Tyr Thr
            675                 680                 685
Leu Leu Asp Met Thr Gly Tyr Tyr Ser Pro Thr Glu Ser Ile Thr Ala
            690                 695                 700
Arg Leu Gly Ile Asn Asn Val Leu Asn Thr Arg Tyr Thr Thr Trp Glu
705                 710                 715                 720
Ala Ala Arg Gln Leu Pro Ser Glu Ala Ala Ser Ser Thr Gln Ser Thr
                725                 730                 735
Arg Tyr Ile Ala Pro Gly Arg Ser Tyr Phe Ala Ser Leu Glu Met Lys
            740                 745                 750
Phe (2) INFORMATION FOR SEQ ID NO:21:

(i) SEQUENCE CHARACTERISTICS:
        (A) LENGTH: 585 amino acids
        (B) TYPE: amino acid
        (C) STRANDEDNESS: single
        (D) TOPOLOGY: linear (xi) SEQUENCE DESCRIPTION: SEQ ID NO:21:

Gln Tyr Thr Arg Lys Gly Glu Asn Lys Ala His Ser Asp Leu Asn Gly
1               5                   10                  15
Ile Asn Gln Ser Leu Tyr Arg Leu Gly Ala Trp Gln Gln Lys Tyr Asp
            20                  25                  30
Leu Arg Lys Pro Asn Glu Leu Phe Ala Gly Thr Ser Tyr Ile Thr Glu
            35                  40                  45
Ser Cys Leu Ala Ser Asp Asp Pro Lys Ser Cys Val Gln Tyr Pro Tyr
            50                  55                  60
Val Tyr Thr Lys Ala Arg Pro Asp Gly Ile Gly Asn Arg Asn Phe Ser
65                  70                  75                  80
Glu Leu Ser Asp Ala Glu Lys Ala Gln Tyr Leu Ala Ser Thr His Pro
                85                  90                  95
```

```
His Glu Val Val Ser Ala Lys Asp Tyr Thr Gly Thr Tyr Arg Leu Leu
                100                 105                 110

Pro Asp Pro Met Asp Tyr Arg Ser Asp Ser Tyr Leu Ala Arg Leu Asn
            115                 120                 125

Ile Lys Ile Thr Pro Asn Leu Val Ser Lys Leu Leu Leu Glu Asp Thr
        130                 135                 140

Lys Gln Thr Tyr Asn Ile Arg Asp Met Arg His Cys Ser Tyr His Gly
145                 150                 155                 160

Ala Arg Leu Gly Asn Asp Gly Lys Pro Ala Asn Gly Gly Ser Ile Val
                165                 170                 175

Leu Cys Asp Asp Tyr Gln Glu Tyr Leu Asn Ala Asn Asp Ala Ser Gln
            180                 185                 190

Ala Ser Phe Arg Pro Gly Ala Asn Asp Ala Pro Ile Pro Lys Leu Ala
        195                 200                 205

Tyr Ala Arg Ser Ser Val Phe Asn Gln Glu His Gly Lys Thr Arg Tyr
        210                 215                 220

Gly Leu Gly Phe Glu Phe Lys Pro Asp Thr Pro Trp Phe Lys Gln Ala
225                 230                 235                 240

Lys Leu Asn Leu His Gln Gln Asn Ile Gln Ile Ile Asn Thr Asp Ser
                245                 250                 255

Asn Ile Ile Ser Lys Thr Tyr Thr Asn Lys Ser Tyr Asn Phe Gly Ala
            260                 265                 270

Ala Val His Xaa Thr Pro Asp Phe Ser Leu Leu Tyr Lys Thr Ala Lys
        275                 280                 285

Gly Phe Arg Thr Pro Ser Phe Tyr Glu Leu Tyr Asn Tyr Asn Ser Thr
        290                 295                 300

Ala Ala Gln His Lys Asn Asp Pro Asp Val Ser Phe Pro Lys Arg Ala
305                 310                 315                 320

Val Asp Val Lys Pro Glu Thr Ser Asn Thr Asn Glu Tyr Gly Phe Arg
                325                 330                 335

Tyr Gln His Pro Trp Gly Asp Ile Glu Met Ser Met Phe Lys Ser Arg
            340                 345                 350

Tyr Lys Asp Met Leu Asp Lys Ala Ile Pro Asn Leu Thr Lys Ala Gln
        355                 360                 365

Gln Glu Tyr Cys Lys Ala His Leu Asp Ser Asn Glu Cys Val Gly Asn
        370                 375                 380

Pro Pro Thr Pro Lys Thr Ser Asp Glu Val Phe Ala Asn Leu Tyr Asn
385                 390                 395                 400

Ala Thr Ile Lys Gly Val Ser Val Lys Gly Lys Leu Asp Leu His Ala
                405                 410                 415

Met Thr Ser Lys Leu Pro Asp Gly Leu Glu Met Thr Leu Gly Tyr Gly
            420                 425                 430

His Thr Lys Leu Gly Lys Phe Xaa Tyr Ile Ala Pro Lys Asp Ala Asp
        435                 440                 445

Gly Trp Tyr Gln Ala Arg Pro Ala Phe Trp Asp Ala Ile Thr Pro Ala
        450                 455                 460

Arg Tyr Val Val Gly Leu Asn Tyr Asp His Pro Ser Gln Val Trp Gly
465                 470                 475                 480

Ile Gly Thr Thr Leu Thr His Ser Lys Gln Lys Asp Glu Asn Glu Leu
                485                 490                 495

Ser Ala Leu Arg Ile Arg Asn Gly Lys Arg Glu Ile Gln Thr Leu Thr
            500                 505                 510
```

-continued

```
His Thr Ile Pro Lys Ala Tyr Thr Leu Leu Asp Met Thr Gly Tyr Tyr
            515                 520                 525

Ser Pro Thr Glu Ser Ile Thr Ala Arg Leu Gly Ile Asn Asn Val Leu
        530                 535                 540

Asn Thr Arg Tyr Thr Thr Trp Glu Ala Ala Arg Gln Leu Pro Ser Glu
545                 550                 555                 560

Ala Ala Ser Ser Thr Gln Ser Thr Arg Tyr Ile Ala Pro Gly Arg Ser
                565                 570                 575

Tyr Phe Ala Ser Leu Glu Met Lys Phe
            580                 585
```

(2) INFORMATION FOR SEQ ID NO:22:

(i) SEQUENCE CHARACTERISTICS:
       (A) LENGTH: 15 amino acids
       (B) TYPE: amino acid
       (C) STRANDEDNESS: single
       (D) TOPOLOGY: linear (xi) SEQUENCE DESCRIPTION: SEQ ID NO:22:

```
Met Val Gln Tyr Thr Tyr Arg Lys Gly Lys Glu Asn Lys Ala His
1               5                   10                  15
```

(2) INFORMATION FOR SEQ ID NO:23:

(i) SEQUENCE CHARACTERISTICS:
       (A) LENGTH: 944 amino acids
       (B) TYPE: amino acid
       (C) STRANDEDNESS: single
       (D) TOPOLOGY: linear (xi) SEQUENCE DESCRIPTION: SEQ ID NO:23:

```
Met Asn Lys Lys His Gly Phe Gln Leu Thr Leu Thr Ala Leu Ala Val
1               5                   10                  15

Ala Ala Ala Phe Pro Ser Tyr Ala Ala Asn Pro Glu Thr Ala Ala Pro
            20                  25                  30

Asp Ala Ala Gln Thr Gln Ser Leu Lys Glu Val Thr Val Arg Ala Ala
        35                  40                  45

Lys Val Gly Arg Arg Ser Lys Glu Ala Val Thr Gly Leu Gly Lys Ile
    50                  55                  60

Ala Lys Thr Ser Glu Thr Leu Asn Lys Glu Gln Val Leu Gly Ile Arg
65                  70                  75                  80

Asp Leu Thr Arg Tyr Asp Pro Gly Val Ala Val Glu Gln Gly Asn
                85                  90                  95

Gly Ala Ser Gly Gly Tyr Ser Ile Arg Gly Val Asp Lys Asn Arg Val
            100                 105                 110

Ala Val Ser Val Asp Gly Val Ala Gln Ile Gln Ala Phe Thr Val Gln
        115                 120                 125

Gly Ser Leu Ser Gly Tyr Gly Gly Arg Gly Gly Ser Gly Ala Ile Asn
    130                 135                 140

Glu Ile Glu Tyr Glu Asn Ile Ser Thr Val Glu Ile Asp Lys Gly Ala
145                 150                 155                 160

Gly Ser Ser Asp His Gly Ser Gly Ala Leu Gly Gly Ala Val Ala Phe
                165                 170                 175

Arg Thr Lys Glu Ala Ala Asp Leu Ile Ser Asp Gly Lys Ser Trp Gly
            180                 185                 190

Ile Gln Ala Lys Thr Ala Tyr Gly Ser Lys Asn Arg Gln Phe Met Lys
        195                 200                 205
```

-continued

```
Ser Leu Gly Ala Gly Phe Ser Lys Asp Gly Trp Glu Gly Leu Leu Ile
    210                 215                 220
Arg Thr Glu Arg Gln Gly Arg Glu Thr His Pro His Gly Asp Ile Ala
225                 230                 235                 240
Asp Gly Val Ala Tyr Gly Ile Asn Arg Leu Asp Ala Phe Arg Gln Thr
                245                 250                 255
Tyr Gly Ile Lys Lys Pro Ser Glu Gly Gly Glu Tyr Phe Leu Ala Glu
            260                 265                 270
Gly Glu Ser Glu Leu Lys Pro Val Ala Lys Val Ala Gly Asn Gly Asn
        275                 280                 285
Tyr Leu Asn Asn Gln Leu Asn Arg Trp Val Lys Glu Arg Ile Glu Gln
    290                 295                 300
Asn Gln Pro Leu Ser Ala Glu Glu Ala Met Val Arg Glu Ala Gln
305                 310                 315                 320
Ala Arg His Glu Asn Leu Ser Ala Gln Ala Tyr Thr Gly Gly Gly Arg
                325                 330                 335
Ile Leu Pro Asp Pro Met Asp Tyr Arg Ser Gly Ser Trp Leu Ala Lys
            340                 345                 350
Leu Gly Tyr Arg Phe Gly Gly Arg His Tyr Val Gly Val Phe Glu
        355                 360                 365
Asp Thr Lys Gln Arg Tyr Asp Ile Arg Asp Met Thr Glu Lys Gln Tyr
    370                 375                 380
Tyr Gly Thr Asp Glu Ala Lys Lys Phe Arg Asp Lys Ser Gly Val Tyr
385                 390                 395                 400
Asp Gly Asp Asp Phe Arg Asp Gly Leu Tyr Phe Val Pro Asn Ile Glu
                405                 410                 415
Glu Trp Lys Gly Asp Gln Lys Leu Ile Arg Gly Ile Gly Leu Lys Tyr
            420                 425                 430
Ser Arg Thr Lys Phe Ile Asp Glu His His Arg Arg Arg Met Gly
        435                 440                 445
Leu Leu Tyr Arg Tyr Glu Asn Glu Lys Tyr Ser Asp Asn Trp Ala Asp
    450                 455                 460
Lys Ala Val Leu Ser Phe Asp Lys Gln Gly Val Ala Thr Asp Asn Asn
465                 470                 475                 480
Thr Leu Lys Leu Asn Cys Ala Val Tyr Pro Ala Val Asp Lys Ser Cys
                485                 490                 495
Arg Ala Ser Ala Asp Lys Pro Tyr Ser Tyr Asp Ser Ser Asp Arg Phe
            500                 505                 510
His Tyr Arg Glu Gln His Asn Val Leu Asn Ala Ser Phe Glu Lys Ser
        515                 520                 525
Leu Lys Asn Lys Trp Thr Lys His His Leu Thr Leu Gly Phe Gly Tyr
    530                 535                 540
Asp Ala Ser Asn Ala Ile Ser Arg Pro Glu Gln Leu Ser His Asn Ala
545                 550                 555                 560
Ala Arg Ile Ser Glu Tyr Ser Asp Tyr Thr Asp Lys Gly Asp Lys Tyr
                565                 570                 575
Leu Leu Gly Lys Pro Glu Val Val Glu Gly Ser Val Cys Gly Tyr Ile
            580                 585                 590
Glu Thr Leu Arg Ser Arg Lys Cys Val Pro Arg Lys Ile Asn Gly Ser
        595                 600                 605
Asn Ile His Ile Ser Leu Asn Asp Arg Phe Ser Ile Gly Lys Tyr Phe
    610                 615                 620
Asp Phe Ser Leu Gly Gly Arg Tyr Asp Arg Lys Asn Phe Thr Thr Ser
```

```
            625                 630                 635                 640

Glu Glu Leu Val Arg Ser Gly Arg Tyr Val Asp Arg Ser Trp Asn Ser
                    645                 650                 655

Gly Ile Val Phe Lys Pro Asn Arg His Phe Ser Leu Ser Tyr Arg Ala
                660                 665                 670

Ser Ser Gly Phe Arg Thr Pro Ser Phe Gln Glu Leu Phe Gly Ile Asp
            675                 680                 685

Ile Tyr His Asp Tyr Pro Lys Gly Trp Gln Arg Pro Ala Leu Lys Ser
        690                 695                 700

Glu Lys Ala Ala Asn Arg Glu Ile Gly Leu Gln Trp Lys Gly Asp Phe
705                 710                 715                 720

Gly Phe Leu Glu Ile Ser Ser Phe Arg Asn Arg Tyr Thr Asp Met Ile
                    725                 730                 735

Ala Val Ala Asp His Lys Thr Lys Leu Pro Asn Gln Ala Gly Gln Leu
                740                 745                 750

Thr Glu Ile Asp Ile Arg Asp Tyr Tyr Asn Ala Gln Asn Met Ser Leu
            755                 760                 765

Gln Gly Val Asn Ile Leu Gly Lys Ile Asp Trp Asn Gly Val Tyr Gly
        770                 775                 780

Lys Leu Pro Glu Gly Leu Tyr Thr Thr Leu Ala Tyr Asn Arg Ile Lys
785                 790                 795                 800

Pro Lys Ser Val Ser Asn Arg Pro Gly Leu Ser Leu Arg Ser Tyr Ala
                    805                 810                 815

Leu Asp Ala Val Gln Pro Ser Arg Tyr Val Leu Gly Phe Gly Tyr Asp
                820                 825                 830

Gln Pro Glu Gly Lys Trp Gly Ala Asn Ile Met Leu Thr Tyr Ser Lys
            835                 840                 845

Gly Lys Asn Pro Asp Glu Leu Ala Tyr Leu Ala Gly Asp Gln Lys Arg
        850                 855                 860

Tyr Ser Thr Lys Arg Ala Ser Ser Ser Trp Ser Thr Ala Asp Val Ser
865                 870                 875                 880

Ala Tyr Leu Asn Leu Lys Lys Arg Leu Thr Leu Arg Ala Ala Ile Tyr
                    885                 890                 895

Asn Ile Gly Asn Tyr Arg Tyr Val Thr Trp Glu Ser Leu Arg Gln Thr
                900                 905                 910

Ala Glu Ser Thr Ala Asn Arg His Gly Gly Asp Ser Asn Tyr Gly Arg
            915                 920                 925

Tyr Ala Ala Pro Gly Arg Asn Phe Ser Leu Ala Leu Glu Met Lys Phe
        930                 935                 940

(2) INFORMATION FOR SEQ ID NO:24:

(i) SEQUENCE CHARACTERISTICS:
        (A) LENGTH: 944 amino acids
        (B) TYPE: amino acid
        (C) STRANDEDNESS: single
        (D) TOPOLOGY: linear (xi) SEQUENCE DESCRIPTION: SEQ ID NO:24:

Met Asn Lys Lys His Gly Phe Pro Leu Thr Leu Thr Ala Leu Ala Ile
1               5                   10                  15

Ala Thr Ala Phe Pro Ala Tyr Ala Ala Gln Ala Gly Ala Ala Ala Leu
            20                  25                  30

Asp Ala Ala Gln Ser Gln Ser Leu Lys Glu Val Thr Val Arg Ala Ala
        35                  40                  45
```

```
Lys Val Gly Arg Arg Ser Lys Pro Glu Ala Thr Gly Leu Gly Lys Ile
     50                  55                  60

Ala Lys Thr Ser Glu Thr Leu Asn Lys Glu Gln Val Leu Gly Ile Arg
 65              70                  75                      80

Asp Leu Thr Arg Tyr Asp Pro Gly Val Ala Val Glu Gln Gly Asn
                 85                  90                  95

Gly Ala Ser Gly Gly Tyr Ser Ile Arg Gly Val Asp Lys Asn Arg Val
            100                 105                 110

Ala Val Ser Val Asp Gly Val Ala Gln Ile Gln Ala Phe Thr Val Gln
         115                 120                 125

Gly Ser Leu Ser Gly Tyr Gly Arg Gly Gly Ser Gly Ala Ile Asn
     130                 135                 140

Glu Ile Glu Tyr Glu Asn Ile Ser Thr Val Glu Ile Asp Lys Gly Ala
145                 150                 155                 160

Gly Ser Ser Asp His Gly Ser Gly Ala Leu Gly Gly Ala Val Ala Phe
                165                 170                 175

Arg Thr Lys Glu Ala Ala Asp Leu Ile Ser Asp Gly Lys Ser Trp Gly
             180                 185                 190

Ile Gln Ala Lys Thr Ala Tyr Gly Ser Lys Asn Arg Gln Phe Met Lys
         195                 200                 205

Ser Leu Gly Ala Gly Phe Ser Lys Asp Gly Trp Glu Gly Leu Leu Ile
     210                 215                 220

Arg Thr Glu Arg Gln Gly Arg Glu Thr Arg Pro His Gly Asp Ile Ala
225                 230                 235                 240

Asp Gly Val Glu Tyr Gly Ile Asp Arg Leu Asp Ala Phe Arg Gln Thr
                245                 250                 255

Tyr Asp Ile Lys Arg Lys Thr Thr Glu Pro Phe Phe Leu Val Glu Gly
             260                 265                 270

Glu Asn Thr Leu Lys Pro Val Ala Lys Leu Ala Gly Tyr Gly Ile Tyr
         275                 280                 285

Leu Asn Arg Gln Leu Asn Arg Trp Val Lys Glu Arg Ile Glu Gln Asn
     290                 295                 300

Gln Pro Leu Ser Ala Glu Glu Ala Gln Val Arg Glu Ala Gln Ala
305                 310                 315                 320

Arg His Glu Asn Leu Ser Ala Gln Ala Tyr Thr Gly Gly Arg Ile
                325                 330                 335

Leu Pro Asp Pro Met Asp Tyr Arg Ser Gly Ser Trp Leu Ala Lys Leu
             340                 345                 350

Gly Tyr Arg Phe Gly Gly Arg His Tyr Val Gly Gly Val Phe Glu Asp
         355                 360                 365

Thr Lys Gln Arg Tyr Asp Ile Arg Asp Met Thr Glu Lys Gln Tyr Tyr
     370                 375                 380

Gly Thr Asp Glu Ala Glu Lys Phe Arg Asp Lys Ser Gly Val Tyr Asp
385                 390                 395                 400

Gly Asp Asp Phe Arg Asp Gly Leu Tyr Phe Val Pro Asn Ile Glu Glu
                405                 410                 415

Trp Lys Gly Asp Lys Asn Leu Val Lys Gly Ile Gly Leu Lys Tyr Ser
             420                 425                 430

Arg Thr Lys Phe Ile Asp Glu His His Arg Arg Arg Met Gly Leu
         435                 440                 445

Leu Tyr Arg Tyr Glu Asn Glu Lys Tyr Ser Asp Asn Trp Ala Asp Lys
     450                 455                 460

Ala Val Leu Ser Phe Asp Lys Gln Gly Val Ala Thr Asp Asn Asn Thr
```

```
465                 470                 475                 480

Leu Lys Leu Asn Cys Ala Val Tyr Pro Ala Val Asp Lys Ser Cys Arg
                485                 490                 495

Ala Ser Ala Asp Lys Pro Tyr Ser Tyr Asp Ser Ser Asp Arg Phe His
                500                 505                 510

Tyr Arg Glu Gln His Asn Val Leu Asn Ala Ser Phe Glu Lys Ser Leu
            515                 520                 525

Lys Asn Lys Trp Thr Lys His His Leu Thr Leu Gly Phe Gly Tyr Asp
        530                 535                 540

Ala Ser Lys Ala Val Ser Arg Pro Glu Gln Leu Ser His Asn Ala Ala
545                 550                 555                 560

Arg Ile Ser Glu Ser Thr Gly Phe Asp Glu Lys Asn Gln Asp Lys Tyr
                565                 570                 575

Arg Leu Gly Lys Pro Glu Val Val Glu Gly Ser Val Cys Gly Tyr Ile
                580                 585                 590

Glu Thr Leu Arg Ser Arg Lys Cys Val Pro Arg Lys Ile Asn Gly Ser
            595                 600                 605

Asn Ile His Ile Ser Leu Asn Asp Arg Phe Ser Ile Gly Lys Tyr Phe
        610                 615                 620

Asp Phe Ser Leu Gly Gly Arg Tyr Asp Arg Lys Asn Phe Thr Thr Ser
625                 630                 635                 640

Glu Glu Leu Val Arg Ser Gly Arg Tyr Ala Asp Arg Ser Trp Asn Ser
                645                 650                 655

Gly Ile Val Phe Lys Pro Asn Arg His Phe Ser Val Ser Tyr Arg Ala
                660                 665                 670

Ser Ser Gly Phe Arg Thr Pro Ser Phe Gln Glu Leu Phe Gly Ile Asp
            675                 680                 685

Ile Tyr His Asp Tyr Pro Lys Gly Trp Gln Arg Pro Ala Leu Lys Ser
        690                 695                 700

Glu Lys Ala Ala Asn Arg Glu Ile Gly Leu Gln Trp Lys Gly Asp Phe
705                 710                 715                 720

Gly Phe Leu Glu Ile Ser Ser Phe Arg Asn Arg Tyr Thr Asp Met Ile
                725                 730                 735

Ala Val Ala Asp Gln Lys Thr Lys Leu Pro Asp Ser Ala Gly Arg Leu
                740                 745                 750

Thr Glu Ile Asp Ile Arg Asp Tyr Tyr Asn Ala Gln Asn Met Ser Leu
            755                 760                 765

Gln Gly Ile Asn Ile Leu Gly Lys Ile Asp Trp Asn Gly Val Tyr Gly
        770                 775                 780

Lys Leu Pro Glu Gly Leu Tyr Thr Thr Leu Ala Tyr Asn Arg Ile Lys
785                 790                 795                 800

Pro Lys Ser Val Ser Asn Arg Pro Asp Leu Ser Leu Arg Ser Tyr Ala
                805                 810                 815

Leu Asp Ala Val Gln Pro Ser Arg Tyr Val Leu Gly Phe Gly Tyr Asp
                820                 825                 830

Gln Pro Glu Gly Lys Trp Gly Ala Asn Ile Met Leu Thr Tyr Ser Lys
            835                 840                 845

Gly Lys Asn Pro Asp Glu Leu Ala Tyr Leu Ala Gly Asp Gln Lys Arg
        850                 855                 860

Tyr Ser Ala Gly Arg Val Thr Ser Ser Trp Lys Thr Ala Asp Val Ser
865                 870                 875                 880

Ala Tyr Leu Asn Leu Lys Lys Arg Leu Thr Leu Arg Ala Ala Ile Tyr
                885                 890                 895
```

```
Asn Ile Gly Asn Tyr Arg Tyr Val Thr Trp Glu Ser Leu Arg Gln Thr
            900                 905                 910

Ala Glu Ser Thr Ala Asn Arg His Gly Gly Asp Ser Asn Tyr Gly Arg
            915                 920                 925

Tyr Ala Ala Pro Gly Arg Asn Phe Ser Leu Ala Leu Glu Met Lys Phe
            930                 935                 940

(2) INFORMATION FOR SEQ ID NO:25:

(i) SEQUENCE CHARACTERISTICS:
         (A) LENGTH: 702 amino acids
         (B) TYPE: amino acid
         (C) STRANDEDNESS: single
         (D) TOPOLOGY: linear (xi) SEQUENCE DESCRIPTION: SEQ ID NO:25:

Met Lys His Ile Pro Leu Thr Thr Leu Cys Val Ala Ile Ser Ala Val
1               5                   10                  15

Leu Leu Thr Ala Cys Gly Gly Ser Gly Gly Ser Asn Pro Pro Ala Pro
            20                  25                  30

Thr Pro Ile Pro Asn Ala Ser Gly Ser Gly Asn Thr Gly Asn Thr Gly
            35                  40                  45

Asn Ala Gly Gly Thr Asp Asn Thr Ala Asn Ala Gly Asn Thr Gly Gly
 50                 55                  60

Thr Asn Ser Gly Thr Gly Ser Ala Asn Thr Pro Glu Pro Lys Tyr Gln
65                  70                  75                  80

Asp Val Pro Thr Glu Lys Asn Glu Lys Asp Lys Val Ser Ser Ile Gln
            85                  90                  95

Glu Pro Ala Met Gly Tyr Gly Met Ala Leu Ser Lys Ile Asn Leu His
            100                 105                 110

Asn Arg Gln Asp Thr Pro Leu Asp Glu Lys Asn Ile Ile Thr Leu Asp
            115                 120                 125

Gly Lys Lys Gln Val Ala Glu Gly Lys Lys Ser Pro Leu Pro Phe Ser
130                 135                 140

Leu Asp Val Glu Asn Lys Leu Leu Asp Gly Tyr Ile Ala Lys Met Asn
145                 150                 155                 160

Val Ala Asp Lys Asn Ala Ile Gly Asp Arg Ile Lys Lys Gly Asn Lys
            165                 170                 175

Glu Ile Ser Asp Glu Glu Leu Ala Lys Gln Ile Lys Glu Ala Val Arg
            180                 185                 190

Lys Ser His Glu Phe Gln Gln Val Leu Ser Ser Leu Glu Asn Lys Ile
            195                 200                 205

Phe His Ser Asn Asp Gly Thr Thr Lys Ala Thr Thr Arg Asp Leu Lys
210                 215                 220

Tyr Val Asp Tyr Gly Tyr Tyr Leu Ala Asn Asp Gly Asn Tyr Leu Thr
225                 230                 235                 240

Val Lys Thr Asp Lys Leu Trp Asn Leu Gly Pro Val Gly Gly Val Phe
            245                 250                 255

Tyr Asn Gly Thr Thr Thr Ala Lys Glu Leu Pro Thr Gln Asp Ala Val
            260                 265                 270

Lys Tyr Lys Gly His Trp Asp Phe Met Thr Asp Val Ala Asn Arg Arg
            275                 280                 285

Asn Arg Phe Ser Glu Val Lys Glu Asn Ser Gln Ala Gly Trp Tyr Tyr
            290                 295                 300

Gly Ala Ser Ser Lys Asp Glu Tyr Asn Arg Leu Leu Thr Lys Glu Asp
```

-continued

```
305                 310                 315                 320
Ser Ala Pro Asp Gly His Ser Gly Glu Tyr Gly His Ser Ser Glu Phe
                325                 330                 335

Thr Val Asn Phe Lys Glu Lys Lys Leu Thr Gly Lys Leu Phe Ser Asn
                340                 345                 350

Leu Gln Asp Arg His Lys Gly Asn Val Thr Lys Thr Glu Arg Tyr Asp
                355                 360                 365

Ile Asp Ala Asn Ile His Gly Asn Arg Phe Arg Gly Ser Ala Thr Ala
            370                 375                 380

Ser Asn Lys Asn Asp Thr Ser Lys His Pro Phe Thr Ser Asp Ala Asn
385                 390                 395                 400

Asn Arg Leu Glu Gly Gly Phe Tyr Gly Pro Lys Gly Glu Glu Leu Ala
                405                 410                 415

Gly Lys Phe Leu Thr Asn Asp Asn Lys Leu Phe Gly Val Phe Gly Ala
                420                 425                 430

Lys Arg Glu Ser Lys Ala Glu Glu Lys Thr Glu Ala Ile Leu Asp Ala
                435                 440                 445

Tyr Ala Leu Gly Thr Phe Asn Thr Ser Asn Ala Thr Thr Phe Thr Pro
                450                 455                 460

Phe Thr Glu Lys Gln Leu Asp Asn Phe Gly Asn Ala Lys Lys Leu Val
465                 470                 475                 480

Leu Gly Ser Thr Val Ile Asp Leu Val Pro Thr Asp Ala Thr Lys Asn
                485                 490                 495

Glu Phe Thr Lys Asp Lys Pro Glu Ser Ala Thr Asn Glu Ala Gly Glu
                500                 505                 510

Thr Leu Met Val Asn Asp Glu Val Ser Val Lys Thr Tyr Gly Lys Asn
                515                 520                 525

Phe Glu Tyr Leu Lys Phe Gly Glu Leu Ser Ile Gly Gly Ser His Ser
                530                 535                 540

Val Phe Leu Gln Gly Glu Arg Thr Ala Thr Gly Glu Lys Ala Val
545                 550                 555                 560

Pro Thr Thr Gly Thr Ala Lys Tyr Leu Gly Asn Trp Val Gly Tyr Ile
                565                 570                 575

Thr Gly Lys Asp Thr Gly Thr Gly Thr Gly Lys Ser Phe Thr Asp Ala
                580                 585                 590

Gln Asp Val Ala Asp Phe Asp Ile Asp Phe Gly Asn Lys Ser Val Ser
                595                 600                 605

Gly Lys Leu Ile Thr Lys Gly Arg Gln Asp Pro Val Phe Ser Ile Thr
                610                 615                 620

Gly Gln Ile Ala Gly Asn Gly Trp Thr Gly Thr Ala Ser Thr Thr Lys
625                 630                 635                 640

Ala Asp Ala Gly Gly Tyr Lys Ile Asp Ser Ser Ser Thr Gly Lys Ser
                645                 650                 655

Ile Ala Ile Lys Asp Ala Asn Val Thr Gly Gly Phe Tyr Gly Pro Asn
                660                 665                 670

Ala Asn Glu Met Gly Gly Ser Phe His Asn Ala Asp Asp Ser Lys
                675                 680                 685

Ala Ser Val Val Phe Gly Thr Lys Arg Gln Gln Glu Val Lys
690                 695                 700
```

(2) INFORMATION FOR SEQ ID NO:26:

(i) SEQUENCE CHARACTERISTICS:
        (A) LENGTH: 5 amino acids (B) TYPE: amino acid
            (C) STRANDEDNESS: single
            (D) TOPOLOGY: linear (xi) SEQUENCE DESCRIPTION: SEQ ID NO:26:

Leu Glu Met Lys Phe
1               5

(2) INFORMATION FOR SEQ ID NO:27:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:27:

Leu Glu Gly Gly Phe Tyr
1               5

(2) INFORMATION FOR SEQ ID NO:28:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:28:

Gln Tyr Thr Arg Lys Gly Glu Asn Lys Ala
1               5                   10

(2) INFORMATION FOR SEQ ID NO:29:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:29:

CAATATACCG TAAAGGTGAA AATAAAGC                                              28

(2) INFORMATION FOR SEQ ID NO:30:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:30:

CAATATACCG TAAAGGTGAA AATAAAGC                                              28

(2) INFORMATION FOR SEQ ID NO:31:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:31:

CAATATACCG TAAAGGTGAA AACAAAGC                                              28

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:32:

CAATATACCG TAAAGGCGAA AATAAAGC                                              28

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:33:

CAATATACCG CAAAGGCGAA AACAAAGC                                              28

(2) INFORMATION FOR SEQ ID NO:34:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:34:

CAATATACCG CAAAGGCGAA AATAAAGC                                              28

(2) INFORMATION FOR SEQ ID NO:35:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:35:

CAATATACCG CAAAGGTGAA AATAAAGC                                              28

(2) INFORMATION FOR SEQ ID NO:36:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:36:

CAATATACCG CAAAGGTGAA AACAAAGC                                              28

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:37:

CTTGAAATGA AGTTTTAA                                                         18

(2) INFORMATION FOR SEQ ID NO:38:

(i) SEQUENCE CHARACTERISTICS:

(A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:38:

GAACTTTACT TCAAAATT                                                         18

(2) INFORMATION FOR SEQ ID NO:39:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:39:

Asp Gly Leu Gly
1

(2) INFORMATION FOR SEQ ID NO:40:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:40:

Met Ser Lys Ser Ile Thr
1               5

(2) INFORMATION FOR SEQ ID NO:41:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:41:

GGAATTCCAT ATGTCAAAAT CTATCACAAA                                            30

(2) INFORMATION FOR SEQ ID NO:42:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:42:

Leu Asp Ala Ile Thr Val Thr Ala Ala
1               5

(2) INFORMATION FOR SEQ ID NO:43:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:43:

TTTAGATGCC ATCACGGTAA CCGCCGCCCC                                            30

(2) INFORMATION FOR SEQ ID NO:44:

```
      (i) SEQUENCE CHARACTERISTICS:
          (A) LENGTH: 30 base pairs
          (B) TYPE: nucleic acid
          (C) STRANDEDNESS: single
          (D) TOPOLOGY: linear (xi) SEQUENCE DESCRIPTION: SEQ ID NO:44:

AAATCTACGG TAGTGCCATT GGCGGCGGGG                                              30

(2) INFORMATION FOR SEQ ID NO:45:

(i) SEQUENCE CHARACTERISTICS:
          (A) LENGTH: 10 amino acids
          (B) TYPE: amino acid
          (C) STRANDEDNESS: single
          (D) TOPOLOGY: linear (xi) SEQUENCE DESCRIPTION: SEQ ID NO:45:

Gly Lys Leu Asp Leu His Ala Met Thr Ser
 1               5                  10

(2) INFORMATION FOR SEQ ID NO:46:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (xi) SEQUENCE DESCRIPTION: SEQ ID NO:46:

GGCAAACTGG ATTTGCATGC CATGACATCA                                              30

(2) INFORMATION FOR SEQ ID NO:47:

(i) SEQUENCE CHARACTERISTICS:
          (A) LENGTH: 6 amino acids
          (B) TYPE: amino acid
          (C) STRANDEDNESS: single
          (D) TOPOLOGY: linear (xi) SEQUENCE DESCRIPTION: SEQ ID NO:47:

Ser Leu Glu Met Lys Phe
 1               5

(2) INFORMATION FOR SEQ ID NO:48:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO:48:

AGTCTTGAAA TGAAGTTTTA A                                                       21

(2) INFORMATION FOR SEQ ID NO:49:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (xi) SEQUENCE DESCRIPTION: SEQ ID NO:49:

TCAGAACTTT ACTTCAAAAT TGCCCTAGGG C                                            31
```

(2) INFORMATION FOR SEQ ID NO:50:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:50:

```
Met Thr Thr His Arg Leu
1               5
```

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:51:

GGAATTCCAT ATGACCACGC ACCGCTTAAA         30

(2) INFORMATION FOR SEQ ID NO:52:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:52:

```
Met Ser Thr Val Lys Thr Pro His
1               5
```

(2) INFORMATION FOR SEQ ID NO:53:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:53:

GGAATTCCAT ATGAGTACTG TCAAAACCCC CCACA         35

(2) INFORMATION FOR SEQ ID NO:54:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:54:

```
Ile Pro Asn Thr Gly His Asp Asn Thr Asn
1               5                   10
```

(2) INFORMATION FOR SEQ ID NO:55:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:55:

AATACCGAAC ACAGGTCATG ACAACACCAA T         31

(2) INFORMATION FOR SEQ ID NO:56:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:56:

TTATGGCTTG TGTCCAGTAC TGTTGTGGTT A                              31

(2) INFORMATION FOR SEQ ID NO:57:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:57:

Asn Glu Pro Thr His Glu Lys Thr Phe Ala
1               5                   10

(2) INFORMATION FOR SEQ ID NO:58:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:58:

AATGAGCCTA CTCATGAAAA AACCTTTGCC                                30

(2) INFORMATION FOR SEQ ID NO:59:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:59:

Gly Ala Val Phe Gly Ala Val Lys Asp Lys
1               5                   10

(2) INFORMATION FOR SEQ ID NO:60:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:60:

GGGCTGTCTT TGGGGCTGTT AAAGATAAAT AA                             32

(2) INFORMATION FOR SEQ ID NO:61:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:61:

CCCGACAGAA ACCCCGACAA TTTCTATTTA TTCCTAGGGC                          40

(2) INFORMATION FOR SEQ ID NO:62:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:62:

Met Cys Arg Ser Asp Asp Ile Ser Val Asn
1               5                   10

(2) INFORMATION FOR SEQ ID NO:63:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:63:

GGAATTCCAT ATGTGCCGCT CTGATGACAT CAGCGTCAAT                          40

(2) INFORMATION FOR SEQ ID NO:64:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:64:

Phe Leu Lys Gln Val
1               5

(2) INFORMATION FOR SEQ ID NO:65:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:65:

TTTTTAAAGC AGGTG                                                     15

(2) INFORMATION FOR SEQ ID NO:66:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:66:

AAAAATTTCG TC                                                        12

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:67:

```
AAGCTTAGCA TGATGGCATC GGCT                                                  24

(2) INFORMATION FOR SEQ ID NO: 68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 68:

TTAGCCCAAG GCAAATCTGG TGCA                                                  24

(2) INFORMATION FOR SEQ ID NO: 69:

(i) SEQUENCE CHARACTERISTICS:
        (A) LENGTH: 2718 base pairs
        (B) TYPE: nucleic acid
        (C) STRANDEDNESS: single
        (D) TOPOLOGY: linear (xi) SEQUENCE DESCRIPTION: SEQ ID NO: 69:

ATGAGTACTG TCAAAGTCCC CCACATTTTC TACCAAAAAC GCACCCTTAG CCTTGCCATC           60

GCCAGTATTT TTGCTGCCGT GGTGATGACA GGCTGCCGCT CTGATGACAT CAGCGTCAAT          120

GCACCCAATG TTACCCAACT GCCCCAAGGC ACGGTTTCAC CAATACCGAA CACAGGTCAT          180

GACAACACCA ATAACACCAA CAATCAGGGC AACAACACGG ATAACAGCAC CAGCACAACT          240

GACCCAAATG GCGATAACAA CCAACTGACA CAAGCACAAA AAACTGCCGC CGCCGCAGGG          300

TTTTTTGTGA TGGGTAAAAT TCGTGATACC AGCGAAAAAA ATGACCCAGA TTATACCAAA          360

GATTTACAAG GCAGCGTACA TACAGCAGGG CAAGGCTTAC AGTACTTAGG CACCAAAGAG          420

CCTCGGCCAG ATGGCACAGG TACAGGTAAA AACTTACGCC AGCCCATCAC AGCTGATGAC          480

ATTACACCAC TTTATTTTGA TAAATTCCCC AAAATATCCG ATCTGCACCT AGAAAACAGC          540

GAGCATGTGT TTGATGCTAA AAAAGCAAAT AACATCAAAA TATATGGTTA TGGTGCATTG          600

TCATCACCTG CCAAAAACCC AACCTACATG AATTATCAAC AAGAACAAAA CATCAAAAAC          660

AAAAAACCAG GCGATGATTA TCAAAACATT CGTTTTGGCT ATATGGAGCT AAGAGAGCTG          720

GACCTAAATA AAAAAGGTGC AGACACCCAG AGCGACAAGA ACCGTGCCAT CATTTTCACC          780

ACACCTACTT TATTTTATCA TGGTGAGAAT GCCAGCACCC ATCTGCCAAA GGCGGGTAAA          840

TTTGACTATG AGGGCAATTG GTTGTATCTG ACCGATGTCA AAAACGCCC ATTTTTAGAT           900

AAAACAGACG ATAAAGTAGG CACTTATTTT AACTCAACCA GAAATCAAA TGAAGGCGAT           960

TTGGTGAGTG CAGCACACAT TTATCTAAAC AGCTTTAAAT ATAAACACAC CCCGGCCACT         1020

TATAGCGTGG ACTTTGATCA AAATACCCTA AAAGGCAAAT TGTCTTATTA TGACAACCCA         1080

AACAAGCAAA CAGCCGATGG GCGTTATATC AGAAGTCAGT TTGATACCGA CAAAAAGGTC         1140

AATGAAGCCG ATGTCTATGA GATTGACGCC AAGATTAATG GCAACCGCTT TACTGGCACA         1200

GCCAAATCTT TGATTGATGA TAACACCAAT ACCGCACCTT TTGTTAAAGA GCTGTTCTCC         1260

AAAAAAGCCA ATCCCAACAA CCCAGACCCC AACTCAGATA CGCTAGAAGG CGGGTTTTAT         1320

GGTGAGTCGG GCGATGAGCT GGCGGGTAAA TTTTTATCCA ATGACAACGC AACTTTTGTG         1380

GTCTTTGGTG GCAAACGAGA CAAAACGACC GAACCTGTCG CCACAAAAAC GGTGTATTTT         1440

AGTACAGGAT TTGAAAAACC CAGCACCAGC TTTGTTGGCA ATGAAGAGAT TGGTAGCATT         1500

ATTGACGGTA AAAAGTTAAA TGATGAAGTC AATAATCAAA TTGAAGATGA AACTGTCCCT         1560
```

```
GTCAGTAATA AAGAATATTA TGAATATAAT TATGGACGAC CCAACAAACA ATTCACCAAA      1620

AAAATAAACG CCAGCGTCCA AAAAAACCCT GCTTATTTTG GTCAGCATGA TAAGTTTTAT      1680

TTTAATGGTA ACTATTATGA CTTATCAGCC AAAGAAGCAA ACAAGCTTGG TGTCTCCCAA      1740

GATACCAGCA CCAATAAGAG TATTTTGGCT AAATACCCAG ATGCCAAAGT AAGCACAGAC      1800

AATAAAGTTA CCAAAATCGT TCTACAACAA GCCAAAGATA AGCCGTATAC CGCCATTCAT      1860

GCCAAAAGCT ATGACCACAT CAGTTTTGGT GAAGTATTGT ATAATGATAA CAAAGGCAAC      1920

CCAACACGCA GTTATTTTGT GCAAGGCGGT CAAGCGGATG TCAGTACTCA GCTGCCCAGT      1980

GCAGGTAAAT TCACCTATAA TGGTCTTTGG GCAGGCTACC TGACCCAGAA AAAAGACAAA      2040

GGTTATAGCA AAGATGAGGA TACCATCAAG CAAAAAGGTC TTAAAGATTA TATATTGACC      2100

AAAGACTTTA TCCCACAAGA TGACGATGAC GATGACGATA GTTTGACCGC ATCTGATGAT      2160

TCACAAGATG ATAATACACA TGGCGATGAT GATTTGATTG CATCTGATGA TTCACAAGAT      2220

GATGACACAG ATGGCGATGA CGATTCAGAT GATTTGGGTG ATGGTGCAGA TGATGACGCC      2280

GCAGGCAAAG TGTATCATGC AGGTAATATT CGCCCTGAAT TTGAAAACAA ATACTTGCCC      2340

ATTAATGAGC CTACTCATGA AAAAACCTTT GCCCTAGATG GTAAAAATAA GGCTAAGTTT      2400

GATGTAAACT TTGACACCAA CAGCCTAACT GGTAAATTAA ACGATGAGAG AGGTGATATC      2460

GTCTTTGATA TCAAAAATGG CAAAATTGAT GGCACAGGAT TTACCGCCAA AGCCGATGTG      2520

CCAAACTATC GTGAAGAAGT GGGTAACAAC CAAGGTGGCG GTTTCTTATA CAACATCAAA      2580

GATATTGATG TTAAGGGGCA ATTTTTTGGC ACAAATGGCA AGAGTTGGC AGGACGGTTA       2640

CATCATGACA AAGGCGATGG CATCACTGAC ACCGCCGAAA AAGCAGGGGC TGTCTTTGGG      2700

GCTGTTAAAG ATAAATAA                                                   2718
```

(2) INFORMATION FOR SEQ ID NO: 70:

(i) SEQUENCE CHARACTERISTICS:
        (A) LENGTH: 905 amino acids
        (B) TYPE: amino acid
        (C) STRANDEDNESS: single
        (D) TOPOLOGY: linear (xi) SEQUENCE DESCRIPTION: SEQ ID NO: 70:

```
Met Ser Thr Val Lys Val Pro His Ile Phe Tyr Gln Lys Arg Thr Leu
1               5                   10                  15

Ser Leu Ala Ile Ala Ser Ile Phe Ala Ala Val Val Met Thr Gly Cys
            20                  25                  30

Arg Ser Asp Asp Ile Ser Val Asn Ala Pro Asn Val Thr Gln Leu Pro
        35                  40                  45

Gln Gly Thr Val Ser Pro Ile Pro Asn Thr Gly His Asp Asn Thr Asn
    50                  55                  60

Asn Thr Asn Asn Gln Gly Asn Asn Thr Asp Asn Ser Thr Ser Thr Thr
65                  70                  75                  80

Asp Pro Asn Gly Asp Asn Asn Gln Leu Thr Gln Ala Gln Lys Thr Ala
                85                  90                  95

Ala Ala Ala Gly Phe Phe Val Met Gly Lys Ile Arg Asp Thr Ser Glu
            100                 105                 110

Lys Asn Asp Pro Asp Tyr Thr Lys Asp Leu Gln Gly Ser Val His Thr
        115                 120                 125

Ala Gly Gln Gly Leu Gln Tyr Leu Gly Thr Lys Glu Pro Arg Pro Asp
    130                 135                 140

Gly Thr Gly Thr Gly Lys Asn Leu Arg Gln Pro Ile Thr Ala Asp Asp
```

```
                145                 150                 155                 160
Ile Thr Pro Leu Tyr Phe Asp Lys Phe Pro Lys Ile Ser Asp Leu His
                    165                 170                 175
Leu Glu Asn Ser Glu His Val Phe Asp Ala Lys Ala Asn Asn Ile
                180                 185                 190
Lys Ile Tyr Gly Tyr Gly Ala Leu Ser Ser Pro Ala Lys Asn Pro Thr
                    195                 200                 205
Tyr Met Asn Tyr Gln Gln Glu Gln Asn Ile Lys Asn Lys Lys Pro Gly
                210                 215                 220
Asp Asp Tyr Gln Asn Ile Arg Phe Gly Tyr Met Glu Leu Arg Glu Leu
225                 230                 235                 240
Asp Leu Asn Lys Lys Gly Ala Asp Asn Gln Ser Asp Lys Asn Arg Ala
                245                 250                 255
Ile Ile Phe Thr Thr Pro Thr Leu Phe Tyr His Gly Glu Asn Ala Ser
                260                 265                 270
Thr His Leu Pro Lys Ala Gly Lys Phe Asp Tyr Glu Gly Asn Trp Leu
                275                 280                 285
Tyr Leu Thr Asp Val Lys Lys Arg Pro Phe Leu Asp Lys Thr Asp Asp
                290                 295                 300
Lys Val Gly Thr Tyr Phe Asn Ser Thr Arg Lys Ser Asn Glu Gly Asp
305                 310                 315                 320
Leu Val Ser Ala Ala His Ile Tyr Leu Asn Ser Phe Lys Tyr Lys His
                    325                 330                 335
Thr Pro Ala Thr Tyr Ser Val Asp Phe Asp Gln Asn Thr Leu Lys Gly
                340                 345                 350
Lys Leu Ser Tyr Tyr Asp Asn Pro Asn Lys Gln Thr Ala Asp Gly Arg
                355                 360                 365
Tyr Ile Arg Ser Gln Phe Asp Thr Asp Lys Lys Val Asn Glu Ala Asp
                370                 375                 380
Val Tyr Glu Ile Asp Ala Lys Ile Asn Gly Asn Arg Phe Thr Gly Thr
385                 390                 395                 400
Ala Lys Ser Leu Ile Asp Asp Asn Thr Asn Thr Ala Pro Phe Val Lys
                    405                 410                 415
Glu Leu Phe Ser Lys Lys Ala Asn Pro Asn Asn Pro Asp Pro Asn Ser
                420                 425                 430
Asp Thr Leu Glu Gly Gly Phe Tyr Gly Glu Ser Gly Asp Glu Leu Ala
                435                 440                 445
Gly Lys Phe Leu Ser Asn Asp Asn Ala Thr Phe Val Val Phe Gly Gly
                450                 455                 460
Lys Arg Asp Lys Thr Thr Glu Pro Val Ala Thr Lys Thr Val Tyr Phe
465                 470                 475                 480
Ser Thr Gly Phe Glu Lys Pro Ser Thr Ser Phe Val Gly Asn Glu Glu
                    485                 490                 495
Ile Gly Ser Ile Ile Asp Gly Lys Gly Leu Asn Asp Glu Val Asn Asn
                500                 505                 510
Gln Ile Glu Asp Glu Thr Val Pro Val Ser Asn Lys Glu Tyr Tyr Glu
                515                 520                 525
Tyr Asn Tyr Gly Arg Pro Asn Lys Gln Phe Thr Lys Ile Asn Ala
                530                 535                 540
Ser Val Gln Lys Asn Pro Ala Tyr Phe Gly Gln His Asp Lys Phe Tyr
545                 550                 555                 560
Phe Asn Gly Asn Tyr Tyr Asp Leu Ser Ala Lys Glu Ala Asn Lys Leu
                    565                 570                 575
```

-continued

```
Gly Val Ser Gln Asp Thr Ser Thr Asn Lys Ser Ile Leu Ala Lys Tyr
            580                 585                 590

Pro Asp Ala Lys Val Ser Thr Asp Asn Lys Val Thr Lys Ile Val Leu
        595                 600                 605

Gln Gln Ala Lys Asp Lys Pro Tyr Thr Ala Ile His Ala Lys Ser Tyr
    610                 615                 620

Asp His Ile Ser Phe Gly Glu Val Leu Tyr Asn Asp Asn Lys Gly Asn
625                 630                 635                 640

Pro Thr Arg Ser Tyr Phe Val Gln Gly Gln Ala Asp Val Ser Thr
            645                 650                 655

Gln Leu Pro Ser Ala Gly Lys Phe Thr Tyr Asn Gly Leu Trp Ala Gly
            660                 665                 670

Tyr Leu Thr Gln Lys Lys Asp Lys Gly Tyr Ser Lys Asp Glu Asp Thr
        675                 680                 685

Ile Lys Gln Lys Gly Leu Lys Asp Tyr Ile Leu Thr Lys Asp Phe Ile
    690                 695                 700

Pro Gln Asp Asp Asp Asp Asp Asp Ser Leu Thr Ala Ser Asp Asp
705                 710                 715                 720

Ser Gln Asp Asp Asn Thr His Gly Asp Asp Leu Ile Ala Ser Asp
            725                 730                 735

Asp Ser Gln Asp Asp Thr Asp Gly Asp Asp Ser Asp Asp Leu
            740                 745                 750

Gly Asp Gly Ala Asp Asp Ala Ala Gly Lys Val Tyr His Ala Gly
            755                 760                 765

Asn Ile Arg Pro Glu Phe Glu Asn Lys Tyr Leu Pro Ile Asn Glu Pro
    770                 775                 780

Thr His Glu Lys Thr Phe Ala Leu Asp Gly Lys Asn Lys Ala Lys Phe
785                 790                 795                 800

Asp Val Asn Phe Asp Thr Asn Ser Leu Thr Gly Lys Leu Asn Asp Glu
            805                 810                 815

Arg Gly Asp Ile Val Phe Asp Ile Lys Asn Gly Lys Ile Asp Gly Thr
        820                 825                 830

Gly Phe Thr Ala Lys Ala Asp Val Pro Asn Tyr Arg Glu Glu Val Gly
    835                 840                 845

Asn Asn Gln Gly Gly Phe Leu Tyr Asn Ile Lys Asp Ile Asp Val
850                 855                 860

Lys Gly Arg Phe Phe Gly Thr Asn Gly Glu Glu Leu Ala Gly Gln Leu
865                 870                 875                 880

His His Asp Lys Gly Asp Gly Ile Thr Asp Thr Ala Glu Lys Ala Gly
            885                 890                 895

Ala Val Phe Gly Ala Val Lys Asp Lys
            900                 905
```

(2) INFORMATION FOR SEQ ID NO: 71:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 71:

```
Leu Glu Gly Gly Phe Tyr Gly
1               5
```

(2) INFORMATION FOR SEQ ID NO: 72:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 72:

```
Gly Lys Asn Leu Arg Gly Pro Ile
1               5
```

(2) INFORMATION FOR SEQ ID NO: 73:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 73:

```
GGTAAAAACT TGCGTCAGCC CATC                                                 24
```

(2) INFORMATION FOR SEQ ID NO: 74:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 74:

```
CCATTTTTGA ACGCAGTCGG GTAG                                                 24
```

(2) INFORMATION FOR SEQ ID NO:75:

(i) SEQUENCE CHARACTERISTICS:
        (A) LENGTH: 941 amino acids
        (B) TYPE: amino acid
        (C) STRANDEDNESS: single
        (D) TOPOLOGY: linear (xi) SEQUENCE DESCRIPTION: SEQ ID NO:75:

```
Met Asn Lys Lys His Ser Phe Pro Leu Thr Leu Thr Ala Leu Ala Ile
1               5                   10                  15

Ala Thr Ala Phe Pro Ser Tyr Ala Ala Asn Ser Glu Thr Ala Ala Gln
            20                  25                  30

Thr Gln Ser Leu Lys Glu Val Thr Val Arg Ala Ala Lys Val Gly Arg
        35                  40                  45

Arg Ser Lys Glu Val Thr Gly Leu Gly Lys Ile Val Lys Thr Ser Glu
    50                  55                  60

Thr Leu Asn Lys Glu Gln Val Leu Gly Ile Arg Asp Leu Thr Arg Tyr
65                  70                  75                  80

Asp Pro Gly Val Ala Val Glu Gln Gly Asn Gly Ala Ser Gly Gly
                85                  90                  95

Tyr Ser Ile Arg Gly Val Asp Lys Asn Arg Val Ala Val Ser Val Asp
            100                 105                 110

Gly Val Ala Gln Ile Gln Ala Phe Thr Val Gln Gly Ser Leu Ser Gly
        115                 120                 125

Tyr Gly Gly Arg Gly Gly Ser Gly Ala Ile Asn Glu Ile Glu Tyr Glu
    130                 135                 140

Asn Ile Ser Thr Val Glu Ile Asp Lys Gly Ala Gly Ser Ser Asp His
145                 150                 155                 160
```

-continued

```
Gly Ser Gly Ala Leu Gly Ala Val Ala Phe Arg Thr Lys Glu Ala
            165                 170                 175
Ala Asp Leu Ile Ser Asp Gly Lys Ser Trp Gly Ile Gln Ala Lys Thr
            180                 185                 190
Ala Tyr Gly Ser Lys Asn Arg Gln Phe Met Lys Ser Leu Gly Ala Gly
            195                 200                 205
Phe Ser Lys Asp Gly Trp Glu Gly Leu Leu Ile Arg Thr Glu Arg Gln
            210                 215                 220
Gly Arg Glu Thr Arg Pro His Gly Asp Ile Ala Asp Gly Val Glu Tyr
225                 230                 235                 240
Gly Ile Asp Arg Leu Asp Ala Phe Arg Gln Thr Tyr Asp Ile Gln Lys
            245                 250                 255
Gln Asn Lys Lys Ala Glu Tyr Phe Leu Ala Glu Gly Glu Ser Glu Leu
            260                 265                 270
Lys Pro Ala Ala Lys Leu Ala Gly Asn Gly Asn Tyr Leu Lys Asn Gln
            275                 280                 285
Leu Asn Arg Trp Val Glu Glu Arg Lys Lys Asn Asn Gln Ser Leu Ser
            290                 295                 300
Ala Glu Glu Glu Ala Met Val Arg Glu Ala Gln Ala Arg His Glu Asn
305                 310                 315                 320
Leu Ser Ala Gln Ala Tyr Thr Gly Gly Gly Arg Ile Leu Pro Asp Pro
            325                 330                 335
Met Asp Tyr Arg Ser Gly Ser Trp Leu Ala Lys Leu Gly Tyr Arg Phe
            340                 345                 350
Gly Gly Arg His Tyr Val Gly Gly Val Phe Glu Asp Thr Lys Gln Arg
            355                 360                 365
Tyr Asp Ile Arg Asp Met Thr Glu Lys Gln Tyr Tyr Gly Thr Asp Glu
            370                 375                 380
Ala Thr Lys Phe Ser Asp Lys Ser Gly Val Tyr Asp Gly Asp Asp Phe
385                 390                 395                 400
Arg Asp Gly Leu Tyr Phe Val Pro Asn Ile Glu Glu Trp Lys Gly Asp
            405                 410                 415
Lys Asn Leu Val Lys Gly Ile Gly Leu Lys Tyr Ser Arg Thr Lys Phe
            420                 425                 430
Ile Asp Glu His His Arg Arg Arg Met Gly Leu Leu Tyr Arg Tyr
            435                 440                 445
Glu Asn Glu Ala Tyr Ser Asp Asn Trp Ala Asp Lys Ala Val Leu Ser
            450                 455                 460
Phe Asp Lys Gln Gly Val Ala Thr Asp Asn Thr Leu Lys Leu Asn
465                 470                 475                 480
Cys Ala Val Tyr Pro Ser Val Asp Lys Ala Cys Arg Ala Ser Ala Asp
            485                 490                 495
Lys Pro Tyr Ser Tyr Asp Ser Ser Asp Arg Phe His Tyr Arg Glu Gln
            500                 505                 510
His Asn Val Leu Asn Ala Leu Phe Glu Lys Ser Leu Lys Asn Lys Trp
            515                 520                 525
Thr Lys His His Leu Thr Leu Gly Phe Gly Tyr Asp Ala Ser Lys Ala
            530                 535                 540
Val Ser Arg Pro Glu Gln Leu Ser His Asn Ala Ala Arg Ile Ser Glu
545                 550                 555                 560
Phe Ser Asp Tyr Ala Asp Asp Gly Lys Tyr Lys Tyr Leu Leu Gly Lys
            565                 570                 575
```

```
Pro Glu Val Val Glu Gly Ser Val Cys Gly Tyr Ile Glu Thr Leu Arg
            580                 585                 590

Ser Arg Lys Cys Val Pro Arg Lys Ile Asn Gly Ser Asn Ile His Ile
        595                 600                 605

Ser Leu Asn Asp Arg Phe Ser Ile Gly Lys Tyr Phe Asp Phe Ser Leu
    610                 615                 620

Gly Gly Arg Tyr Asp Arg Gln Asn Phe Thr Thr Ser Glu Glu Leu Val
625                 630                 635                 640

Arg Ser Gly Arg Tyr Thr Asp Arg Ser Trp Asn Ser Gly Ile Val Phe
                645                 650                 655

Lys Pro Ser Arg His Leu Ser Leu Ser Tyr Arg Ala Ser Ser Gly Phe
            660                 665                 670

Arg Thr Pro Ser Phe Gln Glu Leu Phe Gly Ile Asp Ile Tyr His Asp
        675                 680                 685

Tyr Pro Lys Gly Trp Gln Arg Pro Ala Leu Lys Ser Glu Lys Ala Ala
    690                 695                 700

Asn Arg Glu Ile Gly Leu Gln Trp Lys Gly Asp Phe Gly Phe Leu Glu
705                 710                 715                 720

Ile Ser Ser Phe Arg Asn Arg Tyr Thr Asp Met Ile Ala Val Ala Asp
                725                 730                 735

His Lys Thr Lys Leu Pro Asn Gln Ala Gly Arg Leu Thr Glu Ile Asp
            740                 745                 750

Ile Arg Asp Tyr Tyr Asn Ala Gln Asn Met Ser Leu Gln Gly Val Asn
        755                 760                 765

Ile Leu Gly Lys Ile Asp Trp Asn Gly Val Tyr Gly Lys Leu Pro Glu
    770                 775                 780

Gly Leu Tyr Thr Thr Leu Ala Tyr Asn Arg Ile Lys Pro Lys Ser Val
785                 790                 795                 800

Ser Asn Arg Pro Asp Leu Ser Leu Arg Ser Tyr Ala Leu Asp Ala Gly
                805                 810                 815

Gln Pro Ser Arg Tyr Val Leu Gly Phe Gly Tyr Asp Gln Pro Glu Gly
            820                 825                 830

Lys Trp Gly Ala Asn Ile Met Leu Thr Tyr Ser Lys Gly Lys Asn Pro
        835                 840                 845

Asp Glu Leu Ala Tyr Leu Ala Gly Asp Gln Lys Arg Tyr Ser Thr Lys
    850                 855                 860

Arg Ala Ser Ser Ser Trp Ser Thr Ala Asp Val Ser Ala Tyr Leu Asn
865                 870                 875                 880

Leu Lys Lys Arg Leu Thr Leu Arg Ala Ala Ile Tyr Asn Ile Gly Asn
                885                 890                 895

Tyr Arg Tyr Val Thr Trp Glu Ser Leu Arg Gln Thr Ala Glu Ser Thr
            900                 905                 910

Ala Asn Arg His Gly Gly Asp Ser Asn Tyr Gly Arg Tyr Ala Ala Pro
        915                 920                 925

Gly Arg Asn Phe Ser Leu Ala Leu Glu Met Lys Phe Pro
930                 935                 940
```

(2) INFORMATION FOR SEQ ID NO:76:

(i) SEQUENCE CHARACTERISTICS:
        (A) LENGTH: 76 amino acids
        (B) TYPE: amino acid
        (C) STRANDEDNESS: single
        (D) TOPOLOGY: linear (xi) SEQUENCE DESCRIPTION: SEQ ID NO:76:

```
Gly Phe Tyr Gly Pro Lys Ala Glu Glu Leu Gly Ile Ile Phe Asn
1               5                   10                  15

Asn Asp Gly Lys Ser Leu Gly Ile Thr Glu Gly Thr Glu Asn Lys Val
            20                  25                  30

Glu Ala Asp Val Asp Val Asp Val Asp Val Asp Ala Asp Ala
            35                  40                  45

Asp Val Glu Gln Leu Lys Pro Glu Val Lys Pro Gln Phe Gly Val Val
        50                  55                  60

Phe Gly Ala Lys Lys Asp Asn Lys Glu Val Glu Lys
65                  70                  75
```

(2) INFORMATION FOR SEQ ID NO:77:

(i) SEQUENCE CHARACTERISTICS:
        (A) LENGTH: 183 amino acids
        (B) TYPE: amino acid
        (C) STRANDEDNESS: single
        (D) TOPOLOGY: linear (xi) SEQUENCE DESCRIPTION: SEQ ID NO:77:

```
Leu Lys Gly Ile Arg Thr Ala Glu Ala Asp Ile Pro Gln Thr Gly Lys
1               5                   10                  15

Ala Arg Tyr Thr Gly Thr Trp Glu Ala Arg Ile Ser Lys Pro Ile Gln
            20                  25                  30

Trp Asp Asn His Ala Asp Lys Lys Ala Ala Lys Ala Glu Phe Asp Val
            35                  40                  45

Asp Phe Gly Glu Lys Ser Ile Ser Gly Thr Leu Thr Glu Lys Asn Gly
        50                  55                  60

Val Gln Pro Ala Phe His Ile Glu Asn Gly Val Ile Glu Gly Asn Gly
65                  70                  75                  80

Phe His Ala Thr Ala Arg Thr Arg Asp Asn Gly Ile Asn Leu Ser Gly
                85                  90                  95

Asn Asp Ser Thr Asn Pro Pro Ser Phe Lys Ala Asn Asn Leu Leu Val
                100                 105                 110

Thr Gly Gly Phe Tyr Gly Pro Gln Ala Glu Glu Leu Gly Gly Thr Ile
            115                 120                 125

Phe Asn Asn Asp Gly Lys Ser Leu Gly Ile Thr Glu Asp Thr Glu Asn
        130                 135                 140

Glu Ala Glu Ala Glu Val Glu Asn Glu Ala Gly Val Gly Glu Gln Leu
145                 150                 155                 160

Lys Pro Glu Ala Lys Pro Gln Phe Gly Val Val Phe Gly Ala Lys Lys
                165                 170                 175

Asp Asn Lys Glu Val Glu Lys
            180
```

(2) INFORMATION FOR SEQ ID NO:78:

(i) SEQUENCE CHARACTERISTICS:
        (A) LENGTH: 92 amino acids
        (B) TYPE: amino acid
        (C) STRANDEDNESS: single
        (D) TOPOLOGY: linear (xi) SEQUENCE DESCRIPTION: SEQ ID NO:78:

```
Arg Asp Asn Gly Ile Asn Leu Ser Gly Asn Gly Ser Thr Asn Pro Gln
1               5                   10                  15

Ser Phe Lys Ala Asp Asn Leu Leu Val Thr Gly Gly Phe Tyr Gly Pro
            20                  25                  30
```

-continued

```
Gln Ala Ala Glu Leu Gly Gly Thr Ile Phe Asn Lys Asp Gly Lys Ser
        35                  40                  45

Leu Gly Ile Thr Glu Asp Ile Glu Asn Glu Val Glu Asn Glu Ala Asp
    50                  55                  60

Val Gly Glu Gln Leu Glu Pro Glu Val Lys Pro Gln Phe Gly Val Val
65                  70                  75                  80

Phe Gly Ala Lys Lys Asp Asn Lys Glu Val Glu Lys
                85                  90
```

What we claim is:

1. A purified and isolated nucleic acid molecule having a DNA sequence selected from the group consisting of:

(a) a DNA sequence having SEQ ID No. 69 or the fully complementary DNA sequence thereto;

(b) a DNA sequence encoding an amino acid sequence having SEQ ID No. 70 or the fully complementary DNA sequence thereto; and (c) a DNA sequence encoding a functional lactoferrin receptor protein of Moraxella and which hybridizes under high stringency conditions to any one of the sequences defined in (a) or (b).

2. A vector adapted for transformation of a host comprising the nucleic acid molecule of claim 1.

3. The vector of claim 2 encoding a lactoferin receptor protein and selected from the group consisting of pVH19pc1 and pVH19pcr2.

4. The vector of claim 2 further comprising expression means operatively coupled to the nucleic acid molecule for expression of said lactoferrin receptor protein of a strain of Moraxella by the host containing the vector.

5. A transformed host containing an expression vector as claimed in claimed 4.

* * * * *